US009366371B2

(12) United States Patent
Naftalovitz et al.

(10) Patent No.: US 9,366,371 B2
(45) Date of Patent: Jun. 14, 2016

(54) CLOSED MALE LUER CONNECTOR

(71) Applicant: ELCAM MEDICAL AGRICULTURAL COOPERATIVE ASSOCIATION LTD., D.N. Merom Hagalil (IL)

(72) Inventors: Ziv Naftalovitz, Kibbutz Eilon (IL); Amit Shlezinger, D.N. Merom Hagalil (IL); Tsachi Shaked, D.N. Merom Hagalil (IL); Avi Yogev, D.N. Merom Hagalil (IL); Tomer Gil, D.N. Merom Hagalil (IL)

(73) Assignee: ELCAM MEDICAL AGRICULTURAL COOPERATIVE ASSOCIATION LTD., D.N. Merom Hagalil (IL)

( * ) Notice: Subject to any disclaimer, the term of this patent is extended or adjusted under 35 U.S.C. 154(b) by 129 days.

(21) Appl. No.: 14/251,990

(22) Filed: Apr. 14, 2014

(65) Prior Publication Data

US 2014/0217719 A1    Aug. 7, 2014

Related U.S. Application Data

(63) Continuation of application No. 13/257,558, filed as application No. PCT/IL2010/000227 on Mar. 18, 2010, now Pat. No. 8,757,590.

(60) Provisional application No. 61/162,305, filed on Mar. 22, 2009, provisional application No. 61/259,703, filed on Nov. 10, 2009, provisional application No. 61/290,523, filed on Dec. 29, 2009.

(51) Int. Cl.
*F16L 37/46* (2006.01)
*A61M 39/26* (2006.01)
(Continued)

(52) U.S. Cl.
CPC ............. *F16L 37/46* (2013.01); *A61M 39/26* (2013.01); *F16L 15/006* (2013.01); *F16L 33/24* (2013.01); *A61M 2039/0072* (2013.01); *A61M 2039/267* (2013.01); *A61M 2039/268* (2013.01)

(58) Field of Classification Search
CPC ......... F16L 37/46; F16L 33/24; F16L 15/006; A61M 39/26; A61M 39/22; A61M 39/10
USPC .......... 251/149.1, 149.3, 149.4, 149.6, 149.7; 604/256, 246, 249
See application file for complete search history.

(56) References Cited

U.S. PATENT DOCUMENTS 5,485,982 A * 1/1996 Gunderson ............. F16L 37/42
                                                         251/149.1
5,651,776 A * 7/1997 Appling ................. A61M 39/10
                                                         285/332

(Continued)

*Primary Examiner* — John K Fristoe, Jr.
*Assistant Examiner* — David Colon Morales
(74) *Attorney, Agent, or Firm* — Sughrue Mion, PLLC

(57) ABSTRACT

A fluid flow connector including a housing assembly, having a first end and a second end arranged along a common longitudinal axis, and a resilient fluid flow conduit member having a forward end, disposed alongside the first end of the housing assembly, formed with a selectably closable slit and with at least one side opening. The resilient fluid flow conduit member is positioned in a closed position wherein the slit is closed but the at least one side opening is open and in an open position, allowing the slit to open and leaving the at least one side opening open, whereby when the resilient fluid flow conduit member is in the open position, the selectably closable slit and the at least one side opening each provide a fluid flow pathway between an interior of the resilient fluid flow conduit member and the first end of the housing assembly.

17 Claims, 90 Drawing Sheets

(51) Int. Cl.
*F16L 15/00* (2006.01)
*F16L 33/24* (2006.01)
*A61M 39/00* (2006.01)

(56) References Cited

U.S. PATENT DOCUMENTS

| | | | | |
|---|---|---|---|---|
| 5,676,346 A * | 10/1997 | Leinsing | ............... | A61M 39/26 251/149.1 |
| 5,699,821 A * | 12/1997 | Paradis | ................ | A61J 1/1412 137/1 |
| 5,702,374 A * | 12/1997 | Johnson | ................ | A61M 39/10 128/912 |
| 5,814,024 A * | 9/1998 | Thompson | .......... | A61M 39/045 251/149.1 |
| 6,039,302 A * | 3/2000 | Cote, Sr. | ................ | A61M 39/26 251/149.1 |
| 6,050,978 A * | 4/2000 | Orr | ....................... | A61M 39/26 251/149.1 |
| 6,068,011 A * | 5/2000 | Paradis | ................ | A61J 1/1412 137/1 |
| 6,079,432 A * | 6/2000 | Paradis | ................ | A61M 36/26 137/1 |
| 6,290,206 B1 * | 9/2001 | Doyle | ................... | A61M 39/26 251/149.1 |
| 6,543,745 B1 * | 4/2003 | Enerson | ................. | F16L 29/02 251/149.7 |
| 6,706,022 B1 * | 3/2004 | Leinsing | ............... | A61M 39/26 604/247 |
| 6,726,672 B1 * | 4/2004 | Hanly | ...................... | A61J 1/10 215/247 |
| 6,745,998 B2 * | 6/2004 | Doyle | ................... | A61M 39/045 251/149.3 |
| 6,755,391 B2 * | 6/2004 | Newton | ................ | A61M 39/26 251/149.1 |
| 6,802,490 B2 * | 10/2004 | Leinsing | ............... | A61M 39/26 251/149.6 |
| 6,964,406 B2 * | 11/2005 | Doyle | ................. | A61M 39/045 251/149.3 |
| 7,025,389 B2 * | 4/2006 | Cuschieri | .......... | A61M 39/1011 285/243 |
| 7,044,441 B2 * | 5/2006 | Doyle | ................. | A61M 39/045 251/149.3 |
| 7,100,890 B2 * | 9/2006 | Cote, Sr. | ............... | A61M 39/26 251/149.1 |
| 7,140,592 B2 * | 11/2006 | Phillips | ................ | A61B 5/1427 251/149.1 |
| 7,350,764 B2 * | 4/2008 | Raybuck | ............... | A61M 39/26 251/149.1 |
| 7,361,164 B2 * | 4/2008 | Simpson | ............... | A61M 5/178 604/122 |
| 7,396,348 B2 * | 7/2008 | Newton | ................ | A61M 39/26 604/256 |
| 7,470,262 B2 * | 12/2008 | Hiejima | ................ | A61M 39/26 604/167.04 |
| 7,497,849 B2 * | 3/2009 | Fangrow, Jr. | .......... | A61M 39/02 251/149.1 |
| 7,503,596 B2 * | 3/2009 | Rome | ................ | A61M 39/105 285/353 |
| 7,510,545 B2 * | 3/2009 | Peppel | ................. | A61M 39/045 604/256 |
| 7,530,546 B2 * | 5/2009 | Ryan | ..................... | A61M 39/26 251/149.6 |
| 7,559,530 B2 * | 7/2009 | Korogi | ................. | A61B 5/1438 251/149.6 |
| 7,591,449 B2 * | 9/2009 | Raines | ................. | A61M 39/26 251/149.1 |
| 7,645,274 B2 * | 1/2010 | Whitley | ............ | A61M 39/1011 604/537 |
| 7,648,491 B2 * | 1/2010 | Rogers | ................. | A61J 1/2089 604/411 |
| 7,651,481 B2 * | 1/2010 | Raybuck | ............... | A61M 39/045 604/213 |
| 7,666,170 B2 * | 2/2010 | Guala | .................... | A61M 39/10 604/246 |
| 7,731,155 B2 * | 6/2010 | Funamura | ......... | A61M 39/1011 251/149.6 |
| 7,753,338 B2 * | 7/2010 | Desecki | .............. | A61M 39/045 251/149.6 |
| 7,758,566 B2 * | 7/2010 | Simpson | ........... | A61M 5/36134 604/537 |
| 7,803,139 B2 * | 9/2010 | Fangrow, Jr. | .......... | A61M 39/10 251/149 |
| 7,815,168 B2 * | 10/2010 | Vangsness | .......... | A61M 39/045 251/149 |
| 7,857,805 B2 * | 12/2010 | Raines | ............... | A61M 39/1011 604/533 |
| 7,976,532 B2 * | 7/2011 | Kitani | .................... | A61M 39/26 604/533 |
| 7,998,134 B2 * | 8/2011 | Fangrow | ............. | A61M 39/1011 604/535 |
| 2004/0199126 A1 * | 10/2004 | Harding | .............. | A61M 39/045 604/256 |
| 2005/0222541 A1 * | 10/2005 | Lopez | ................. | A61M 39/045 604/249 |
| 2006/0058734 A1 * | 3/2006 | Phillips | ................ | A61M 39/26 604/93.01 |
| 2007/0218757 A1 * | 9/2007 | Guala | ................. | A61M 39/045 439/589 |
| 2008/0097407 A1 * | 4/2008 | Plishka | ............... | A61M 39/045 604/533 |
| 2008/0172004 A1 * | 7/2008 | Plishka | ............... | A61M 39/26 604/249 |
| 2009/0062776 A1 * | 3/2009 | Funamura | ............. | A61M 39/10 604/539 |
| 2009/0105692 A1 * | 4/2009 | Lopez | ............. | A61M 39/1055 604/535 |
| 2009/0143746 A1 * | 6/2009 | Mudd | ................... | A61M 5/347 604/243 |
| 2009/0156975 A1 * | 6/2009 | Robinson | ............. | A61B 5/1427 604/4.01 |
| 2009/0177170 A1 * | 7/2009 | Kitani | ................... | A61M 39/26 604/256 |
| 2009/0292274 A1 * | 11/2009 | Guala | ................. | A61M 39/26 604/533 |
| 2010/0030163 A1 * | 2/2010 | Carrez | ................. | A61M 39/22 604/256 |
| 2010/0063482 A1 * | 3/2010 | Mansour | ............... | A61M 39/26 604/539 |
| 2010/0211020 A1 * | 8/2010 | Layton, Jr. | ............. | A61M 39/16 604/247 |
| 2010/0217208 A1 * | 8/2010 | Snow | ................... | A61M 39/06 604/246 |

* cited by examiner

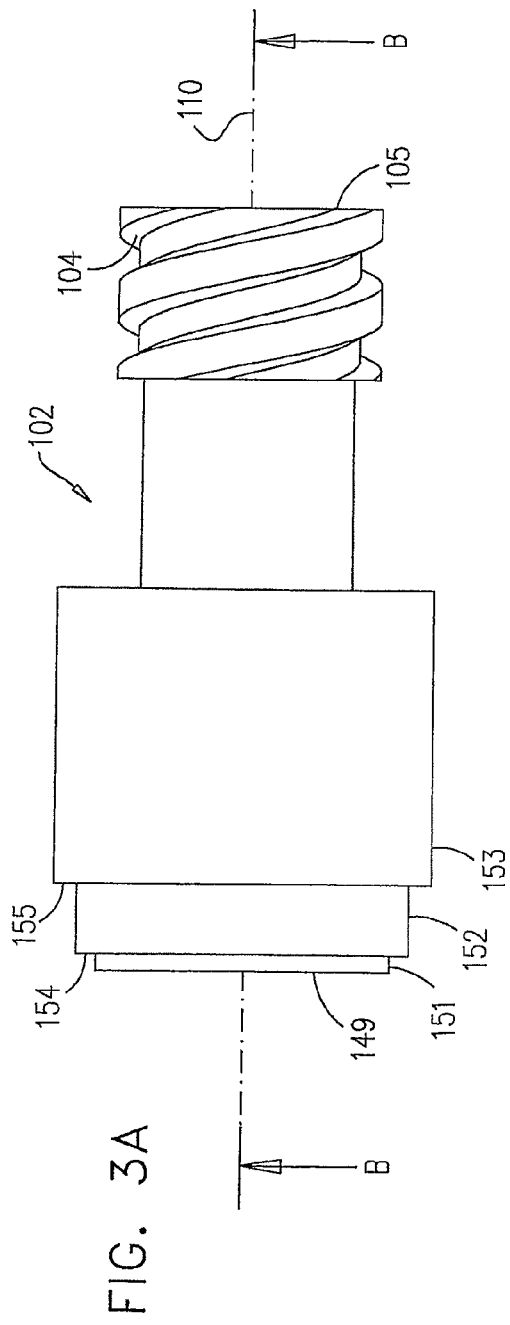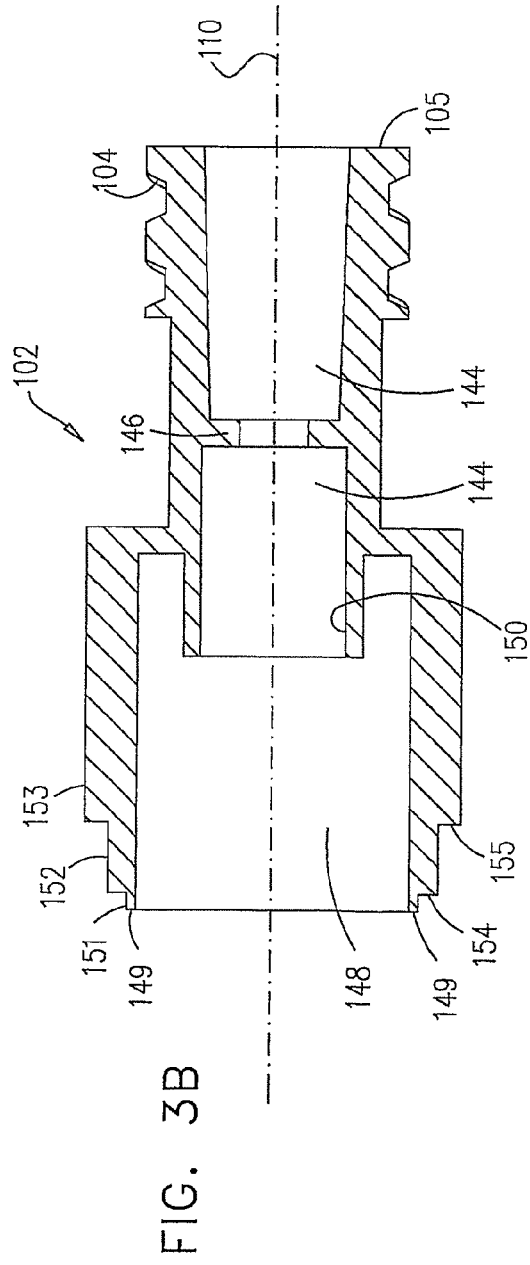
FIG. 3A
FIG. 3B

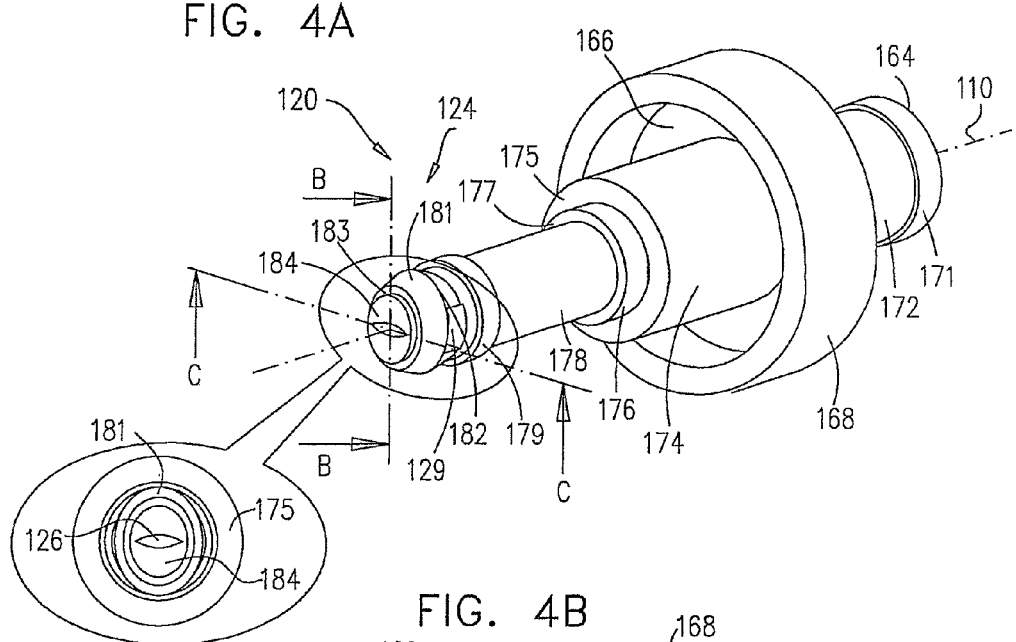
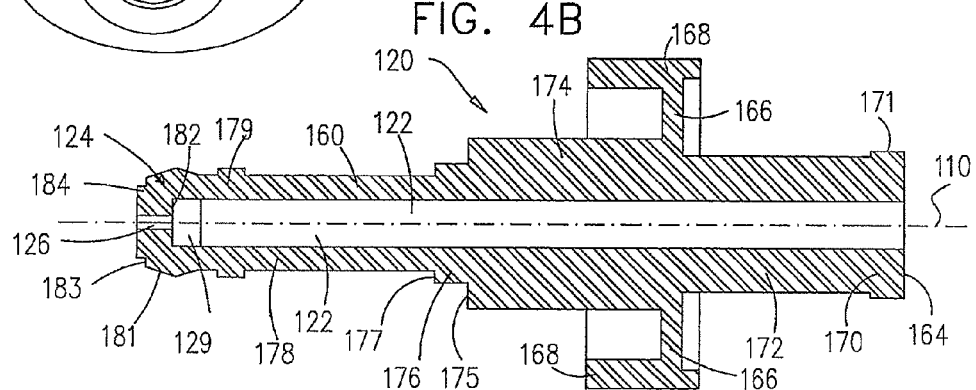
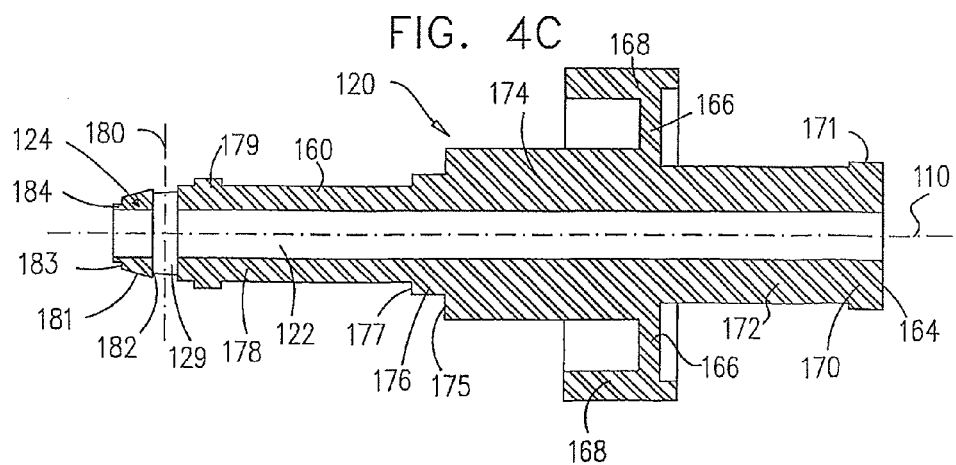

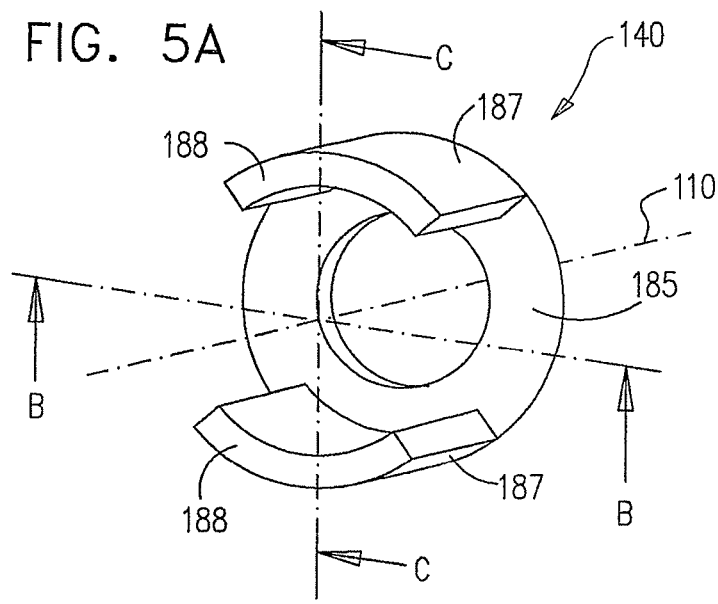
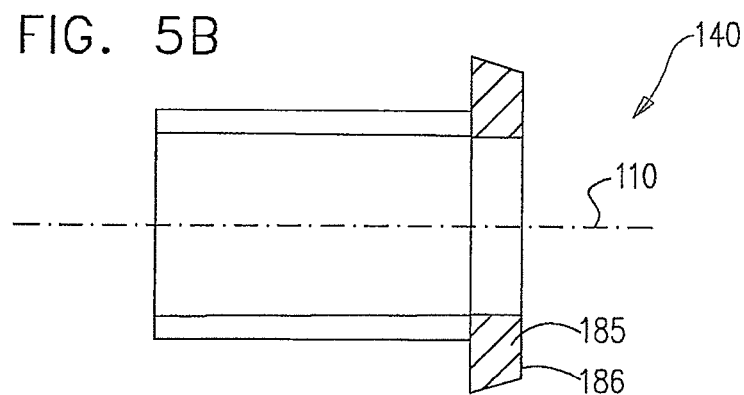
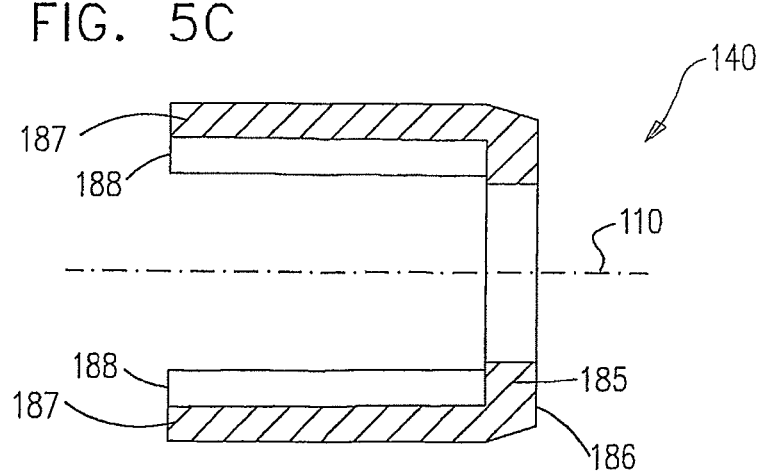

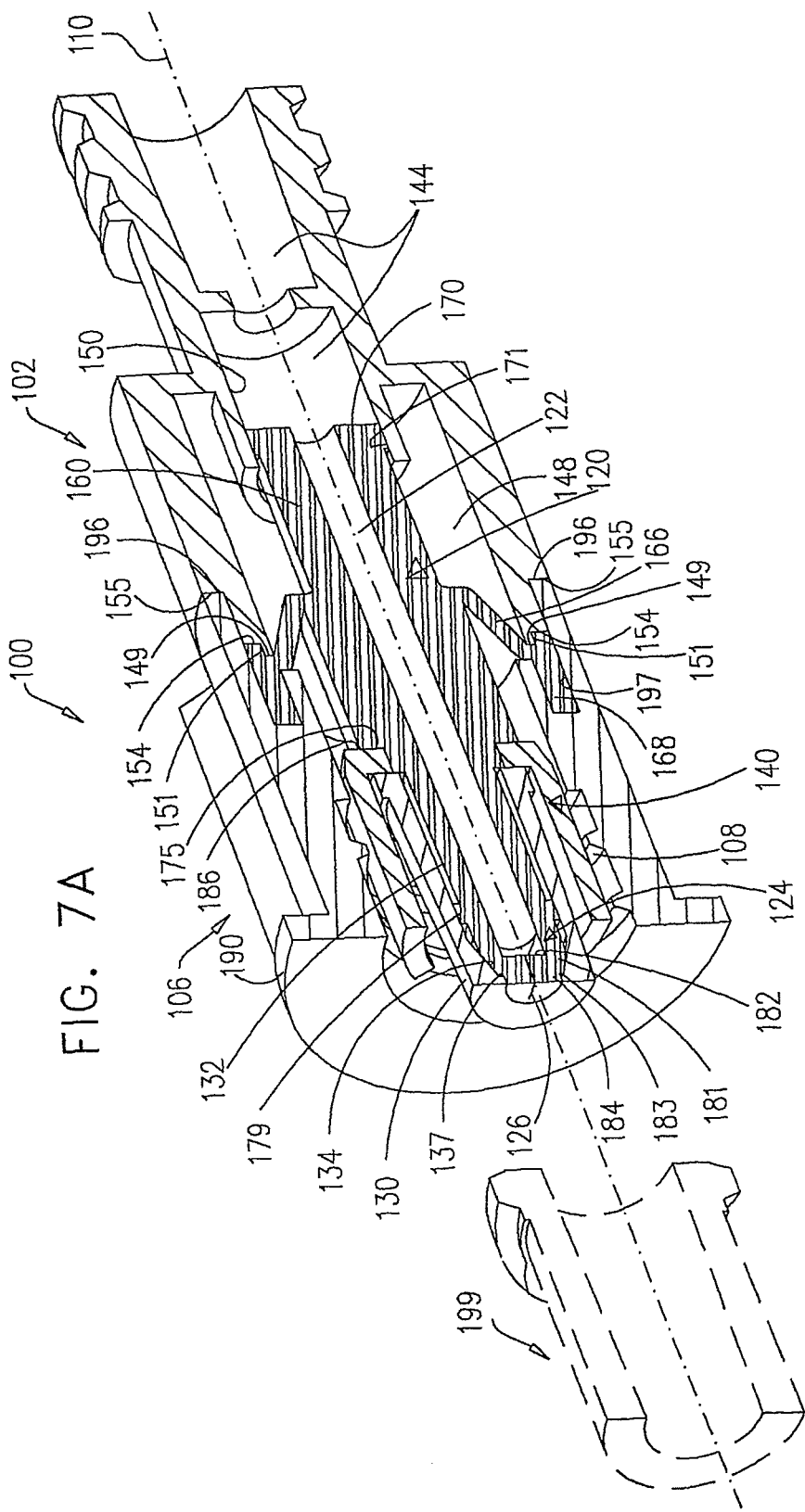

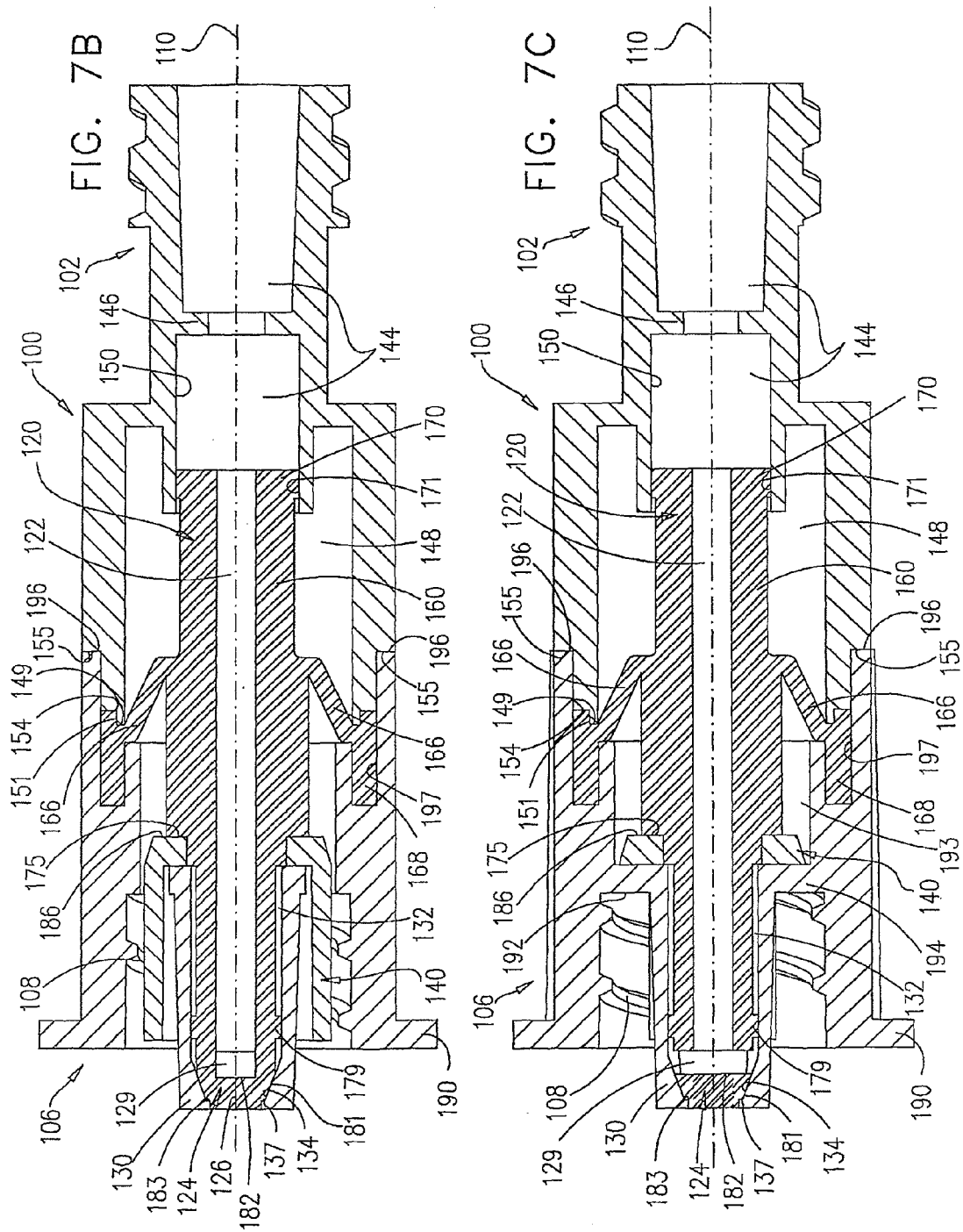

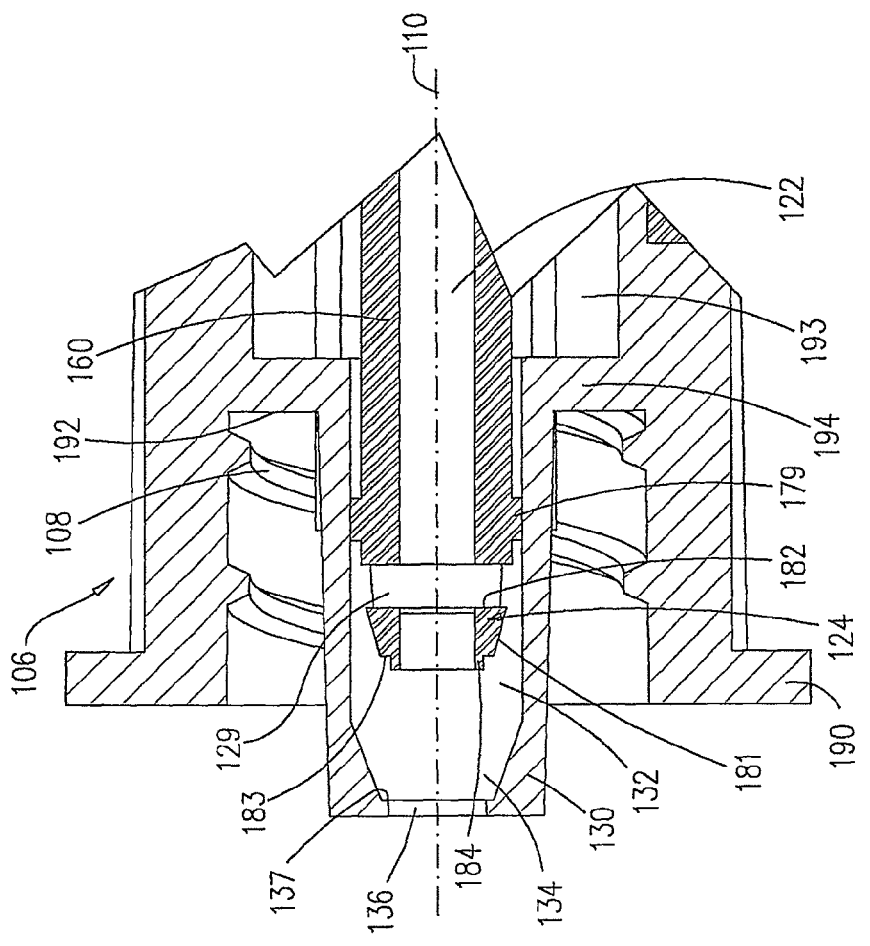
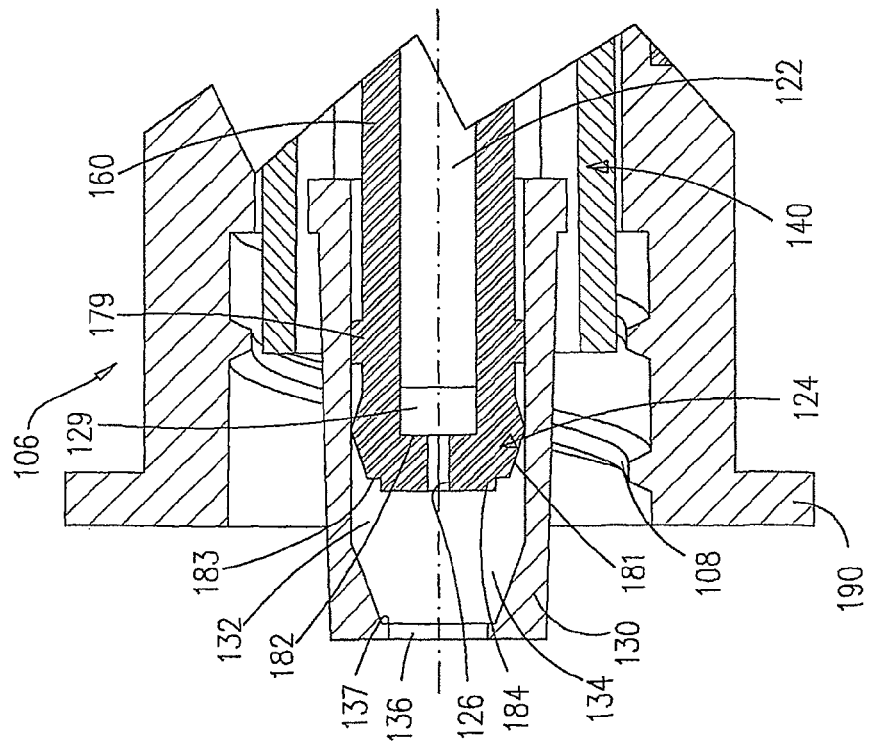

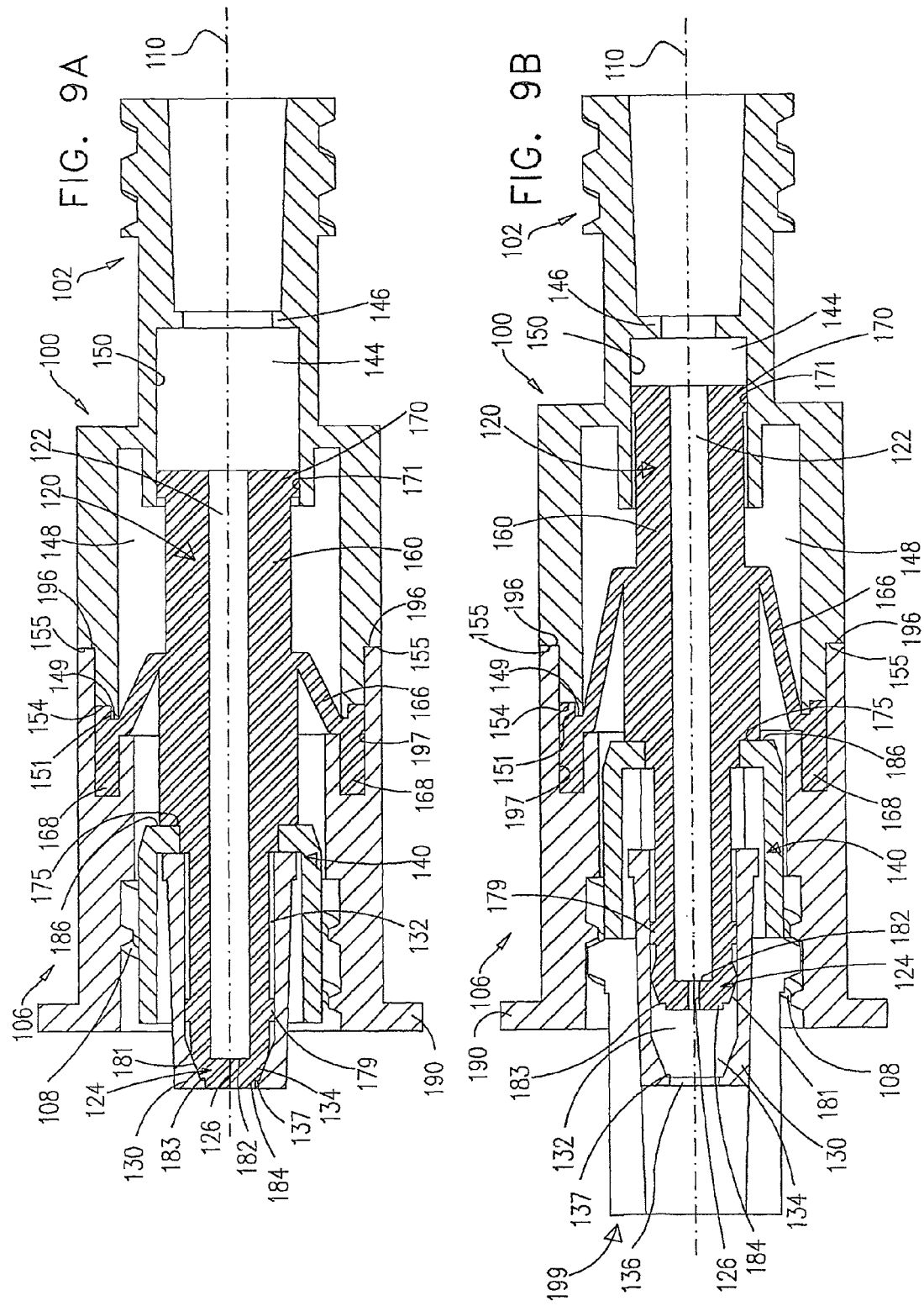

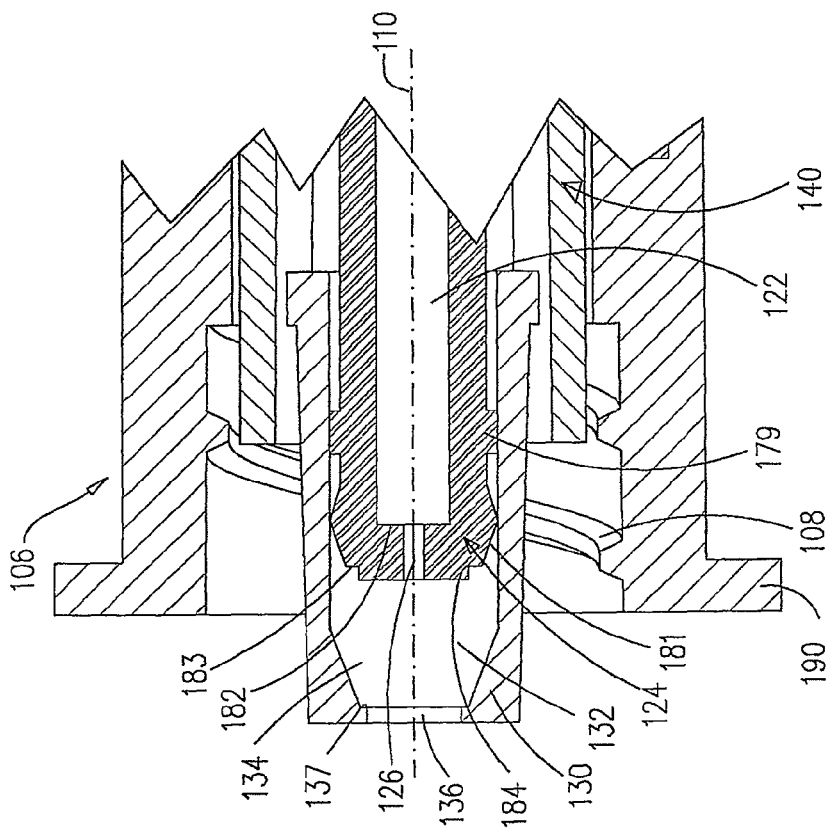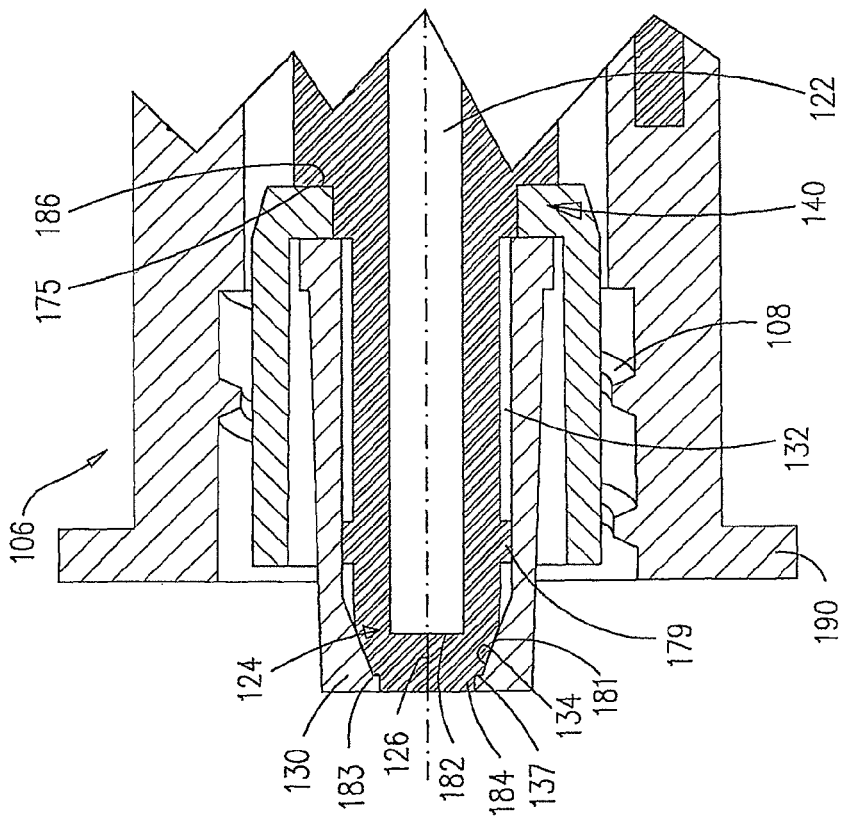

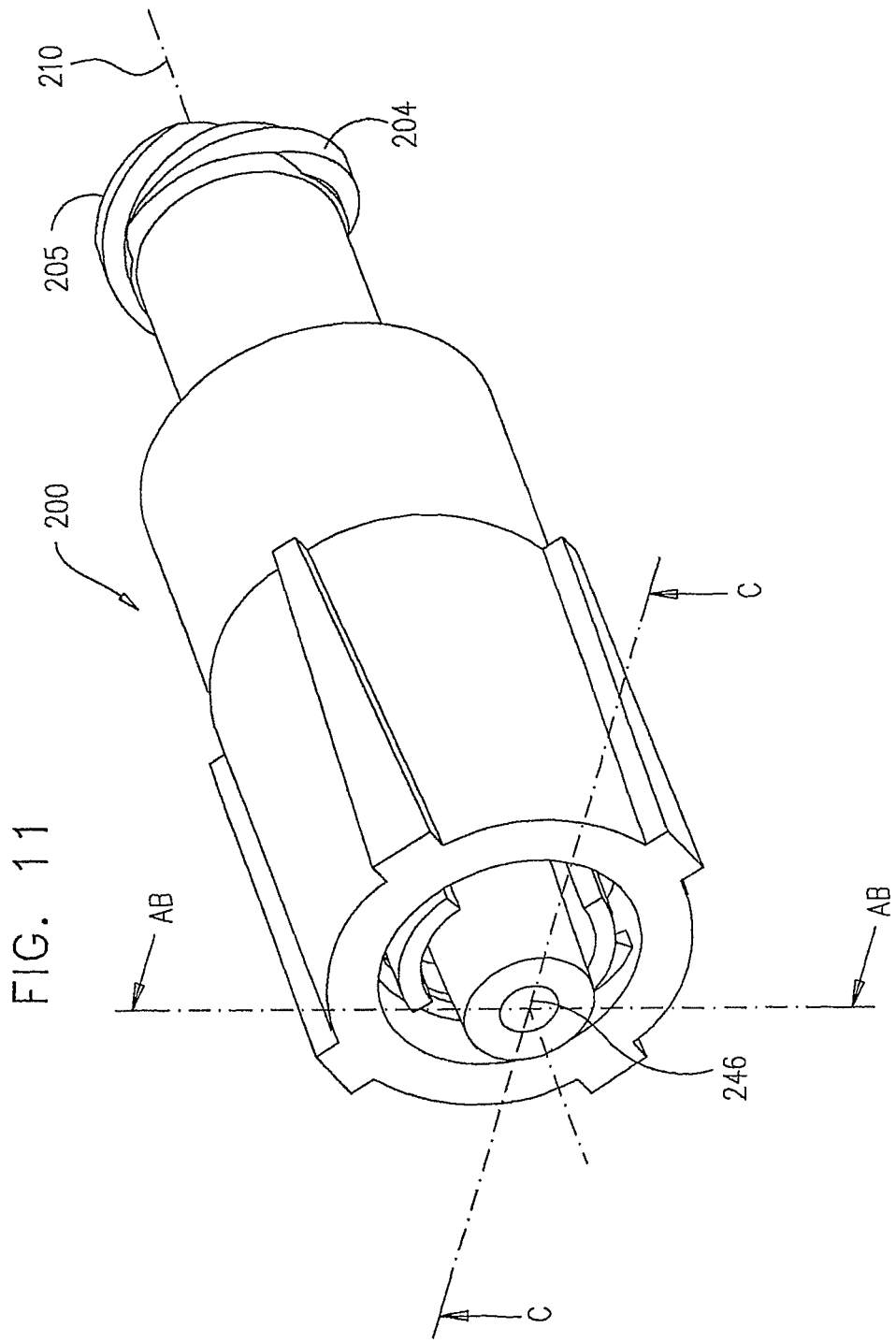

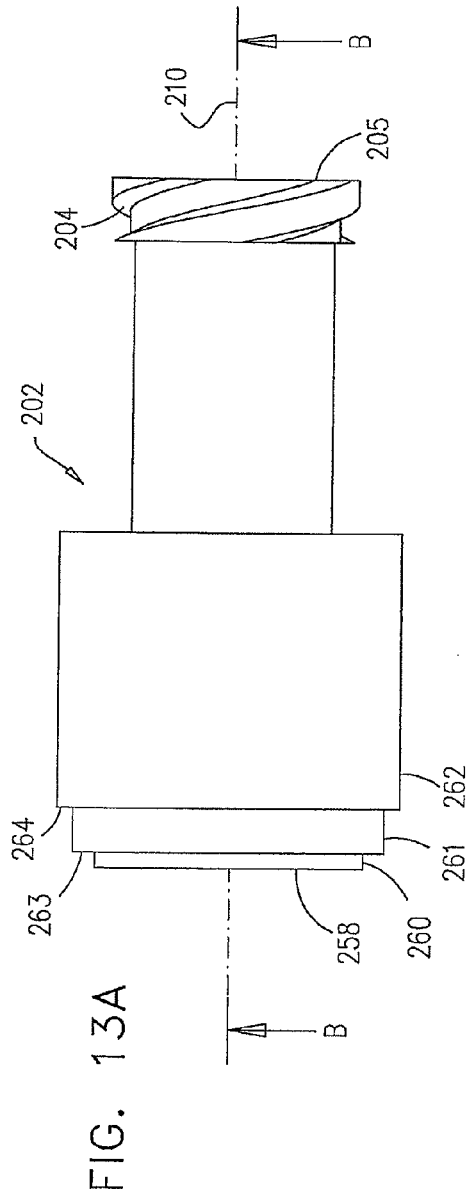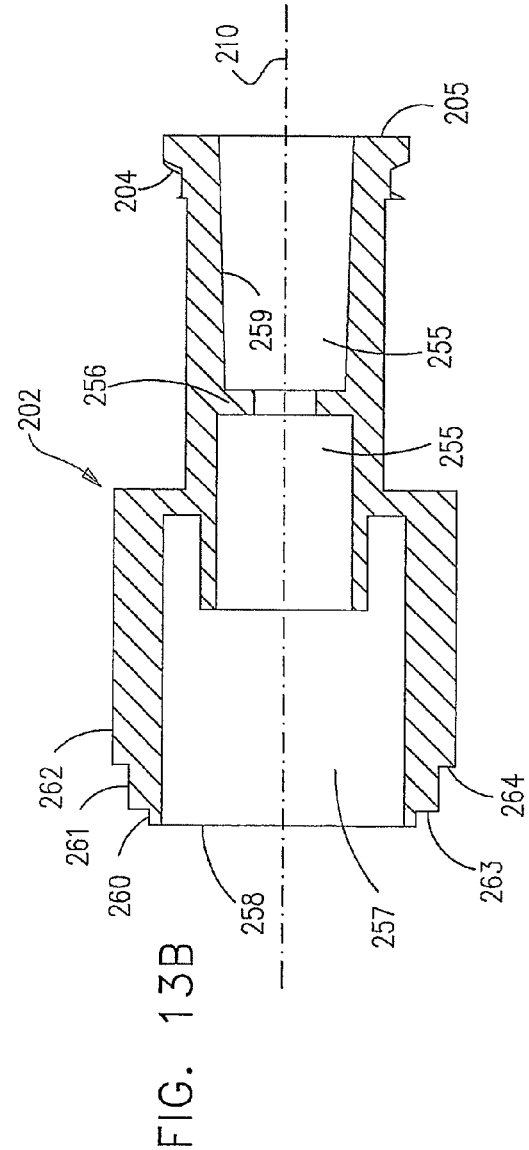
FIG. 13A
FIG. 13B

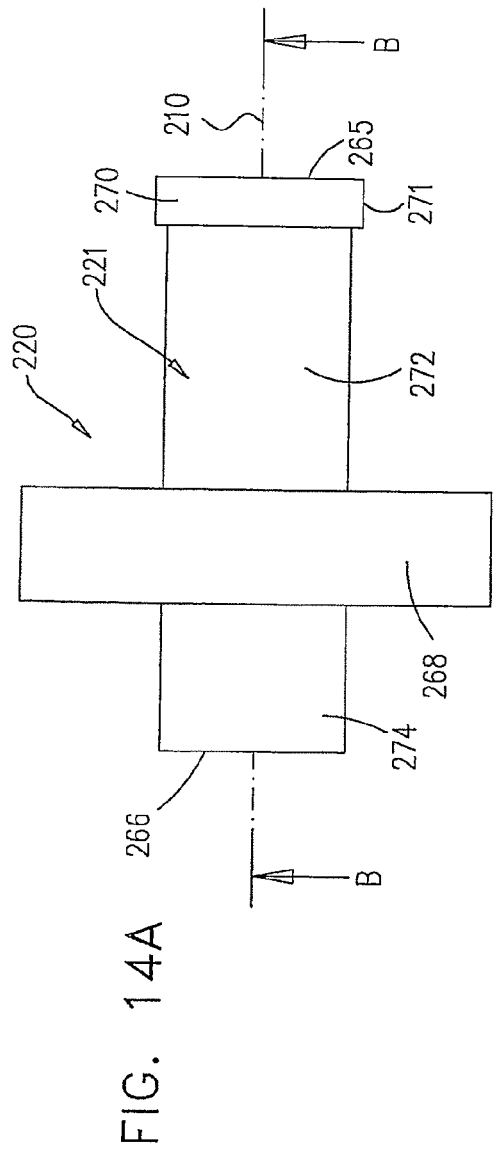
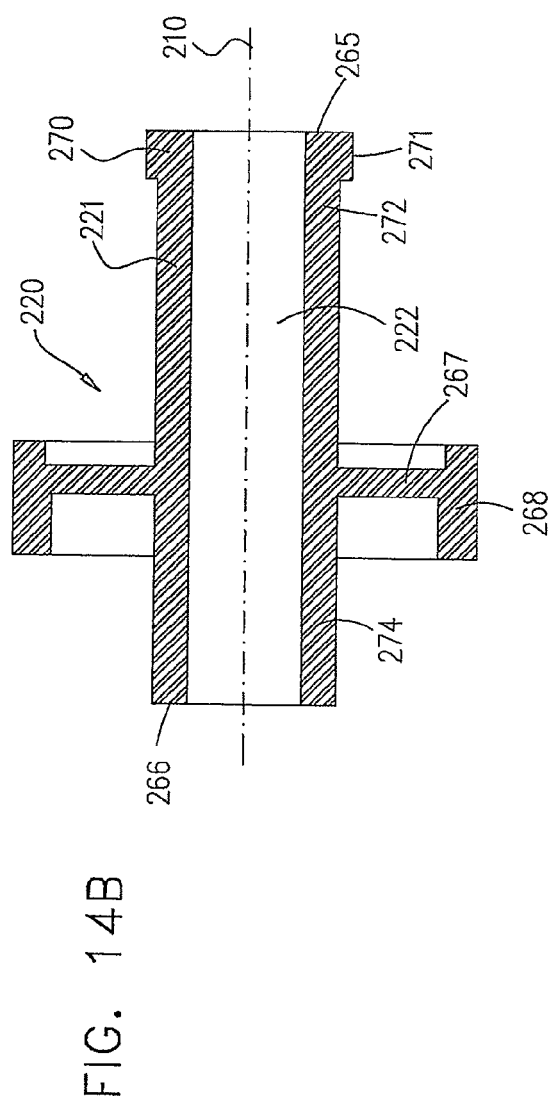
FIG. 14A
FIG. 14B

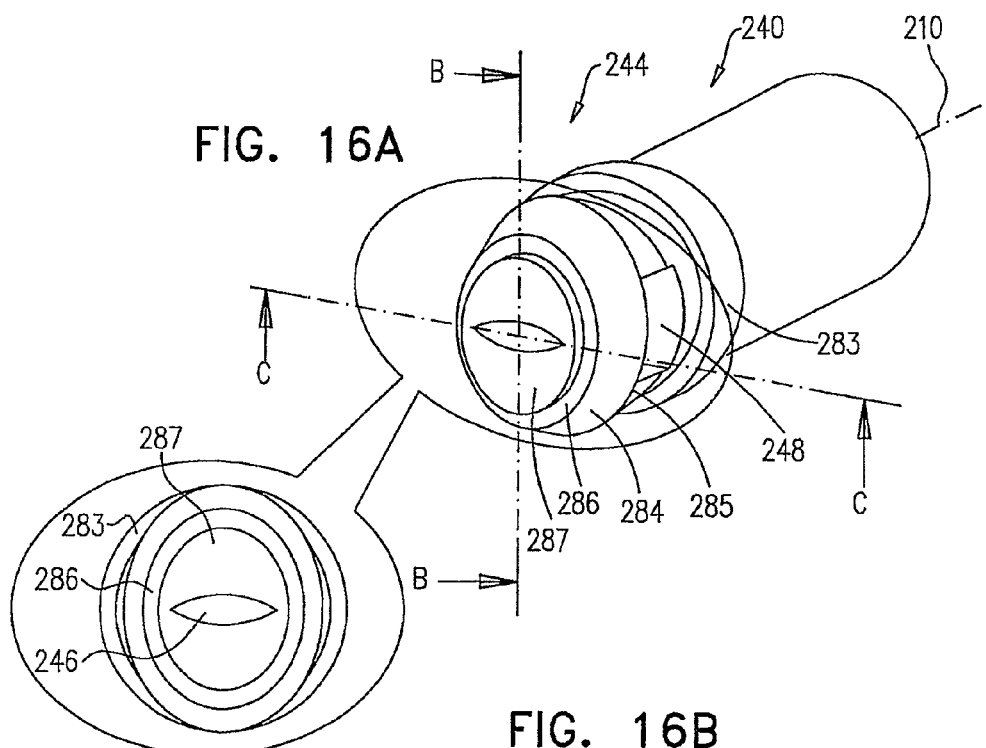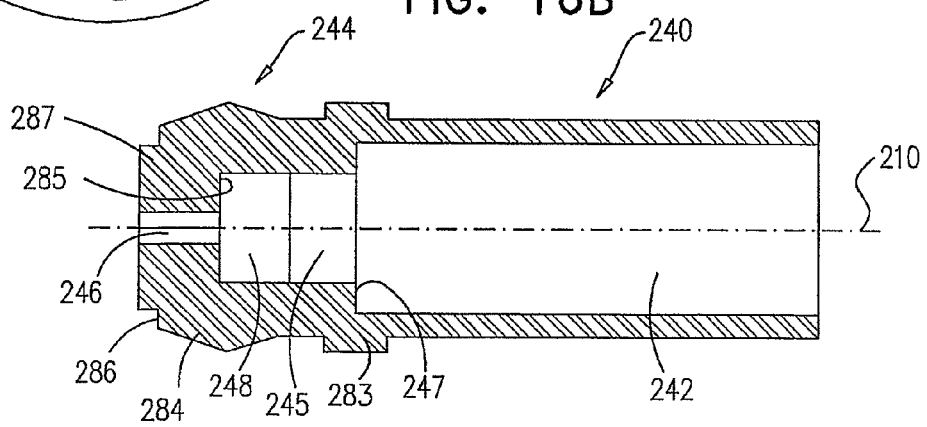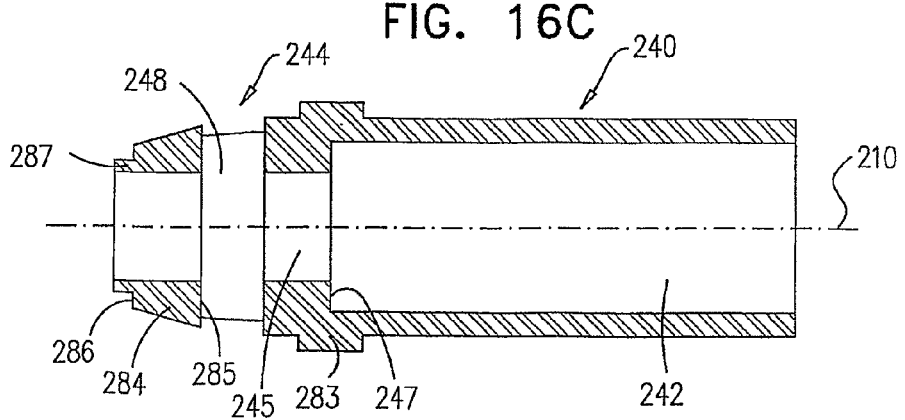

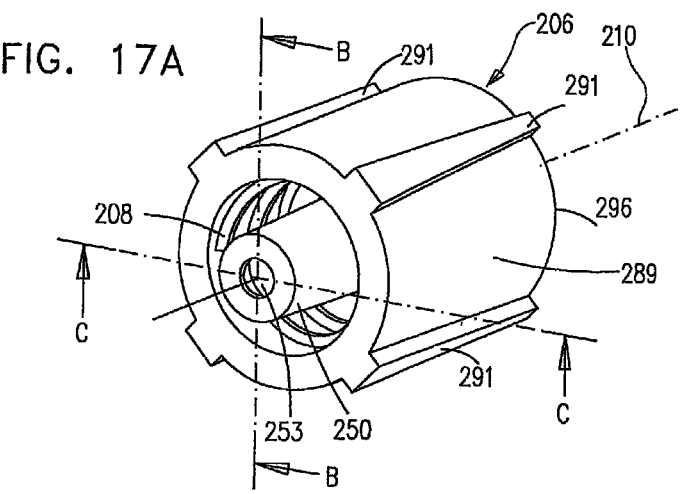
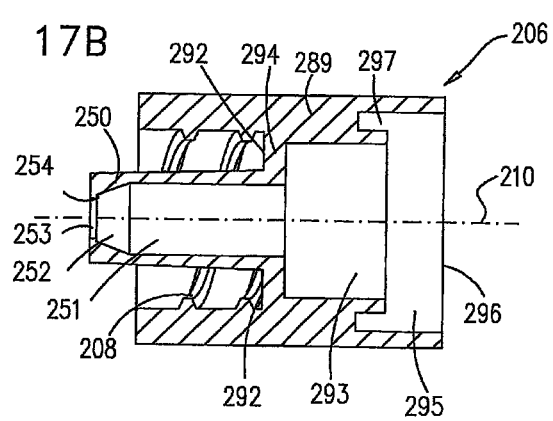
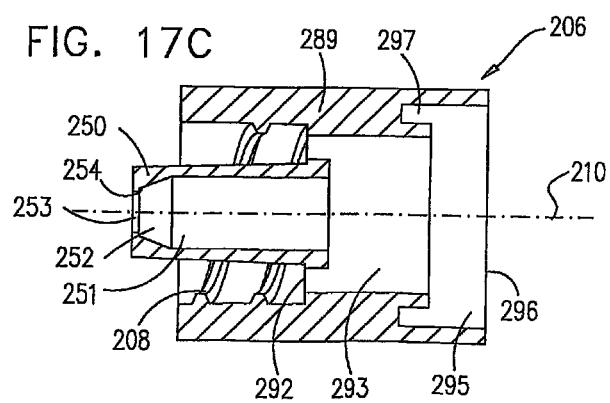

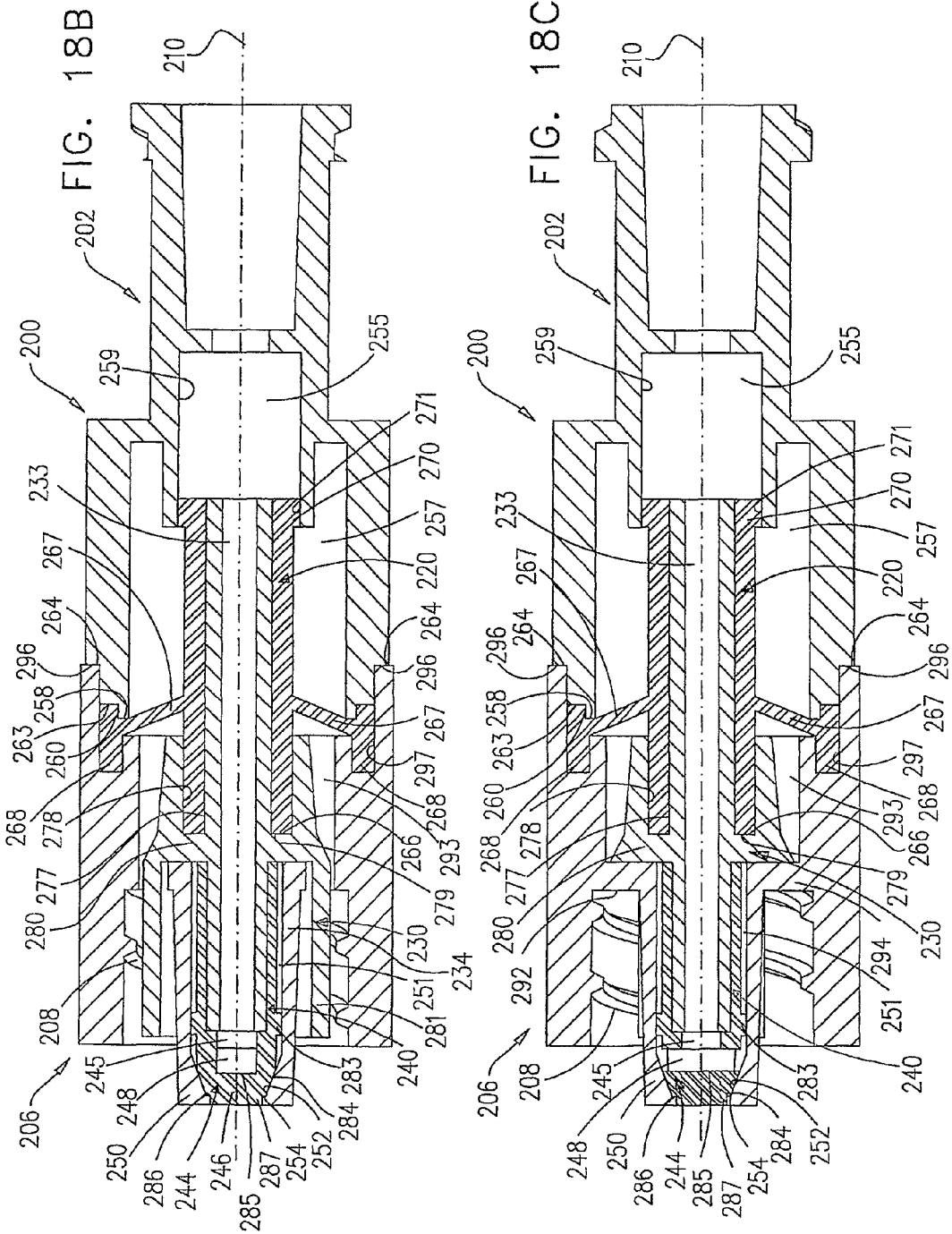

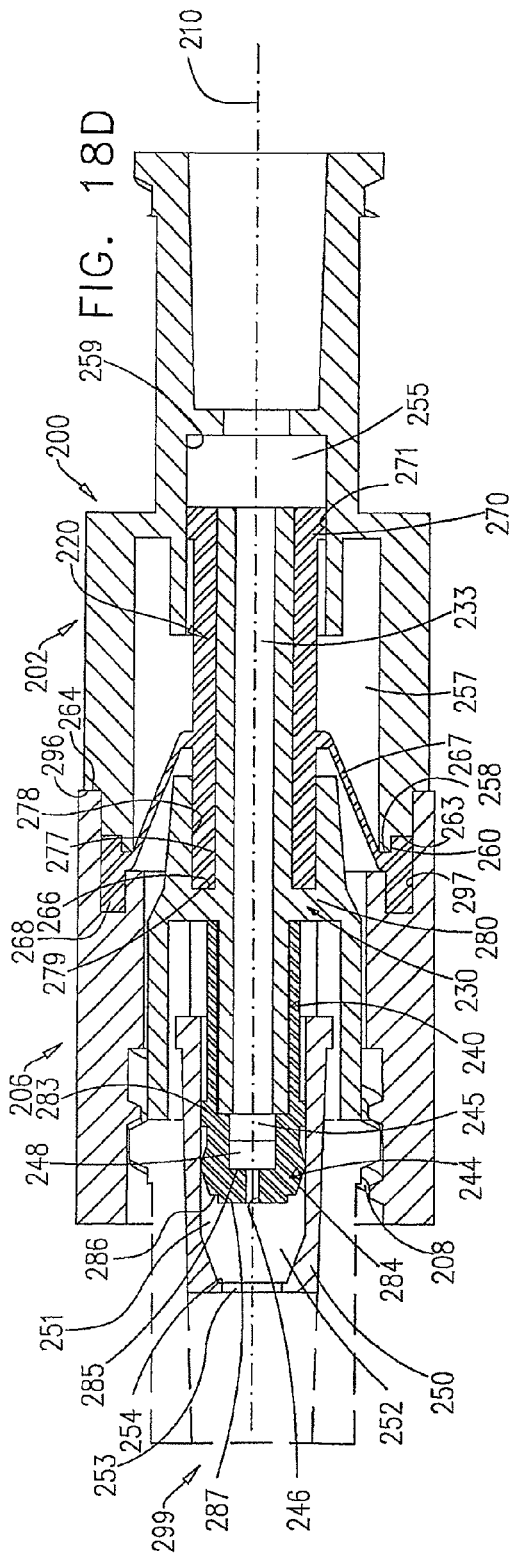
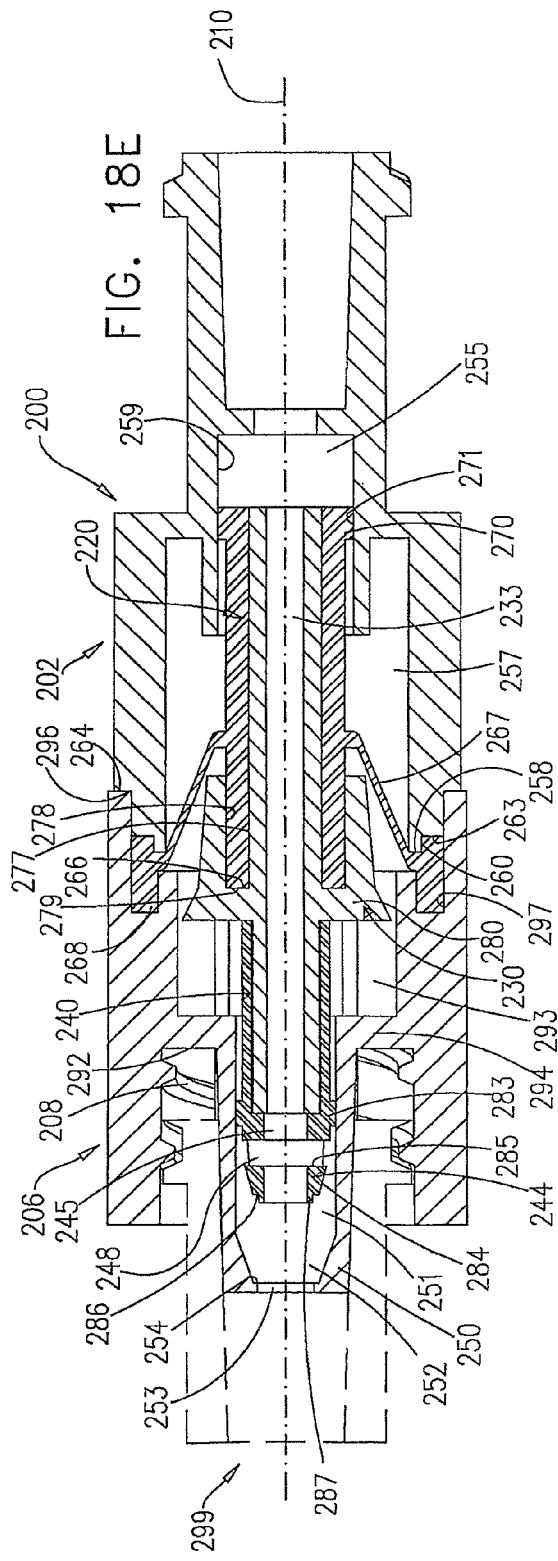

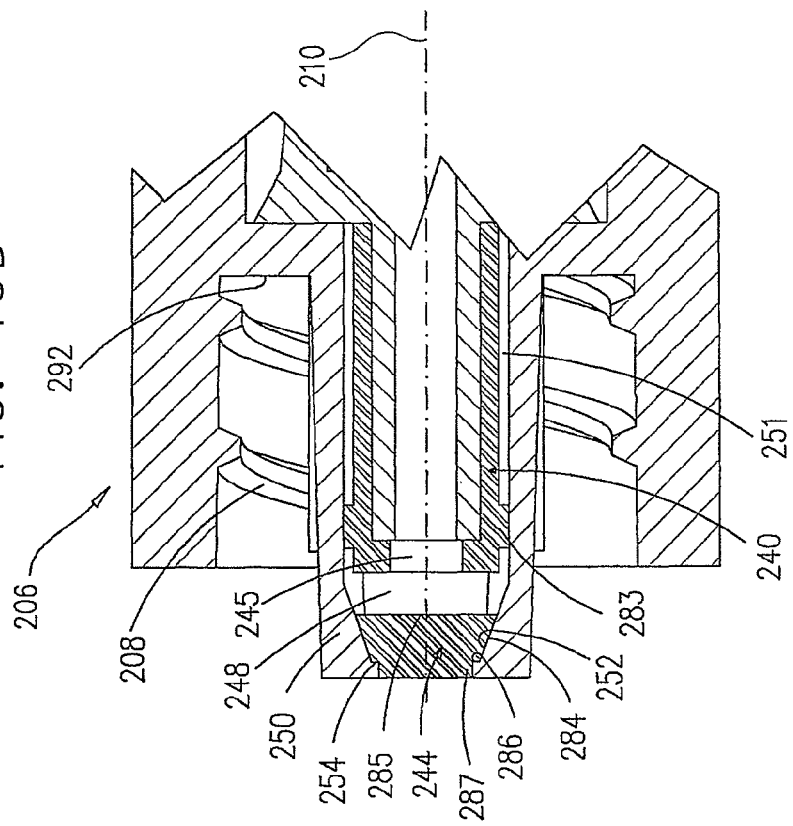
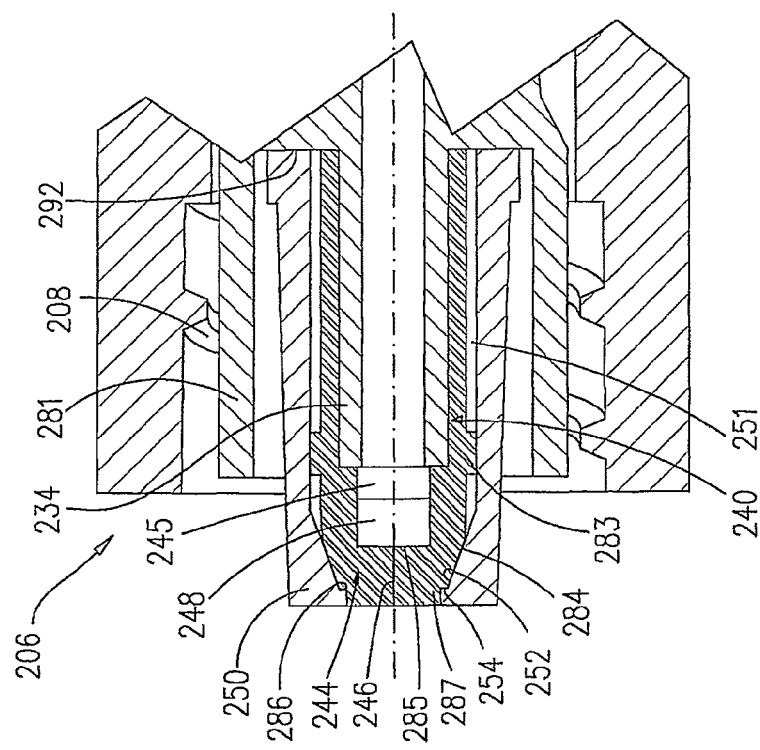

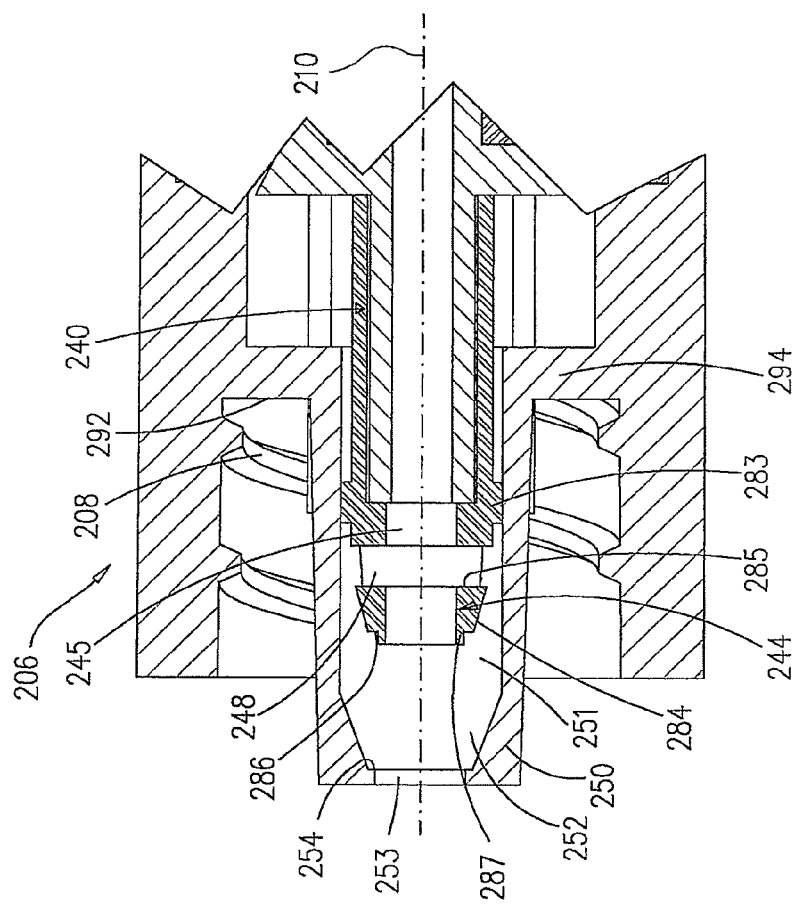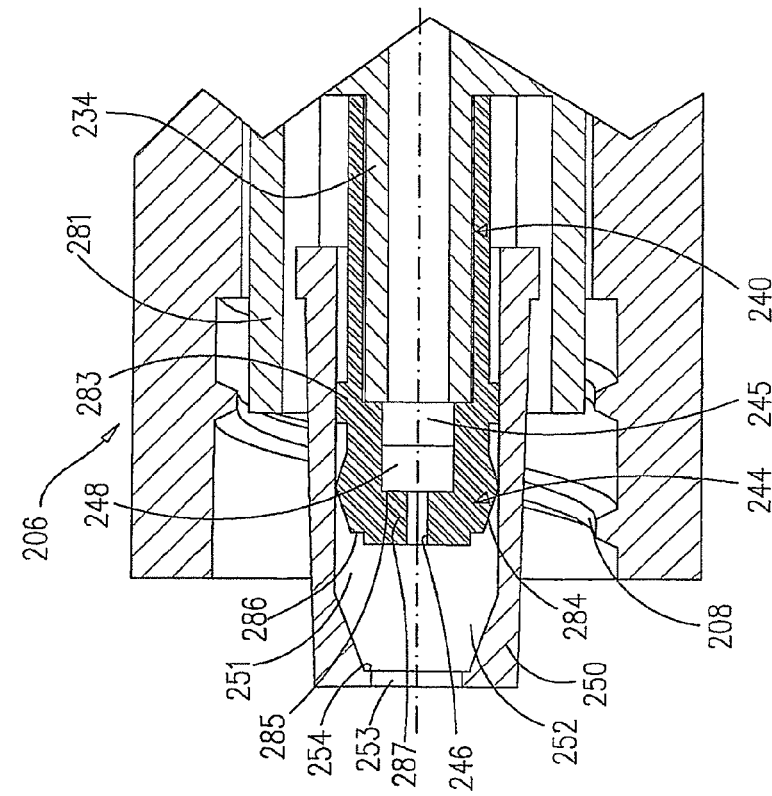

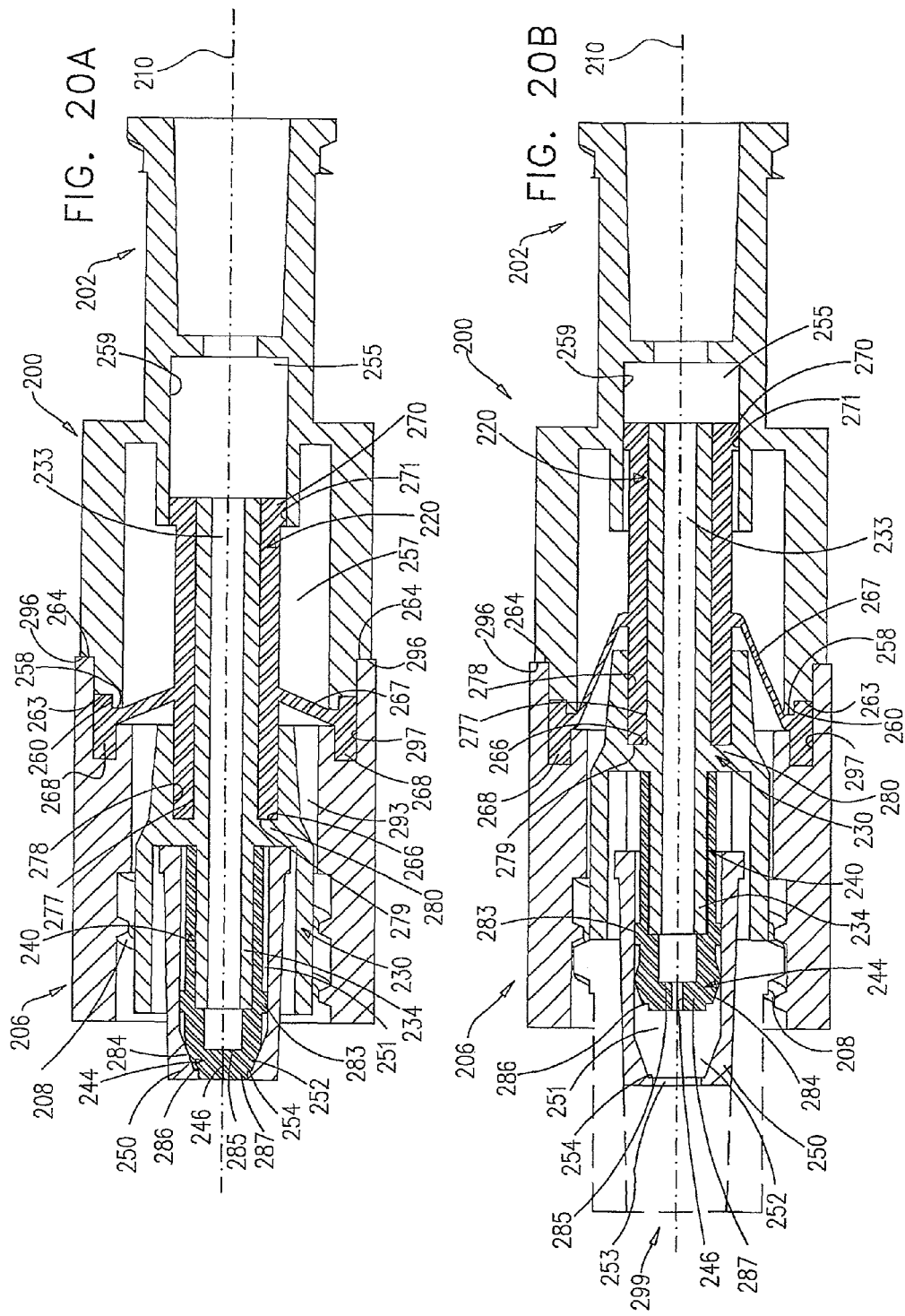

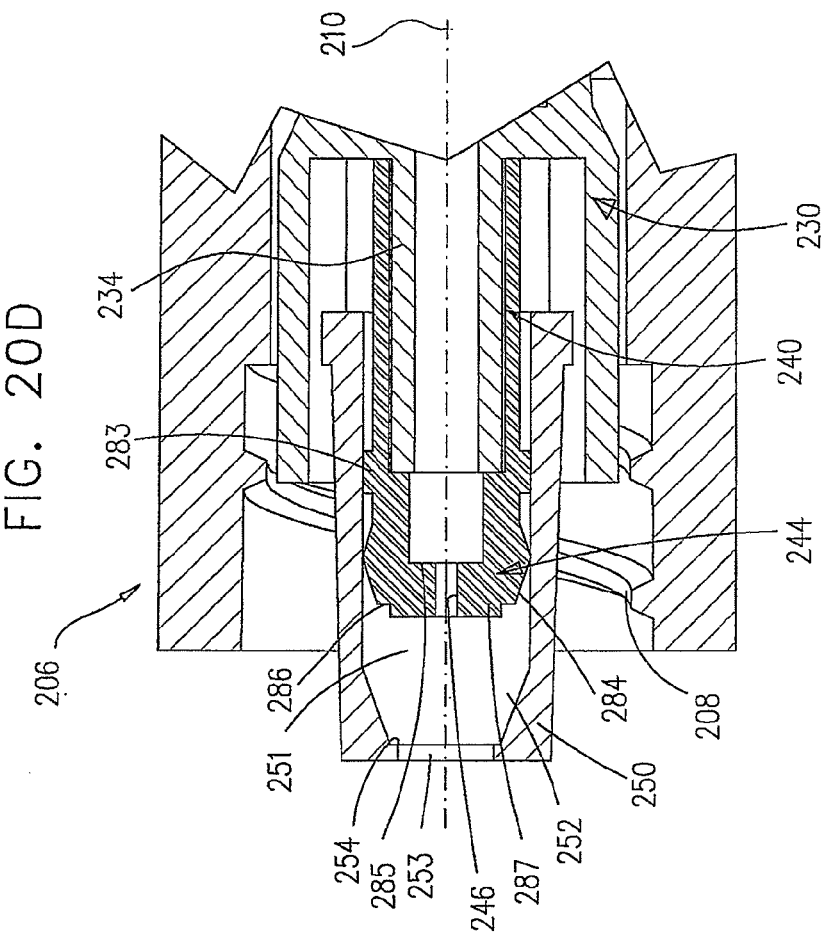
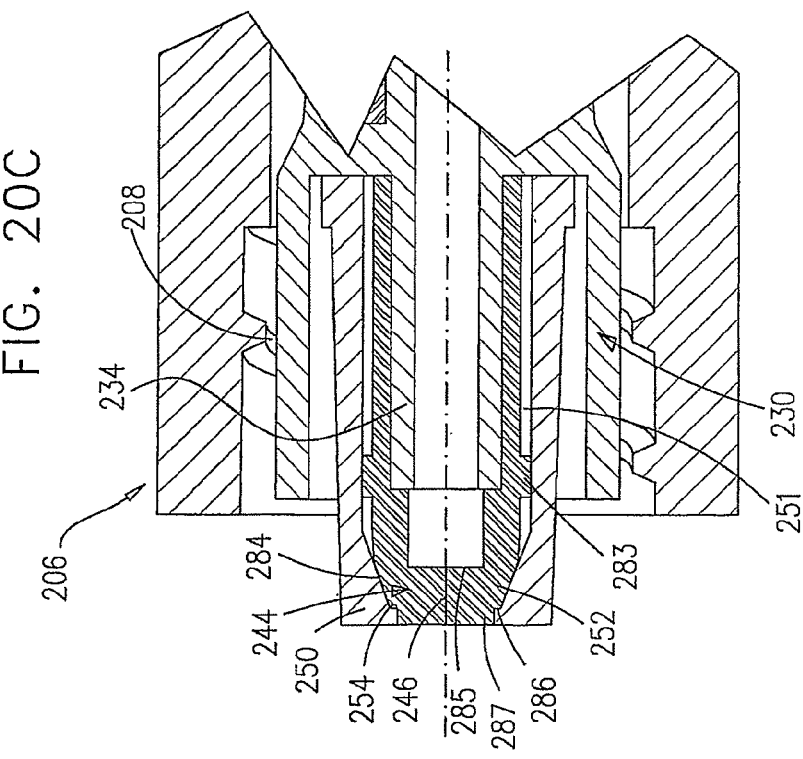

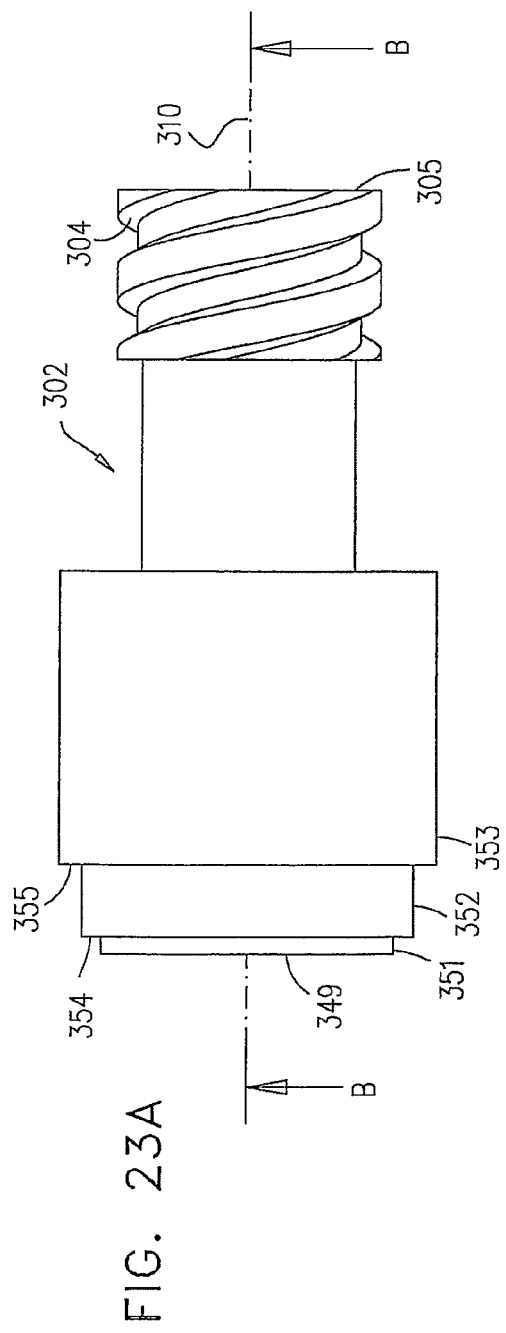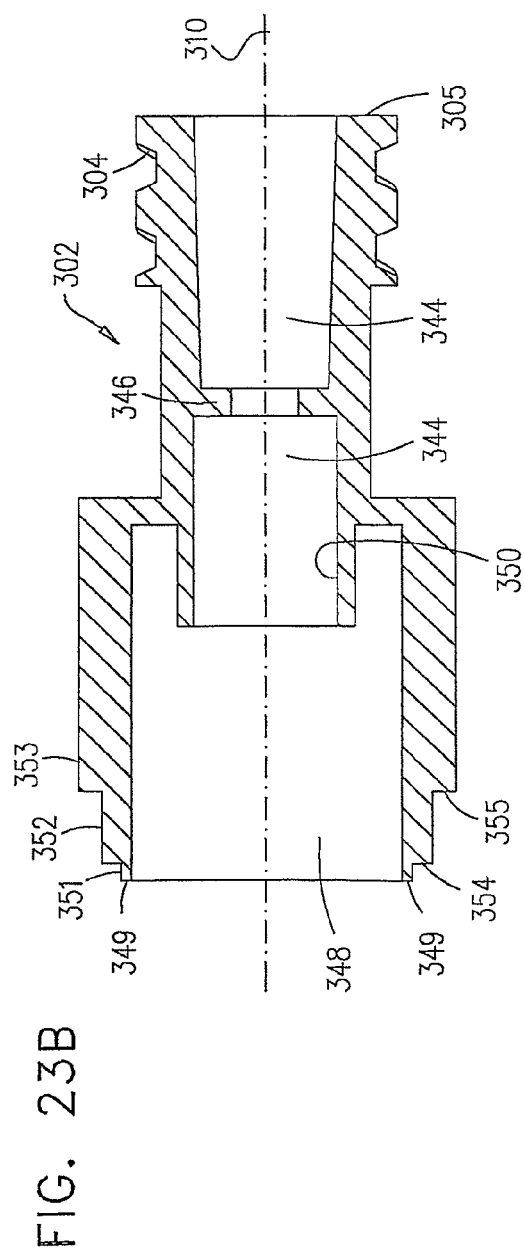
FIG. 23A
FIG. 23B

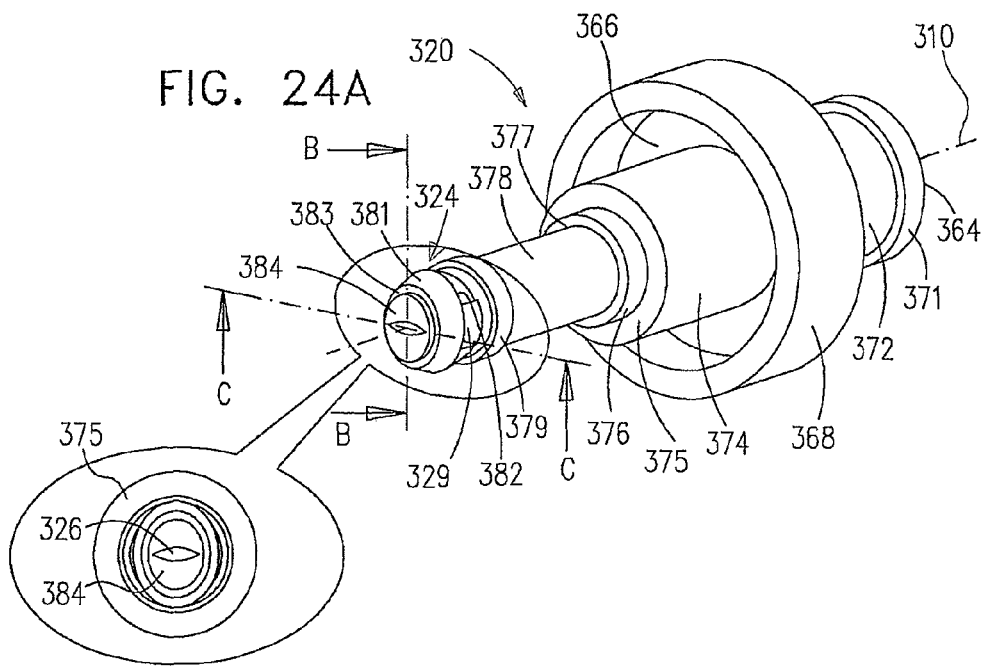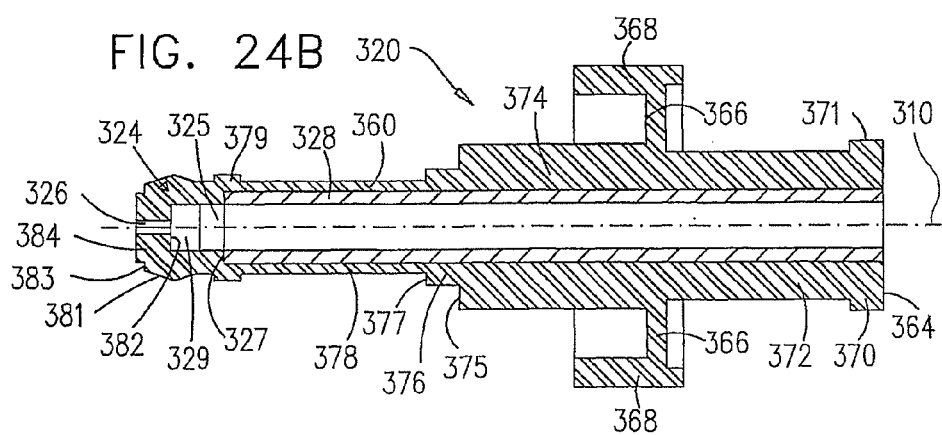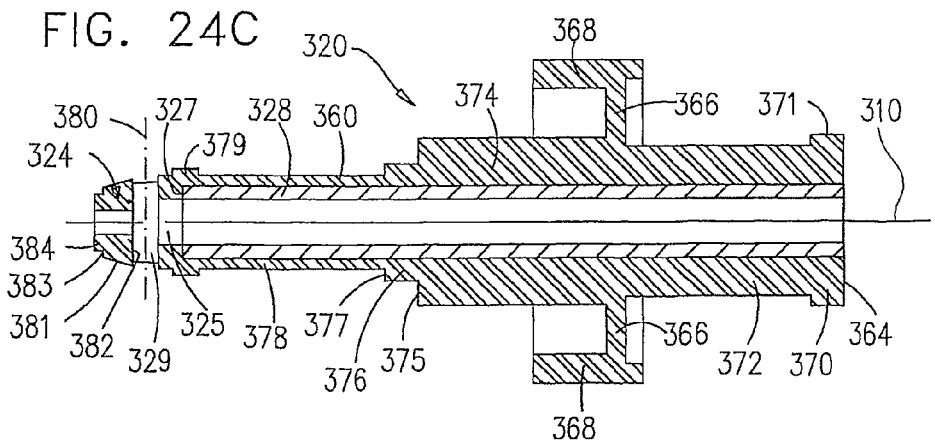

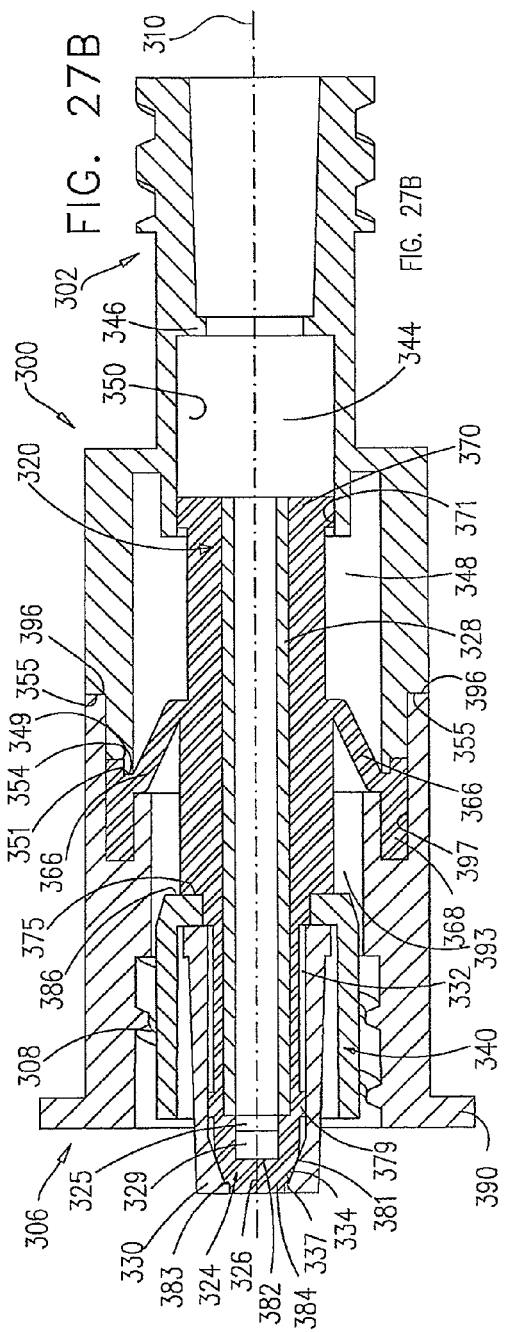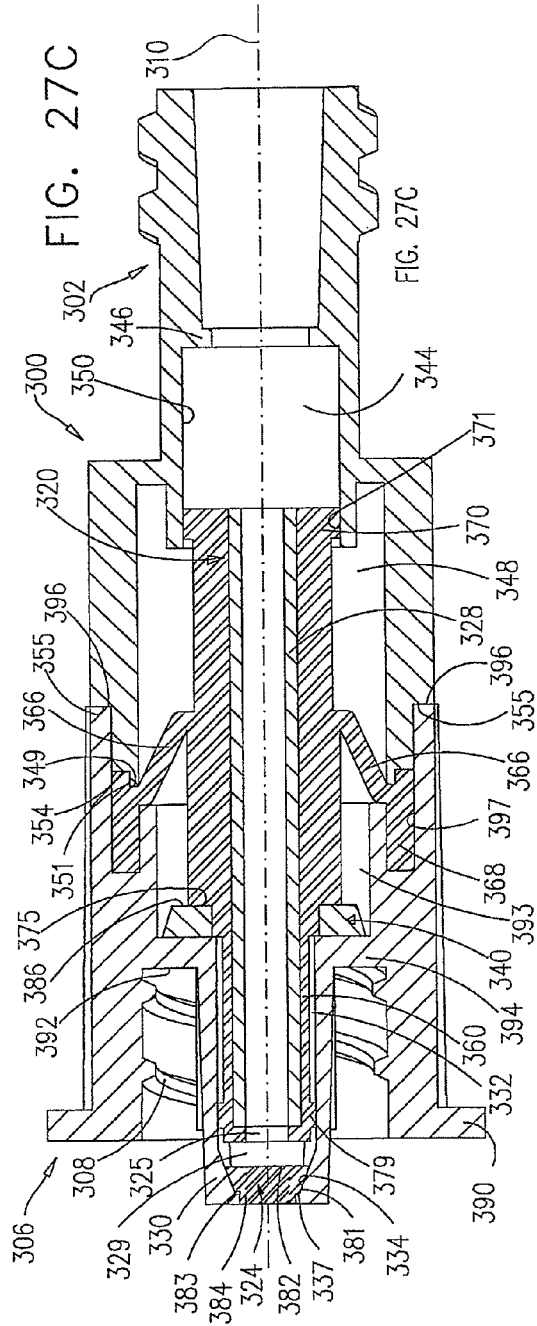

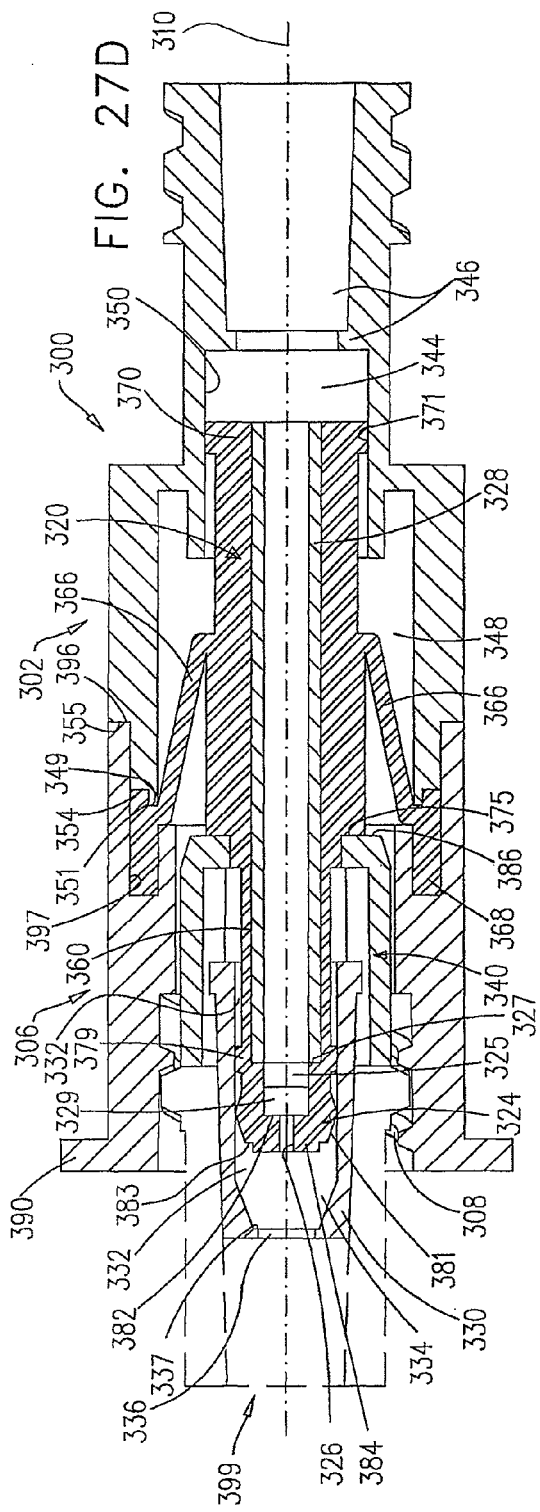
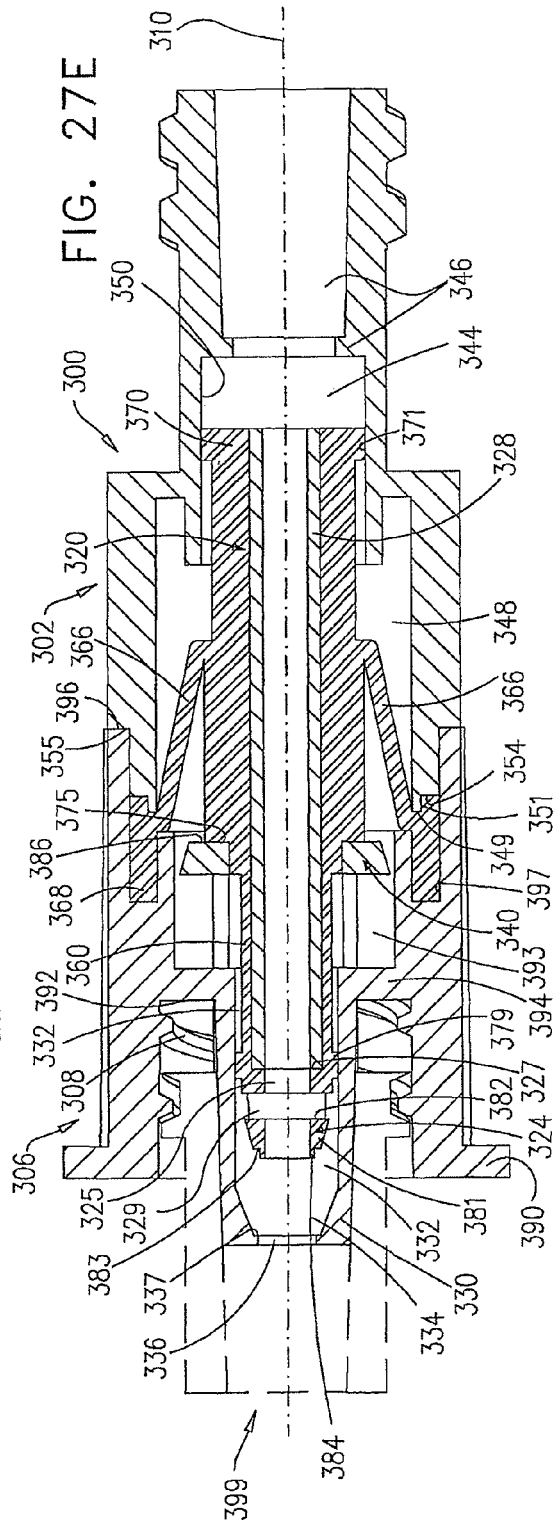

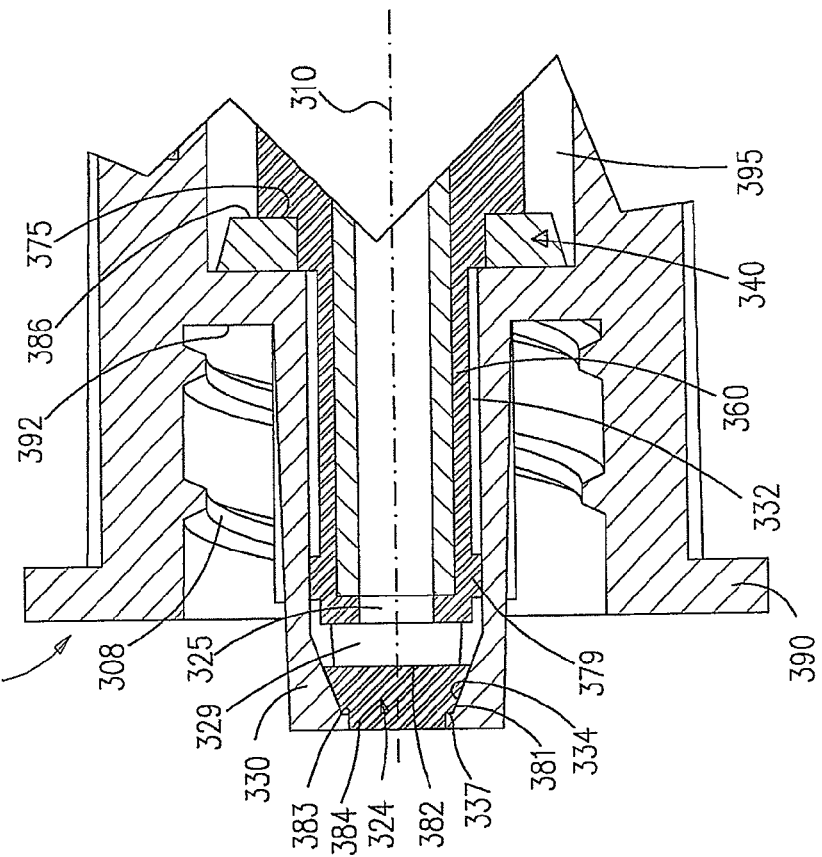
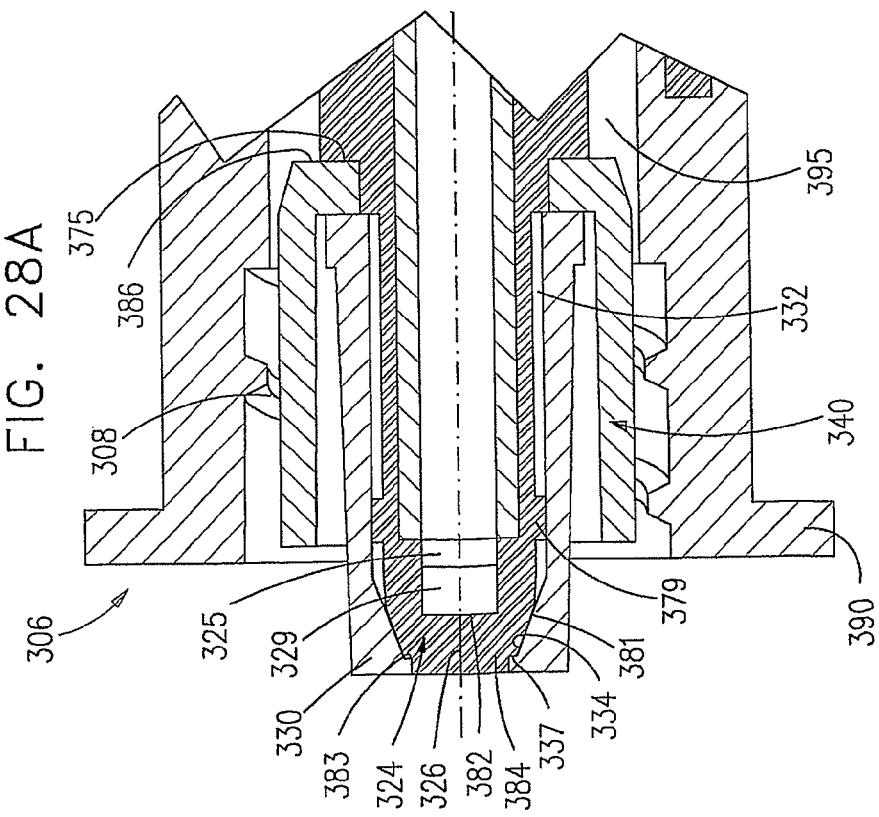

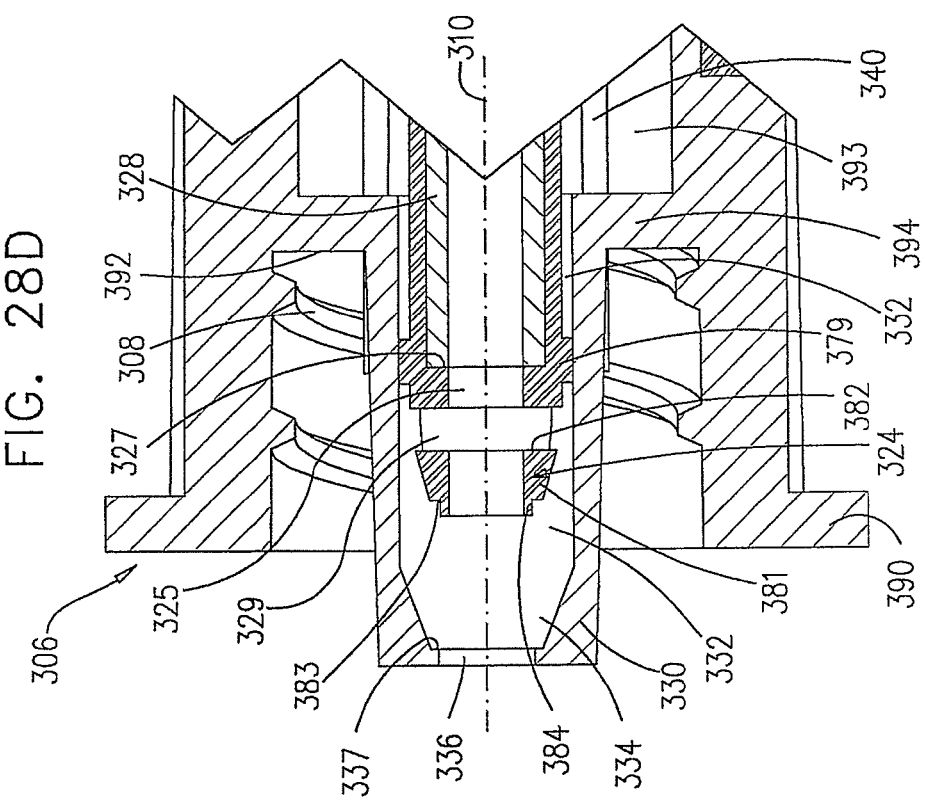
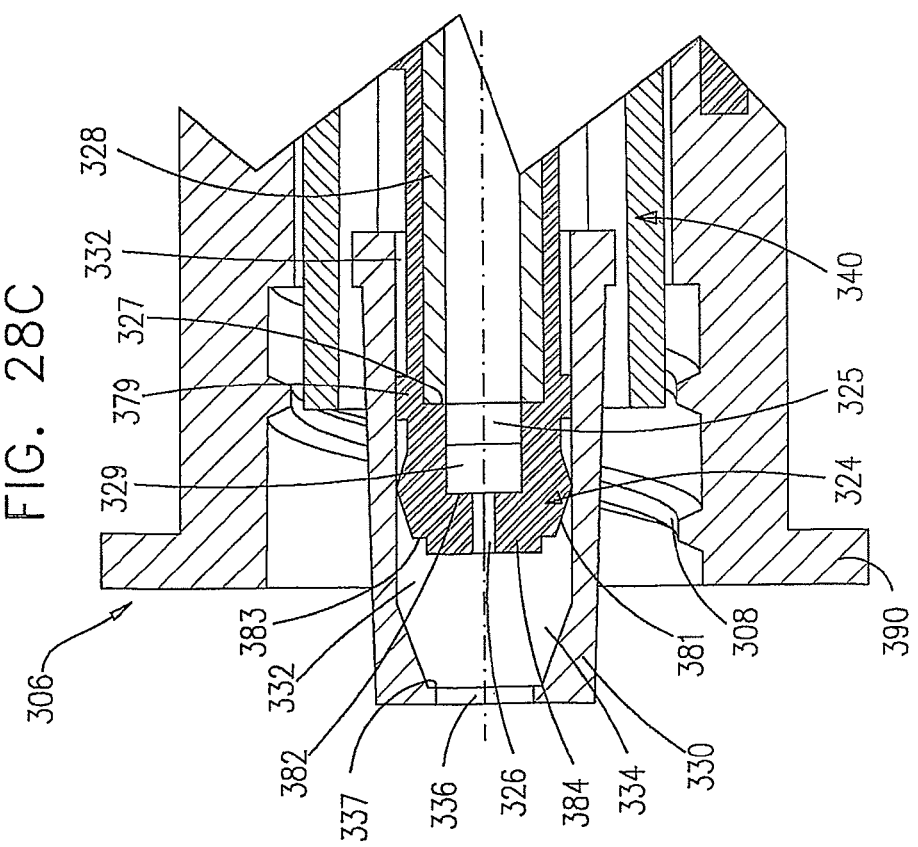

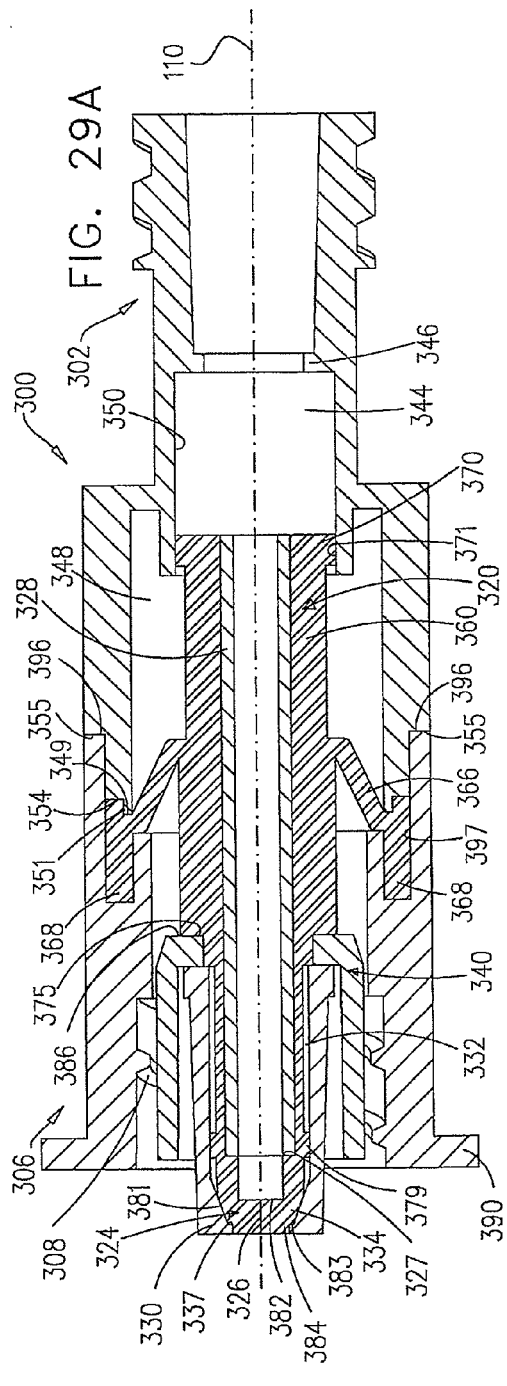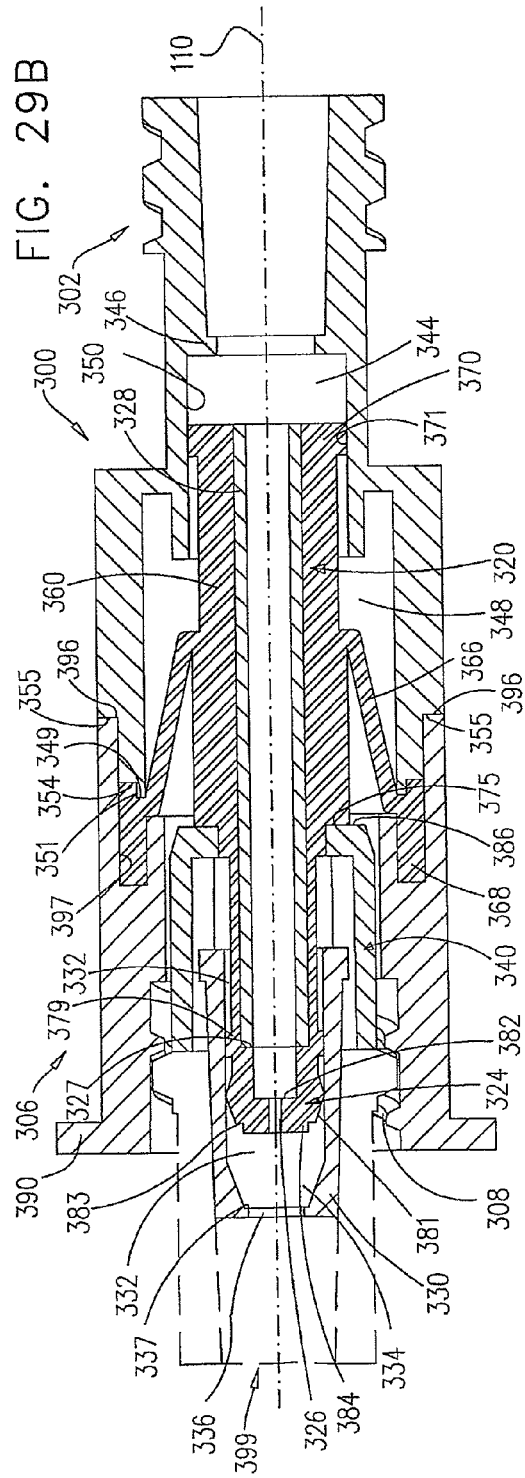

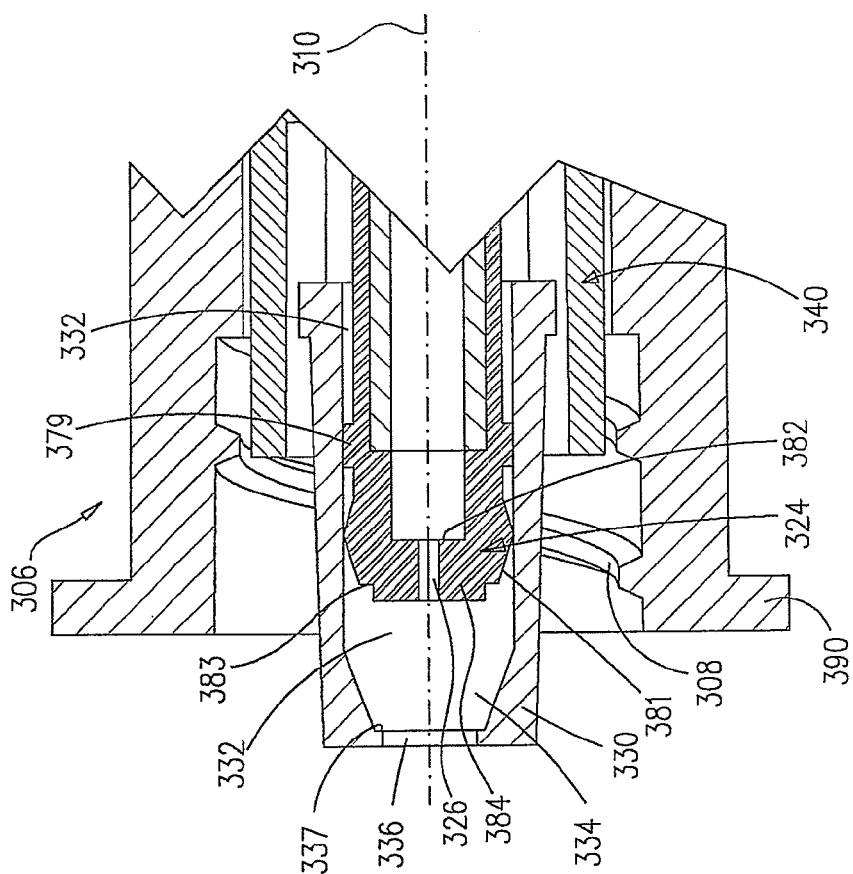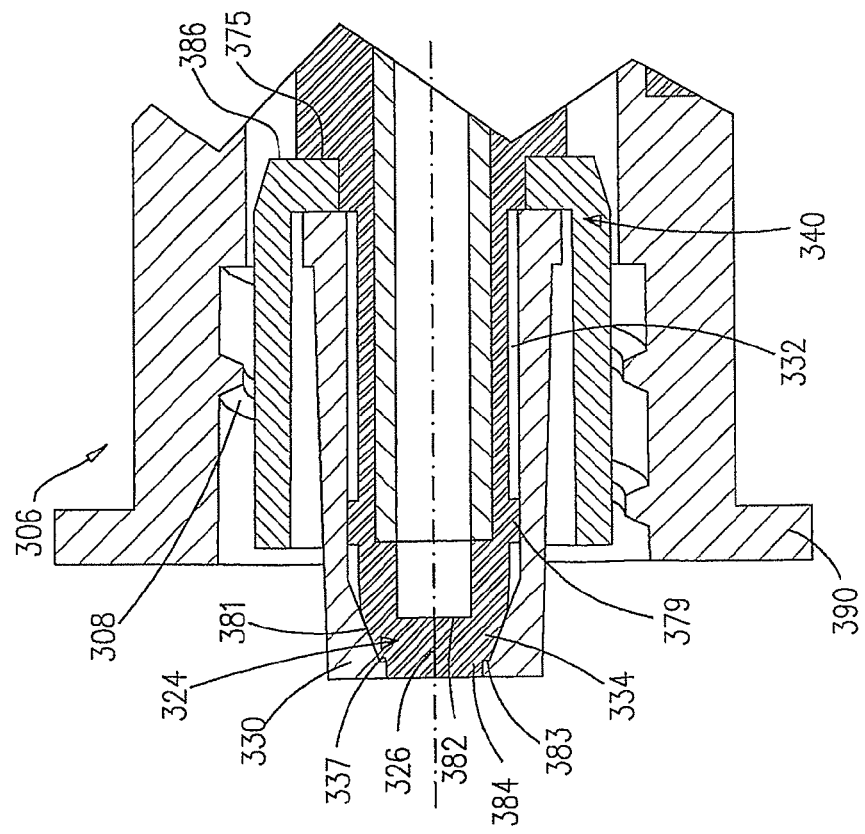

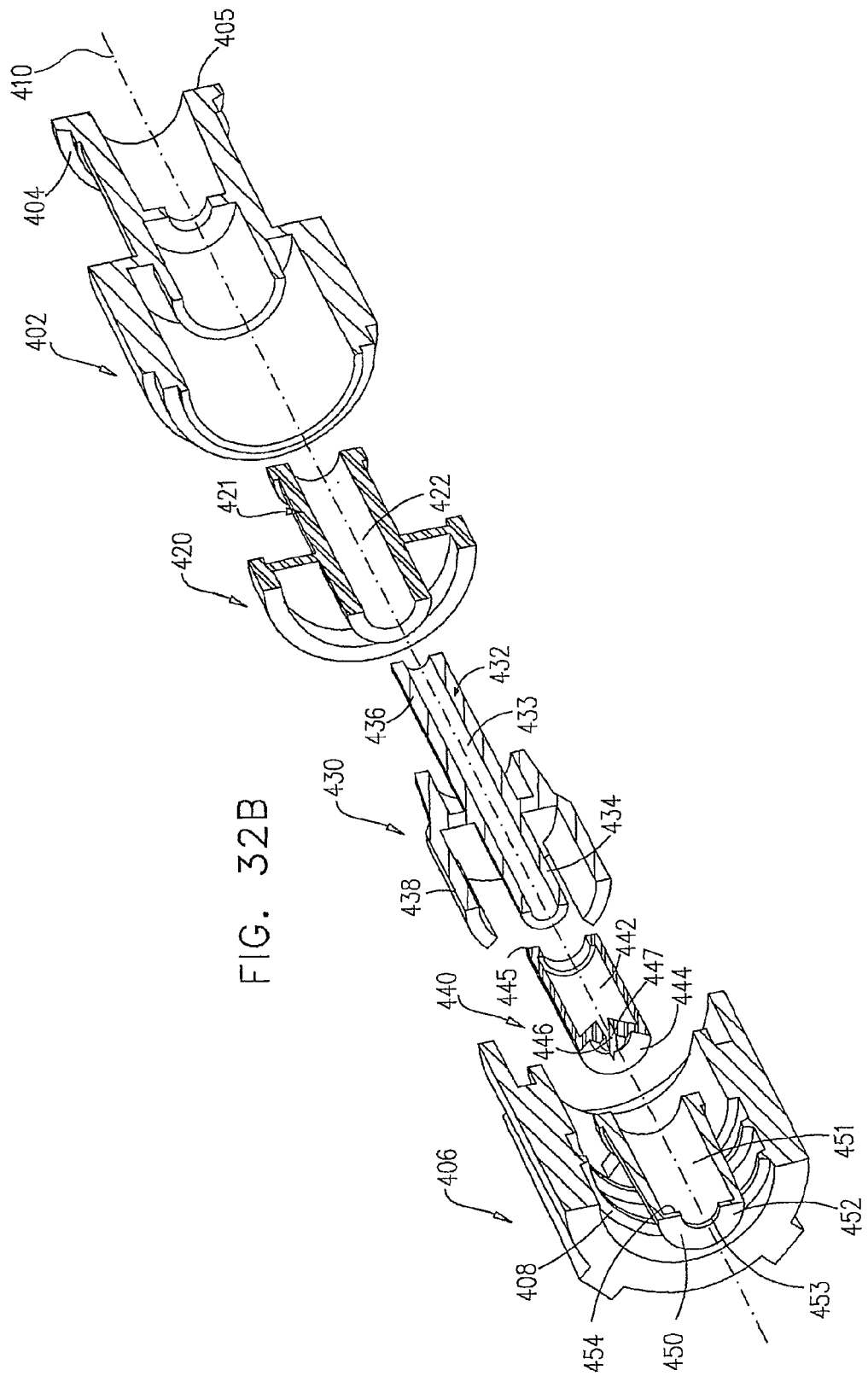

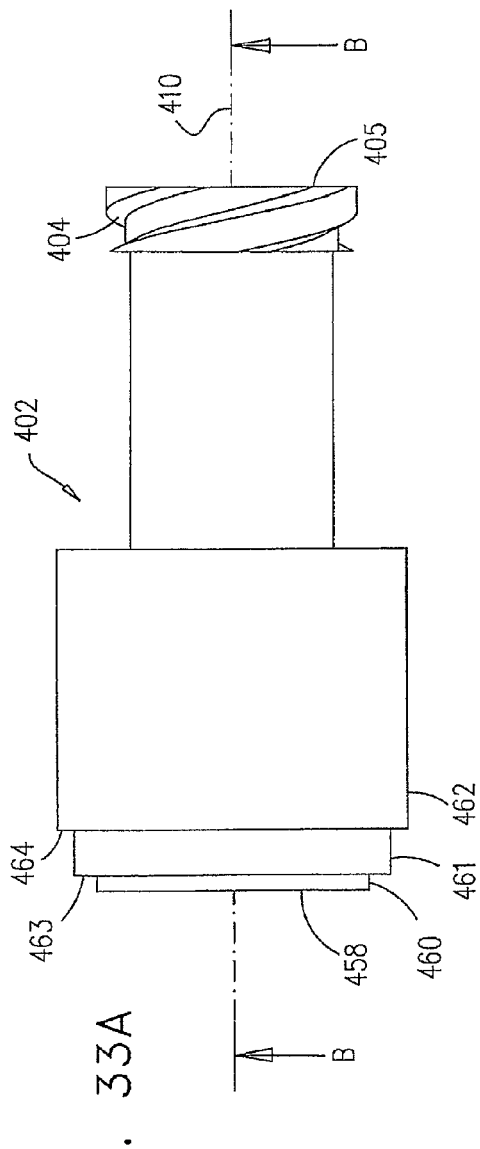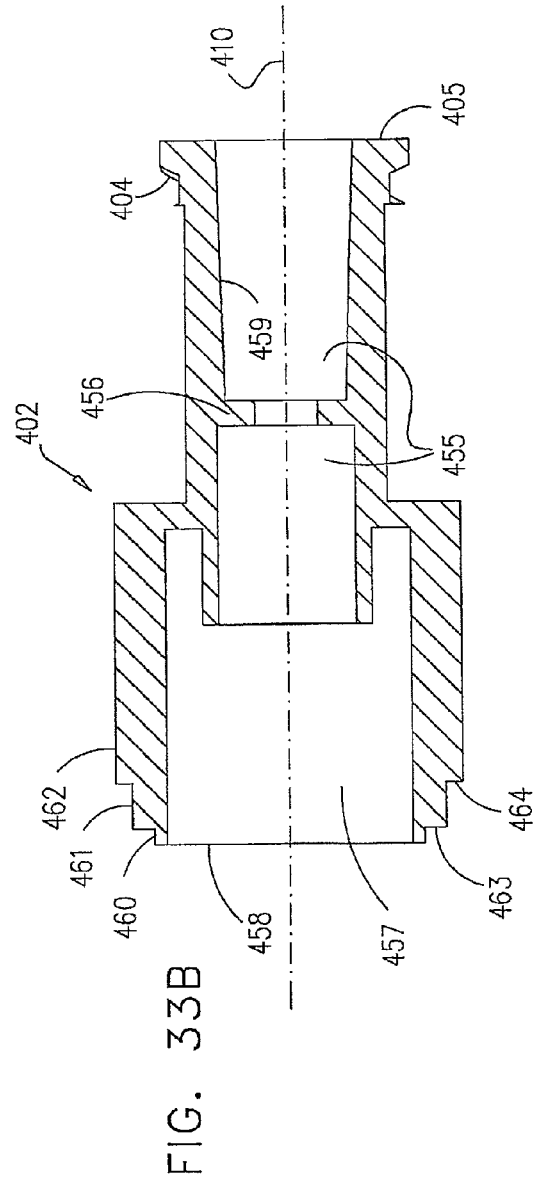

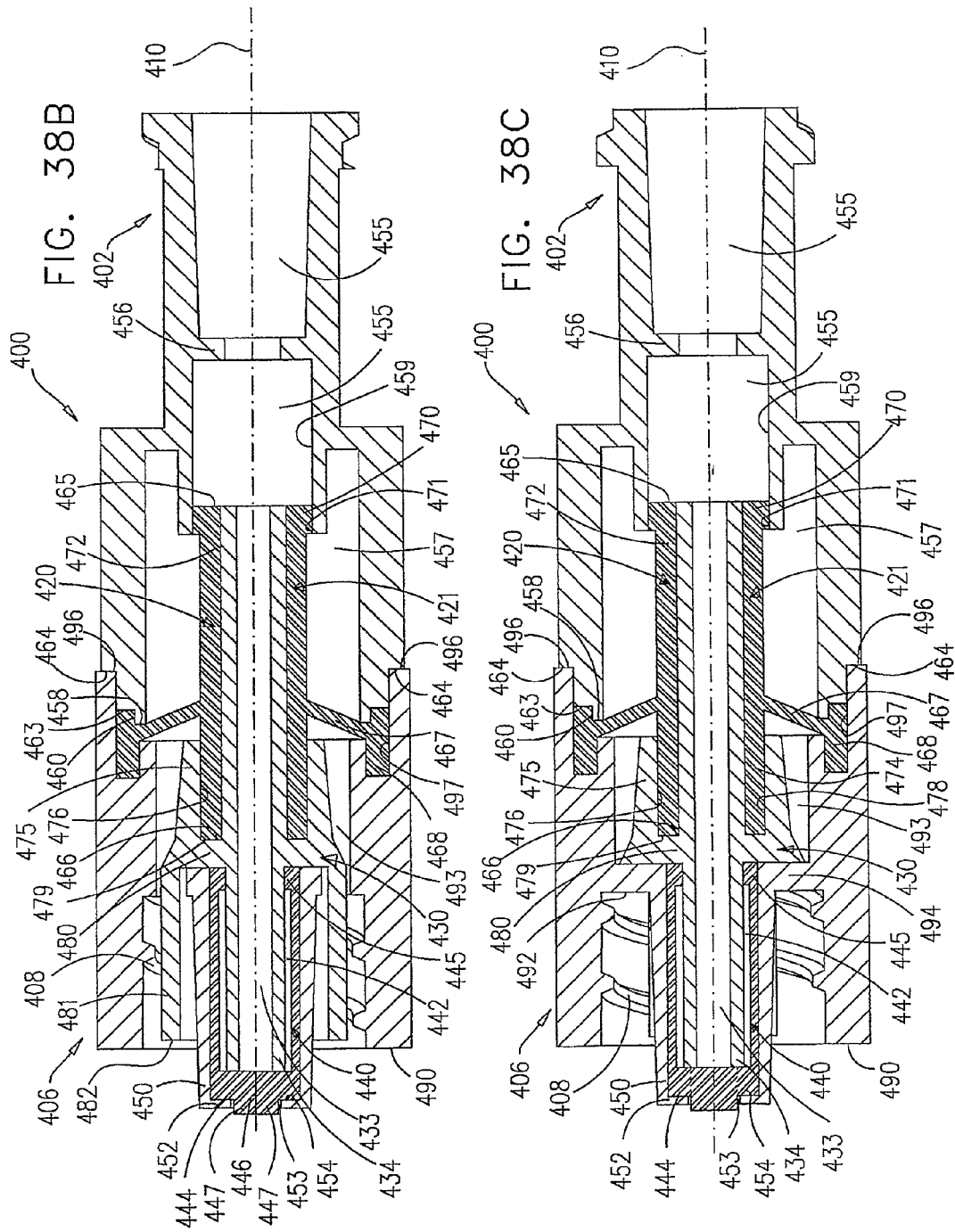

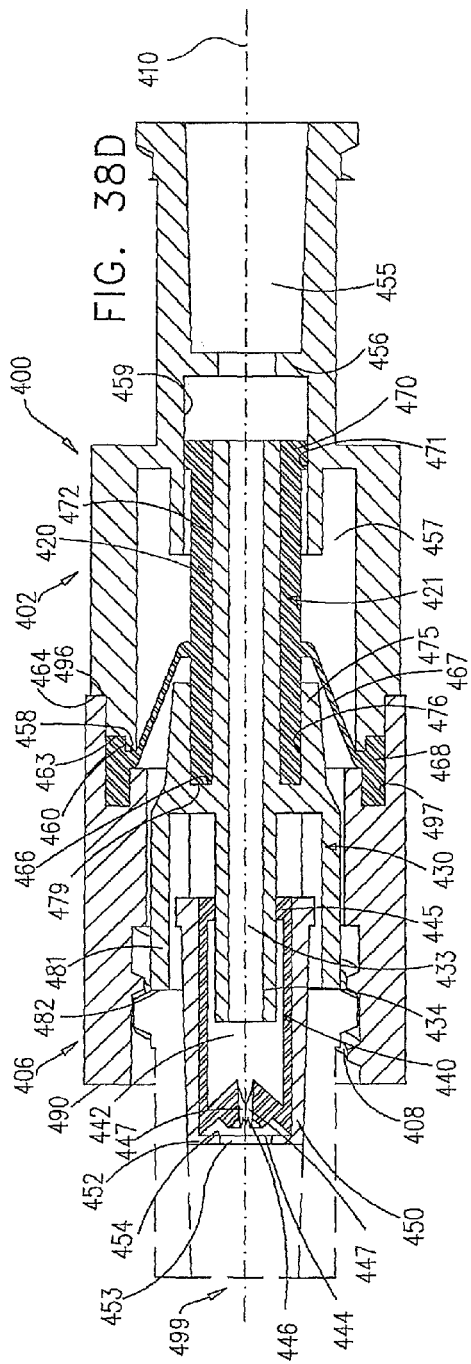
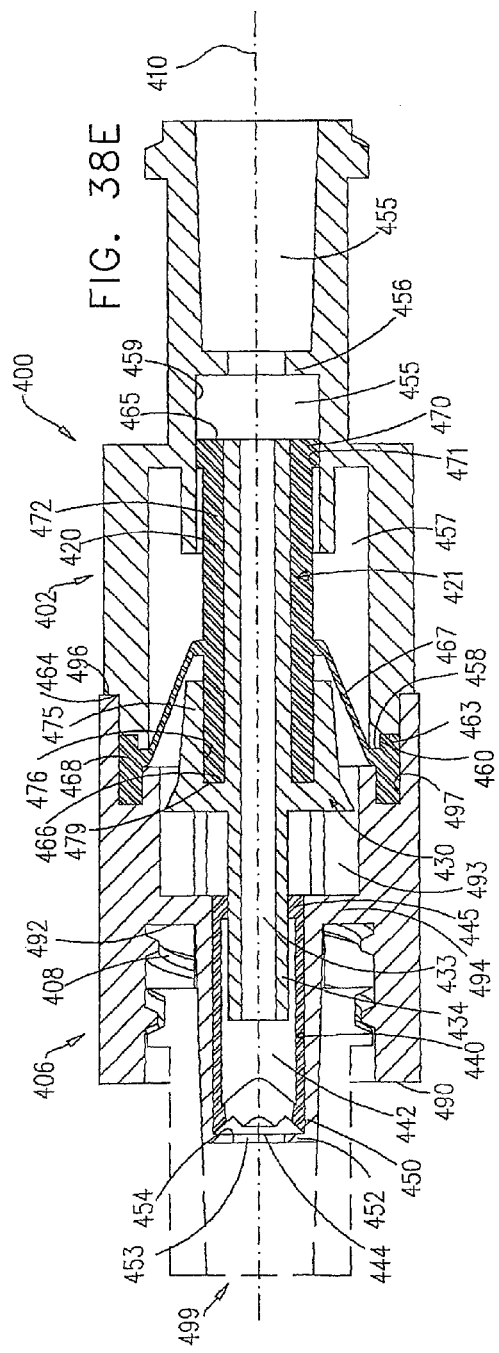

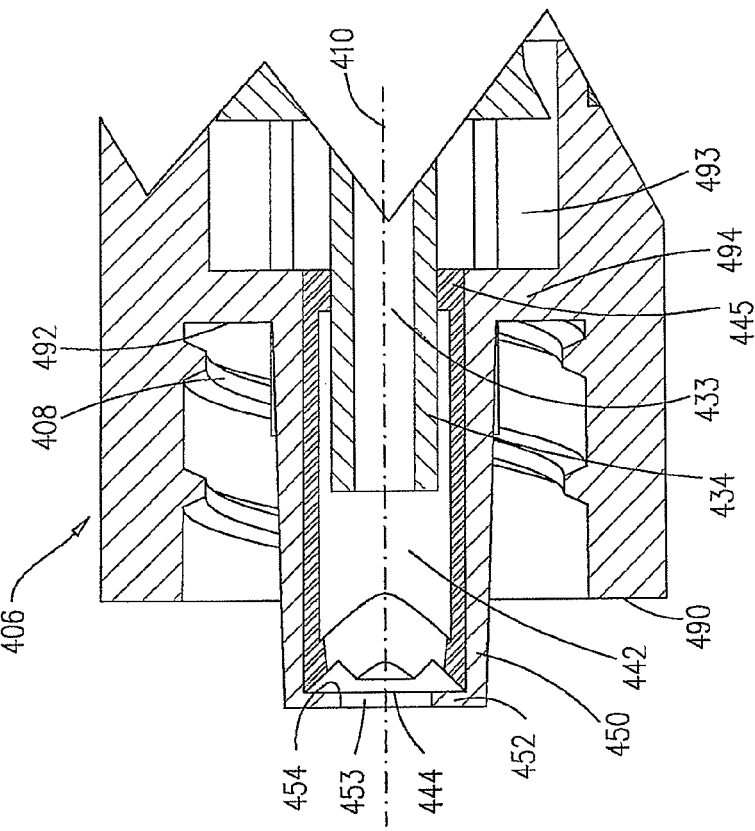
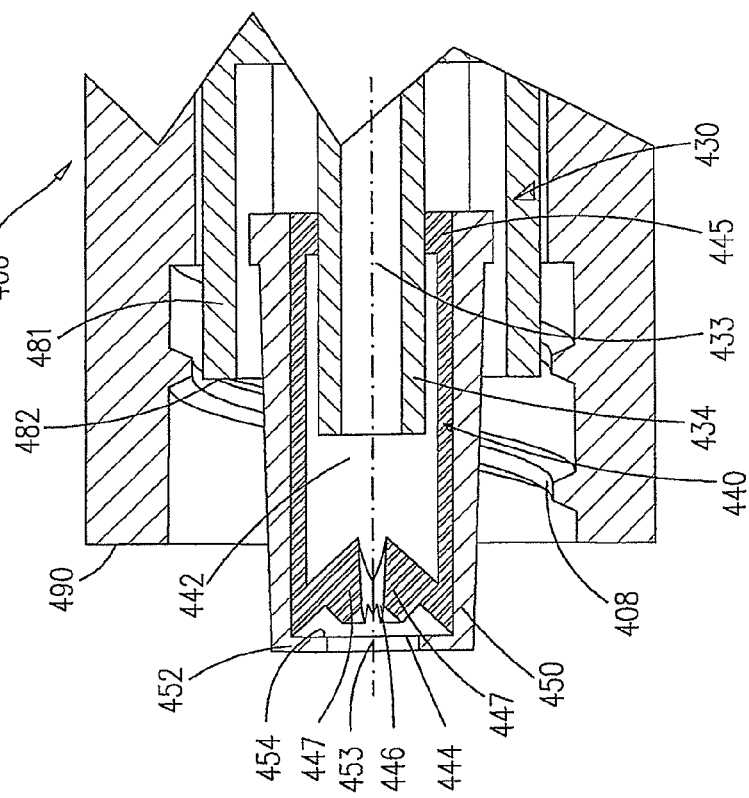

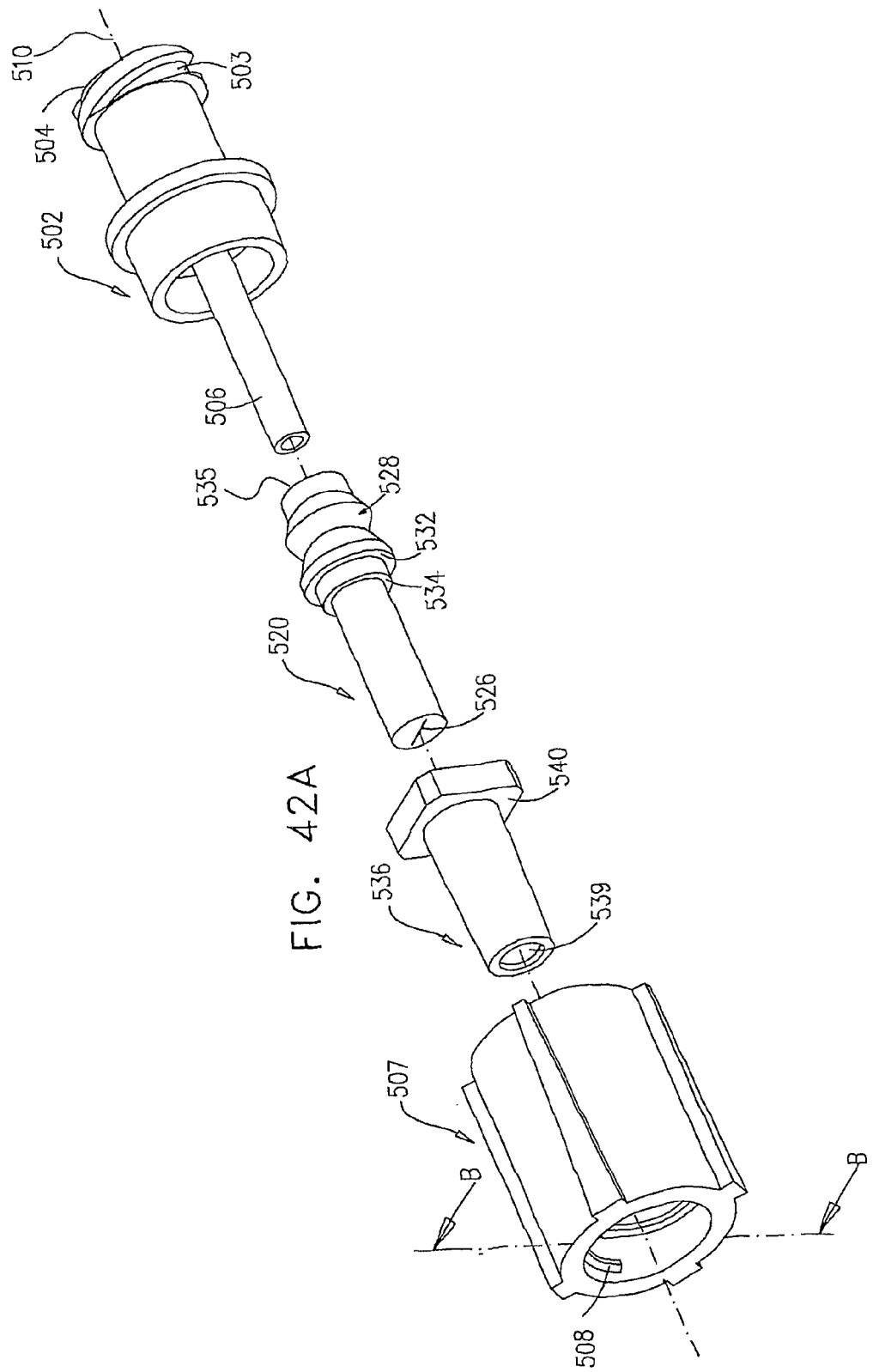

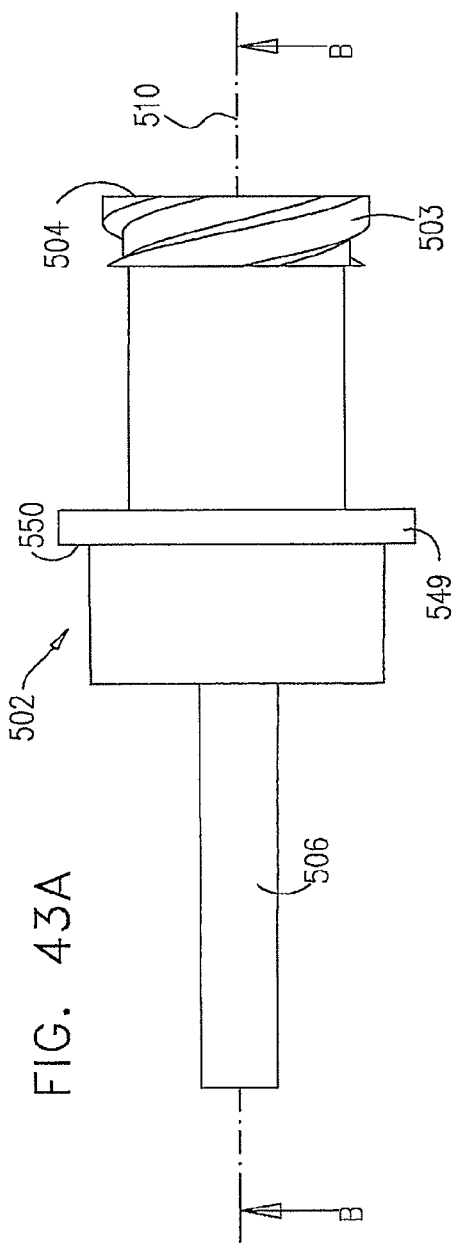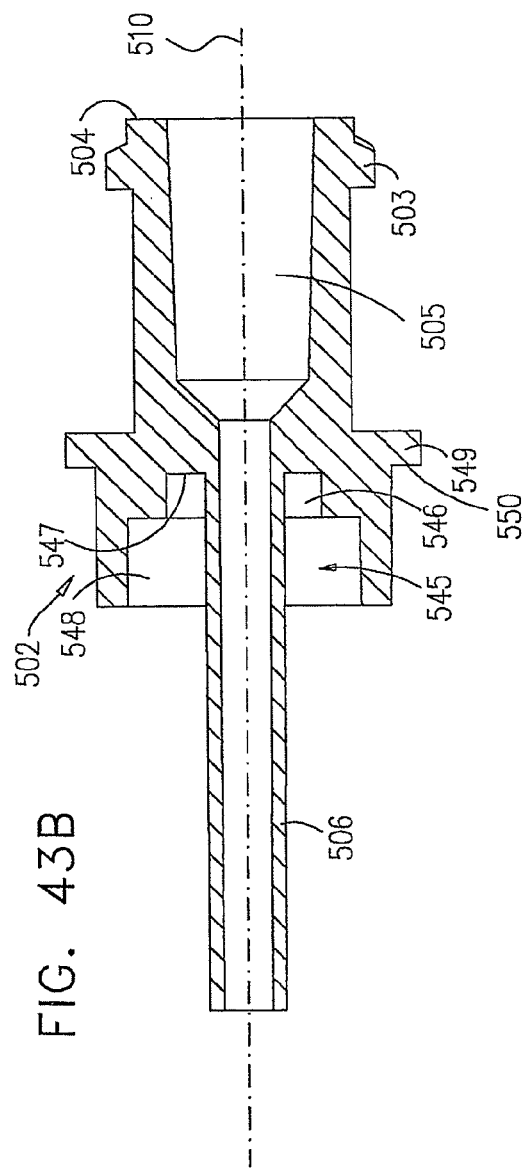
FIG. 43A
FIG. 43B

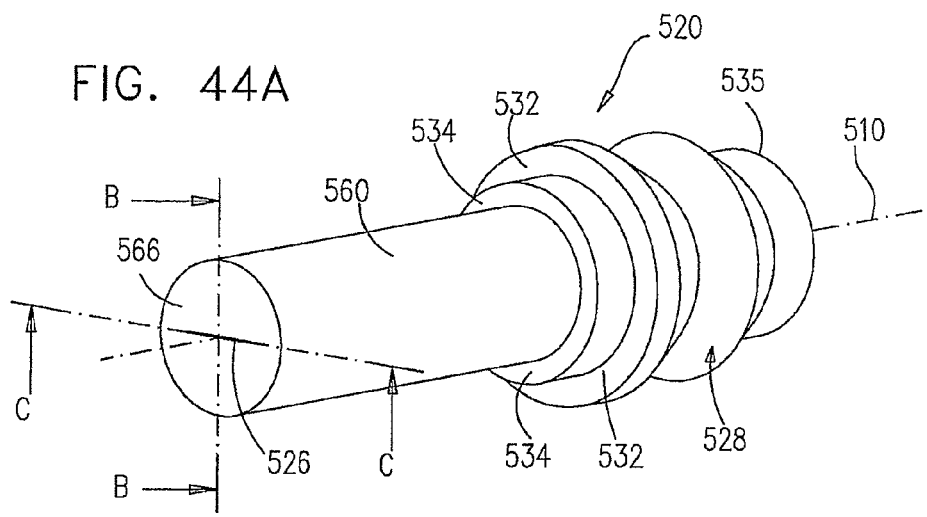
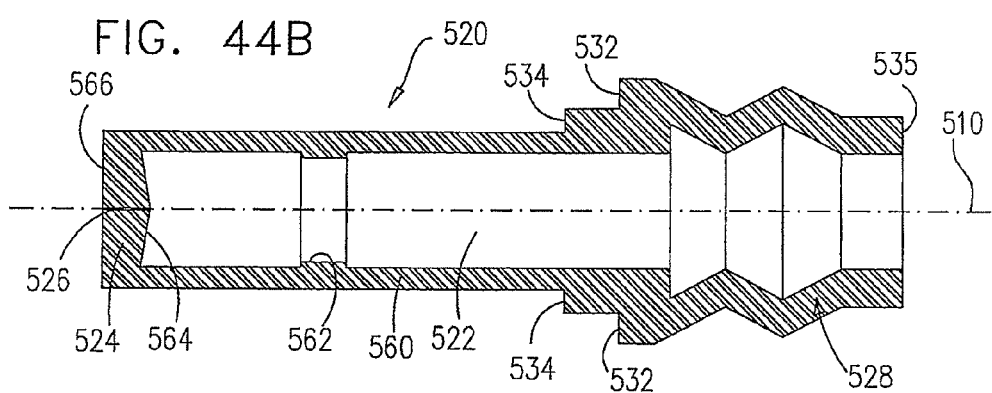
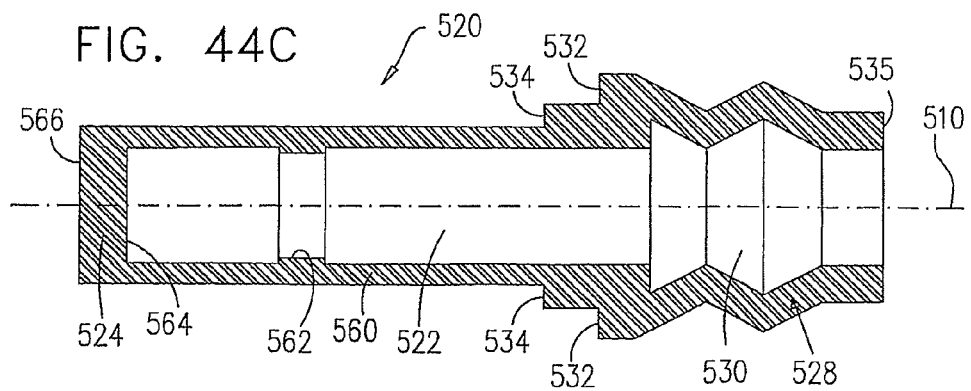

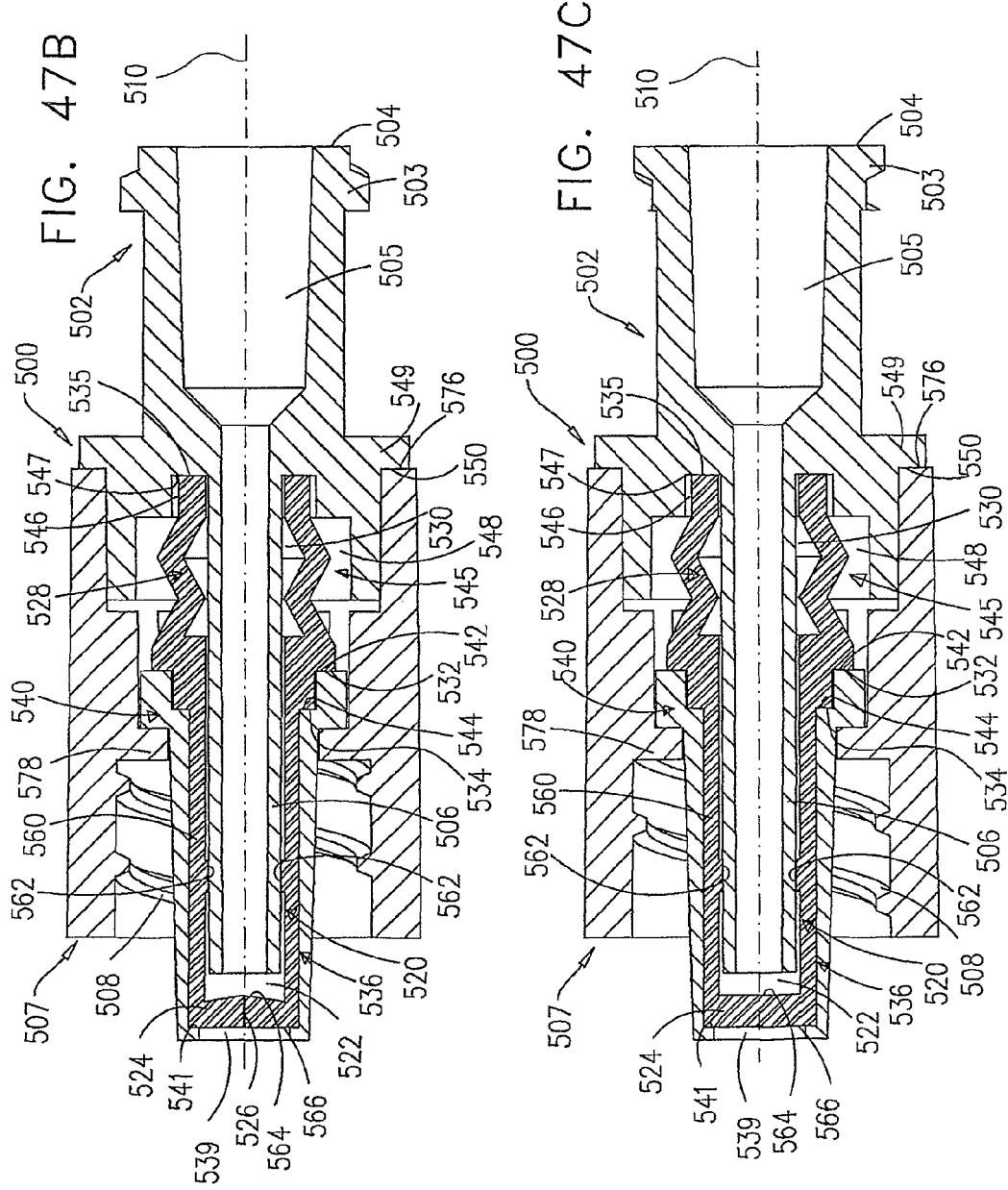

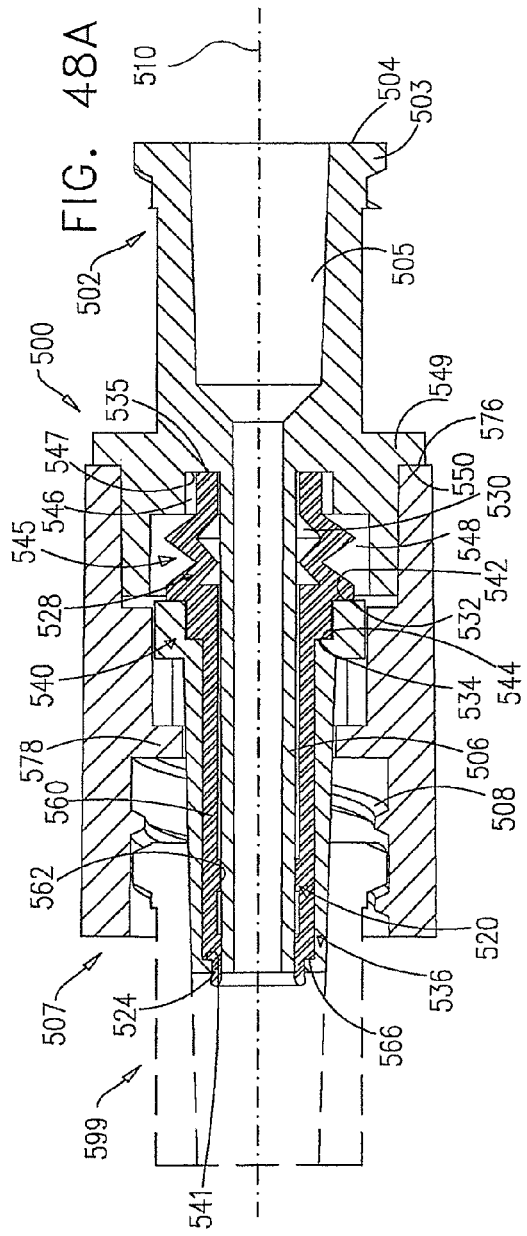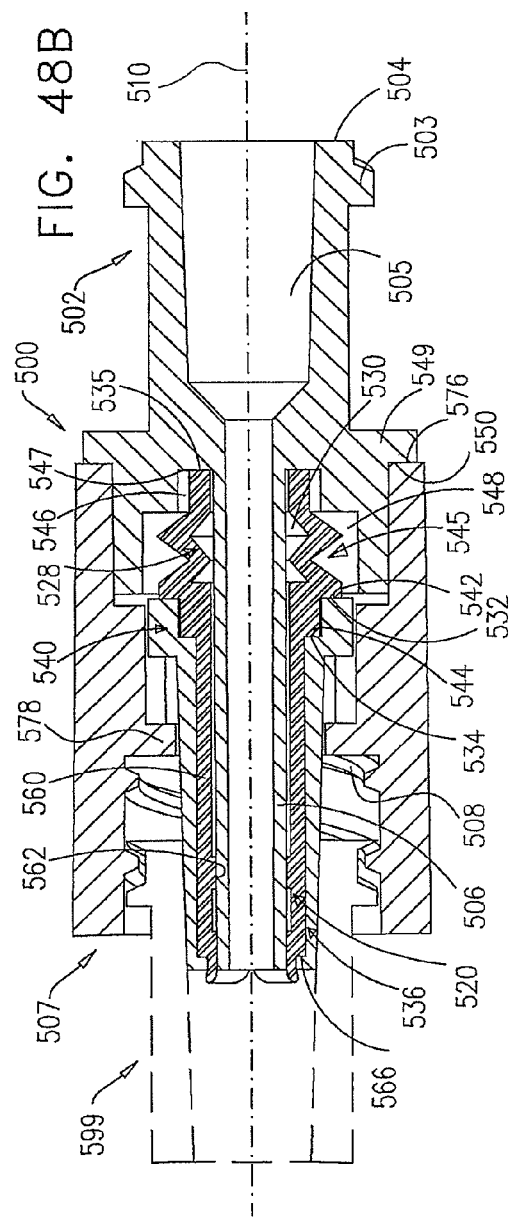

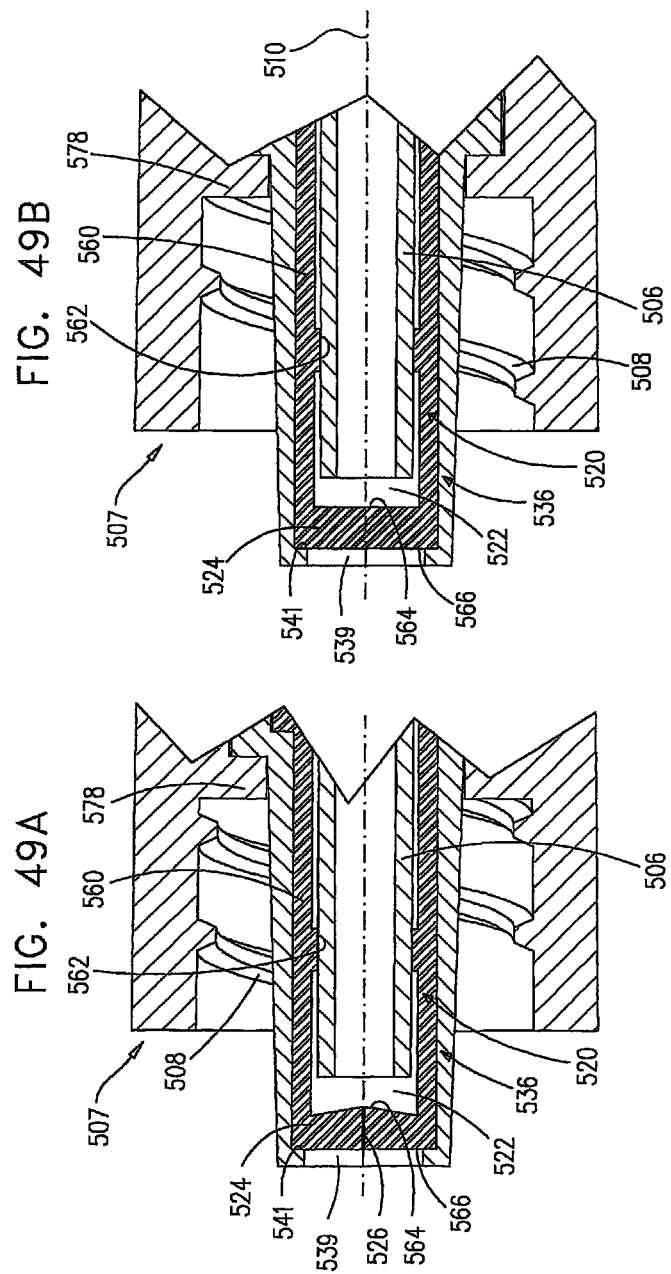

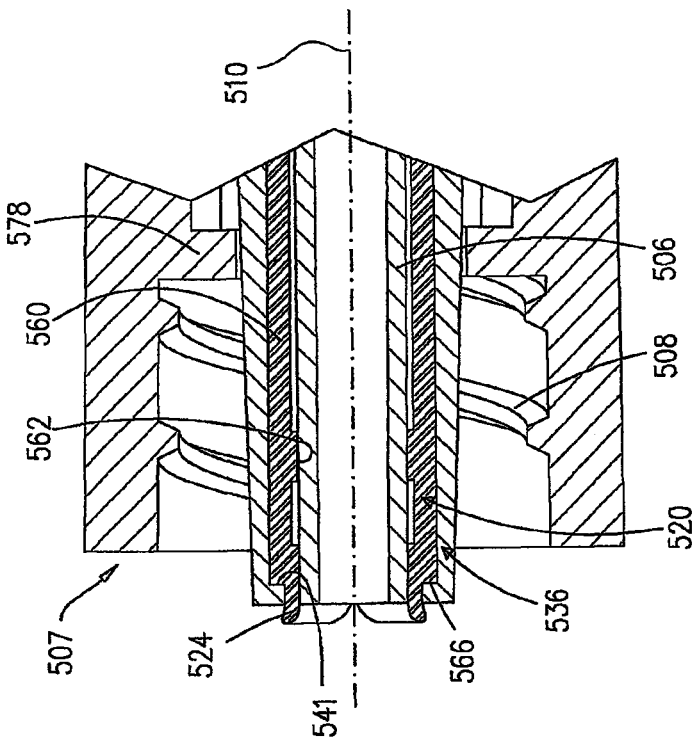
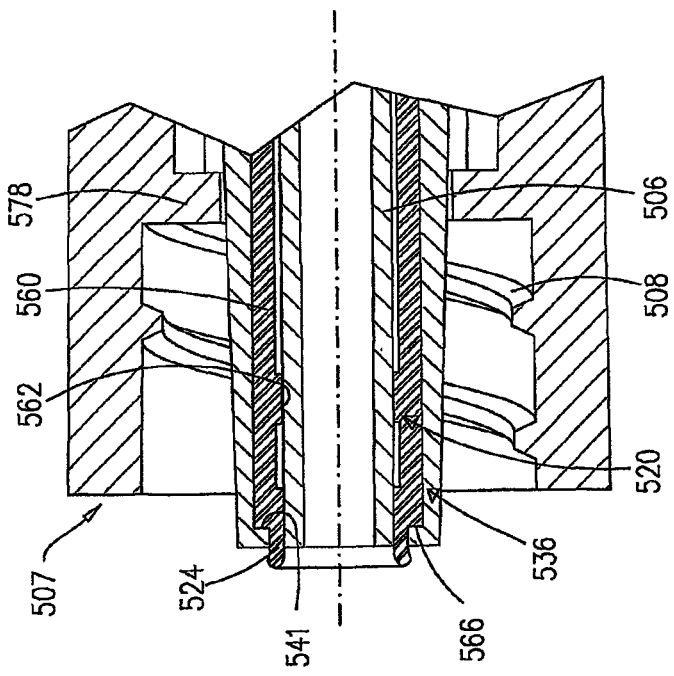

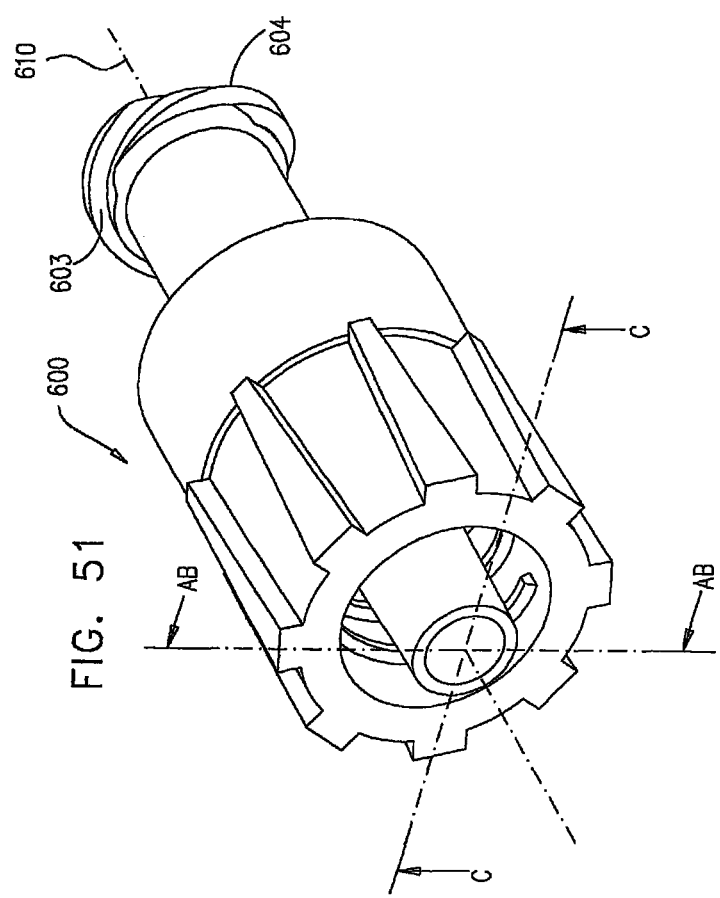

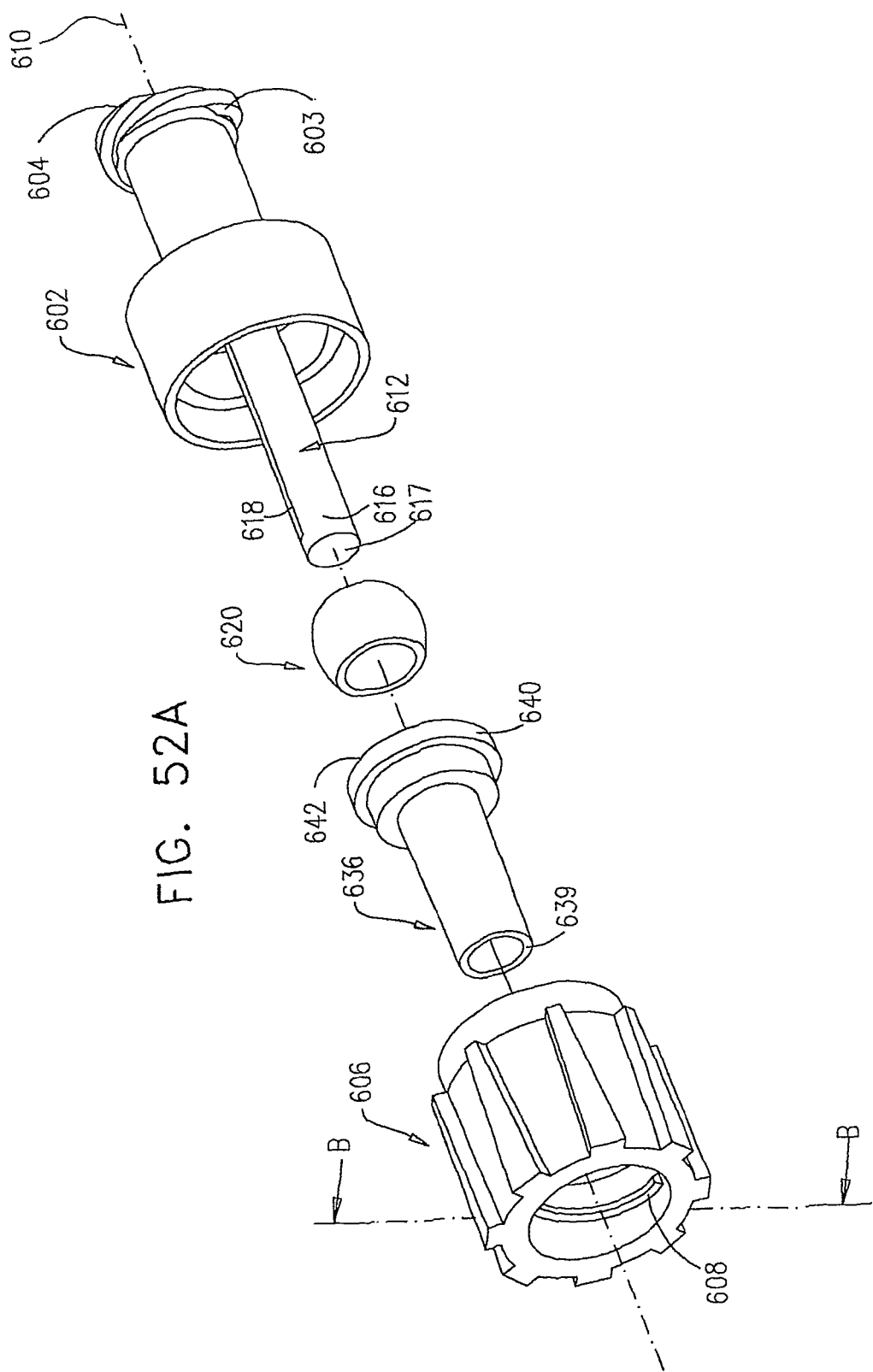

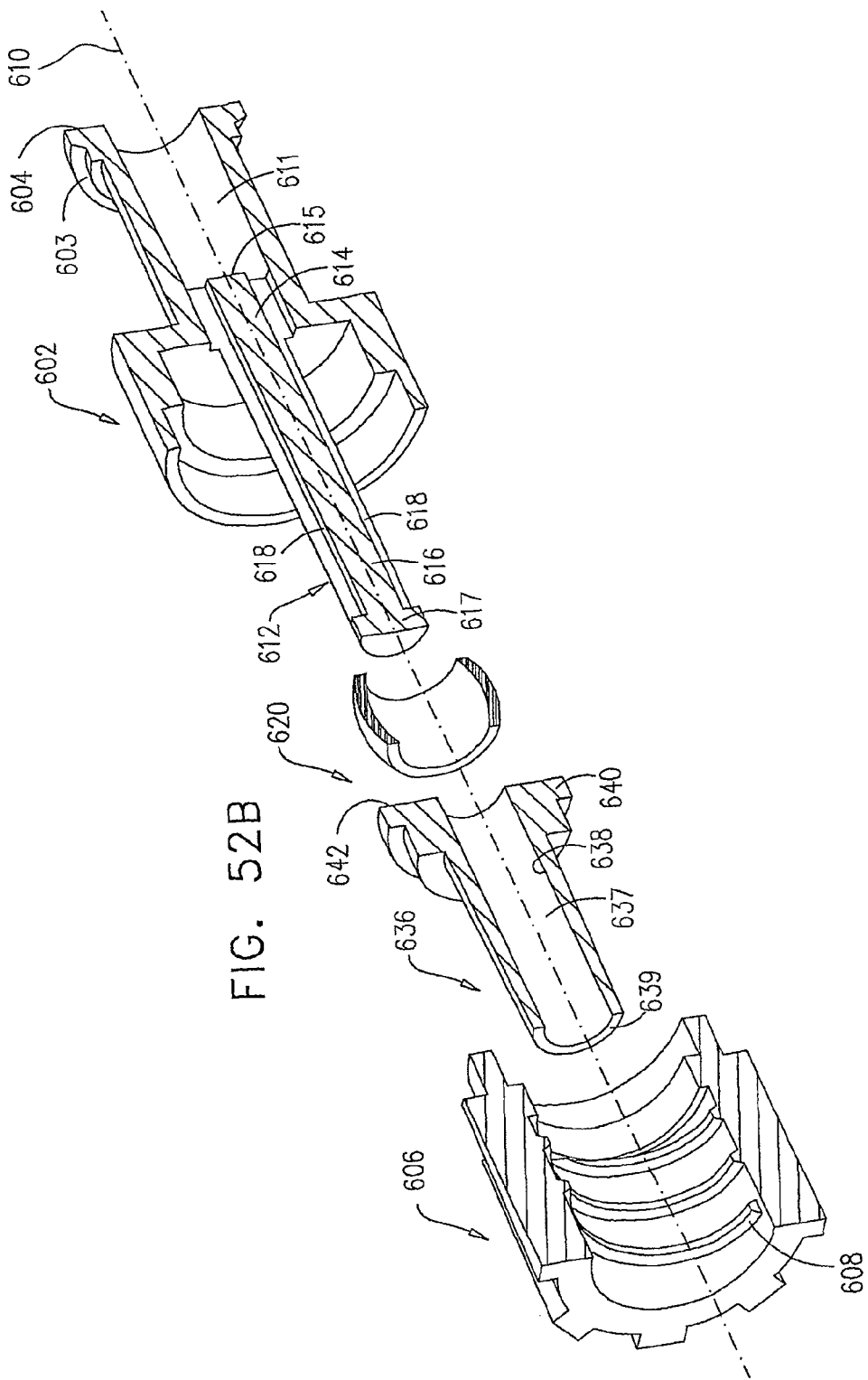

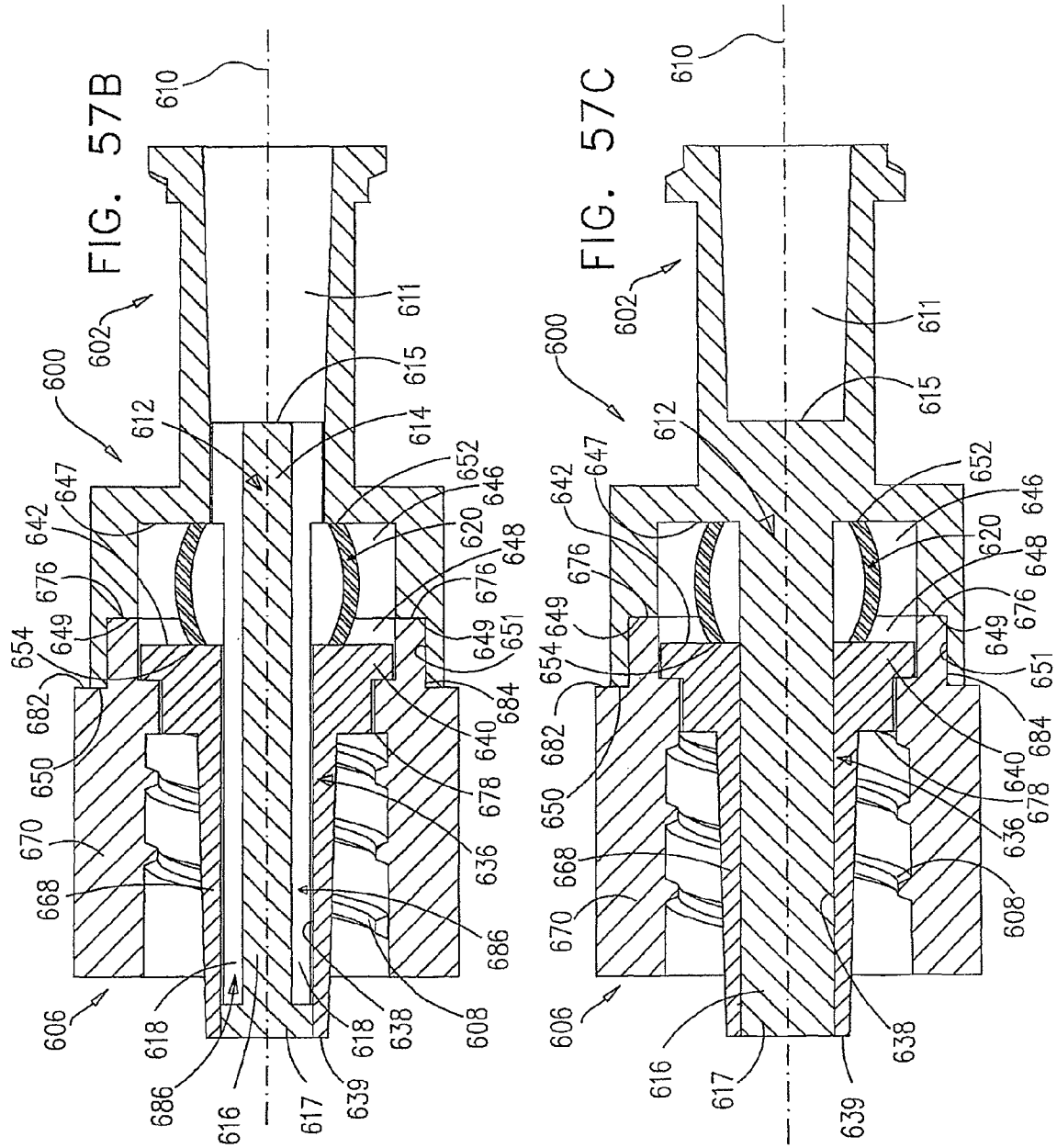

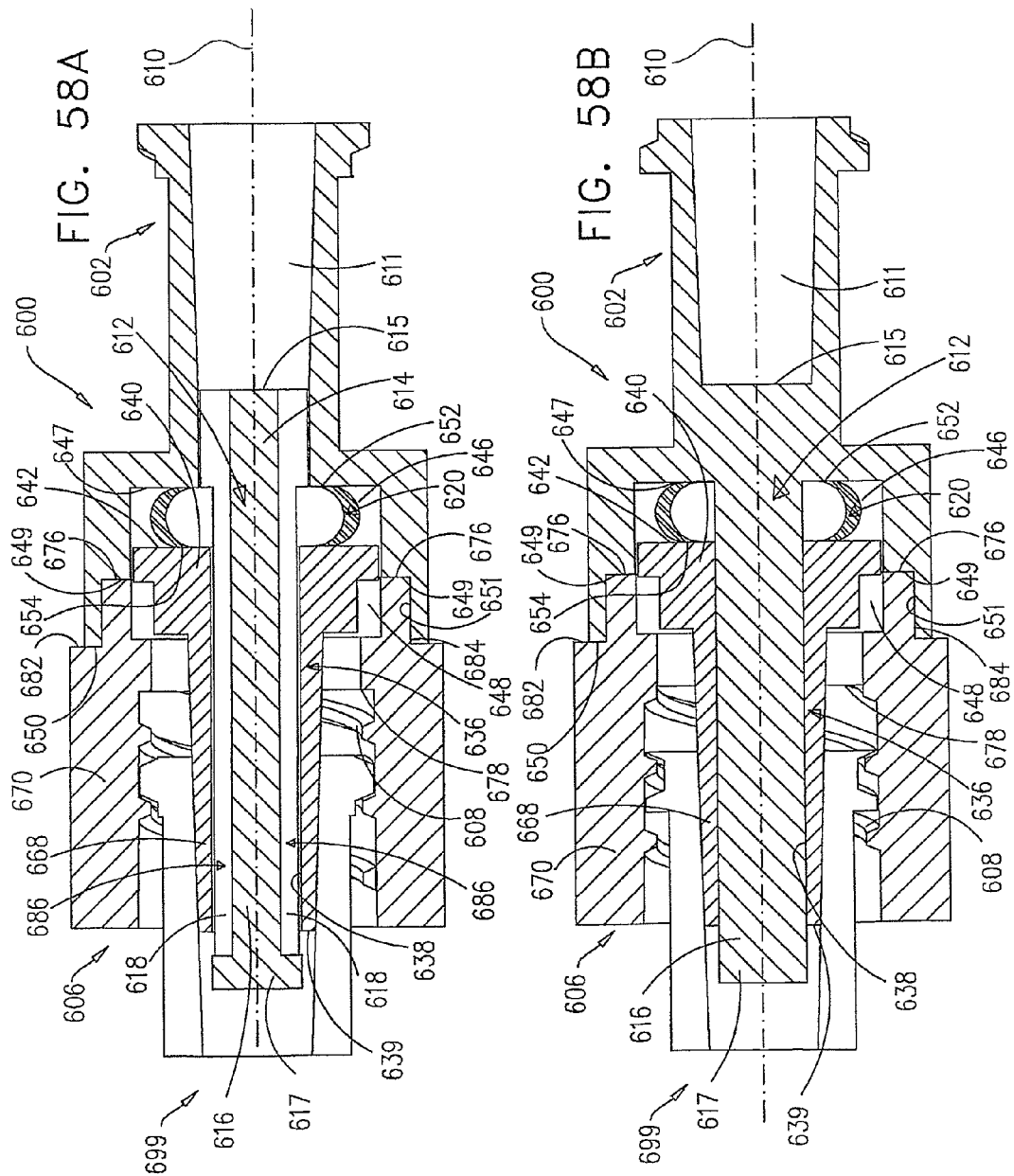

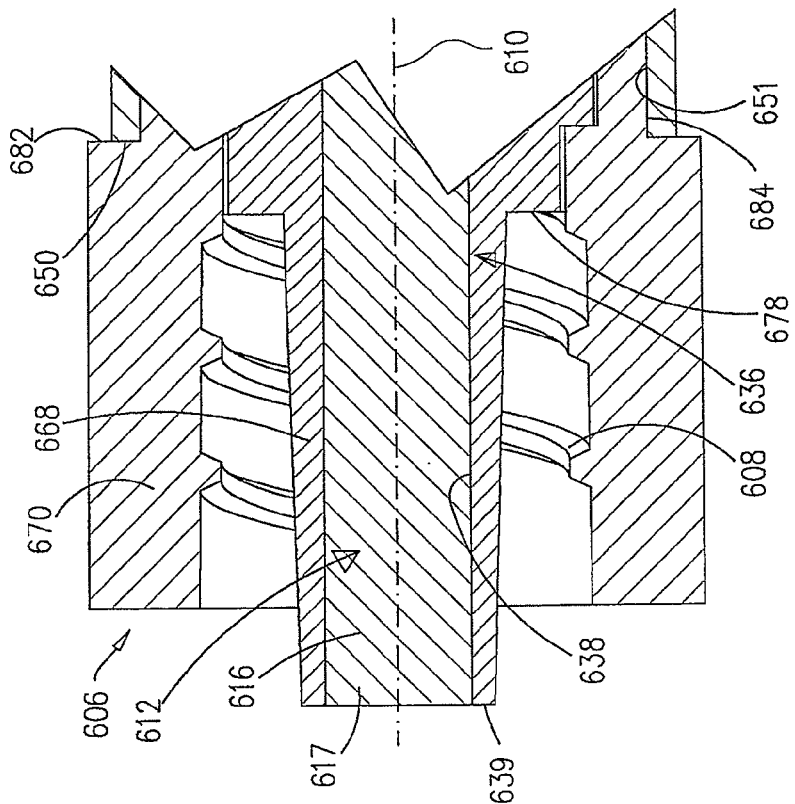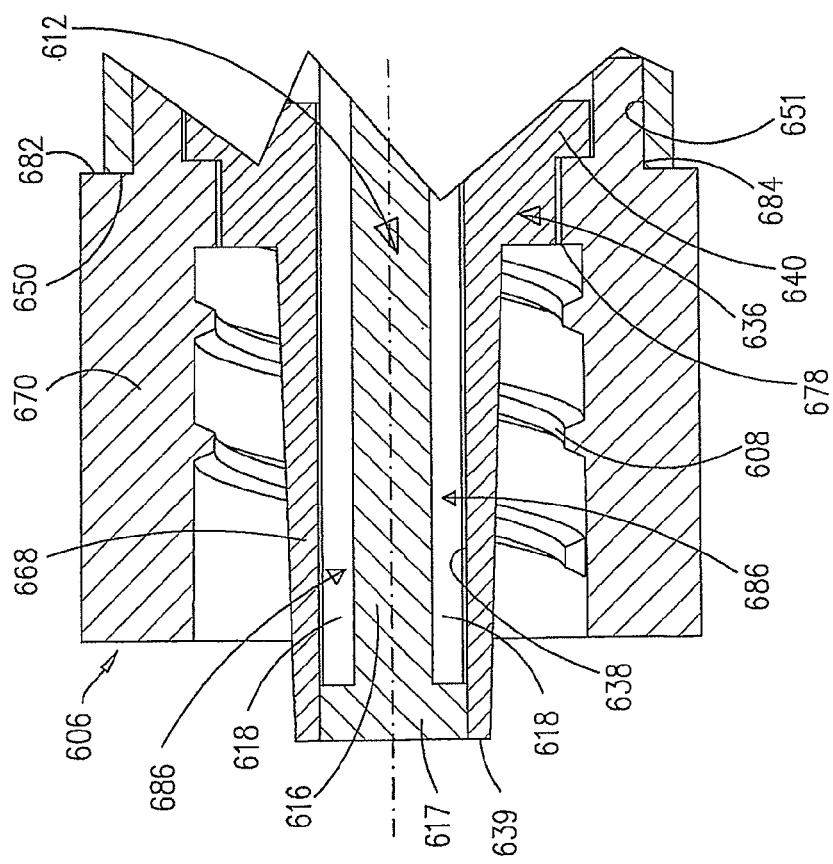

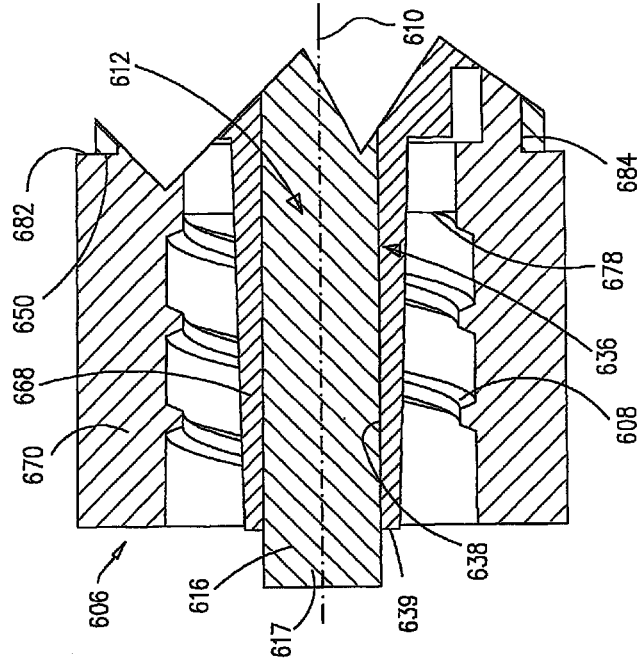
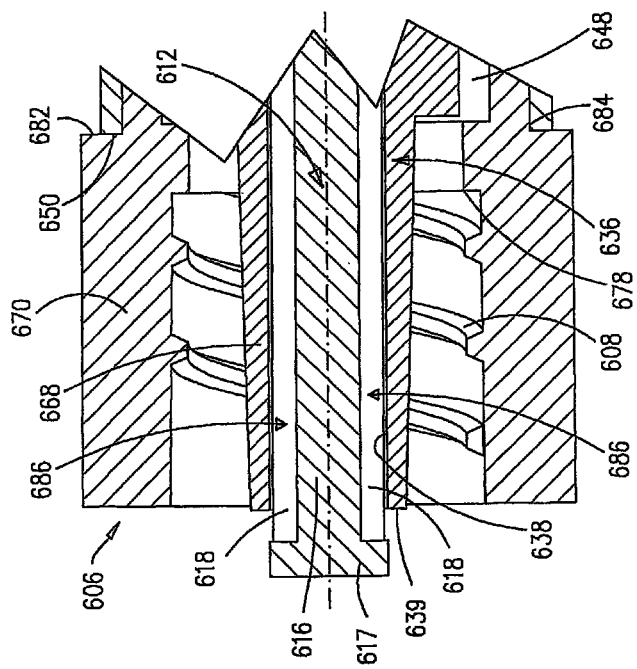

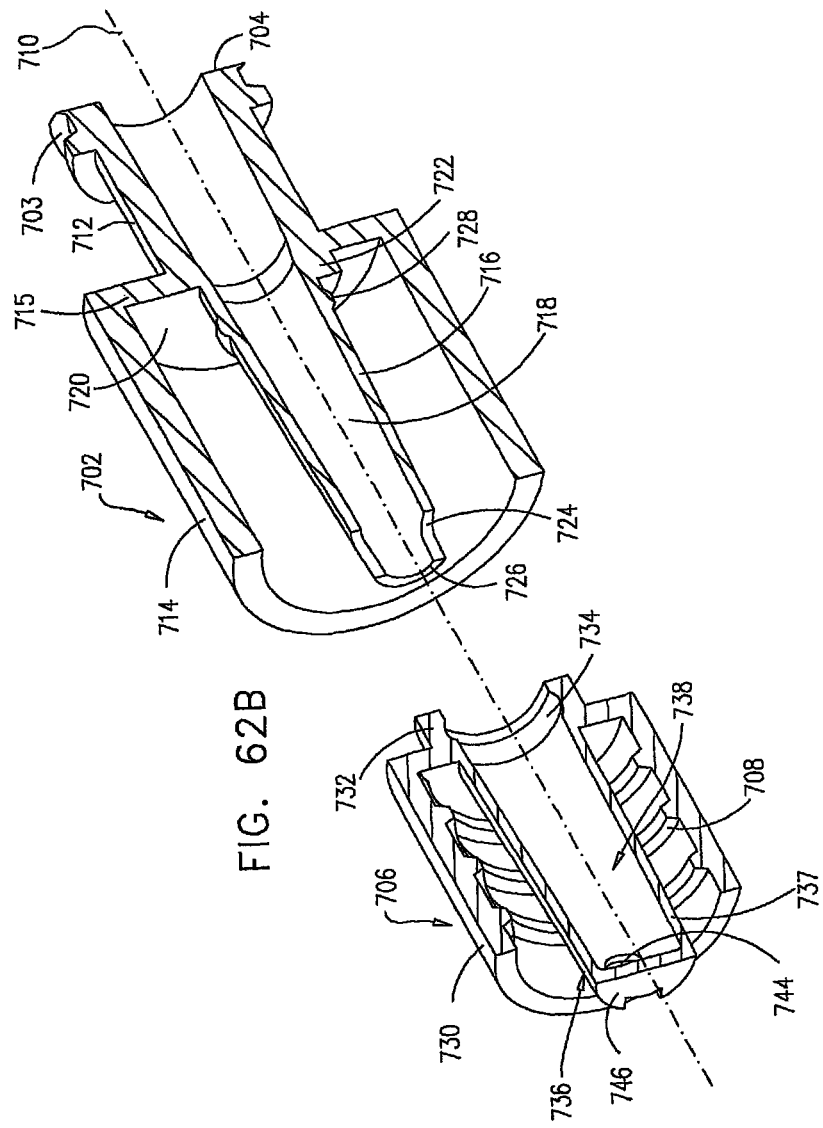

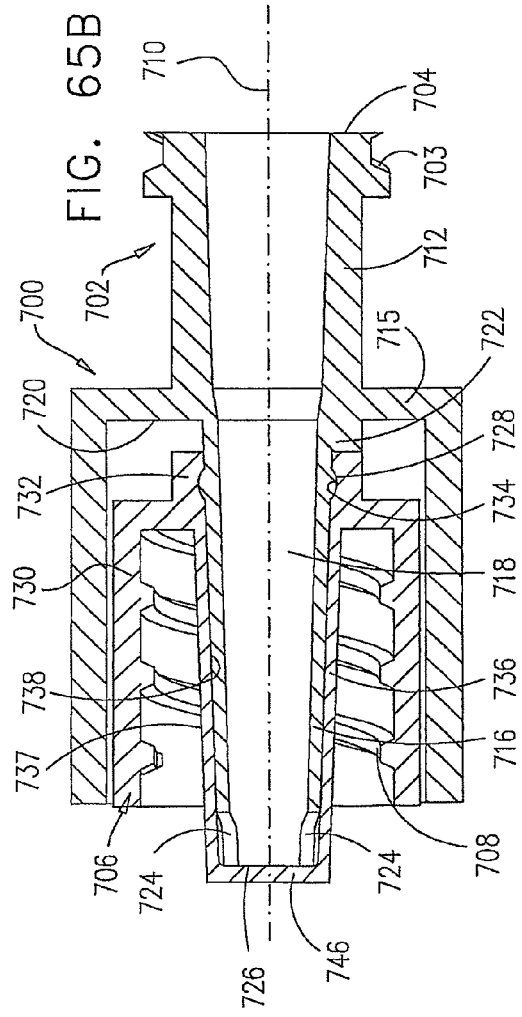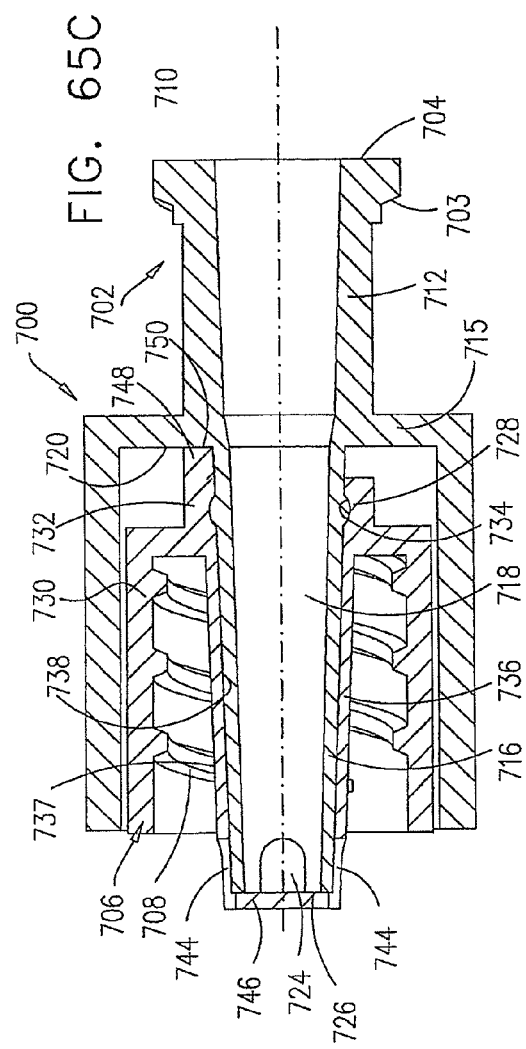

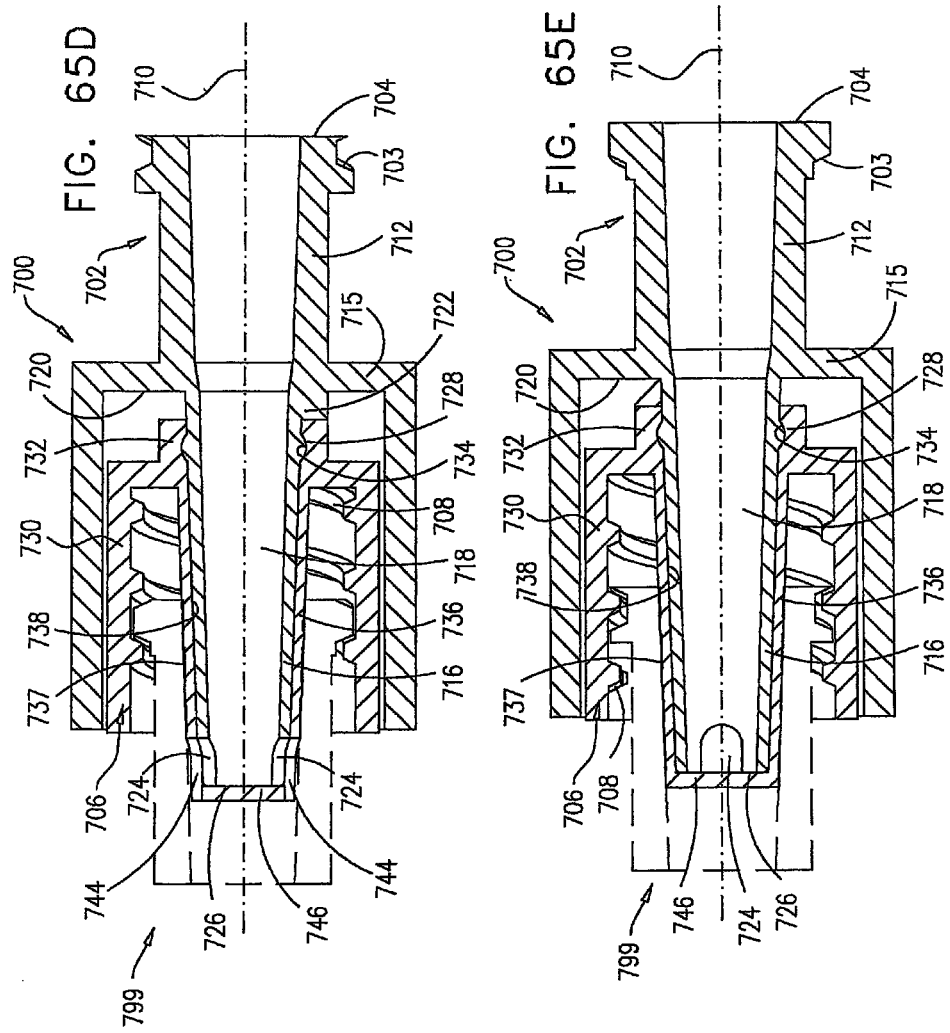

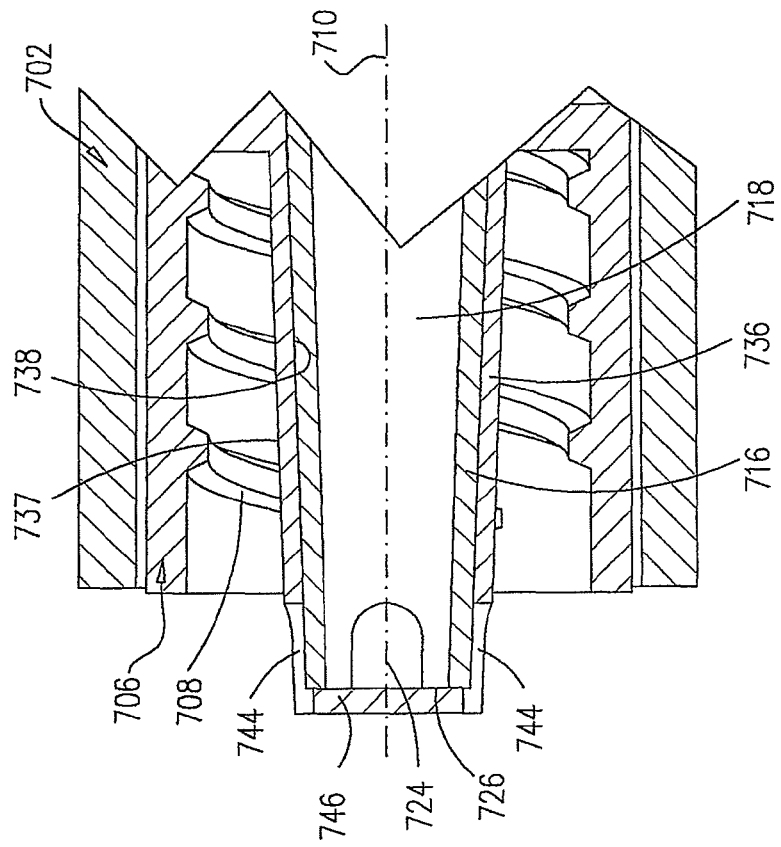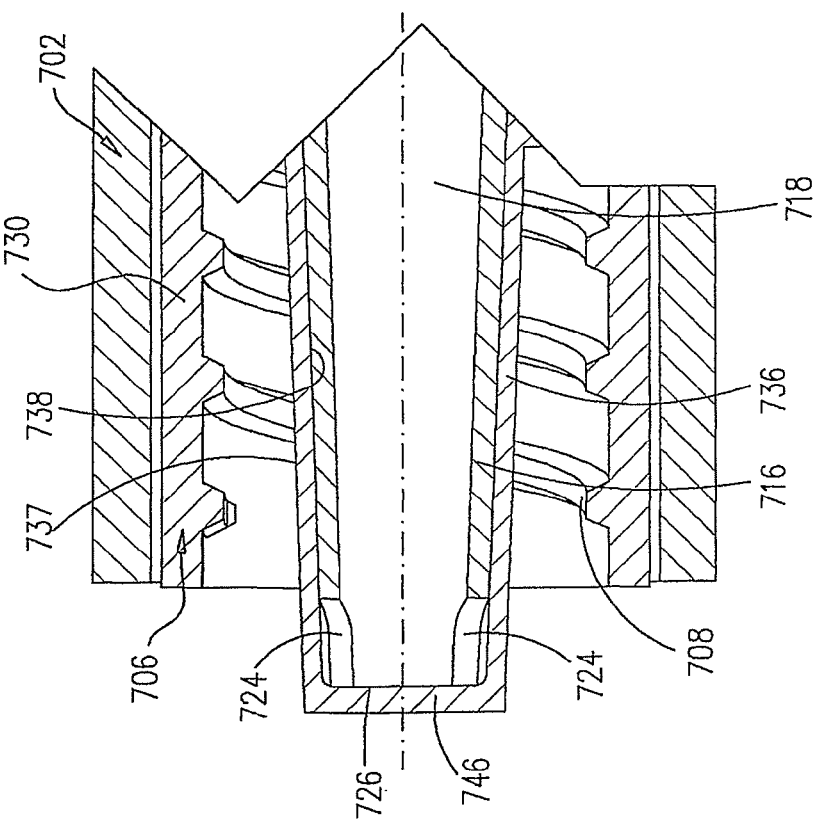

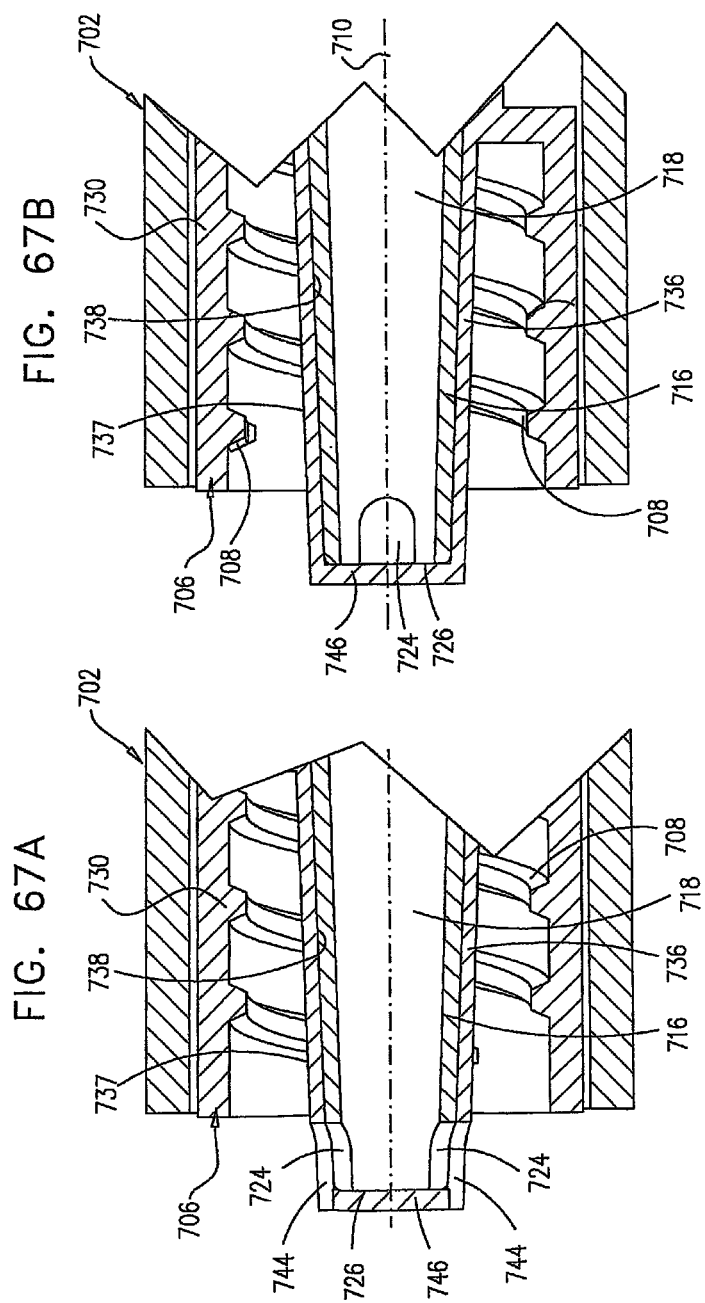

CLOSED MALE LUER CONNECTOR

REFERENCE TO RELATED APPLICATIONS

This is a Continuation Application of application Ser. No. 13/257,558 filed Nov. 28, 2011, which is a National Stage Application of PCT/IL2010/000227 filed Mar. 18, 2010, which claims the benefit of priority of U.S. Provisional Application No. 61/162,305, filed Mar. 22, 2009, U.S. Provisional Application No. 61/259,703, filed Nov. 10, 2009, and U.S. Provisional Application No. 61/290,523, filed Dec. 29, 2009. The entire disclosures of the prior applications are hereby incorporated by reference.

Reference is made to U.S. Provisional Patent Application Ser. No. 61/259,703, filed Nov. 10, 2009 and entitled "VALVED LUER CONNECTOR", to U.S. Provisional Patent Application Ser. No. 61/290,523, filed Dec. 29, 2009 and entitled "VALVED LUER CONNECTOR", and to U.S. Provisional Patent Application Ser. No. 61/162,305, filed Mar. 22, 2009 and entitled "VALVED MALE LUER CONNECTORS", the disclosures of which are hereby incorporated by reference and priority of which is hereby claimed pursuant to 37 CFR 1.78(a)(4) and (5)(i).

FIELD OF THE INVENTION

The present invention relates to fluid flow connectors and more particularly to fluid flow connectors for medical applications.

BACKGROUND OF THE INVENTION

The following publications are believed to represent the current state of the art:

U.S. Pat. Nos. 5,699,821; 6,068,011; 6,039,302; 6,706,022; 6,745,998; 6,964,406; 7,044,441; 7,100,890; 7,104,520; 7,140,592; 7,182,313; 7,306,198; 7,497,848; 7,530,546 and 7,559,530.

U.S. Patent Publication Nos. 2007/0088324; 2007/10088324; 2008/183155 and 2009/0177170.

SUMMARY OF THE INVENTION

The present invention seeks to provide an improved fluid flow connector.

There is thus provided in accordance with a preferred embodiment of the present invention a fluid flow connector including a housing assembly having a first end and a second end arranged along a common longitudinal axis and a resilient fluid flow conduit member disposed within the housing assembly, the resilient fluid flow conduit member having a forward end disposed alongside the first end of the housing assembly, the forward end being formed with a selectably closable slit and with at least one side opening, the resilient fluid flow conduit member being positionable in a closed position wherein the slit is closed but the at least one side opening is open and the resilient fluid flow conduit member being positionable in an open position, thereby allowing the slit to open and leaving the at least one side opening open, whereby when the resilient fluid flow conduit member is in the open position, the selectably closable slit and the at least one side opening each provide a fluid flow pathway between an interior of the resilient fluid flow conduit member and the first end of the housing assembly.

There is also provided in accordance with another preferred embodiment of the present invention a fluid flow connector including a housing assembly having an externally threaded end and an internally threaded end arranged along a common longitudinal axis at opposite ends thereof and a resilient fluid flow conduit member disposed within the housing assembly and arranged for displacement along the common longitudinal axis, the resilient fluid flow conduit member defining a fluid flow pathway extending interiorly thereof along the longitudinal axis between a rearward end thereof adjacent the externally threaded end of the housing assembly and a forward end thereof adjacent the internally threaded end of the housing assembly. The resilient fluid flow conduit member has at least one opening at the forward end thereof, enabling fluid communication between the fluid flow pathway and a location outside of the forward end, and a displacement engagement location formed rearwardly of the forward end for engagement of the resilient fluid flow conduit member by a displacement actuator to provide rearward displacement of the resilient fluid flow conduit member relative to the housing assembly between a closed position and an open position along the longitudinal axis. The resilient fluid flow conduit member also has a generally cylindrical portion extending rearwardly of the displacement engagement location and having a forward part and a rearward part and a radially outwardly extending tensionable connecting portion integrally joined to the generally cylindrical portion at a joining location rearwardly spaced from the displacement engagement location intermediate the forward part and the rearward part.

There is further provided in accordance with yet another preferred embodiment of the present invention a fluid flow connector including a housing assembly having a first end and a second end arranged along a common longitudinal axis, a rigid fluid flow conduit member disposed within the housing assembly, the rigid fluid flow conduit member having a forward end disposed alongside the first end of the housing assembly, a forward resilient selectable sealing element associated with the forward end of the rigid fluid flow conduit member, the forward resilient selectable sealing element being formed with a selectably closable slit and a rearward resilient displacement biasing element associated with the rigid fluid flow conduit member and with the housing assembly for urging the rigid fluid flow conduit member and the forward resilient selectable sealing member forwardly into engagement with the first end of the housing assembly, thereby closing the selectably closable slit.

There is even further provided in accordance with still another preferred embodiment of the present invention a fluid flow connector including a housing assembly having a first end and a second end arranged along a common longitudinal axis, a resilient member disposed within the housing assembly, the resilient member having a forward end disposed alongside the first end of the housing assembly, the forward end being formed with a selectably closable slit and with at least one side opening and a rigid fluid flow conduit member being fixedly disposed within the resilient member and adapted for displacement along the longitudinal axis together therewith. The resilient member is positionable in a closed position wherein the slit is closed but the at least one side opening is open and in an open position, allowing the slit to open and leaving the at least one side opening open. When the resilient member is in the open position, the selectably closable slit and the at least one side opening each provide a fluid flow pathway between an interior of the resilient member and the first end of the housing assembly.

There is yet further provided in accordance with another preferred embodiment of the present invention a fluid flow connector including a housing assembly having an externally threaded end and an internally threaded end arranged along a common longitudinal axis at opposite ends thereof, a resilient member disposed within the housing assembly and arranged for displacement along the common longitudinal axis and a rigid fluid flow conduit member disposed within the resilient member. The rigid fluid flow conduit member defines a fluid flow pathway extending interiorly thereof along the longitudinal axis between a rearwardly facing end thereof adjacent the externally threaded end of the housing assembly and a forwardly facing end thereof adjacent the internally threaded end of the housing assembly. The rigid fluid flow conduit member is fixedly disposed within the resilient member and adapted for displacement along the longitudinal axis together therewith. The resilient member has at least one opening at a forward end thereof, enabling fluid communication between the fluid flow pathway and a location outside of the forward end and a displacement engagement location formed rearwardly of the forward end for engagement of the resilient member by a displacement actuator to provide rearward displacement of the resilient member relative to the housing assembly between a closed position and an open position along the longitudinal axis. The resilient member also has a generally cylindrical portion extending rearwardly of the displacement engagement location and having a forward part and a rearward part and a radially outwardly extending tensionable connecting portion integrally joined to the generally cylindrical portion at a joining location rearwardly spaced from the displacement engagement location intermediate the forward part and the rearward part.

There is also provided in accordance with yet another preferred embodiment of the present invention a fluid flow connector including a housing assembly having a first end and a second end arranged along a common longitudinal axis, a forward resilient member locked within the housing assembly, the forward resilient member having a forward end disposed alongside the first end, the forward end including at least two slit wall portions defining a selectably closable slit therebetween, a rigid fluid flow conduit member at least partially disposed within the forward resilient member rearwardly of the forward end and a rearward resilient displacement biasing element associated with the rigid fluid flow conduit member and with the housing assembly. The rigid fluid flow conduit member is positionable in a forward position in engagement with the at least two slit wall portions of the forward resilient member, causing the slit to be closed and in a rearward position out of engagement with the at least two slit wall portions of the forward resilient member, causing the slit to be open.

There is further provided in accordance with still another preferred embodiment of the present invention a fluid flow connector including a housing assembly having a first end and a second end arranged along a common longitudinal axis, a forward conduit and actuator element at least partially disposed within the housing assembly, the forward conduit and actuator element having a forward edge, a resilient fluid flow conduit sealing and biasing element locked within the forward conduit and actuator element, the resilient fluid flow conduit sealing and biasing element having a forward end positioned alongside the forward edge, the forward end being formed with a selectably closable slit extending along the longitudinal axis and a rigid fluid flow conduit member disposed within the resilient fluid flow conduit sealing and biasing element. The forward conduit and actuator element and the resilient fluid flow conduit sealing and biasing element are positionable in a forward position wherein the selectably closable slit is closed and in a rearward position, wherein the rigid fluid flow conduit member at least partially extends through the selectably closable slit, causing the selectably closable slit to open.

Preferably, the resilient fluid flow conduit member is arranged for displacement between the closed position and the open position along the common longitudinal axis. Additionally or alternatively, the selectably closable slit extends along the longitudinal axis.

In accordance with a preferred embodiment of the present invention the first end is an internally threaded end and the second end is an externally threaded end. Alternatively or additionally, the at least one side opening extends generally perpendicularly to the longitudinal axis.

Preferably, the resilient fluid flow conduit member is pre-tensioned and thereby urged to the closed position. Additionally, the resilient fluid flow conduit member is displaceable, against the urging produced by its being pre-tensioned, to the open position.

In accordance with a preferred embodiment of the present invention, the resilient fluid flow conduit member includes a displacement engagement location formed rearwardly of the forward end for engagement of the resilient fluid flow conduit member by a displacement actuator to provide rearward displacement of the resilient fluid flow conduit member relative to the housing assembly along the longitudinal axis, a generally cylindrical portion extending rearwardly of the displacement engagement location and having a forward part and a rearward part and a radially outwardly extending tensionable connecting portion integrally joined to the generally cylindrical portion at a joining location rearwardly spaced from the displacement engagement location intermediate the forward part and the rearward part. Additionally, the tensionable connecting portion terminates in a generally circularly cylindrical mounting portion. Additionally, the generally circularly cylindrical mounting portion is locked within the housing assembly intermediate the first end and the second end.

Preferably, the resilient fluid flow conduit member is formed with an elongate bore which defines a fluid flow conduit and the slit and the at least one side opening communicate with the elongate bore.

Preferably, when the resilient fluid flow conduit member is positioned in the closed position, the forward end engages a forward conduit having a forwardly facing aperture, thereby closing the slit but leaving the at least one side opening open for fluid communication between an interior of the resilient fluid flow conduit member and an exterior of the resilient fluid flow conduit member within the forward conduit, thereby sealing the forwardly facing aperture. Alternatively or additionally, when the resilient fluid flow conduit member is positioned in the open position, the forward end does not engage the forward conduit, thereby allowing the slit to open and leaving the at least one side opening open for fluid communication between the interior of the resilient fluid flow conduit member and the exterior of the resilient fluid flow conduit member within the forward conduit and thereby unsealing the forwardly facing aperture.

Preferably, the forward conduit is formed with an interior bore having a forwardly tapered portion. Additionally, when the resilient fluid flow conduit member is positioned in the closed position, the forward end sealingly engages the forwardly tapered portion of the interior bore, thereby squeezing the forward end transversely to the longitudinal axis and thereby closing the slit and sealing the aperture but leaving the at least one side opening open for fluid communication between the interior of the resilient fluid flow conduit member and the exterior thereof within the interior bore of the forward conduit. Alternatively or additionally, when the resilient fluid flow conduit member is positioned in the open position, the forward end is rearwardly positioned out of engagement with the forwardly tapered portion of the interior bore, thereby unsealing the forwardly facing aperture, and thereby allowing the slit to open and leaving the at least one side opening open, thereby providing fluid communication between the elongate bore of the resilient fluid flow conduit member, the exterior of the resilient fluid flow conduit member, the interior bore of the forward conduit and the forwardly facing aperture, both via the slit and via the at least one side opening.

In accordance with a preferred embodiment of the present invention, the displacement actuator is arranged to be displaced rearwardly along the longitudinal axis by engagement therewith of a rearwardly facing end of an external conduit, which engages the first end.

Preferably, the resilient fluid flow conduit member is symmetric about the longitudinal axis in all respects other than with respect to the slit and the at least one side opening. Additionally or alternatively, the forward end is formed with a forwardly tapered portion and with a tip portion, forwardly of the forwardly tapered portion, the tip portion having an oval cross section, which is compressible into a circular cross section and the slit extends through the forwardly tapered portion and through the tip portion.

In accordance with a preferred embodiment of the present invention when the resilient fluid flow conduit member is positioned in the closed position, axial pressure engagement of the forwardly tapered portion of the forward end with the forwardly tapered portion of the interior bore of the forward conduit is operative to squeeze the forward end of the resilient fluid flow conduit member transversely to the longitudinal axis, thereby closing the slit and changing a generally oval configuration of the forwardly tapered portion of the resilient fluid flow conduit member to a generally circular configuration. Additionally or alternatively, when the resilient fluid flow conduit member is positioned in the open position, elimination of axial pressure engagement of the forwardly tapered portion of the forward end with the forwardly tapered portion of the interior bore of the forward conduit causes the forward end of the resilient fluid flow conduit member to no longer be squeezed transversely to the longitudinal axis, thereby allowing the slit to open and allowing the cross section of the tapered portion to return to the generally oval configuration.

Preferably, the first end of the housing assembly is formed with a forwardmost flange and rearwardly tapered mutually spaced generally axial ribs extending rearwardly from the flange. In accordance with a preferred embodiment of the present invention, the forward conduit is joined to an inwardly facing wall of the housing assembly by a plurality of radially extending ribs.

In accordance with a preferred embodiment of the present invention the resilient fluid flow conduit member is formed with a sealing ring extending radially outward therefrom, slightly rearwardly of the forward end. Additionally or alternatively, the resilient fluid flow conduit member is formed with a radially outer sealing surface extending radially outward from a rearward end thereof.

Preferably, the housing assembly includes a rearward conduit extending forwardly from the second end.

In accordance with a preferred embodiment of the present invention the radially outer sealing surface of the resilient fluid flow conduit member and an inner facing surface of the rearward conduit are in slidable sealing engagement, the sealing engagement preventing fluid which enters the fluid flow connector via the rearward conduit from entering a volume rearward of the connecting portion, thereby preventing the volume from acting as a "dead space" which could undesirably retain the fluid. Additionally, the sealing ring of the resilient fluid flow conduit member and the interior bore of the forward conduit are in slidable sealing engagement, the sealing engagement preventing fluid which passes through the slit and the at least one side opening from entering a volume within the interior bore rearward of the sealing ring, thereby preventing the volume from acting as a "dead space" which could undesirably retain the fluid. In accordance with a preferred embodiment of the present invention, the slidable sealing engagement between the radially outer sealing surface of the resilient fluid flow conduit member and an inner facing surface of the rearward conduit and the slidable sealing engagement between the sealing ring of the resilient fluid flow conduit member and the interior bore of the forward conduit together maintain a pressurized fluid seal for pressurized fluid in the rearward conduit and in the resilient fluid flow conduit member.

Preferably, when the resilient fluid flow conduit member is positioned in the open position, a fluid flow connection is open for fluid supplied via the second end and the resilient fluid flow conduit member to the first end via the slit and the at least one side opening.

In accordance with a preferred embodiment of the present invention, the tensionable connecting portion terminates in a generally circularly cylindrical mounting portion.

Preferably, the resilient fluid flow conduit member defines a generally incompressible fluid flow pathway extending axially along an interior thereof between the rearward end thereof and the forward end thereof.

In accordance with a preferred embodiment of the present invention, the at least one opening at the forward end thereof includes a selectably closable slit extending along the longitudinal axis.

Preferably, the resilient fluid flow conduit member is formed with an elongate bore which defines a fluid flow conduit and the at least one opening communicates with the elongate bore.

In accordance with a preferred embodiment of the present invention, the rigid fluid flow conduit member is arranged for displacement along the common longitudinal axis. Additionally, the forward resilient selectable sealing element is arranged for displacement along the common longitudinal axis and the selectably closable slit extends along the longitudinal axis.

Preferably, the first end is an internally threaded end and the second end is an externally threaded end. Additionally or alternatively, the rearward resilient displacement biasing element is arranged for partial displacement along the common longitudinal axis.

In accordance with a preferred embodiment of the present invention, the rearward resilient displacement biasing element is formed with a generally cylindrical portion and the generally cylindrical portion is formed with an elongate bore. Additionally or alternatively, the rigid fluid flow conduit member includes a cylindrical portion formed with a fluid conduit defining bore, having a forward part and a rearward part, and a circumferential actuator portion. Additionally, the rearward part is partially sealingly disposed within the elongate bore.

Preferably, the rigid fluid flow conduit member is arranged to be displaced rearwardly along the longitudinal axis by engagement of a rearwardly facing end of an external conduit with the actuator portion. In accordance with a preferred embodiment of the present invention, the external conduit threadably engages the internally-threaded end.

Preferably, the forward resilient selectable sealing element is arranged along the longitudinal axis and is sealingly disposed over the forward part of the cylindrical portion of the rigid fluid flow conduit member. Additionally or alternatively, the forward resilient selectable sealing element is formed with an elongate bore and has a forward section extending forwardly of the elongate bore, the forward section being disposed alongside the first end. Additionally, the forward section is formed with an interior bore.

In accordance with a preferred embodiment of the present invention, the housing assembly includes a forward conduit integrally formed therewith, the forward conduit being formed with an interior bore having a forwardly tapered portion and a forwardly facing aperture. Additionally or alternatively, the rearward resilient displacement biasing element is pre-tensioned and thereby urges the rigid fluid flow conduit member and the forward resilient selectable sealing element associated therewith, forwardly along the longitudinal axis to a closed position.

Preferably, when the fluid flow connector is in the closed position, the forward section sealingly engages the forwardly tapered portion of the interior bore, thereby squeezing the forward section transversely to the longitudinal axis, thereby sealing the forwardly facing aperture and closing the slit.

In accordance with a preferred embodiment of the present invention, rearward displacement of the rigid fluid flow conduit member produces corresponding rearward displacement of the rearward resilient displacement biasing element along the longitudinal axis and also produces rearward displacement of the forward resilient selectable sealing element such that the forward section moves rearwardly out of engagement with the forwardly tapered portion of the interior bore, thereby allowing the slit to open and unsealing the forwardly facing aperture, thereby positioning the fluid flow connector in an open position and thereby providing fluid communication between the fluid conduit defining bore, the interior bore of the forward section and an exterior thereof, the interior bore of the forward conduit and the forwardly facing aperture.

Preferably, the housing assembly includes a rearward conduit extending forwardly from the second end along the axis. Additionally or alternatively, the rearward resilient displacement biasing element also includes a tensionable connecting portion extending radially outwardly therefrom, the tensionable connecting portion being in the form of a disc when in an unstressed condition and terminating in a generally circularly cylindrical mounting portion. Additionally, the rearward resilient displacement biasing element is maintained in a pre-tensioned state wherein the generally circularly cylindrical mounting portion is locked within the housing assembly intermediate the first end and the second end.

In accordance with a preferred embodiment of the present invention, the forward section is formed with a tapered portion and with a tip portion, forwardly of the tapered portion, the tip portion having an oval cross section, which is compressible into a circular cross section and the slit extends through the tapered portion and through the tip portion.

Preferably, when the fluid flow connector is in the closed position, axial pressure engagement of the tapered portion of the forward section with the forwardly tapered portion of the interior bore of the forward conduit is operative to squeeze the forward section transversely to the longitudinal axis, thereby closing the slit and changing the cross section of the tip portion from the oval cross section to the circular cross section. In accordance with a preferred embodiment of the present invention, when the fluid flow connector in the open position, elimination of axial pressure engagement of the tapered portion of the forward section with the forwardly tapered portion of the interior bore of the forward conduit causes the forward section to no longer be squeezed transversely to the longitudinal axis, thereby allowing the slit to open and allowing the tip portion to return to the oval cross section.

Preferably, the rearward resilient displacement biasing element is formed with a radially outer sealing surface extending radially outward from a rearward end thereof. Additionally or alternatively, the forward resilient selectable sealing element is formed with a sealing ring extending radially outward of the forward end and slightly rearwardly thereof.

In accordance with a preferred embodiment of the present invention, the radially outer sealing surface and an inner facing surface of the rearward conduit are in slidable sealing engagement, the sealing engagement preventing fluid which enters the fluid flow connector via the rearward conduit from entering a volume rearward of the connecting portion, thereby preventing the volume from acting as a "dead space" which could undesirably retain the fluid. Preferably, the sealing ring and the interior bore of the forward conduit are in slidable sealing engagement, the sealing engagement preventing fluid which passes through the slit from entering a volume within the interior bore rearward of the sealing ring, thereby preventing the volume from acting as a "dead space" which could undesirably retain the fluid.

In accordance with a preferred embodiment of the present invention, the slidable sealing engagement between the radially outer sealing surface and the inner facing surface of the rearward conduit and between the sealing ring and the interior bore of the forward conduit together maintain a pressurized fluid seal for pressurized fluid in the forward conduit, the fluid conduit defining bore and the interior bore of the forward section. Preferably, engagement of the external conduit with the first end rearwardly displaces the rigid fluid flow conduit member, producing corresponding rearward displacement of the rearward resilient displacement biasing element along the axis, resulting in increased tensioning of the tensionable connecting portion.

Preferably, when the fluid flow connector is in the open position, a fluid flow connection is open for fluid supplied via the second end and the rigid fluid flow conduit member to the first end via the slit.

Preferably, the forward resilient selectable sealing element is also formed with at least one side opening which extends generally perpendicularly to the longitudinal axis. Additionally, the at least one side opening communicates with an interior of the forward resilient selectable sealing element and with an interior of the rigid fluid flow conduit member.

In accordance with a preferred embodiment of the present invention, when the fluid flow connector is in the open position, a fluid flow connection is open for fluid supplied via the second end and the rigid fluid flow conduit member to the first end via the slit and the at least one side opening. Preferably, when the fluid flow connector is in the closed position, the forward section sealingly engages the forwardly tapered portion of the interior bore, squeezing the forward section transversely to the longitudinal axis, thereby sealing the forwardly facing aperture and closing the slit but and leaving the at least one side opening open for fluid communication between the fluid conduit defining bore, the interior bore of the forward resilient selectable sealing element and an exterior thereof, the interior bore of the forward conduit and the forwardly facing aperture.

In accordance with a preferred embodiment of the present invention, rearward displacement of the rigid fluid flow conduit member produces corresponding rearward displacement of the rearward resilient displacement biasing element along the longitudinal axis and also produces rearward displacement of the forward resilient selectable sealing element such that the forward section moves rearwardly out of engagement with the forwardly tapered portion of the interior bore to the open position, thereby unsealing the forwardly facing aperture and allowing the slit to open and leaving the at least one side opening open, whereby both the slit and the at least one side opening provide fluid communication between the fluid conduit defining bore, the interior bore of the forward resilient selectable sealing element and an exterior thereof, the interior bore of the forward conduit and the forwardly facing aperture.

In accordance with a preferred embodiment of the present invention, the sealing ring and the interior bore of the forward conduit are in slidable sealing engagement, the sealing engagement preventing fluid which passes through the slit and the at least one side opening from entering a volume within the interior bore rearward of the sealing ring, thereby preventing the volume from acting as a "dead space" which could undesirably retain the fluid.

Preferably, the rearward resilient displacement biasing element is an integrally formed silicone rubber element which is symmetric about the longitudinal axis. Additionally or alternatively, the housing assembly includes rearwardly tapered mutually spaced generally axial ribs on an exterior thereof.

In accordance with a preferred embodiment of the present invention, the forward conduit is joined to an inwardly facing circularly cylindrical wall of the housing assembly by a plurality of radially extending ribs. Preferably, the actuator portion includes a transverse wall disposed at a location intermediate the forward part and the rearward part, and a pair of cylindrical sections which extend forwardly of the wall and form part of an imaginary cylinder aligned about the axis, the cylindrical sections defining forwardly facing engagement surfaces.

Preferably, the forward resilient member also includes a generally cylindrical portion which remains generally static with respect to the housing assembly irrespective of whether the slit is open or closed.

In accordance with a preferred embodiment of the present invention, the rearward resilient displacement biasing element is arranged for partial displacement between the forward position and the rearward position along the common longitudinal axis.

Preferably, when the rigid fluid flow conduit member is positioned in the rearward position wherein the rigid fluid flow conduit member is engaged by a displacement actuator, the rigid fluid flow conduit member is thereby disengaged from the at least two slit wall portions, causing the slit to be open. Additionally, when the rigid fluid flow conduit member is positioned in the forward position wherein the rigid fluid flow conduit member is not engaged by the displacement actuator, the rigid fluid flow conduit member engages the at least two slit wall portions causing the slit to be closed.

In accordance with a preferred embodiment of the present invention, the rearward resilient displacement biasing element includes a generally cylindrical portion formed with an elongate bore. Additionally or alternatively, the rigid fluid flow conduit member includes a circumferential actuator portion and a cylindrical portion, the cylindrical portion is formed with a fluid conduit defining bore and the cylindrical portion includes a forward part and a rearward part.

Preferably, the rearward part is partially sealingly disposed within the elongate bore. Additionally or alternatively, the forward resilient member is arranged along the longitudinal axis and is slidingly disposed over the forward part of the cylindrical portion.

In accordance with a preferred embodiment of the present invention, the forward resilient member is formed with an interior bore and a rearwardly facing sealing aperture. Preferably, the forward resilient member is tightly and sealingly disposed within the interior bore of the forward conduit.

Preferably, part of the rearward resilient displacement biasing element is pre-tensioned and urges the rigid fluid flow conduit member forwardly along the longitudinal axis to the forward position, wherein a forward end of the rigid fluid flow conduit member engages the at least two slit wall portions of the selectably closable slit, whereby the at least two slit wall portions are forwardly displaced and squeezed transversely to the longitudinal axis, thereby closing the slit.

In accordance with a preferred embodiment of the present invention, engagement of a forward end of the rigid fluid flow conduit member with the at least two slit wall portions under the urging of the rearward resilient displacement biasing element in the forward position is operative to forwardly displace and tightly dispose the at least two slit wall portions at least partially within the forwardly facing aperture and to seal the forwardly facing aperture.

Preferably, the rigid fluid flow conduit member is arranged to be displaced rearwardly along the axis between the forward position and the rearward position by engagement of the actuator portion by a rearwardly facing end of an external conduit. Additionally or alternatively, the rearwardly facing end of the external conduit engages the actuator portion via the internally-threaded end.

In accordance with a preferred embodiment of the present invention, rearward displacement of the rigid fluid flow conduit member to the rearward position produces corresponding rearward displacement of the rearward resilient displacement biasing element along the axis such that the forward end of the rigid fluid flow conduit member moves rearwardly out of engagement with the at least two slit wall portions, thereby allowing the slit to open. Preferably, disengagement of the rigid fluid flow conduit member from the at least two slit wall portions in the rearward position is operative to unseal the forwardly facing aperture and allows the slit to open for fluid communication between the fluid conduit defining bore of the rigid fluid flow conduit member, the interior bore of the forward resilient member and the forwardly facing aperture.

Preferably, the housing assembly includes a forwardmost face and rearwardly tapered mutually spaced generally axial ribs extending rearwardly from the forwardmost face.

In accordance with a preferred embodiment of the present invention, the rearwardly facing sealing aperture and an exterior of the forward part of the cylindrical portion of the rigid fluid flow conduit member are in slidable sealing engagement, the sealing engagement preventing fluid which passes through the fluid conduit defining bore from entering a volume within the interior bore rearward of the sealing aperture, thereby preventing the volume from acting as a "dead space" which could undesirably retain the fluid. Additionally, the slidable sealing engagement between the radially outer sealing surface and the inner facing surface of the rearward conduit and the slidable sealing engagement between the rearwardly facing sealing aperture and the exterior of the forward part of the cylindrical portion of the rigid fluid flow conduit member together maintain a pressurized fluid seal for pressurized fluid in the rearward conduit and in the fluid conduit defining bore.

Preferably, when the fluid flow connector is in the rearward position, a fluid flow connection is open for fluid supplied via the rearward conduit and the fluid conduit defining bore to the external conduit via the slit and the aperture.

Preferably, the forward conduit and actuator element is arranged for displacement between the forward position and the rearward position along the common longitudinal axis. Additionally or alternatively, the resilient fluid flow conduit sealing and biasing element is arranged for partial displacement between the forward position and the rearward position along the common longitudinal axis.

In accordance with a preferred embodiment of the present invention, when the forward conduit and actuator element and the resilient fluid flow conduit sealing and biasing element are positioned in the rearward position, wherein the forward conduit and actuator element is engaged by a displacement actuator, the rigid fluid flow conduit member at least partially extends through the selectably closable slit thereby opening the selectably closable slit. Additionally, when the forward conduit and actuator element and the resilient fluid flow conduit sealing and biasing element are positioned in the forward position, wherein the forward conduit and actuator element is not engaged by the displacement actuator, the selectably closable slit is closed.

Preferably, the rigid fluid flow conduit member is integrally formed within the housing assembly and extends forwardly from the rearward conduit.

In accordance with a preferred embodiment of the present invention, the resilient fluid flow conduit sealing and biasing element is formed with an elongate bore and a forward end wall having a rearwardly facing surface, the slit being formed within the forward end wall. Additionally, the resilient fluid flow conduit sealing and biasing element is formed with a selectably compressible accordion type rearward portion disposed rearwardly of the elongate bore, the selectably compressible accordion type rearward portion defining an inner volume, communicating with the elongate bore.

Preferably, when the forward conduit and actuator element and the resilient fluid flow conduit sealing and biasing element are positioned in the rearward position and the forward conduit and actuator element is engaged by the displacement actuator, the selectably compressible accordion type rearward portion is rearwardly compressed against a forwardly facing circumferential surface of the housing assembly.

In accordance with a preferred embodiment of the present invention, the forward conduit and actuator element is formed with an interior bore and a forwardly facing aperture.

Preferably, the forward conduit and actuator element is arranged to be displaced rearwardly from the forward position to the rearward position along the axis by engagement of the forward conduit and actuator element by a rearwardly facing end of an external conduit.

Preferably, the engagement of the external conduit with the forward conduit and actuator element is via the internally-threaded end.

In accordance with a preferred embodiment of the present invention, the resilient fluid flow conduit sealing and biasing element includes a generally elongate portion having an elongate bore formed therewithin along the axis, the elongate bore including an integrally formed interior facing sealing ring. Additionally, the rigid fluid flow conduit member is slidably and sealingly disposed within the elongate bore in engagement with the sealing ring. Alternatively or additionally, the sealing ring and an exterior surface of the rigid fluid flow conduit member are in slidable sealing engagement.

Preferably, the fluid flow connector maintains a pressurized fluid seal for pressurized fluid in the rearward conduit, the rigid fluid flow conduit member, and a volume inside the resilient fluid flow conduit sealing and biasing element forward of the sealing ring, the pressurized fluid seal being provided by the sealing ring and by the rearwardly facing surface of the forward end wall. In accordance with a preferred embodiment of the present invention, when the forward conduit and actuator element and the resilient fluid flow conduit sealing and biasing element are positioned in the rearward position, the rigid fluid flow conduit member extends through the slit, and at least partially extends through the forwardly facing aperture, thereby stretchingly displacing the forward end wall forwardly and radially outward from the slit to a longitudinal orientation, tightly and circumferentially disposed between an exterior surface of the rigid fluid flow conduit member and the aperture, thereby unsealing the rigid fluid flow conduit member.

In accordance with a preferred embodiment of the present invention, when the forward conduit and actuator element and the resilient fluid flow conduit sealing and biasing element are in the rearward position, a fluid flow connection is open for fluid supplied via the rearward conduit and the rigid fluid flow conduit member to the external conduit via the slit and the aperture, wherein a volume of the fluid flow connection does not substantially change upon opening or closing of the fluid flow connection, thus providing a generally neutral fluid displacement characteristic.

There is yet further provided in accordance with another preferred embodiment of the present invention a fluid flow connector including a housing assembly having a first end and a second end arranged along a common longitudinal axis, a forward conduit and actuator element disposed within the housing assembly, the forward conduit and actuator element being arranged for displacement along the common longitudinal axis, the forward conduit and actuator element having a forward end disposed alongside the first end, a rigid inner rod at least partially disposed within the forward conduit and actuator element and arranged along the common longitudinal axis, thereby defining together with an interior of the forward conduit and actuator element a fluid flow conduit therebetween, the rigid inner rod having a forward end disposable in sealing engagement with an interior of the forward conduit and actuator element at the forward end thereof and a resilient selectably compressible biasing element disposed within the housing assembly rearward of the forward conduit and actuator element. The forward conduit and actuator element is positionable in a forward position wherein the forward conduit and actuator element is in the sealing engagement with the rigid inner rod, thereby sealing the fluid flow conduit and in a rearward position wherein the forward conduit and actuator element is out of engagement with the forward end of the rigid inner rod, thereby unsealing the fluid flow conduit.

Preferably, the forward conduit and actuator element is arranged for displacement between the forward position and the rearward position along the common longitudinal axis. Additionally or alternatively, engagement of the forward conduit and actuator element by a displacement actuator is operative to displace the forward conduit and actuator element from the forward position to the rearward position. Additionally, the displacement actuator is an external conduit.

In accordance with a preferred embodiment of the present invention, the first end is an internally-threaded end and the second end is an externally-threaded end. Additionally, the engagement of the forward conduit and actuator element by the displacement actuator is via the internally-threaded end.

Preferably, the resilient selectably compressible biasing element is pre-tensioned to urge the forward conduit and actuator element forwardly into the forward position. Additionally, when the forward conduit and actuator element is positioned in the rearward position, the resilient selectably compressible biasing element is compressed rearwardly, against the urging produced by its being pre-tensioned.

Preferably, the housing assembly is formed with a rearward conduit extending forwardly from the second end thereof, the rigid inner rod extending forwardly of the rearward conduit.

In accordance with a preferred embodiment of the present invention, the rigid inner rod is formed with at least two elongate longitudinal recesses extending from a rearwardly facing end of the inner rod to slightly rearward of a forwardly facing end portion thereof. Additionally or alternatively, the forward conduit and actuator element is formed with an interior bore having an inner facing surface.

Preferably, the forward conduit and actuator element is formed with a generally truncated conical forward section. Additionally or alternatively, the resilient selectably compressible biasing element is an integrally formed silicone rubber element. Alternatively or additionally, the resilient selectably compressible biasing element is symmetric about the longitudinal axis.

Preferably, the housing assembly includes a generally cylindrical forward body portion having rearwardly tapered mutually spaced generally axial ribs. Additionally or alternatively, the resilient selectably compressible biasing element is maintained in a non-compressed state and is held in place between a forwardly facing interior surface of the housing assembly and the forward conduit and actuator element, rearwardly thereof, which is in turn retained against forward movement by a rearwardly facing interior surface of the housing assembly.

Preferably, the at least two elongate longitudinal recesses of the rigid inner rod and the inner facing surface of the interior bore of the forward conduit and actuator element define at least two longitudinal fluid flow conduits therebetween.

In accordance with a preferred embodiment of the present invention, when the forward conduit and actuator element is positioned in the forward position, the forwardly facing end portion of the rigid inner rod and the inner facing surface of the interior bore of the forward conduit and actuator element are in sealing engagement therebetween, thereby sealing the longitudinal fluid flow conduits and maintaining a pressurized fluid seal for pressurized fluid in the longitudinal fluid flow conduits and the rearward conduit. Preferably, when the forward conduit and actuator element is positioned in the rearward position upon engagement thereof by the external conduit, the inner facing surface of the interior bore is displaced rearwardly out of engagement with the forwardly facing end portion of the cylindrical inner rod, thereby allowing fluid communication between the fluid flow conduit and the external conduit. Preferably, when the forward conduit and actuator element is positioned in the rearward position, the fluid flow connector is open for flow of fluid supplied via the rearward conduit and the fluid flow conduits to the external conduit.

There is also provided in accordance with still another preferred embodiment of the present invention a fluid flow connector including a housing member including a rigid fluid flow conduit defining portion, defining a rigid fluid flow conduit, the rigid fluid flow conduit defining portion having a first end and a second end arranged along a common longitudinal axis, the first end being formed with at least one fluid flow conduit side opening and a rigid hollow member sealingly disposed about the rigid fluid flow conduit defining portion, the rigid hollow member having a forward end disposed alongside the first end, the forward end being formed with at least one rigid hollow member side opening. The rigid hollow member is positionable in a first position wherein the at least one rigid hollow member side opening of the rigid hollow member is not disposed at least partially in alignment with the at least one fluid flow conduit side opening of the rigid fluid flow conduit defining portion, thereby sealing the rigid fluid flow conduit and in a second position wherein the at least one rigid hollow member side opening of the rigid hollow member is disposed at least partially in alignment with the at least one fluid flow conduit side opening of the rigid fluid flow conduit defining portion, thereby unsealing the rigid fluid flow conduit.

Preferably, the rigid hollow member is arranged about the rigid fluid flow conduit defining portion for rotational displacement between the first position and the second position. Additionally or alternatively, rotational engagement of the rigid hollow member by a displacement actuator is operative to rotationally displace the rigid hollow member from the first position to the second position. Additionally, the displacement actuator is an external conduit.

In accordance with a preferred embodiment of the present invention, the forward end includes an internally-threaded portion and the second end is an externally-threaded end. Additionally, the rotational engagement of the rigid hollow member by the displacement actuator is via the internally-threaded portion.

Preferably, the housing member and the rigid hollow member are arranged along the common longitudinal axis and are snap fitted together.

In accordance with a preferred embodiment of the present invention, the rigid fluid flow conduit defining portion is formed as an elongate generally conical hollow forwardly open shaft defining a forwardly tapered conduit therewithin extending forwardly along the axis. Additionally, the housing member includes a forwardly extending rotation limiting protrusion which lies adjacent the shaft along a part of a periphery thereof. Additionally or alternatively, the shaft is formed with an annular protrusion on an outer surface thereof. Additionally, the rigid hollow member includes an annular recess configured for snap fit rotational engagement with the annular protrusion.

Preferably, the rigid hollow member includes a rotation limiting portion which cooperates with the forwardly extending rotation limiting protrusion to limit the extent of rotation about the axis of the rigid hollow member relative to the housing member.

In accordance with a preferred embodiment of the present invention, when the rigid hollow member is positioned in the first position, mutual sealing of the rigid fluid flow conduit defining portion within the rigid hollow member seals the forwardly tapered conduit, thereby maintaining a pressurized fluid seal for pressurized fluid therein.

Preferably, upon threaded rotational engagement of the internally-threaded portion by the external conduit, an inner conical surface of the external conduit frictionally and lockingly engages an outer generally conical surface of the rigid hollow member, thereby rotating the rigid hollow member about the axis relative to the housing member, until mutually facing surfaces of the rotation limiting protrusion and the rotation limiting portion come into touching engagement, whereby the at least one rigid hollow member side opening lies in alignment with the at least one fluid flow conduit side opening, thereby opening the forwardly tapered conduit and permitting fluid flow therethrough.

BRIEF DESCRIPTION OF THE DRAWINGS

The present invention will be understood and appreciated more fully from the following detailed description, taken in conjunction with the drawings in which:

FIGS. 3A and 3B are simplified respective side view and sectional illustrations of a rearward housing portion of the fluid flow connector of FIG. 1, FIG. 3B being taken along lines B-B in FIG. 3A;

FIG. 4A is a simplified pictorial view of a resilient double pathway fluid flow conduit sealing and biasing (RDPFFCSB) element forming part of the fluid flow connector of FIG. 1;

FIGS. 4B and 4C are simplified respective sectional illustrations of the resilient double pathway fluid flow conduit sealing and biasing (RDPFFCSB) element, taken along mutually perpendicular section lines B-B and C-C in FIG. 4A;

FIG. 5A is a simplified pictorial view of an actuator element forming part of the fluid flow connector of FIG. 1;

FIGS. 5B and 5C are simplified respective sectional illustrations of the actuator element, taken along mutually perpendicular section lines B-B and C-C in FIG. 5A;

FIGS. 7A and 7B are simplified sectional illustrations of the fluid flow connector of FIG. 1, taken along lines AB-AB in FIG. 1 in a closed operative orientation as seen in respective perspective and side views;

FIG. 7C is a simplified sectional illustration of the fluid flow connector of FIG. 1 in a closed operative orientation, taken along lines C-C, perpendicular to lines AB-AB in FIG. 1;

FIGS. 8A, 8B, 8C and 8D are simplified partial enlargements of respective FIGS. 7B, 7C, 7D and 7E;

FIGS. 9A and 9B are simplified sectional illustrations corresponding to FIGS. 7B and 7D for an alternative embodiment of the fluid flow connector of FIG. 1 which does not include side openings;

FIGS. 10A and 10B are simplified partial enlargements corresponding to FIGS. 8A and 8C for the alternative embodiment of the fluid flow connector of FIG. 1 which does not include side openings;

FIG. 11 is a simplified pictorial illustration of a fluid flow connector constructed and operative in accordance with another preferred embodiment of the invention;

FIGS. 13A and 13B are simplified respective side view and sectional illustrations of a rearward housing portion of the fluid flow connector of FIG. 11, FIG. 13B being taken along lines B-B in FIG. 13A;

FIGS. 14A and 14B are simplified respective side view and sectional illustrations of a resilient fluid flow conduit biasing (RFFCB) element, forming part of the fluid flow connector of FIG. 11, FIG. 14B being taken along lines B-B in FIG. 14A;

FIG. 16A is a simplified side view illustration of a resilient double pathway fluid flow conduit sealing (RSDPFFCS) element forming part of the fluid flow connector of FIG. 11;

FIGS. 16B and 16C are simplified respective sectional illustrations of the resilient double pathway fluid flow conduit sealing (RSDPFFCS) element, taken along mutually perpendicular section lines B-B and C-C in FIG. 16A;

FIG. 17A is a simplified side view of a forward housing portion of the fluid flow connector of FIG. 11;

FIGS. 17B and 17C are simplified respective sectional illustrations of the forward housing portion, taken along mutually perpendicular section lines B-B and C-C in FIG. 17A;

FIGS. 18A and 18B are simplified sectional illustrations of the fluid flow connector of FIG. 11, taken along lines AB-AB in FIG. 11 in a closed operative orientation as seen in respective perspective and side views;

FIG. 18C is a simplified sectional illustration of the fluid flow connector of FIG. 11 in a closed operative orientation, taken along lines C-C, perpendicular to lines AB-AB in FIG. 11;

FIG. 18D is a simplified sectional illustration of the fluid flow connector of FIG. 11 in an open operative orientation in engagement with a female luer portion, taken along lines AB-AB in FIG. 11;

FIG. 18E is a simplified sectional illustration of the fluid flow connector of FIG. 11 in an open operative orientation in engagement with a female luer portion, taken along lines C-C, perpendicular to lines AB-AB in FIG. 11;

FIGS. 19A and 19B are simplified partial enlargements of respective FIGS. 18B and 18C;

FIGS. 19C and 19D are simplified partial enlargements of respective FIGS. 18D and 18E;

FIGS. 20A and 20B are simplified sectional illustrations corresponding to FIGS. 18B and 18D for an alternative embodiment of the fluid flow connector of FIG. 11 which does not include side openings;

FIGS. 20C and 20D are simplified partial enlargements corresponding to FIGS. 19A and 19C for the alternative embodiment of the fluid flow connector of FIG. 11 which does not include side openings;

FIGS. 23A and 23B are simplified respective side view and sectional illustrations of a rearward housing portion of the fluid flow connector of FIG. 21, FIG. 23B being taken along lines B-B in FIG. 23A;

FIG. 24A is a simplified pictorial view of a resilient double pathway fluid flow conduit sealing and biasing (RDPFFCSB) element and an elongate rigid fluid flow conduit element inserted therein, forming part of the fluid flow connector of FIG. 21;

FIGS. 24B and 24C are simplified respective sectional illustrations of the resilient double pathway fluid flow conduit sealing and biasing (RDPFFCSB) element and elongate rigid fluid flow conduit element inserted therein, taken along mutually perpendicular section lines B-B and C-C in FIG. 24A;

FIGS. 27A and 27B are simplified respective pictorial and side view sectional illustrations of the fluid flow connector of FIG. 21, taken along lines AB-AB in FIG. 21 in a closed operative orientation;

FIG. 27C is a simplified sectional illustration of the fluid flow connector of FIG. 21 in a closed operative orientation, taken along lines C-C, perpendicular to lines AB-AB in FIG. 21;

FIG. 27D is a simplified sectional illustration of the fluid flow connector of FIG. 21, taken along lines AB-AB in FIG. 21, in an open operative orientation in engagement with a female luer portion;

FIG. 27E is a simplified sectional illustration of the fluid flow connector of FIG. 21, taken along lines C-C, perpendicular to lines AB-AB in FIG. 21, in an open operative orientation in engagement with a female luer portion;

FIGS. 28A, 28B, 28C and 28D are simplified partial enlargements of respective FIGS. 27B, 27C, 27D and 27E;

FIGS. 29A and 29B are simplified sectional illustrations corresponding to FIGS. 27B and 27D for an alternative embodiment of the fluid flow connector of FIG. 21 which does not include side openings;

FIGS. 30A and 30B are simplified partial enlargements corresponding to FIGS. 28A and 28C for the alternative embodiment of the fluid flow connector of FIG. 21 which does not include side openings;

FIGS. 32A and 32B are simplified respective pictorial and sectional exploded view illustrations of the fluid flow connector of FIG. 31, FIG. 32B being taken along lines B-B in FIG. 32A;

FIGS. 33A and 33B are simplified respective side view and sectional illustrations of a rearward housing portion of the fluid flow connector of FIG. 31, FIG. 33B being taken along lines B-B in FIG. 33A;

FIGS. 34A and 34B are simplified respective side view and sectional illustrations of a resilient fluid flow conduit biasing (RFFCB) element, forming part of the fluid flow connector of FIG. 31, FIG. 34B being taken along lines B-B in FIG. 34A;

FIGS. 38A and 38B are simplified sectional illustrations of the fluid flow connector of FIG. 31, taken along lines AB-AB in FIG. 31 in a closed operative orientation as seen in respective perspective and side views;

FIG. 38C is a simplified sectional illustration of the fluid flow connector of FIG. 31 in a closed operative orientation, taken along lines C-C, perpendicular to lines AB-AB in FIG. 31;

FIG. 38D is a simplified sectional illustration of the fluid flow connector of FIG. 31 in an open operative orientation in engagement with a female luer portion, taken along lines AB-AB in FIG. 31;

FIG. 38E is a simplified sectional illustration of the fluid flow connector of FIG. 31 in an open operative orientation in engagement with a female luer portion, taken along lines C-C, perpendicular to lines AB-AB in FIG. 31;

FIGS. 40A and 40B are simplified partial enlargements of respective FIGS. 38D and 38E;

FIGS. 42A and 42B are simplified respective pictorial and sectional exploded view illustrations of the fluid flow connector of FIG. 41, FIG. 42B being taken along lines B-B in FIG. 42A;

FIGS. 43A and 43B are simplified respective side view and sectional illustrations of a rearward housing portion, forming part of the fluid flow connector of FIG. 41, FIG. 43B being taken along lines B-B in FIG. 43A;

FIG. 44A is a simplified side view of a resilient fluid flow conduit sealing and biasing (RFFCSB) element forming part of the fluid flow connector of FIG. 41;

FIGS. 44B and 44C are simplified respective sectional illustrations of the resilient fluid flow conduit sealing and biasing (RFFCSB) element, taken along mutually perpendicular section lines B-B and C-C in FIG. 44A;

FIGS. 47A and 47B are simplified sectional illustrations of the fluid flow connector of FIG. 41, taken along lines AB-AB in FIG. 41 in a closed operative orientation as seen in respective perspective and side views;

FIG. 47C is a simplified sectional illustration of the fluid flow connector of FIG. 41 in a closed operative orientation, taken along lines C-C, perpendicular to lines AB-AB in FIG. 41;

FIG. 48A is a simplified sectional illustration of the fluid flow connector of FIG. 41 in an open operative orientation in engagement with a female luer portion, taken along lines AB-AB in FIG. 41;

FIG. 48B is a simplified sectional illustration of the fluid flow connector of FIG. 41 in an open operative orientation in engagement with a female luer portion, taken along lines C-C, perpendicular to lines AB-AB in FIG. 41;

FIGS. 49A and 49B are simplified partial enlargements of respective FIGS. 47B and 47C;

FIGS. 50A and 50B are simplified partial enlargements of respective FIGS. 48A and 48B;

FIG. 51 is a simplified pictorial illustration of a fluid flow connector constructed and operative in accordance with yet another preferred embodiment of the invention;

FIGS. 52A and 52B are simplified respective pictorial and sectional exploded view illustrations of the fluid flow connector of FIG. 51, FIG. 52B being taken along lines B-B in FIG. 52A;

FIGS. 57A and 57B are simplified sectional illustrations of the fluid flow connector of FIG. 51, taken along lines AB-AB in FIG. 51 in a closed operative orientation as seen in respective perspective and side views;

FIG. 57C is a simplified sectional illustration of the fluid flow connector of FIG. 51 in a closed operative orientation, taken along lines C-C, perpendicular to lines AB-AB in FIG. 51;

FIG. 58A is a simplified sectional illustration of the fluid flow connector of FIG. 51 in an open operative orientation in engagement with a female luer portion, taken along lines AB-AB in FIG. 51;

FIG. 58B is a simplified sectional illustration of the fluid flow connector of FIG. 51 in an open operative orientation in engagement with a female luer portion, taken along lines C-C, perpendicular to lines AB-AB in FIG. 51;

FIGS. 59A and 59B are simplified partial enlargements of respective FIGS. 57B and 57C;

FIGS. 60A and 60B are simplified partial enlargements of respective FIGS. 58A and 58B;

FIGS. 62A and 62B are simplified respective pictorial and sectional exploded view illustrations of the fluid flow connector of FIG. 61, FIG. 62B being taken along lines B-B in FIG. 62A;

FIGS. 65A and 65B are simplified sectional illustrations of the fluid flow connector of FIG. 61, taken along lines AB-AB in FIG. 61 in a closed operative orientation as seen in respective perspective and side views;

FIG. 65C is a simplified sectional illustration of the fluid flow connector of FIG. 61 in a closed operative orientation, taken along lines C-C, perpendicular to lines AB-AB in FIG. 61;

FIG. 65D is a simplified sectional illustration of the fluid flow connector of FIG. 61 in an open operative orientation in engagement with a female luer portion, taken along lines AB-AB in FIG. 61;

FIG. 65E is a simplified sectional illustration of the fluid flow connector of FIG. 61 in an open operative orientation in engagement with a female luer portion, taken along lines C-C, perpendicular to lines AB-AB in FIG. 61;

FIGS. 66A and 66B are simplified partial enlargements of respective FIGS. 65B and 65C; and FIGS. 67A and 67B are simplified partial enlargements of respective FIGS. 65D and 65E.

DETAILED DESCRIPTION OF PREFERRED EMBODIMENTS

Figure 1:
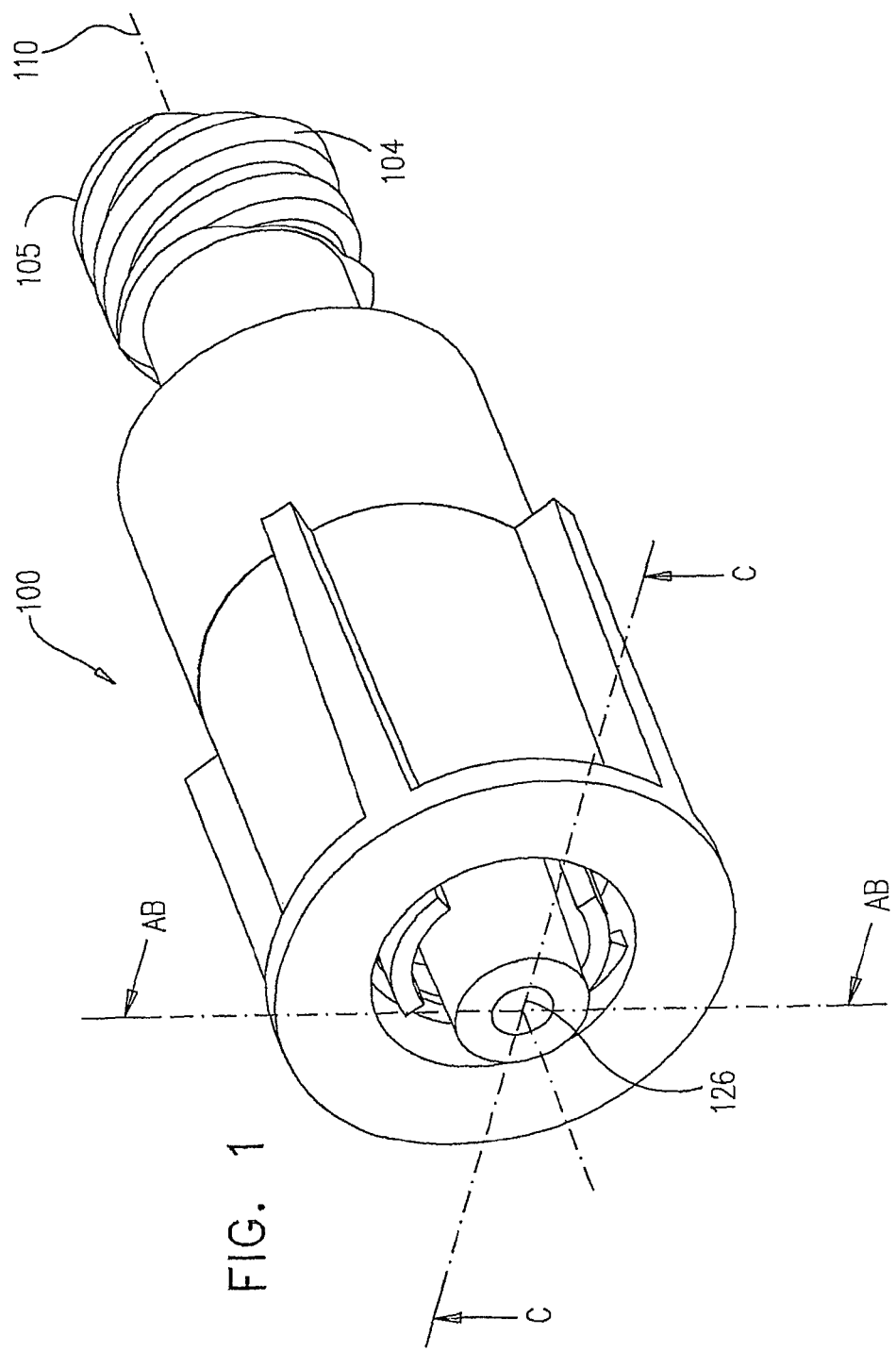
FIG. 1 is a simplified pictorial illustration of a fluid flow connector constructed and operative in accordance with a preferred embodiment of the invention.
Figure 2A:
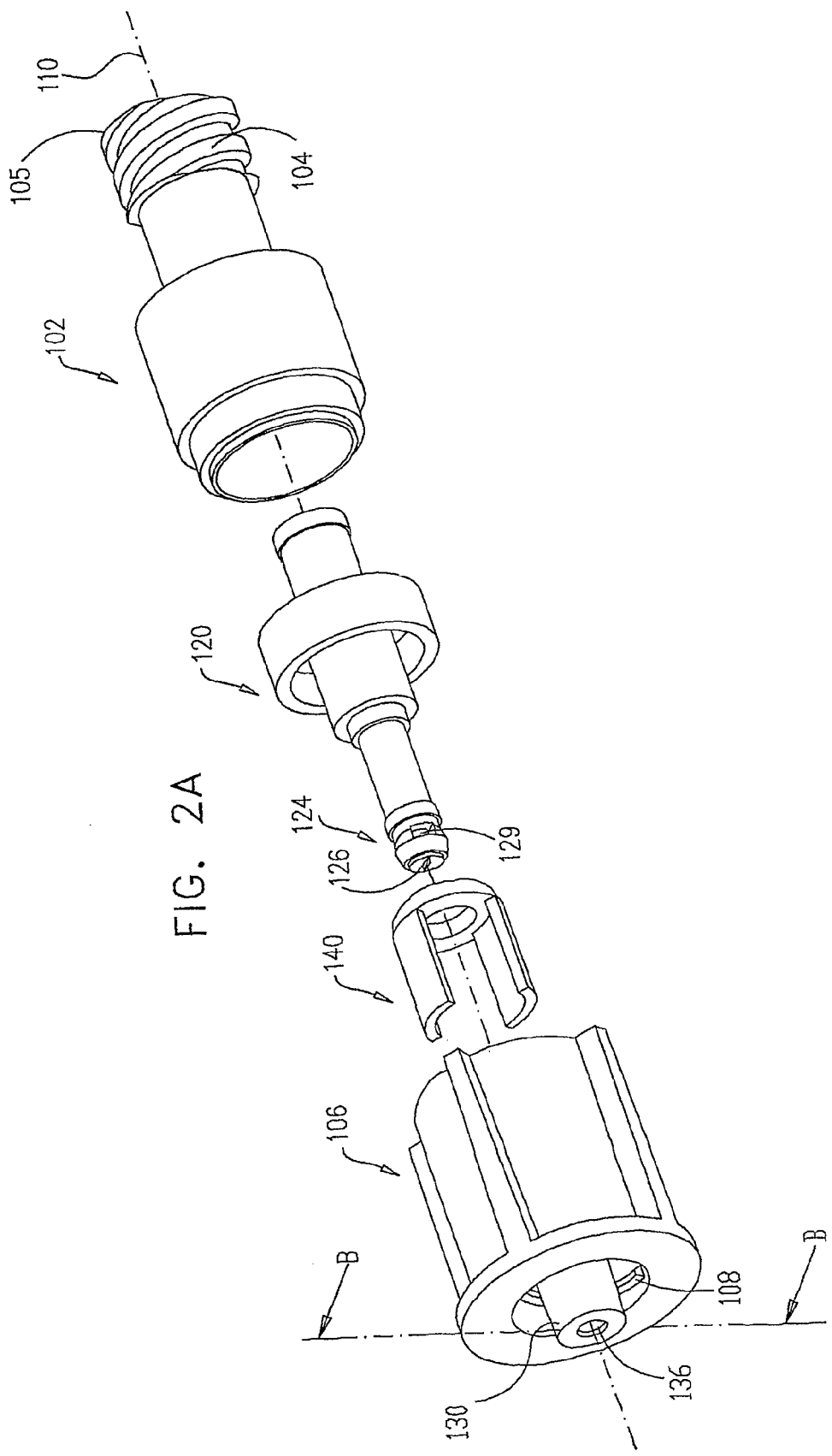
FIGS. 2A and 2B are simplified respective pictorial and sectional exploded view illustrations of the fluid flow connector of FIG. 1, FIG. 2B being taken along lines B-B in FIG. 2A.
Figure 2B:
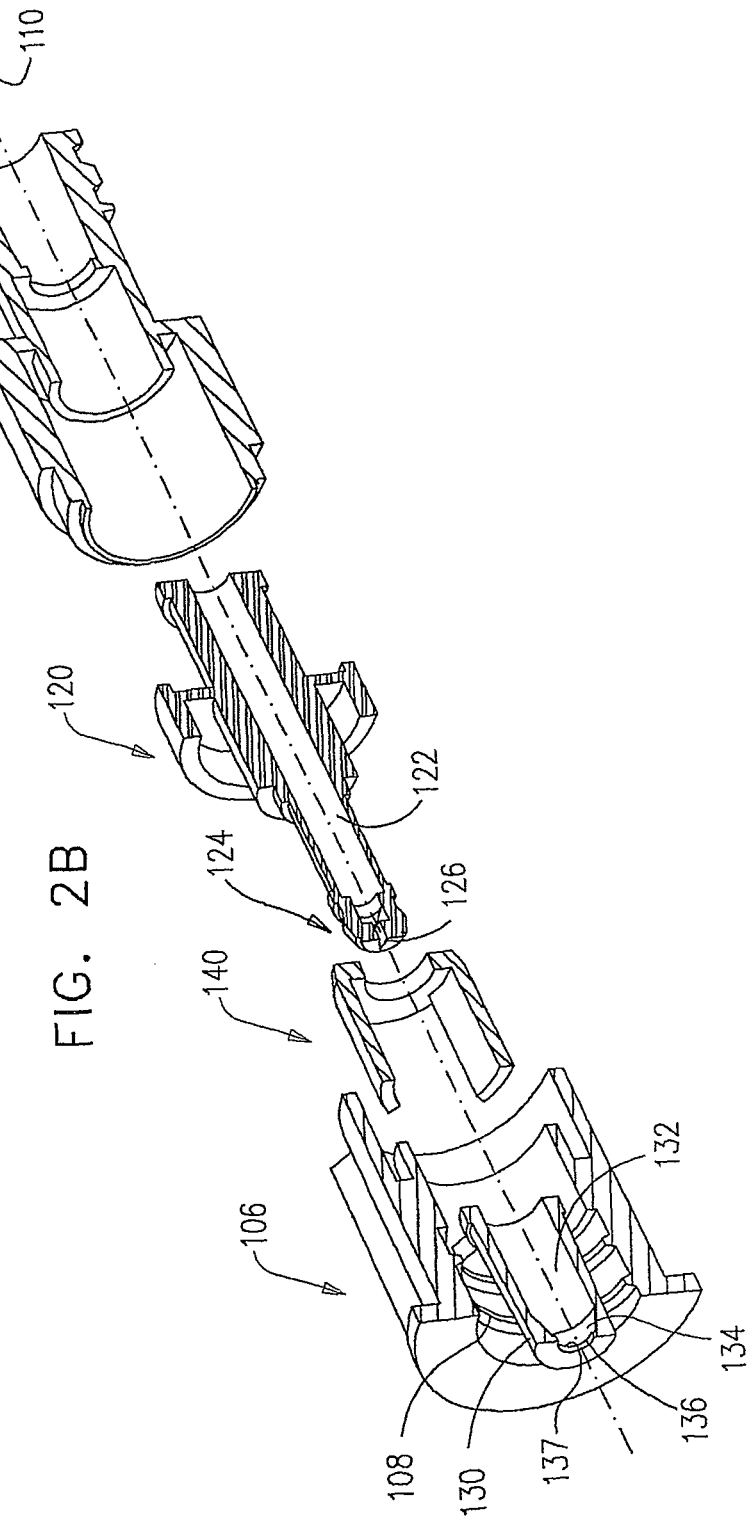

Reference is now made to FIG. 1, which is a simplified pictorial illustration of a fluid flow connector constructed and operative in accordance with a preferred embodiment of the invention and to FIGS. 2A and 2B, which are simplified respective pictorial and sectional exploded view illustrations of the fluid flow connector of FIG. 1, FIG. 2B being taken along lines B-B in FIG. 2A.

As seen in FIGS. 1, 2A & 2B, there is provided a fluid flow connector 100 having a housing assembly including a rearward housing portion 102, having an externally-threaded portion 104 at a rearward end 105 thereof, and a forward housing portion 106 having an internally-threaded portion 108 at a forward end thereof. Rearward and forward housing portions 102 and 106 are preferably arranged along a common longitudinal axis 110 and are preferably heat welded together.

A resilient double pathway fluid flow conduit sealing and biasing (RDPFFCSB) element 120 is disposed within the housing assembly and is arranged along longitudinal axis 110. The RDPFFCSB element 120 is formed with an elongate bore 122 which defines a fluid flow conduit and has a forward section 124 disposed alongside the internally-threaded portion 108 of the forward housing portion 106. The forward section 124 of the RDPFFCSB element 120 is preferably formed with a selectably closable slit 126 extending along longitudinal axis 110 and communicating with elongate bore 122.

In accordance with a preferred embodiment of the present invention, rearward of selectably closable slit 126 the RDPFFCSB element 120 includes at least one, and preferably two, coaxial side openings 129, which extend generally perpendicularly to longitudinal axis 110 and communicate with elongate bore 122.

Preferably, the forward housing portion 106 includes a forward conduit 130, preferably integrally formed therewith. Forward conduit 130 is formed with an interior bore 132 having a forwardly tapered portion 134 and a forwardly facing aperture 136. A rearwardly facing shoulder 137 is defined by the periphery of aperture 136.

Preferably, part of the RDPFFCSB element 120 is pre-tensioned and thereby urges the forward section 124 forwardly along longitudinal axis 110 to a closed position. In the closed position, the forward section 124 sealingly engages the forwardly tapered portion 134 of the interior bore 132. This engagement squeezes the forward section 124 transversely to longitudinal axis 110, thereby closing the slit 126 but leaving the side openings 129 open for fluid communication between elongate bore 122 at the interior of RDPFFCSB element 120 and the exterior thereof within the interior of the forward conduit 130.

Engagement of the forward section 124 of the RDPFFCSB element 120 with the forward conduit 130 under the urging of part of RDPFFCSB element 120 is operative to seal forwardly facing aperture 136.

An actuator element 140 is provided for engagement with RDPFFCSB element 120. The actuator element 140 is arranged to be displaced rearwardly along longitudinal axis 110 by engagement therewith of a rearwardly facing end of a female luer (not shown), which may threadably engage internally-threaded portion 108 of forward housing portion 106.

Rearward displacement of actuator element 140 produces corresponding rearward displacement of part of RDPFFCSB element 120 along longitudinal axis 110, such that forward section 124 moves rearwardly out of engagement with the forwardly tapered portion 134 of the interior bore 132, thereby unsealing forwardly facing aperture 136 and allowing slit 126 to open, while leaving side openings 129 open for fluid communication between interior bore 122 of RDPFFCSB element 120, the exterior of RDPFFCSB element 120, the interior bore 132 of the forward conduit 130, and forwardly facing aperture 136.

It is a particular feature of this embodiment of the present invention that when RDPFFCSB element 120 is in this open position, fluid communication between elongate bore 122 and forwardly facing aperture 136 is provided both via selectably closable slit 126 and via side openings 129, whereby the fluid flow provided via side openings 129 preferably is generally double the fluid flow provided via selectably closable slit 126.

Reference is now made to FIGS. 3A and 3B, which are a simplified respective side view and sectional illustration of a preferred structure of rearward housing portion 102 of the fluid flow connector 100 of FIG. 1, FIG. 3B being taken along lines B-B in FIG. 3A. As seen in FIGS. 3A & 3B, rearward housing portion 102 is an integrally formed element which is symmetric about a longitudinal axis, such as axis 110 (FIGS. 1-2B).

As noted hereinabove with reference to FIGS. 1-2B, the rearward housing portion 102 includes an externally-threaded portion 104 at a rearward end 105 thereof. Rearward housing portion 102 also includes a rearward conduit 144 extending forwardly from rearward end 105 along axis 110. An internally directed flange 146 is disposed at a location intermediate along rearward conduit 144 and serves as a stop, limiting forward penetration of a male luer (not shown) into conduit 144 from rearward end 105.

Rearward housing portion 102 also includes a forward conduit 148 which extends rearwardly from a forward end 149 of rearward housing portion 102 along axis 110. As seen clearly in FIG. 3B, rearward conduit 144 has an inner facing surface 150 and rearward conduit 144 extends partially into forward conduit 148.

The exterior of rearward housing portion 102 is formed with a plurality of stepped circumferential radially outwardly facing surfaces adjacent forward end 149, including a first circumferential ring 151, adjacent forward end 149, a second circumferential ring 152, having an outer diameter greater than that of first circumferential ring 151, rearwardly of ring 151, and a cylindrical wall 153 extending rearwardly of ring 152. A plurality of stepped circumferential forwardly facing surfaces are also defined adjacent forward end 149, including a ring 154 intermediate surfaces 151 and 152, and a ring 155, intermediate surfaces 152 and 153.

Reference is now made to FIGS. 4A, 4B and 4C, which illustrate resilient double pathway fluid flow conduit sealing and biasing (RDPFFCSB) element 120 forming part of the fluid flow connector of FIGS. 1-2B in an unstressed orientation. As seen in FIGS. 4A-4C, RDPFFCSB element 120 is an integrally formed element, preferably formed of silicone rubber, which is symmetric about a longitudinal axis, such as axis 110 (FIGS. 1-2B), in all respects other than with respect to selectably closable slit 126 and side openings 129.

The RDPFFCSB element 120 preferably includes a generally elongate portion 160 having an elongate bore 122 formed at the center thereof along axis 110, extending from a rearwardly facing end 164 to forward section 124 (FIGS. 2A & 2B) thereof. Extending radially outward from generally elongate portion 160 is a tensionable connecting portion 166, typically in the form of a disc when in an unstressed condition. Tensionable connecting portion 166 preferably terminates in a generally circularly cylindrical mounting portion 168.

Generally elongate portion 160 preferably includes a rear portion 170, having a circular cross section of a first diameter and a radially outer surface 171, a rearward intermediate portion 172, forward of rear portion 170 and having a circular cross section of a second diameter, less than the first diameter, which terminates at a junction with tensionable connecting portion 166. Forward of the junction with tensionable connecting portion 166 is a forward intermediate portion 174, preferably having a circular cross section of a third diameter, greater than the first and second diameters, which terminates at a circumferential shoulder 175. Forward of circumferential shoulder 175 is a ring portion 176, preferably having a circular cross section of a fourth diameter, less than the second diameter, which terminates at a circumferential shoulder 177.

Forward of shoulder 177 is a forward portion 178 which extends to forward section 124 (FIGS. 2A & 2B). Extending radially outward of forward portion 178 slightly rearwardly of forward section 124 is a sealing ring 179.

As noted above, forward section 124 (FIGS. 2A & 2B) includes a pair of side openings 129 (FIGS. 2A & 2B) which preferably extend along an axis 180, intersecting and orthogonal to axis 110, from elongate bore 122 to the periphery of forward section 124.

Forward of side openings 129 is a tapered portion 181, whose rearwardly facing wall 182 defines the forward extent of elongate bore 122. Tapered portion 181 terminates in a circumferential shoulder 183, forwardly of which is provided a tip portion 184, preferably having an oval cross section which is compressible into a circular cross section of a fifth diameter, less than the fourth diameter.

Tip portion 184 and tapered portion 181 are preferably formed with slit 126 (FIGS. 1-2B) extending along axis 110 and communicating between elongate bore 122 and the outside, forward of tip portion 184. As seen in FIG. 4B, slit 126 is open when in an unstressed orientation.

It is appreciated that elongate bore 122 defines a generally incompressible fluid flow pathway extending between rearwardly facing end 164 and rearwardly facing wall 182.

Reference is now made to FIGS. 5A-5C, which illustrate actuator element 140, forming part of the fluid flow connector 100 of FIG. 1. Actuator element 140 preferably includes a rearward apertured disc 185, having a circumferential rearmost surface 186, integrally formed with a pair of cylindrical sections 187 which extend forwardly of disc 185 and form part of an imaginary cylinder aligned about axis 110. Cylindrical sections 187 define forwardly facing engagement surfaces 188.

Figure 6A:
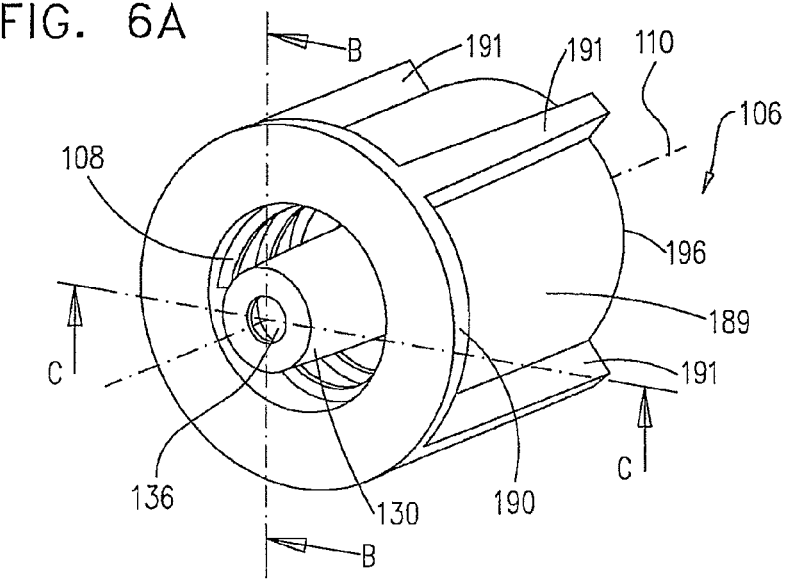
FIG. 6A is a simplified pictorial view of a forward housing portion of the fluid flow connector of FIG. 1.
Figure 6B:
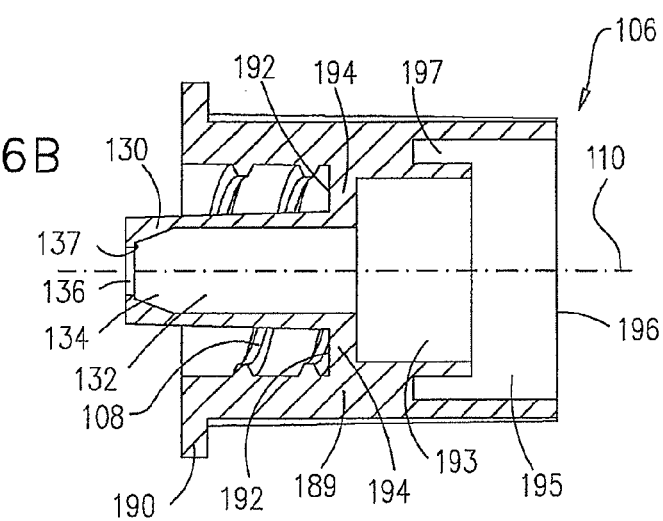
FIGS. 6B and 6C are simplified respective sectional illustrations of the forward housing portion, taken along mutually perpendicular section lines B-B and C-C in FIG. 6A.
Figure 6C:
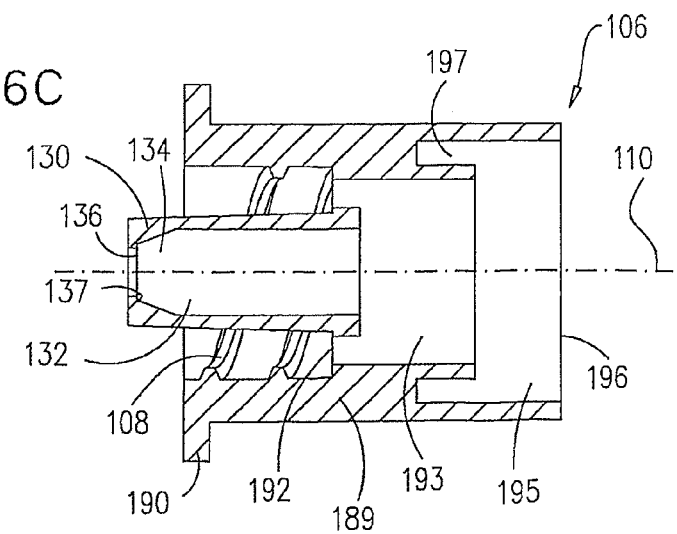

Reference is now made to FIGS. 6A-6C, which illustrate forward housing portion 106 (FIGS. 1-2B) of the fluid flow connector 100 of FIG. 1. Forward housing portion 106 preferably includes a generally cylindrical body 189 having a forwardmost flange 190 and rearwardly tapered mutually spaced generally axial ribs 191 extending rearwardly from flange 190.

As seen in FIGS. 6A-6C, forward housing portion 106 is an integrally formed element which is generally symmetric about a longitudinal axis, such as axis 110 (FIGS. 1-2B), in most respects. As noted hereinabove with reference to FIGS. 1-2B, the forward housing portion 106 includes an internally-threaded portion 108 at a forward end thereof and a forward conduit 130 extending rearwardly therethrough along axis 110. Forward conduit 130 is preferably formed with an interior bore 132 having a forwardly tapered portion 134 and a forwardly facing aperture 136.

Internally-threaded portion 108 terminates rearwardly at shoulders 192 and communicates with a rearwardly extending generally circularly cylindrical internal bore 193. Forward conduit 130 is joined to the inwardly facing circularly cylindrical wall of bore 193 by a plurality of radially extending ribs 194, forwardly facing surfaces of which define shoulders 192.

Forward housing portion 106 also includes a rearward conduit 195 which extends forwardly from a rearward face 196 of forward housing portion 106 along axis 110. As seen clearly in FIGS. 6B & 6C, rearward conduit 195 has an inner diameter greater than that of rearwardly extending generally circularly cylindrical internal bore 193, and rearwardly extending generally circularly cylindrical internal bore 193 extends partially into rearward conduit 195, defining a circumferential recess 197.

Reference is now made to FIGS. 7A, 7B, 7C, 8A and 8B, which are simplified sectional illustrations of the fluid flow connector 100 of FIG. 1 in a closed operative orientation, and to FIGS. 7D, 7E, 8C and 8D, which are simplified sectional illustrations of fluid flow connector 100 of FIG. 1 in an open operative orientation in engagement with a female luer portion 199.

Referring initially specifically to FIGS. 7A, 7B, 7C, 8A and 8B, it is seen that RDPFFCSB element 120 is maintained in a pre-tensioned state wherein generally circularly cylindrical mounting portion 168 is locked in place between rearward housing portion 102 and forward housing portion 106, which are welded together, as by ultrasonic welding. Specifically it is seen that rearward face 196 of forward housing portion 106 lies against ring 155 of rearward housing portion 102 and that cylindrical mounting portion 168 is locked in a circumferential volume defined by circumferential recess 197 of forward housing portion 106, end 149 and surfaces 151 and 154 of rearward housing portion 102.

Axial pretensioning of RDPFFCSB element 120 along axis 110 is achieved by axial pressure engagement of the shoulder 183 of the RDPFFCSB element 120 with shoulder 137 of the forward conduit 130 and by axial pressure engagement of tapered portion 181 of RDPFFCSB element 120 with forwardly tapered portion 134 of the interior bore 132 of the forward conduit 130. This arrangement stretches and thus tensions tensionable connecting portion 166, as seen from a comparison of FIGS. 7A-7C with FIGS. 4A-4C.

Axial pressure engagement of tapered portion 181 of RDPFFCSB element 120 with forwardly tapered portion 134 of the interior bore 132 of the forward conduit 130 is operative to squeeze the forward section 124 of the RDPFFCSB element 120 transversely to longitudinal axis 110, thereby closing the slit 126 and changing the cross section of the tapered portion 181 from a generally oval configuration as seen in FIG. 4A to a generally circular configuration as seen in FIG. 7A.

Slidable sealing engagement is provided between radially outer surface 171 of rear portion 170 of RDPFFCSB element 120 and inner facing surface 150 of rearward conduit 144. This sealing engagement preferably prevents fluid which enters the fluid flow connector via rearward conduit 144 from entering the volume within the forward conduit 148 lying rearward of connecting portion 166 and cylindrical mounting portion 168. Accordingly this volume is prevented from acting as a "dead space" which could undesirably retain such fluid.

Slidable sealing engagement is also provided between sealing ring 179 of RDPFFCSB element 120 and interior bore 132 of forward conduit 130. This sealing engagement preferably prevents fluid which passes through side openings 129 from entering the volume within interior bore 132 of forward conduit 130 lying rearward of sealing ring 179 and within internal bore 193. Accordingly this volume is prevented from acting as a "dead space" which could undesirably retain such fluid.

It is appreciated that the fluid flow connector 100 in the state shown in FIGS. 7A-7C, 8A and 8B is capable of maintaining a pressurized fluid seal for pressurized fluid in rearward conduit 144 and elongate bore 122. It is further appreciated that an increase in fluid pressure preferably enhances the effectiveness of the pressurized fluid seal.

Reference is now made specifically to FIGS. 7D, 7E, 8C and 8D, which are simplified sectional illustrations of the fluid flow connector 100 of FIG. 1 in an open operative orientation in engagement with a female luer portion 199.

It is seen that threaded engagement of the female luer portion 199 with the internally-threaded portion 108 causes actuator element 140 to be rearwardly displaced. It is noted that circumferential rearmost surface 186 of actuator element 140 engages shoulder 175 of RDPFFCSB element 120, producing corresponding rearward displacement thereof. Rearward displacement of shoulder 175 produces corresponding rearward displacement of a generally elongate portion 160 of RDPFFCSB element 120 along axis 110, resulting in increased tensioning of tensionable connecting portion 166 of RDPFFCSB element 120.

Rearward displacement of generally elongate portion 160 of RDPFFCSB element 120 along axis 110 also produces disengagement of shoulder 183 of the RDPFFCSB element 120 from shoulder 137 of the forward conduit 130 and disengagement of tapered portion 181 of RDPFFCSB element 120 from forwardly tapered portion 134 of the interior bore 132 of the forward conduit 130.

The resulting elimination of axial pressure engagement of tapered portion 181 of RDPFFCSB element 120 with forwardly tapered portion 134 of the interior bore 132 of the forward conduit 130 causes the forward section 124 of the RDPFFCSB element 120 to no longer be squeezed transversely to longitudinal axis 110, thereby allowing the slit 126 to open and allowing the cross section of the tapered portion 181 to return to a generally oval configuration as seen in FIG. 4A.

Slidable sealing engagement continues to be provided between radially outer surface 171 of rear portion 170 of RDPFFCSB element 120 and inner facing surface 150 of rearward conduit 144. This sealing engagement preferably prevents fluid which enters the fluid flow connector via rearward conduit 144 from entering the volume within the forward conduit 148 lying rearward of connecting portion 166 and cylindrical mounting portion 168. Accordingly this volume is prevented from acting as a "dead space" which could undesirably retain such fluid.

Slidable sealing engagement also continues to be provided between sealing ring 179 of RDPFFCSB element 120 and interior bore 132 of forward conduit 130. This sealing engagement preferably prevents fluid which passes through the slit 126 and side openings 129 from entering the volume within interior bore 132 of forward conduit 130 lying rearward of sealing ring 179 and within internal bore 193. Accordingly this volume is prevented from acting as a "dead space" which could undesirably retain such fluid.

It is appreciated that the fluid flow connector 100, in the state shown in FIGS. 7D, 7E, 8C and 8D, provides a fluid flow connection for fluid supplied via rearward conduit 144 and elongate bore 122, as by a male luer or a syringe, to female luer portion 199 via slit 126, side openings 129 and aperture 136.

Figure 7D:
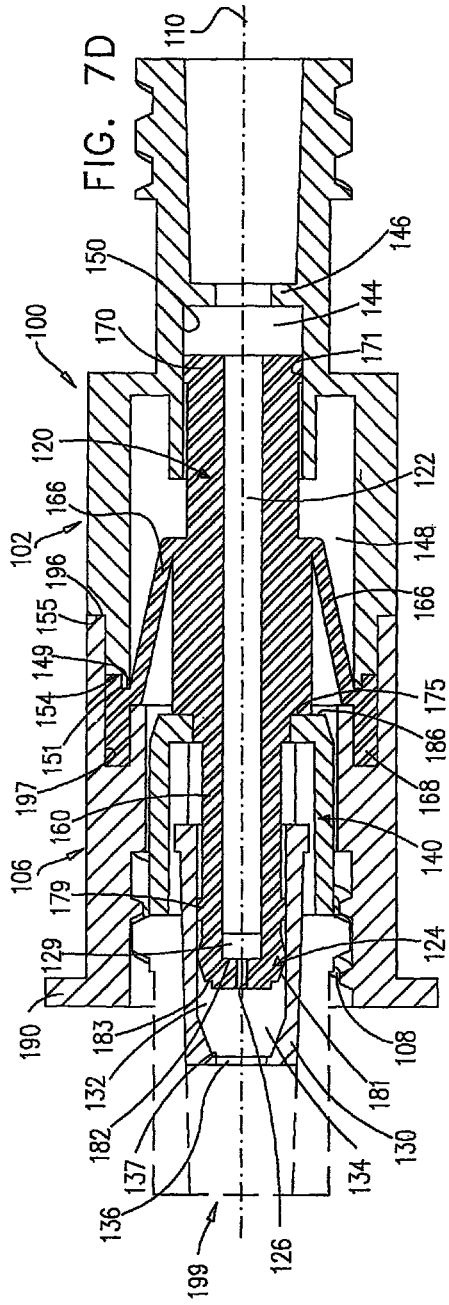
FIG. 7D is a simplified sectional illustration of the fluid flow connector of FIG. 1 taken along lines AB-AB in FIG. 1, in an open operative orientation in engagement with a female luer portion.
Figure 7E:
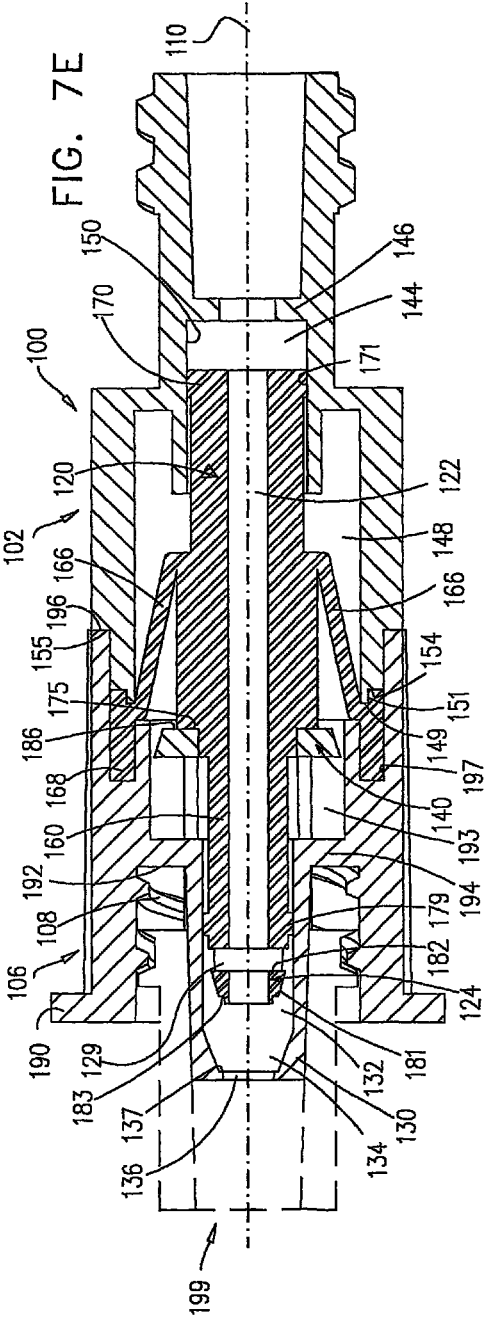
FIG. 7E is a simplified sectional illustration of the fluid flow connector of FIG. 1, taken along lines C-C, perpendicular to lines AB-AB in FIG. 1, in an open operative orientation in engagement with a female luer portion.
Figure 8A:
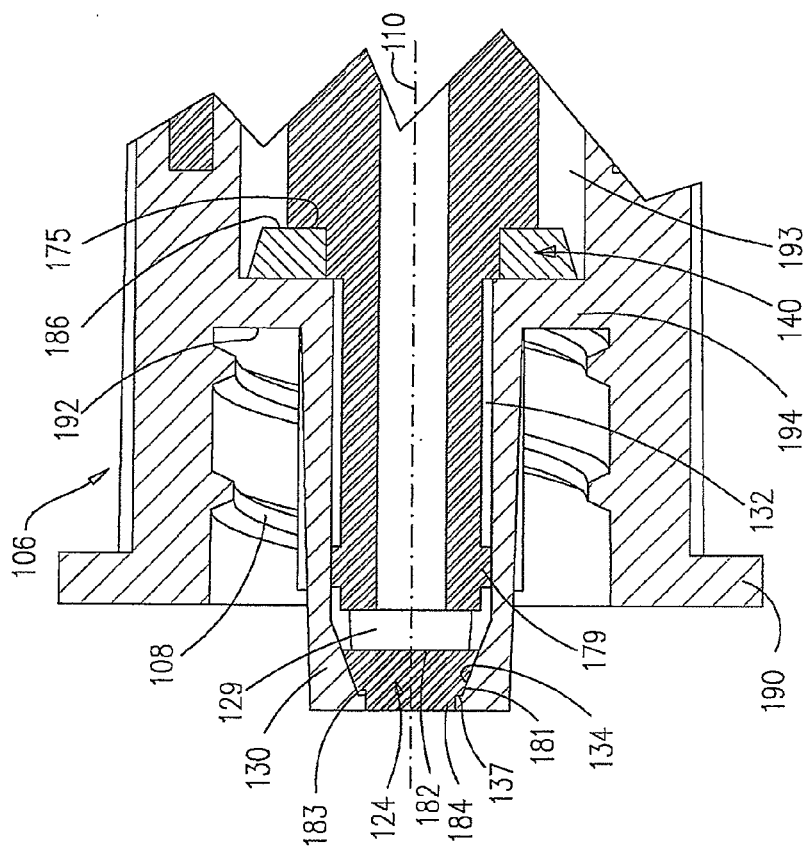
Figure 8B:
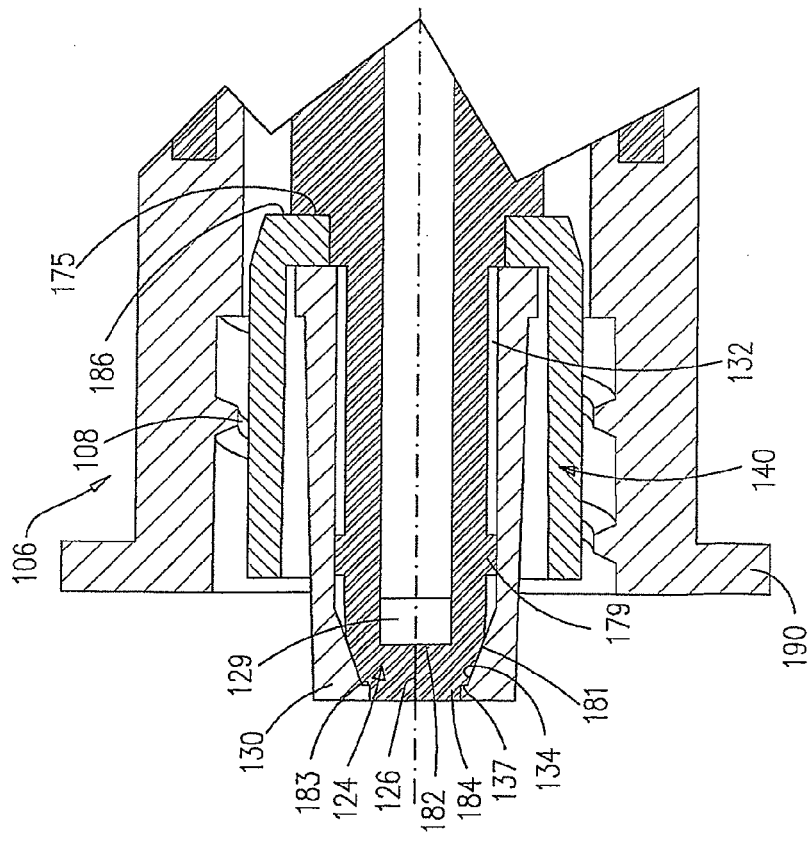

Reference is now made to FIGS. 9A and 9B, which are simplified sectional illustrations corresponding to FIGS. 7B and 7D for an alternative embodiment of the fluid flow connector 100 of FIG. 1 which does not include side openings, and to FIGS. 10A and 10B, which are simplified partial enlargements, corresponding to FIGS. 8A and 8C, for the alternative embodiment of the fluid flow connector of FIG. 1 which does not include side openings.

The alternative embodiment shown in FIGS. 1, 3A, 3B, 5A-5C, 6A-6C, 9A, 9B, 10A and 10B is generally identical in structure and operation to the embodiment of FIGS. 1-8D, with the sole exception that side openings 129 in the embodiment of FIGS. 1-8D are obviated in the embodiment of FIGS. 1, 3A, 3B, 5A-5C, 6A-6C, 9A, 9B, 10A and 10B.

Figure 12A:
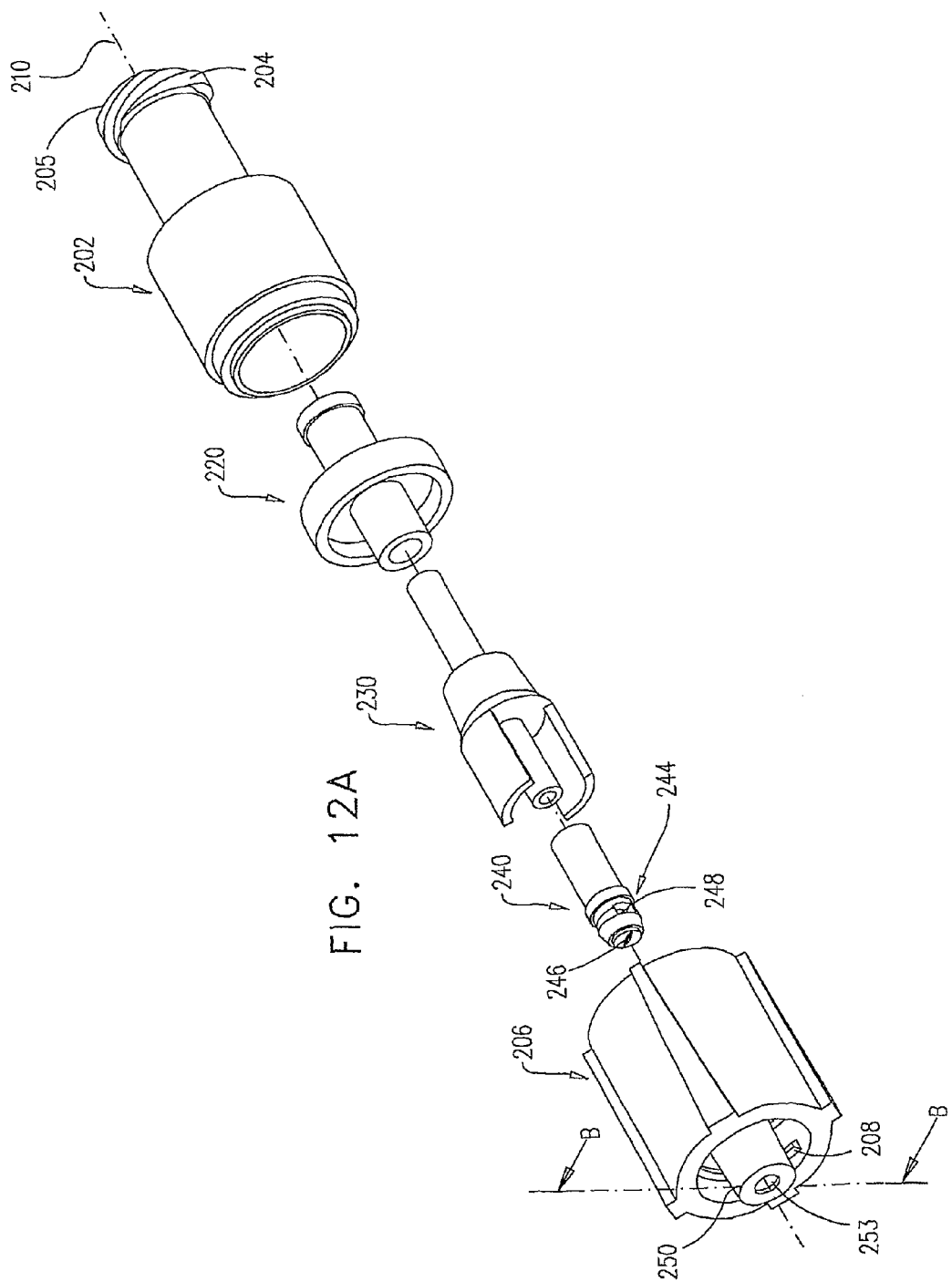
FIGS. 12A and 12B are simplified respective pictorial and sectional exploded view illustrations of the fluid flow connector of FIG. 11, FIG. 12B being taken along lines B-B in FIG. 12A.
Figure 12B:
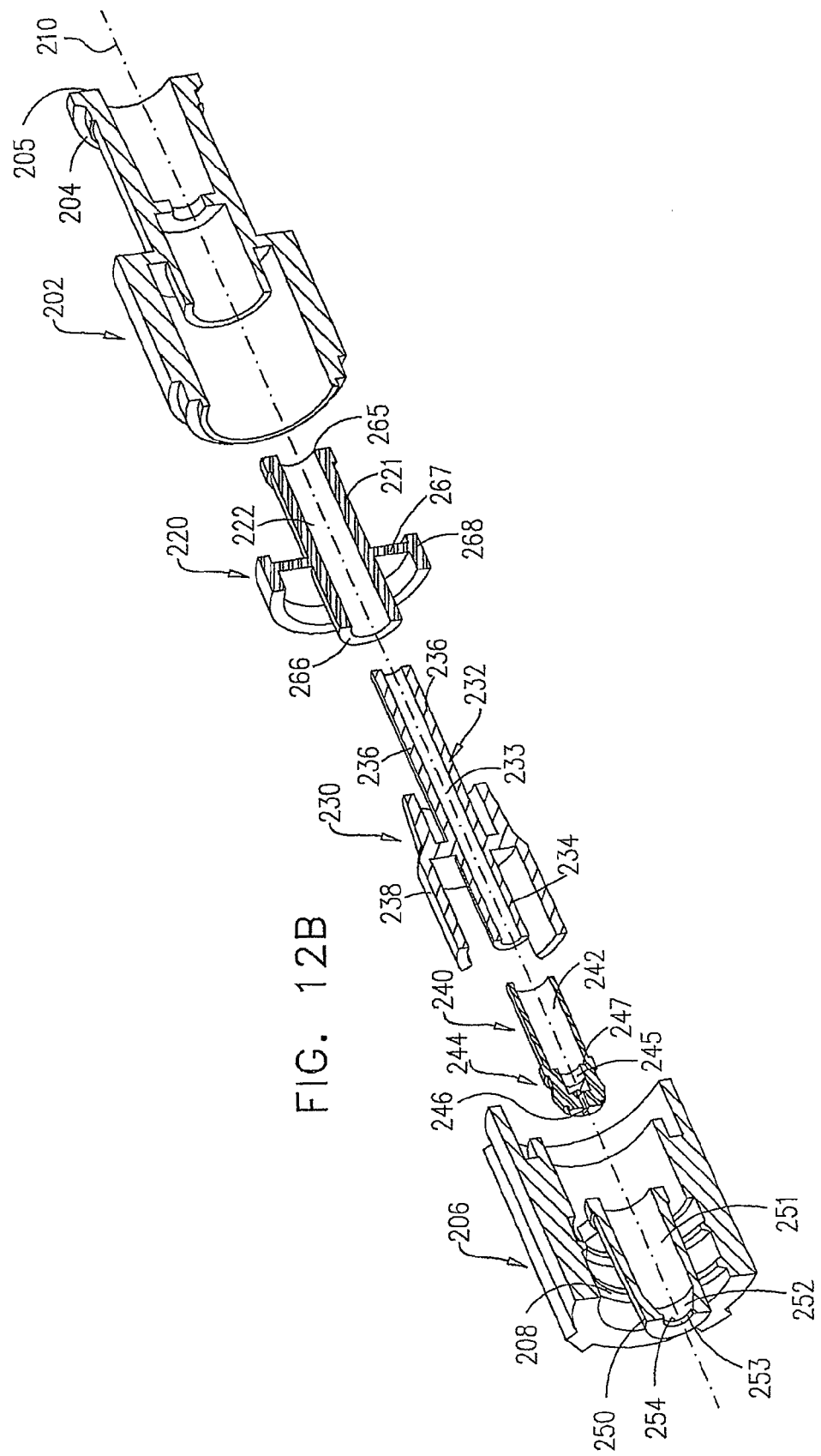

Reference is now made to FIG. 11, which is a simplified pictorial illustration of a fluid flow connector constructed and operative in accordance with another preferred embodiment of the invention and to FIGS. 12A and 12B, which are simplified respective pictorial and sectional exploded view illustrations of the fluid flow connector of FIG. 11, FIG. 12B being taken along lines B-B in FIG. 12A.

As seen in FIGS. 11, 12A & 12B, there is provided a fluid flow connector 200 having a housing assembly including a rearward housing portion 202, having an externally-threaded portion 204 at a rearward end 205 thereof, and a forward housing portion 206 having an internally-threaded portion 208 at a forward end thereof. Rearward and forward housing portions 202 and 206 are preferably arranged along a common longitudinal axis 210 and are preferably heat welded together.

A resilient fluid flow conduit biasing (RFFCB) element 220 is disposed within the housing assembly and is arranged along longitudinal axis 210. The RFFCB element 220 includes a generally cylindrical portion 221 formed with an elongate bore 222.

An elongate rigid fluid flow conduit and actuator element 230 includes a cylindrical portion 232, formed with a fluid conduit defining bore 233 and having a forward part 234 and a rearward part 236 as well as a circumferential actuator portion 238. Rearward part 236 of element 230 is partially sealingly disposed within elongate bore 222.

A resilient double pathway fluid flow conduit sealing (RSDPFFCS) element 240 is disposed within the housing assembly, is arranged along longitudinal axis 210 and is preferably sealingly disposed over the forward part 234 of cylindrical portion 232. The RDPFFCS element 240 is formed with an elongate bore 242, and preferably has a forward section 244 extending forwardly of elongate bore 242 disposed alongside the internally-threaded portion 208 of the forward housing portion 206.

The forward section 244 of the RDPFFCS element 240 is preferably formed with an interior bore 245 and a selectably closable slit 246 extending along longitudinal axis 210. As seen in FIG. 12B, elongate bore 242 has a circular cross section of a diameter greater than that of interior bore 245, thereby defining a rearwardly facing shoulder 247 therebetween.

Forward part 234 of rigid fluid flow conduit and actuator element 230 is tightly and sealingly disposed within elongate bore 242, rearwardly of shoulder 247.

In accordance with a preferred embodiment of the present invention, rearward of selectably closable slit 246 the RDPFFCS element 240 includes at least one and preferably two coaxial side openings 248 which extend generally perpendicularly to longitudinal axis 210 and communicate with interior bore 245 and with fluid conduit defining bore 233 of element 230.

Preferably, the forward housing portion 206 includes a forward conduit 250, preferably integrally formed therewith. Forward conduit 250 is formed with an interior bore 251 having a forwardly tapered portion 252 and a forwardly facing aperture 253. A rearwardly facing shoulder 254 is defined by the periphery of aperture 253.

Preferably, part of the RFFCB element 220 is pre-tensioned and thereby urges element 230 and thus RDPFFCS element 240, which is tightly mounted thereon, forwardly along longitudinal axis 210 to a closed position. In the closed position, the forward section 244 sealingly engages the forwardly tapered portion 252 of the interior bore 251. This engagement squeezes the forward section 244 transversely to longitudinal axis 210, thereby closing the slit 246 but leaving the side openings 248 open for fluid communication between fluid conduit defining bore 233 of element 230 and elongate bore 242 and the exterior thereof within the interior bore 251 of forward conduit 250.

Engagement of the forward section 244 of the RDPFFCS element 240 with the forward conduit 250 under the urging of RFFCB element 220 is operative to seal forwardly facing aperture 253.

Actuator portion 238 is arranged to be displaced rearwardly along longitudinal axis 210 by engagement therewith of a rearwardly facing end of a female luer (not shown), which may threadably engage internally-threaded portion 208 of forward housing portion 206.

Rearward displacement of actuator portion 238 produces corresponding rearward displacement of RFFCB element 220 along longitudinal axis 210 and also produces rearward displacement of RDPFFCS element 240 such that forward section 244 moves rearwardly out of engagement with the forwardly tapered portion 252 of the interior bore 251, thereby unsealing forwardly facing aperture 253 and allowing slit 246 to open and leaving side openings 248 open for fluid communication between the fluid conduit defining bore 233 of element 230, interior bore 245 and the exterior of RDPFFCS element 240, interior bore 251 of the forward conduit 250 and forwardly facing aperture 253.

It is a particular feature of this embodiment of the present invention that when RDPFFCS element 240 is in this open position, fluid communication between fluid conduit defining bore 233 of element 230 and forwardly facing aperture 253 is provided both via selectably closable slit 246 and via side openings 248, whereby the fluid flow provided via side openings 248 preferably is generally double the fluid flow provided via selectably closable slit 246.

Reference is now made to FIGS. 13A and 13B which are simplified respective side views and sectional illustrations of a preferred structure of rearward housing portion 202 of the fluid flow connector 200 of FIG. 11, FIG. 13B being taken along lines B-B in FIG. 13A. As seen in FIGS. 13A & 13B, rearward housing portion 202 is an integrally formed element which is symmetric about a longitudinal axis, such as axis 210 (FIGS. 11-12B).

As noted hereinabove with reference to FIGS. 11-12B, the rearward housing portion 202 includes an externally-threaded portion 204 at a rearward end 205 thereof. Rearward housing portion 202 also includes a rearward conduit 255 extending forwardly from rearward end 205 along axis 210. An internally directed flange 256 is disposed at a location intermediate along rearward conduit 255 and serves as a stop, limiting forward penetration of a male luer (not shown) into conduit 255 from rearward end 205.

Rearward housing portion 202 also includes a forward conduit 257 which extends rearwardly from a forward end 258 of rearward housing portion 202 along axis 210. As seen clearly in FIG. 13B, rearward conduit 255 has an inner facing surface 259 and rearward conduit 255 extends partially into forward conduit 257. The exterior of rearward housing portion 202 is formed with a plurality of stepped circumferential radially outwardly facing surfaces adjacent forward end 258, including a first circumferential ring 260, adjacent forward end 258, a second circumferential ring 261, having an outer diameter greater than that of first circumferential ring 260, rearwardly of ring 260, and a cylindrical wall 262 extending rearwardly of ring 261. A plurality of stepped circumferential forwardly facing surfaces are also defined adjacent forward end 258, including a ring 263 intermediate surfaces 260 and 261, and a ring 264, intermediate surfaces 261 and 262.

Reference is now made to FIGS. 14A and 14B, which illustrate resilient fluid flow conduit biasing (RFFCB) element 220, forming part of the fluid flow connector of FIGS. 11-12B, in an unstressed orientation. As seen in FIGS. 14A & 14B, RFFCB element 220 is an integrally formed element, preferably formed of silicone rubber, which is symmetric about a longitudinal axis, such as axis 210 (FIGS. 11-12B).

As noted above, the RFFCB element 220 preferably includes a generally cylindrical portion 221 (FIGS. 12A & 12B) having an elongate bore 222 formed at the center thereof along axis 210, extending from a rearwardly facing end 265 to a forwardly facing end 266, cylindrical portion 232 of element 230 (not shown) being partially and sealingly disposed therewithin. Extending radially outward from cylindrical portion 221 is a tensionable connecting portion 267, typically in the form of a disc when in an unstressed condition. Tensionable connecting portion 267 preferably terminates in a generally circularly cylindrical mounting portion 268.

Cylindrical portion 221 preferably includes a rear portion 270, having a circular cross section of a first diameter and a radially outer surface 271, and a rearward portion 272, forward of rear portion 270 and having a circular cross section of a second diameter, less than the first diameter, which terminates at a junction with tensionable connecting portion 267. Forward of the junction with tensionable connecting portion 267 is a forward portion 274, which terminates at forward end 266.

Figure 15A:
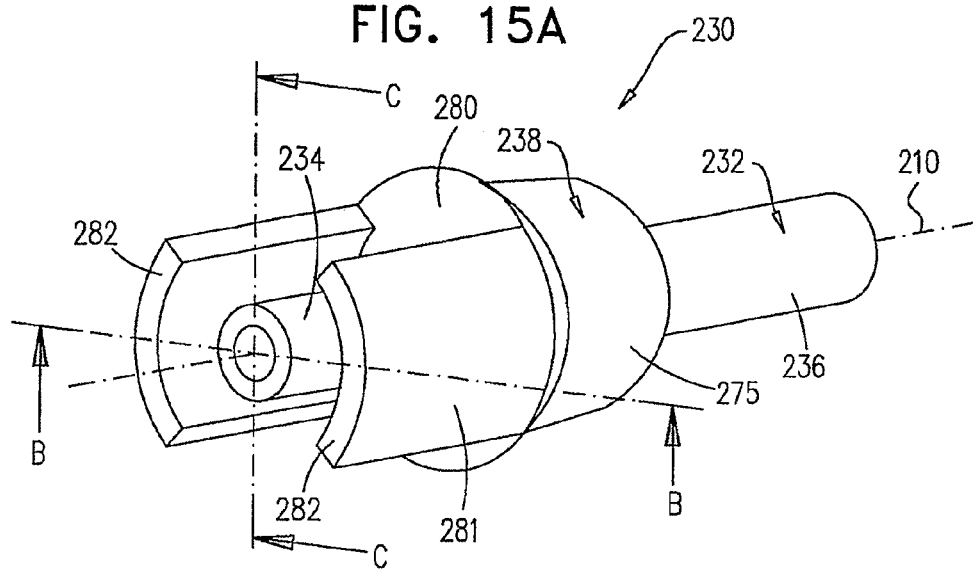
FIG. 15A is a simplified side view of a rigid fluid flow conduit and actuator element forming part of the fluid flow connector of FIG. 11.
Figure 15B:
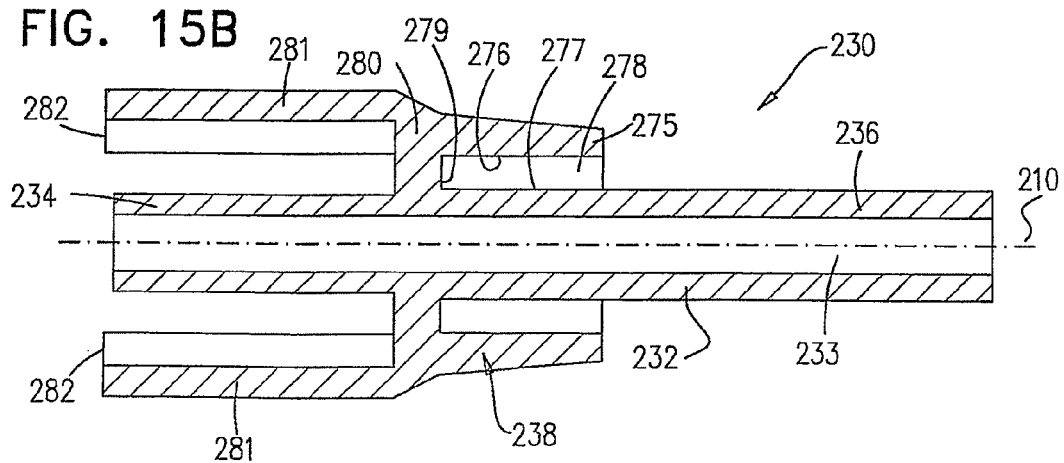
FIGS. 15B and 15C are simplified respective sectional illustrations of the rigid fluid flow conduit and actuator element, taken along mutually perpendicular section lines B-B and C-C in FIG. 15A.
Figure 15C:
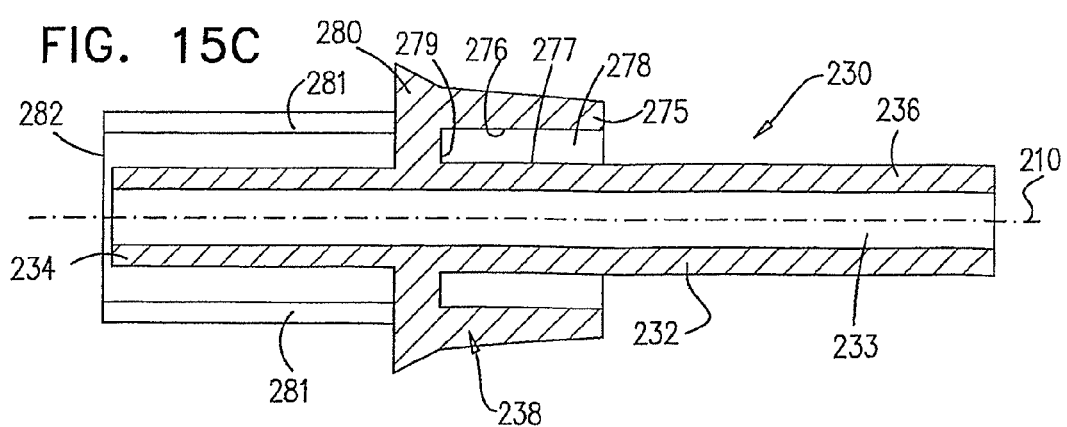

Reference is now made to FIGS. 15A-15C, which illustrate elongate rigid fluid flow conduit and actuator element 230. As noted above, element 230 includes a cylindrical portion 232, formed with a fluid conduit defining bore 233 and having a forward part 234 and a rearward part 236 as well as a circumferential actuator portion 238. Rearward part 236 of element 230 is partially sealingly disposed within elongate bore 222 of RFFCB element 220 (not shown).

Actuator portion 238 preferably includes a rearwardly facing cylindrical portion 275 whose interior facing surface 276 is spaced from an exterior facing surface 277 of rearward part 236 of cylindrical portion 232 and defines therewith a generally cylindrical recess 278 having an axially rearwardly facing wall surface 279 of a transverse wall 280. Forwardly of wall 280 are a pair of cylindrical sections 281 which extend forwardly of wall 280 and form part of an imaginary cylinder aligned about axis 210. Cylindrical sections 281 define forwardly facing engagement surfaces 282.

Reference is now made to FIGS. 16A-16C, which illustrate resilient double pathway fluid flow conduit sealing (RSDPFFCS) element 240. As noted above, RDPFFCS element 240 is formed with an elongate bore 242, and preferably has a forward section 244 extending forwardly of elongate bore 242. The forward section 244 of the RDPFFCS element 240 is preferably formed with an interior bore 245 and a selectably closable slit 246 extending along longitudinal axis 210. As seen in FIG. 12B, elongate bore 242 has a circular cross section: of a diameter greater than that of interior bore 245, thereby defining a rearwardly facing shoulder 247 therebetween.

As noted above, rearward of selectably closable slit 246, the RDPFFCS element 240 includes at least one, and preferably two, coaxial side openings 248 which extend generally perpendicularly to longitudinal axis 210 and communicate with interior bore 245 and with fluid conduit defining bore 233 of element 230. Extending radially outward of forward section 244 and slightly rearwardly thereof is a sealing ring 283.

Forward of side openings 248 is a tapered portion 284, whose rearwardly facing wall 285 defines the forward extent of interior bore 245. Tapered portion 284 terminates in a circumferential shoulder 286, forwardly of which is provided a tip portion 287, preferably having an oval cross section, which is compressible into a circular cross section.

Slit 246 preferably extends through tip portion 287 and tapered portion 284 along axis 210. As seen in FIGS. 16B & 16C, slit 246 is open when in an unstressed orientation.

Reference is now made to FIGS. 17A, 17B and 17C, which illustrate the forward housing portion 206 (FIGS. 11-12B) of the fluid flow connector 200 of FIG. 11. Forward housing portion 206 preferably includes a generally cylindrical body 289 having rearwardly tapered mutually spaced generally axial ribs 291.

As seen in FIGS. 17A-17C, forward housing portion 206 is an integrally formed element which is generally symmetric about a longitudinal axis, such as axis 210 (FIGS. 11-12B), in most respects. As noted hereinabove with reference to FIGS. 11-12B, the forward housing portion 206 includes an internally-threaded portion 208 at a forward end thereof and a forward conduit 250 extending rearwardly therethrough along axis 210. Forward conduit 250 is preferably formed with an interior bore 251 having a forwardly tapered portion 252 and a forwardly facing aperture 253.

Internally-threaded portion 208 terminates rearwardly at a circumferential shoulder 292 and communicates with a rearwardly extending generally circularly cylindrical internal bore 293. Forward conduit 250 is joined to the inwardly facing circularly cylindrical wall of bore 293 by a plurality of radially extending ribs 294, rearwardly of shoulder 292.

Forward housing portion 206 also includes a rearward conduit 295 which extends forwardly from a rearward face 296 of forward housing portion 206 along axis 210. As seen clearly in FIGS. 17B & 17C, rearward conduit 295 has an inner diameter greater than that of rearwardly extending generally circularly cylindrical internal bore 293, and rearwardly extending generally circularly cylindrical internal bore 293 extends partially into rearward conduit 295, defining a circumferential recess 297.

Reference is now made to FIGS. 18A, 18B, 18C, 19A and 19B, which are simplified sectional illustrations of the fluid flow connector 200 of FIG. 11 in a closed operative orientation, and to FIGS. 18D, 18E, 19C and 19D, which are simplified sectional illustrations of the fluid flow connector 200 of FIG. 11 in an open operative orientation in engagement with a female luer portion 299.

Referring initially specifically to FIGS. 18A, 18B, 18C, 19A and 19B, it is seen that RFFCB element 220 is maintained in a pre-tensioned state wherein generally circularly cylindrical mounting portion 268 is locked in place between rearward housing portion 202 and forward housing portion 206, which are welded together, as by ultrasonic welding. Specifically, it is seen that rearward face 296 of forward housing portion 206 lies against ring 264 of rearward housing portion 202 and cylindrical mounting portion 268 is locked in a circumferential volume defined by circumferential recess 297 of forward housing portion 206, end 258 and surfaces 260 and 263 of rearward housing portion 202.

Forward portion 274 of RFFCB element 220 is seated in generally cylindrical recess 278 of element 230 such that forwardly facing edge 266 of RFFCB element 220 lies in engagement with rearwardly facing wall surface 279 of wall 280.

Axial pretensioning of RFFCB element 220 along axis 210 is achieved by axial pressure engagement of rearwardly facing wall surface 279 with forwardly facing edge 266 of RFFCB element 220 and by axial pressure engagement of tapered portion 284 of RDPFFCS element 240 with forwardly tapered portion 252 of the interior bore 251 of forward conduit 250, due to tight engagement between RDPFFCS element 240 and the forward section 234 of element 230. This arrangement stretches and thus tensions tensionable connecting portion 267, as seen from a consideration of FIGS. 18A-18C, 19A & 19B with FIGS. 14A & 14B.

Figure 18A:
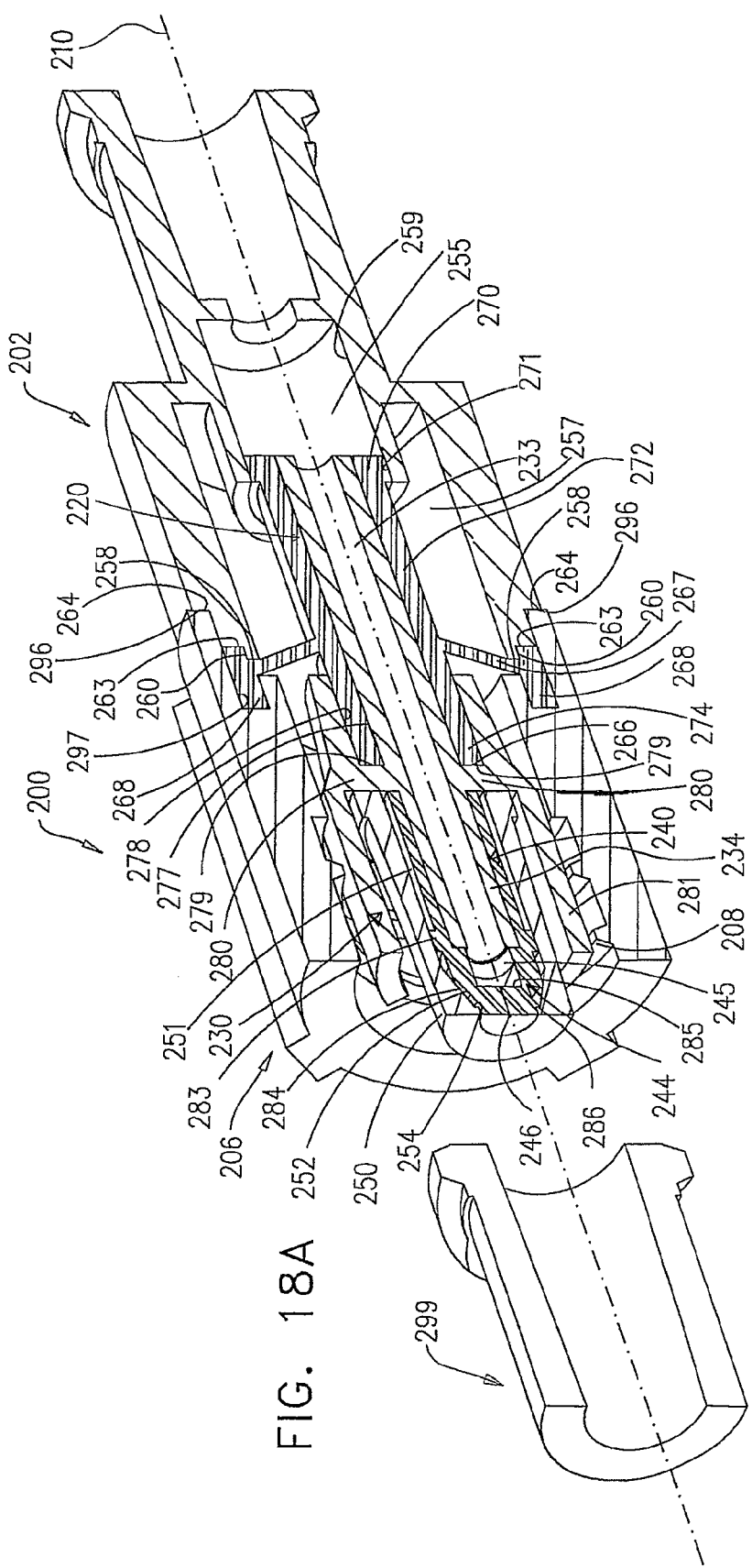

Axial pressure engagement of tapered portion 284 of RDPFFCS element 240 with forwardly tapered portion 252 of the interior bore 251 of the forward conduit 250 is operative to squeeze the forward section 244 of the RDPFFCS element 240 transversely to longitudinal axis 210, thereby closing the slit 246 and changing the cross section of the tapered portion 284 from a generally oval configuration, as seen in FIG. 16A, to a generally circular configuration, as seen in FIG. 18A.

Slidable sealing engagement is provided between radially outer surface 271 of rear portion 270 of RFFCB element 220 and inner facing surface 259 of rearward conduit 255. This sealing engagement preferably prevents fluid which enters the fluid flow connector via rearward conduit 255 from entering the volume within the forward conduit 260 lying rearward of connecting portion 267 and cylindrical mounting portion 268. Accordingly this volume is prevented from acting as a "dead space" which could undesirably retain such fluid.

Slidable sealing engagement is also provided between sealing ring 283 of RDPFFCS element 240 and interior bore 251 of forward conduit 250. This sealing engagement preferably prevents fluid which passes through side openings 248 from entering the volume within interior bore 251 of forward conduit 250 lying rearward of sealing ring 283 and within internal bore 293. Accordingly this volume is prevented from acting as a "dead space" which could undesirably retain such fluid.

It is appreciated that the fluid flow connector 200 in the state shown in FIGS. 18A-18C, 19A and 19B is capable of maintaining a pressurized fluid seal for pressurized fluid in forward conduit 250, fluid conduit defining bore 233, and interior bore 245. It is further appreciated that an increase in fluid pressure preferably enhances the effectiveness of the pressurized fluid seal.

Reference is now made specifically to FIGS. 18D, 18E, 19C and 19D which are simplified sectional illustrations of the fluid flow connector 200 of FIG. 11 in an open operative orientation in engagement with a female luer portion 299.

It is seen that threaded engagement of the female luer portion 299 with the internally-threaded portion 208 causes elongate rigid fluid flow conduit and actuator element 230 to be rearwardly displaced. It is noted that rearwardly facing wall surface 279 of element 230 engages forwardly facing end 266 of RFFCB element 220, producing corresponding rearward displacement thereof along axis 210, resulting in increased tensioning of tensionable connecting portion 267 of RFFCB element 220.

Rearward displacement of element 230 also produces corresponding rearward displacement of RDPFFCS element 240 which is tightly mounted thereon, along axis 210.

Rearward displacement of RDPFFCS element 240 along axis 210 produces disengagement of shoulder 286 of the RDPFFCS element 240 from shoulder 254 of the forward conduit 250 and disengagement of tapered portion 284 of RDPFFCS element 240 from forwardly tapered portion 252 of the interior bore 251 of the forward conduit 250.

The resulting elimination of axial pressure engagement of tapered portion 284 of RDPFFCS element 240 with forwardly tapered portion 252 of the interior bore 251 of the forward conduit 250 causes the forward section 244 of the RDPFFCS element 240 to no longer be squeezed transversely to longitudinal axis 210, thereby allowing the slit 246 to open and allowing the cross section of the tapered portion 284 to return to a generally oval configuration as seen in FIG. 16A.

Slidable sealing engagement continues to be provided between radially outer surface 271 of rear portion 270 of RFFCB element 220 and inner facing surface 259 of rearward conduit 255. This sealing engagement preferably prevents fluid which enters the fluid flow connector via rearward conduit 255 from entering the volume within the forward conduit 260 lying rearward of connecting portion 267 and cylindrical mounting portion 268. Accordingly this volume is prevented from acting as a "dead space" which could undesirably retain such fluid.

Slidable sealing engagement also continues to be provided between sealing ring 283 of RDPFFCS element 240 and interior bore 251 of forward conduit 250. This sealing engagement preferably prevents fluid which passes through side openings 248 and slit 246 from entering the volume within interior bore 251 of forward conduit 250 lying rearward of sealing ring 283 and within internal bore 293. Accordingly this volume is prevented from acting as a "dead space" which could undesirably retain such fluid.

It is appreciated that the fluid flow connector 200, in the state shown in FIGS. 18D, 18E, 19C and 19D, provides a fluid flow connection for fluid supplied via rearward conduit 255 and fluid conduit defining bore 233, as by a male luer or a syringe, to female luer portion 299 via slit 246, side openings 248 and aperture 253.

Reference is now made to FIGS. 20A and 20B, which are simplified sectional illustrations corresponding to FIGS. 18B and 18D for an alternative embodiment of the fluid flow connector 200 of FIG. 11 which does not include side openings, and to FIGS. 20C and 20D, which are simplified partial enlargements, corresponding to FIGS. 19A and 19C, for the alternative embodiment of the fluid flow connector 200 of FIG. 11 which does not include side openings.

The alternative embodiment shown in FIGS. 11, 13A-15C, 17A-18A and 20A-20D is generally identical in structure and operation to the embodiment of FIGS. 11-19D, with the sole exception that side openings 248 in the embodiment of FIGS. 11-19D are obviated in the embodiment of FIGS. 11, 13A-15C, 17A-18A and 20A 20D.

Figure 21:
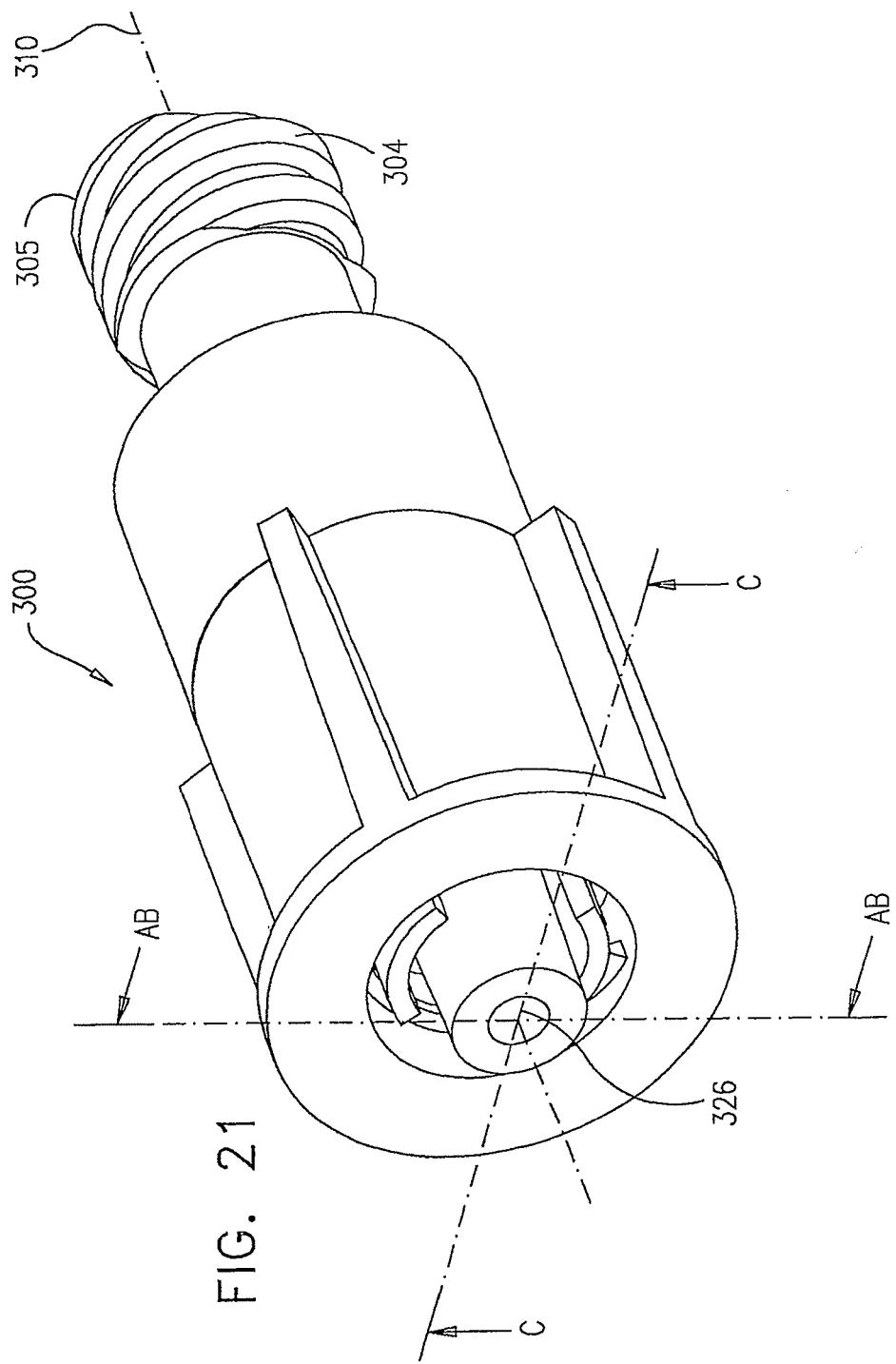
FIG. 21 is a simplified pictorial illustration of a fluid flow connector constructed and operative in accordance with yet another preferred embodiment of the invention.
Figure 22A:
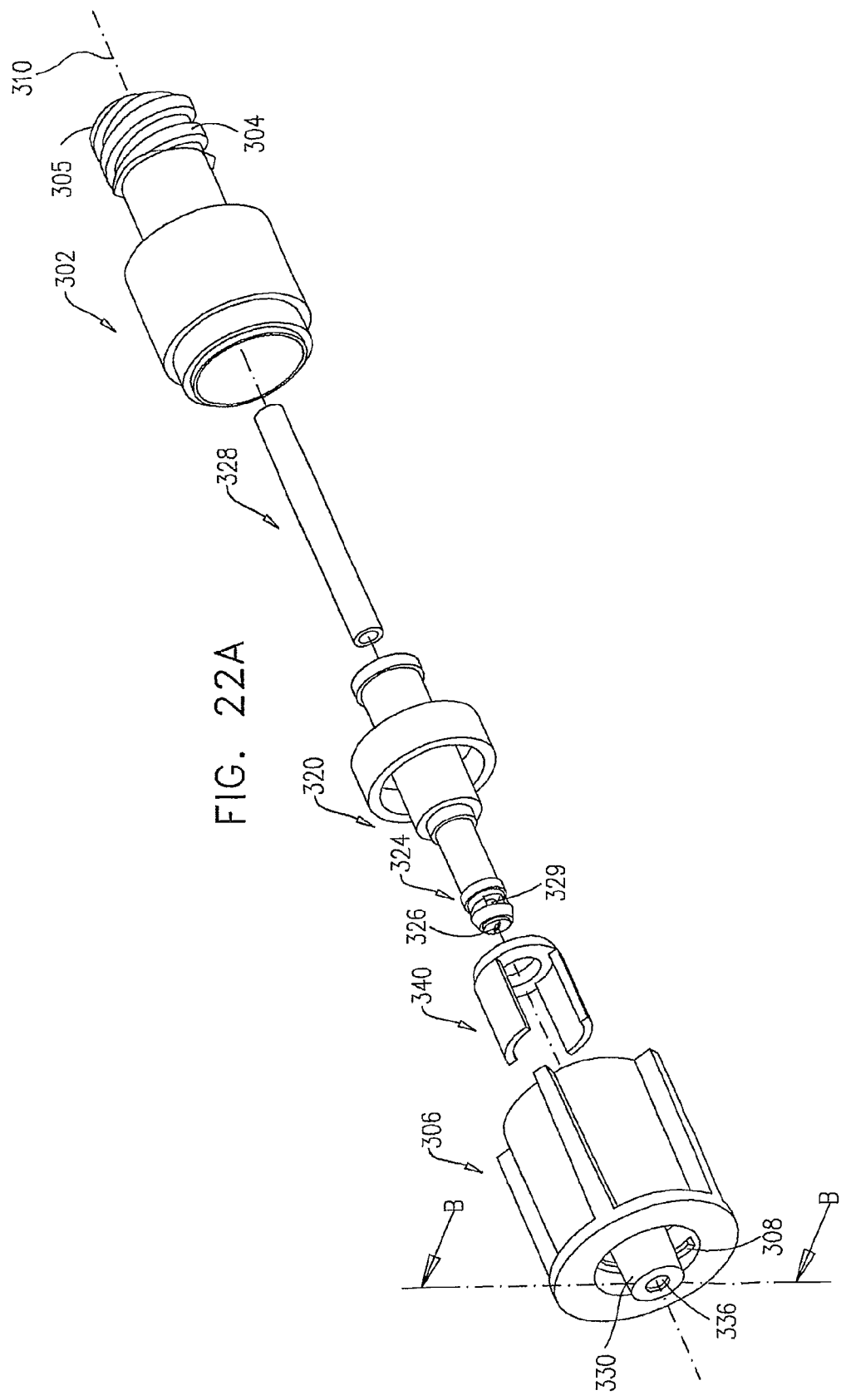
FIGS. 22A and 22B are simplified respective pictorial and sectional exploded view illustrations of the fluid flow connector of FIG. 21, FIG. 22B being taken along lines B-B in FIG. 22A.
Figure 22B:
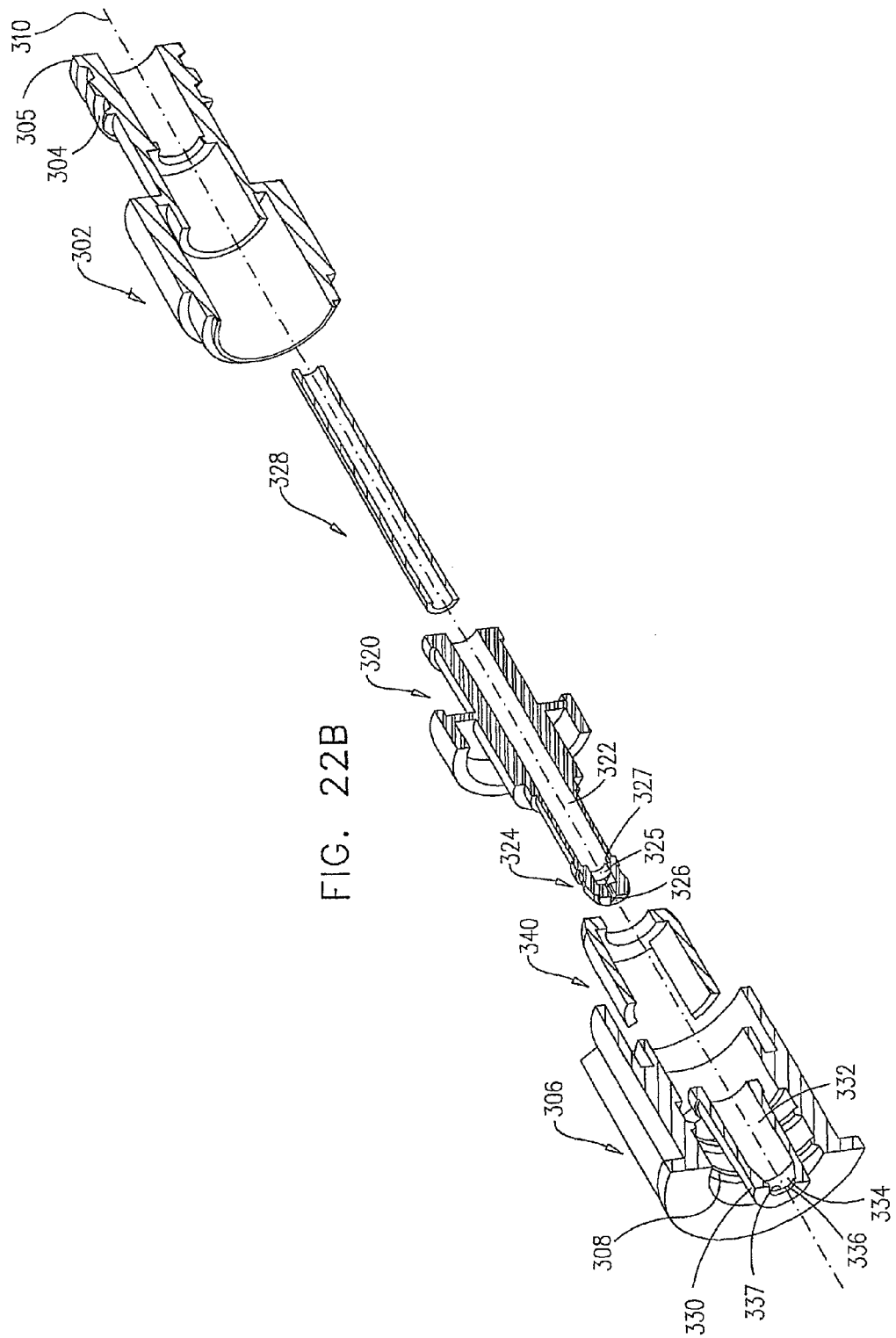

Reference is now made to FIG. 21, which is a simplified pictorial illustration of a fluid flow connector constructed and operative in accordance with yet another preferred embodiment of the invention and to FIGS. 22A and 22B, which are simplified respective pictorial and sectional exploded view illustrations of the fluid flow connector of FIG. 21, FIG. 22B being taken along lines B-B in FIG. 22A.

As seen in FIGS. 21, 22A & 22B, there is provided a fluid flow connector 300 having a housing assembly including a rearward housing portion 302, having an externally-threaded portion 304 at a rearward end 305 thereof, and a forward housing portion 306 having an internally-threaded portion 308 at a forward end thereof. Rearward and forward housing portions 302 and 306 are preferably arranged along a common longitudinal axis 310 and are preferably heat welded together.

A resilient double pathway fluid flow conduit sealing and biasing (RDPFFCSB) element 320 is disposed within the housing assembly and is arranged along longitudinal axis 310. The RDPFFCSB element 320 is formed with an elongate bore 322, and preferably has a forward section 324 extending forwardly of elongate bore 322 disposed alongside the internally-threaded portion 308 of the forward housing portion 306.

The forward section 324 of the RDPFFCSB element 320 is preferably formed with an interior bore 325 and a selectably closable slit 326 extending along longitudinal axis 310. As seen in FIG. 22B, elongate bore 322 has a circular cross section of a diameter greater than that of interior bore 325, thereby defining a rearwardly facing shoulder 327 therebetween.

An elongate rigid fluid flow conduit element 328 is tightly and sealingly disposed within elongate bore 322, rearwardly of shoulder 327. The interior of fluid flow conduit element 328 is in communication with interior bore 325.

In accordance with a preferred embodiment of the present invention, rearwardly of selectably closable slit 326, the RDPFFCSB element 320 includes at least one and preferably two coaxial side openings 329 which extend generally perpendicularly to longitudinal axis 310 and communicate with interior bore 325 and with the interior of fluid flow conduit element 328.

Preferably, the forward housing portion 306 includes a forward conduit 330, preferably integrally formed therewith. Forward conduit 330 is preferably formed with an interior bore 332 having a forwardly tapered portion 334 and a forwardly facing aperture 336. A rearwardly facing shoulder 337 is defined by the periphery of aperture 336.

Preferably, part of the RDPFFCSB element 320 is pretensioned and thereby urges another part of RDPFFCSB element 320 forwardly along longitudinal axis 310 to a closed position. In the closed position, the forward section 324 sealingly engages the forwardly tapered portion 334 of the interior bore 332. This engagement squeezes the forward section 324 transversely to longitudinal axis 310, thereby closing the slit 326 but leaving the side openings 329 open for fluid communication between the interior of fluid flow conduit element 328 and interior bore 325 at the interior of RDPFFCSB element 320, the exterior of element 328 being tightly retained within the interior of RDPFFCSB element 320.

Engagement of the forward section 324 of the RDPFFCSB element 320 with the forward conduit 330 under the urging of part of RDPFFCSB element 320 is operative to seal forwardly facing aperture 336.

An actuator element 340 is provided for engagement with RDPFFCSB element 320. The actuator element 340 is arranged to be displaced rearwardly along longitudinal axis 310 by engagement therewith of a rearwardly facing end of a female luer (not shown), which may threadably engage internally-threaded portion 308 of forward housing portion 306.

Rearward displacement of actuator element 340 produces corresponding rearward displacement of part of RDPFFCSB element 320 along longitudinal axis 310, such that forward section 324 moves rearwardly out of engagement with the forwardly tapered portion 334 of the interior bore 332, thereby unsealing forwardly facing aperture 336 and allowing slit 326 to open, while leaving side openings 329 open for fluid communication between the interior of fluid flow conduit element 328, interior bore 325 of forward section 324, the exterior of RDPFFCSB element 320, interior bore 332 of the forward conduit 330, and forwardly facing aperture 336.

It is a particular feature of this embodiment of the present invention that when RDPFFCSB element 320 is in this open position, fluid communication between the interior of fluid flow conduit element 328 and forwardly facing aperture 336 is provided both via selectably closable slit 326 and via side openings 329.

Reference is now made to FIGS. 23A and 23B, which are a simplified respective side view and a sectional illustration of a preferred structure of rearward housing portion 302 of the fluid flow connector 300 of FIG. 21, FIG. 23B being taken along lines B-B in FIG. 23A. As seen in FIGS. 23A & 23B, rearward housing portion 302 is an integrally formed element which is symmetric about a longitudinal axis, such as axis 310 (FIGS. 21-22B).

As noted hereinabove with reference to FIGS. 21-22B, the rearward housing portion 302 includes an externally-threaded portion 304 at a rearward end 305 thereof. Rearward housing portion 302 also includes a rearward conduit 344 extending forwardly from rearward end 305 along axis 310. An internally directed flange 346 is disposed at a location intermediate along rearward conduit 344 and serves as a stop, limiting forward penetration of a male luer (not shown) into conduit 344 from rearward end 305.

Rearward housing portion 302 also includes a forward conduit 348 which extends rearwardly from a forward end 349 of rearward housing portion 302 along axis 310. As seen clearly in FIG. 23B, rearward conduit 344 has an inner facing surface 350 and rearward conduit 344 extends partially into forward conduit 348. The exterior of rearward housing portion 302 is formed with a plurality of stepped circumferential radially outwardly facing surfaces adjacent forward end 349, including a first circumferential ring 351, adjacent forward end 349, a second circumferential ring 352, having an outer diameter greater than that of first circumferential ring 351, rearwardly of ring 351, and a cylindrical wall 353 extending rearwardly of ring 352. A plurality of stepped circumferential forwardly facing surfaces are also defined adjacent forward end 349, including a ring 354 intermediate surfaces 351 and 352, and a ring 355, intermediate surfaces 352 and 353.

Reference is now made to FIGS. 24A, 24B and 24C which illustrate resilient double pathway fluid flow conduit sealing and biasing (RDPFFCSB) element 320, forming part of the fluid flow connector of FIGS. 21-22B in an unstressed orientation having elongate rigid fluid flow conduit element 328 inserted therein. As seen in FIGS. 24A-24C, RDPFFCSB element 320 is an integrally formed element, preferably formed of silicone rubber, which is symmetric about a longitudinal axis, such as axis 310 (FIGS. 21-22B), in all respects other than with respect to selectably closable slit 326 and side openings 329.

The RDPFFCSB element 320 preferably includes a generally elongate portion 360 having an elongate bore 322 formed at the center thereof along axis 310, extending from a rearwardly facing end 364 to rearwardly facing shoulder 327 (FIGS. 22A & 22B), elongate rigid fluid flow conduit element 328 being tightly and sealingly disposed therewithin. Extending radially outward from generally elongate portion 360 is a tensionable connecting portion 366, typically in the form of a disc when in an unstressed condition. Tensionable connecting portion 366 preferably terminates in a generally circularly cylindrical mounting portion 368.

Generally elongate portion 360 preferably includes a rear portion 370 having a circular cross section of a first diameter and a radially outer surface 371, a rearward intermediate portion 372, forward of rear portion 370 and having a circular cross section of a second diameter, less than the first diameter, which terminates at a junction with tensionable connecting portion 366. Forward of the junction with tensionable connecting portion 366 is a forward intermediate portion 374, preferably having a circular cross section of a third diameter, greater than the second diameter, which terminates at a circumferential shoulder 375. Forward of circumferential shoulder 375 is a ring portion 376, preferably having a circular cross section of a fourth diameter, less than the second diameter, which terminates at a circumferential shoulder 377.

Forward of shoulder 377 is a forward portion 378 which extends to forward section 324 (FIGS. 22A & 22B). Extending radially outward of forward portion 378, slightly rearwardly of forward section 324 is a sealing ring 379.

As noted above, forward section 324 (FIGS. 22A & 22B) includes a pair of side openings 329 (FIGS. 22A & 22B) which preferably extend along an axis 380, intersecting and orthogonal to axis 310, from interior bore 325 to the periphery of forward section 324.

Forwardly of side openings 329 is a tapered portion 381, whose rearwardly facing wall 382 defines the forward extent of interior bore 325. Tapered portion 381 terminates in a circumferential shoulder 383, forwardly of which is provided a tip portion 384, preferably having an oval cross section which is compressible into a circular cross section of a fifth diameter, less than the fourth diameter.

Tip portion 384 and tapered portion 381 are preferably formed with slit 326 (FIGS. 21-22B) extending along axis 310 and communicating between interior bore 325 and the outside, forward of tip portion 384. As seen in FIG. 24B, slit 326 is open when in an unstressed orientation.

It is appreciated that elongate bore 322 defines a generally incompressible fluid flow pathway extending between rearwardly facing end 364 and rearwardly facing wall 382.

Figure 25A:
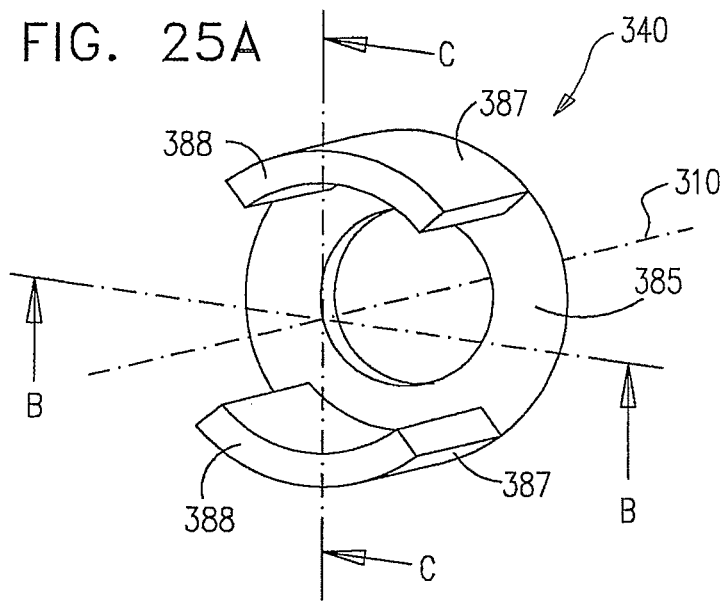
FIG. 25A is a simplified pictorial view of an actuator element forming part of the fluid flow connector of FIG. 21.
Figure 25B:
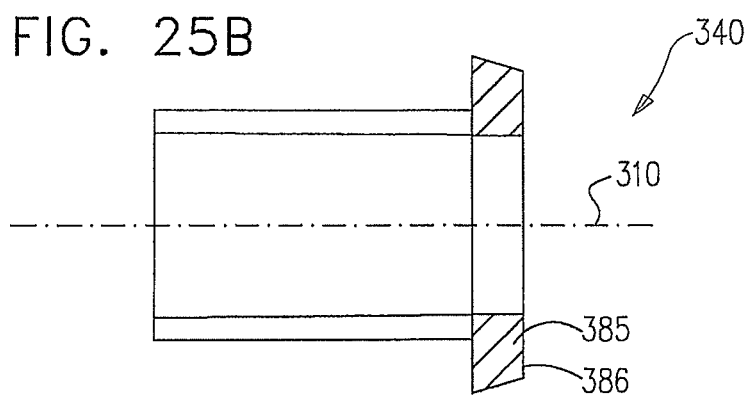
FIGS. 25B and 25C are simplified respective sectional illustrations of the actuator element, taken along mutually perpendicular section lines B-B and C-C in FIG. 25A.
Figure 25C:
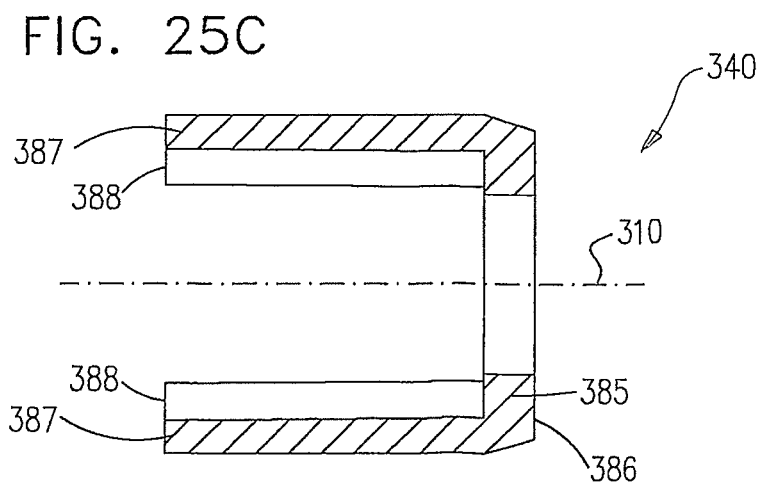

Reference is now made to FIGS. 25A-25C, which illustrate actuator element 340, forming part of the fluid flow connector 300 of FIG. 21. Actuator element 340 preferably includes a rearward apertured disc 385, having a circumferential rearmost surface 386, integrally formed with a pair of cylindrical sections 387, which extend forwardly of disc 385 and form part of an imaginary cylinder aligned about axis 310. Cylindrical sections 387 define forwardly facing engagement surfaces 388.

Figure 26A:
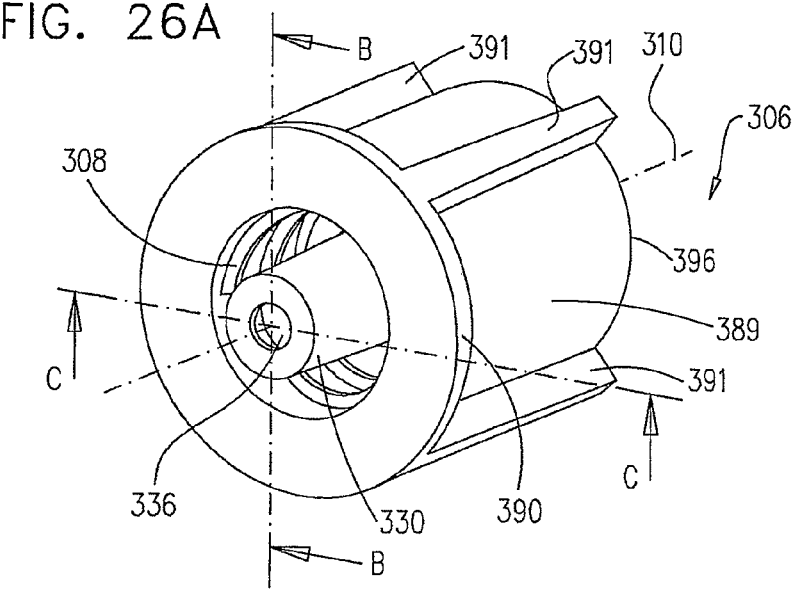
FIG. 26A is a simplified pictorial view of a forward housing portion of the fluid flow connector of FIG. 21.
Figure 26B:
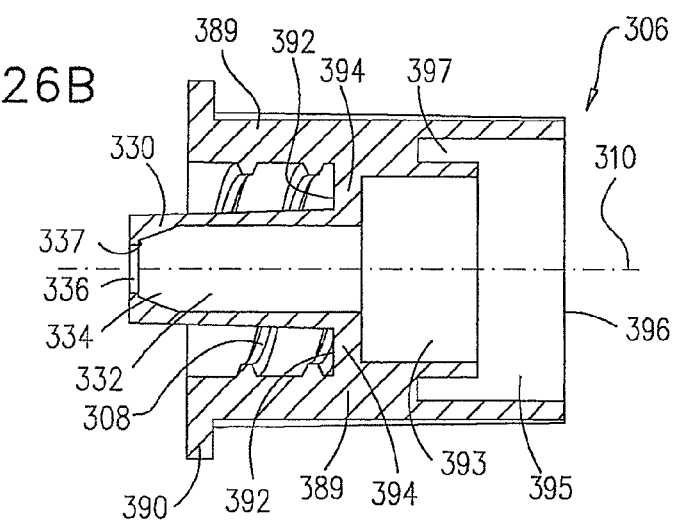
FIGS. 26B and 26C are simplified respective sectional illustrations of the forward housing portion, taken along mutually perpendicular section lines B-B and C-C in FIG. 26A.
Figure 26C:
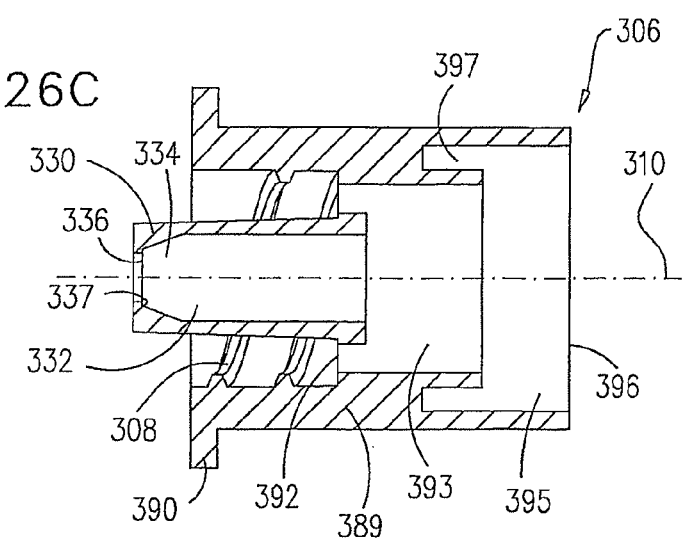

Reference is now made to FIGS. 26A-26C, which illustrate forward housing portion 306 (FIGS. 21-22B) of the fluid flow connector 300 of FIG. 21. Forward housing portion 306 preferably includes a generally cylindrical body 389 having a forwardmost flange 390 and rearwardly tapered mutually spaced generally axial ribs 391 extending rearwardly from flange 390.

As seen in FIGS. 26A-26C, forward housing portion 306 is an integrally formed element which is generally symmetric about a longitudinal axis, such as axis 310 (FIGS. 21-22B), in most respects. As noted hereinabove with reference to FIGS. 21-22B, the forward housing portion 306 includes an internally-threaded portion 308 at a forward end thereof and a forward conduit 330 extending rearwardly therethrough along axis 310. Forward conduit 330 is preferably formed with an interior bore 332 having a forwardly tapered portion 334 and a forwardly facing aperture 336.

Internally-threaded portion 308 terminates rearwardly at circumferential shoulders 392 and communicates with a rearwardly extending generally circularly cylindrical internal bore 393. Forward conduit 330 is joined to the inwardly facing circularly cylindrical wall of bore 393 by a plurality of radially extending ribs 394, forwardly facing surfaces of which define shoulders 392.

Forward housing portion 306 also includes a rearward conduit 395 which extends forwardly from a rearward face 396 of forward housing portion 306 along axis 310. As seen clearly in FIGS. 26B & 26C, rearward conduit 395 has an inner diameter greater than that of rearwardly extending generally circularly cylindrical internal bore 393, and rearwardly extending generally circularly cylindrical internal bore 393 extends partially into rearward conduit 395, defining a circumferential recess 397.

Reference is now made to FIGS. 27A, 27B, 27C, 28A and 28B, which are simplified sectional illustrations of the fluid flow connector 300 of FIG. 21 in a closed operative orientation, and to FIGS. 27D, 27E, 28C and 28D, which are simplified sectional illustrations of the fluid flow connector 300 of FIG. 21 in an open operative orientation in engagement with a female luer portion 399.

Referring initially specifically to FIGS. 27A, 27B, 27C, 28A and 28B, it is seen that RDPFFCSB element 320 is maintained in a pre-tensioned state wherein generally circularly cylindrical mounting portion 368 is locked in place between rearward housing portion 302 and forward housing portion 306, which are welded together, as by ultrasonic welding. Specifically it is seen that rearward face 396 of forward housing portion 306 lies against ring 355 of rearward housing portion 302 and cylindrical mounting portion 368 is locked in a circumferential volume defined by circumferential recess 397 of forward housing portion 306, end 349 and surfaces 351 and 354 of rearward housing portion 302.

Axial pretensioning of RDPFFCSB element 320 along axis 310 is achieved by axial pressure engagement of the shoulder 383 of RDPFFCSB element 320 with shoulder 337 of the forward conduit 330 and by axial pressure engagement of tapered portion 381 of RDPFFCSB element 320 with forwardly tapered portion 334 of the interior bore 332 of the forward conduit 330. This arrangement stretches and thus tensions tensionable connecting portion 366, as seen from a comparison of FIGS. 27A 27C, 28A & 28B with FIGS. 24A-24C.

Figure 27A:
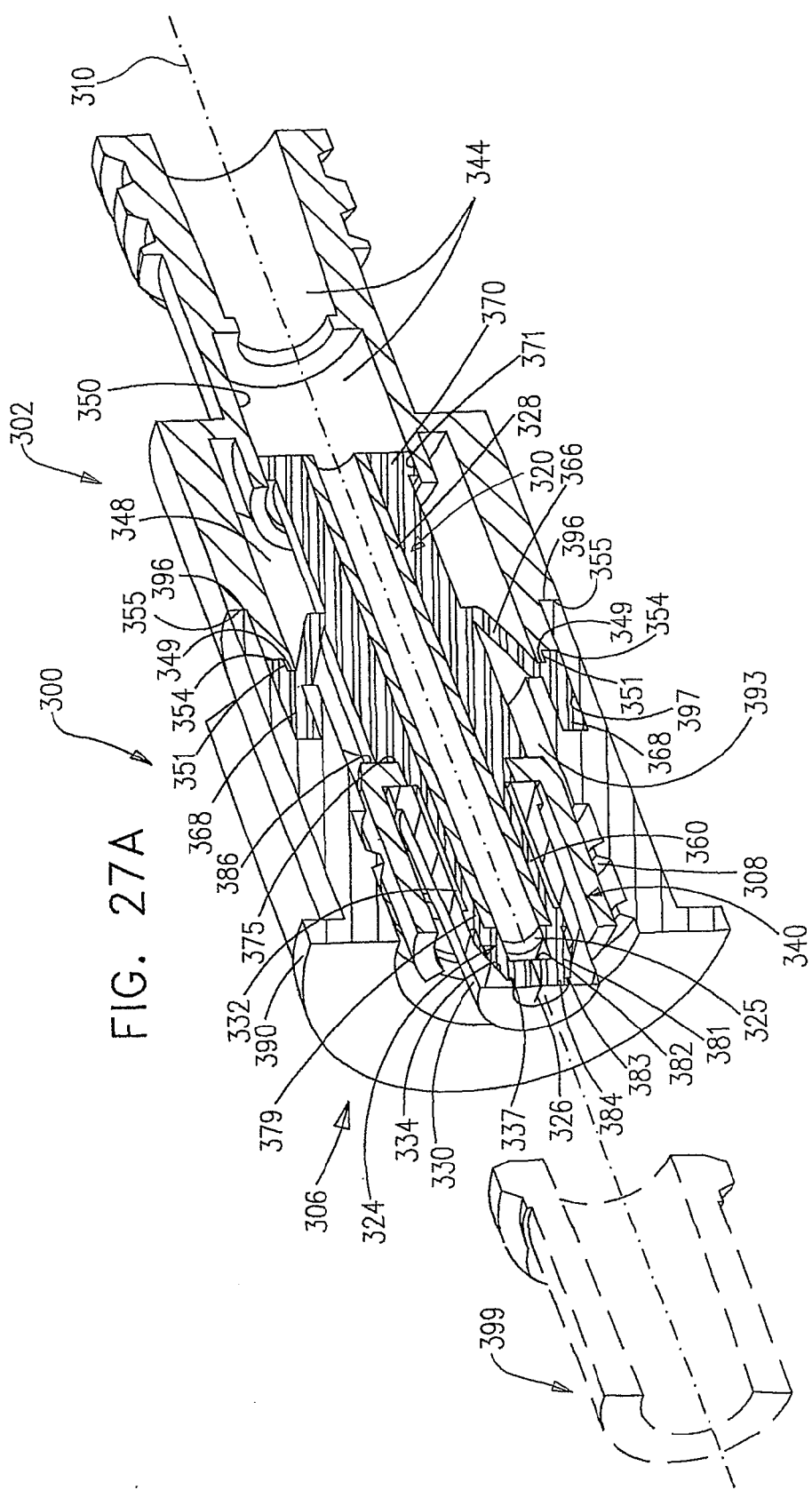

Axial pressure engagement of tapered portion 381 of RDPFFCSB element 320 with forwardly tapered portion 334 of the interior bore 332 of the forward conduit 330 is operative to squeeze the forward section 324 of the RDPFFCSB element 320 transversely to longitudinal axis 310, thereby closing the slit 326 and changing the cross section of the tapered portion 381 from a generally oval configuration as seen in FIG. 24A to a generally circular configuration as seen in FIG. 27A.

Slidable sealing engagement is provided between radially outer surface 371 of rear portion 370 of RDPFFCSB element 320 and inner facing surface 350 of rearward conduit 344. This sealing engagement preferably prevents fluid which enters the fluid flow connector via rearward conduit 344 from entering the volume within the forward conduit 348 lying rearward of connecting portion 366 and cylindrical mounting portion 368. Accordingly this volume is prevented from acting as a "dead space" which could undesirably retain such fluid.

Slidable sealing engagement is also provided between sealing ring 379 of RDPFFCSB element 320 and interior bore 332 of forward conduit 330. This sealing engagement preferably prevents fluid which passes through side openings 329 from entering the volume within interior bore 332 of forward conduit 330 lying rearward of sealing ring 379 and within internal bore 395. Accordingly this volume is prevented from acting as a "dead space" which could undesirably retain such fluid.

It is appreciated that the fluid flow connector 300 in the state shown in FIGS. 27A-27C, 28A and 28B is capable of maintaining a pressurized fluid seal for pressurized fluid in rearward conduit 344, fluid flow conduit element 328, and interior bore 325. It is further appreciated that an increase in fluid pressure preferably enhances the effectiveness of the pressurized fluid seal.

Reference is now made specifically to FIGS. 27D, 27E, 28C and 28D which are simplified sectional illustrations of the fluid flow connector 300 of FIG. 21 in an open operative orientation in engagement with a female luer portion 399.

It is seen that threaded engagement of female luer portion 399 with the internally-threaded portion 308 causes actuator element 340 to be rearwardly displaced. It is noted that circumferential rearmost surface 386 of actuator element 340 engages shoulder 375 of RDPFFCSB element 320, producing corresponding rearward displacement thereof. Rearward displacement of shoulder 375 produces corresponding rearward displacement of a generally elongate portion 360 of RDPFFCSB element 320 along axis 310, resulting in increased tensioning of tensionable connecting portion 366 of RDPFFCSB element 320.

Rearward displacement of generally elongate portion 360 of RDPFFCSB element 320 also produces corresponding rearward displacement of rearwardly facing shoulder 327, resulting in corresponding rearward displacement of rigid fluid flow conduit element 328 which is tightly and sealingly disposed within elongate bore 322 of RDPFFCSB element 320, along axis 310.

Rearward displacement of generally elongate portion 360 of RDPFFCSB element 320 along axis 310 also produces disengagement of shoulder 383 of the RDPFFCSB element 320 from shoulder 337 of the forward conduit 330 and disengagement of tapered portion 381 of RDPFFCSB element 320 from forwardly tapered portion 334 of the interior bore 332 of the forward conduit 330.

The resulting elimination of axial pressure engagement of tapered portion 381 of RDPFFCSB element 320 with forwardly tapered portion 334 of the interior bore 332 of the forward conduit 330 causes the forward section 324 of the RDPFFCSB element 320 to no longer be squeezed transversely to longitudinal axis 310, thereby allowing the slit 326 to open and allowing the cross section of the tapered portion 381 to return to a generally oval configuration as seen in FIG. 24A.

Slidable sealing engagement continues to be provided between radially outer surface 371 of rear portion 370 of RDPFFCSB element 320 and inner facing surface 350 of rearward conduit 344. This sealing engagement preferably prevents fluid which enters the fluid flow connector via rearward conduit 344 from entering the volume within the forward conduit 348 lying rearward of connecting portion 366 and cylindrical mounting portion 368. Accordingly this volume is prevented from acting as a "dead space" which could undesirably retain such fluid.

Slidable sealing engagement also continues to be provided between sealing ring 379 of RDPFFCSB element 320 and interior bore 332 of forward conduit 330. This sealing engagement preferably prevents fluid which passes through side openings 329 and slit 326 from entering the volume within interior bore 332 of forward conduit 330 lying rearward of sealing ring 379 and within internal bore 395. Accordingly this volume is prevented from acting as a "dead space" which could undesirably retain such fluid.

It is appreciated that the fluid flow connector 300, in the state shown in FIGS. 27D, 27E, 28C and 28D, provides a fluid flow connection for fluid supplied via rearward conduit 344, elongate rigid fluid flow conduit element 328 and interior bore 325, as by a male luer or a syringe, to female luer portion 399 via slit 326, side openings 329 and aperture 336.

Reference is now made to FIGS. 29A and 29B, which are simplified sectional illustrations corresponding to FIGS. 27B and 27D for an alternative embodiment of the fluid flow connector 300 of FIG. 21 which does not include side openings and to FIGS. 30A and 30B, which are simplified partial enlargements, corresponding to FIGS. 28A and 28C, for the alternative embodiment of the fluid flow connector 300 of FIG. 21 which does not include side openings.

The alternative embodiment shown in FIGS. 21, 23A, 23B, 25A-25C, 26A-26C, 29A, 29B, 30A and 30B is generally identical in structure and operation to the embodiment of FIGS. 21-28D, with the sole exception that side openings 329 in the embodiment of FIGS. 21-28D are obviated in the embodiment of FIGS. 21, 23A, 23B, 25A-25C, 26A-26C, 29A, 29B, 30A and 30B.

Figure 31:
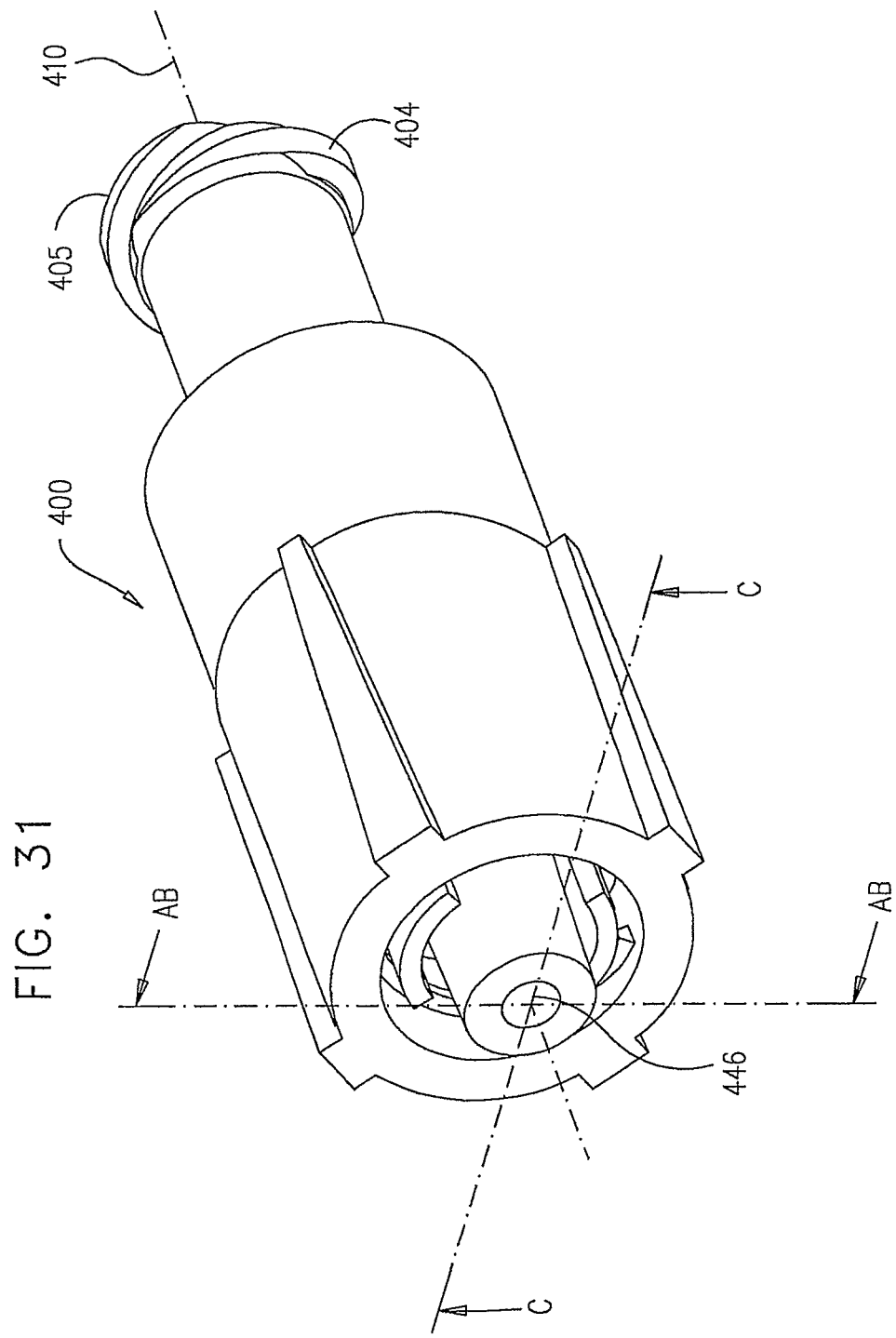
FIG. 31 is a simplified pictorial illustration of a fluid flow connector constructed and operative in accordance with yet another preferred embodiment of the invention.
Figure 32A:
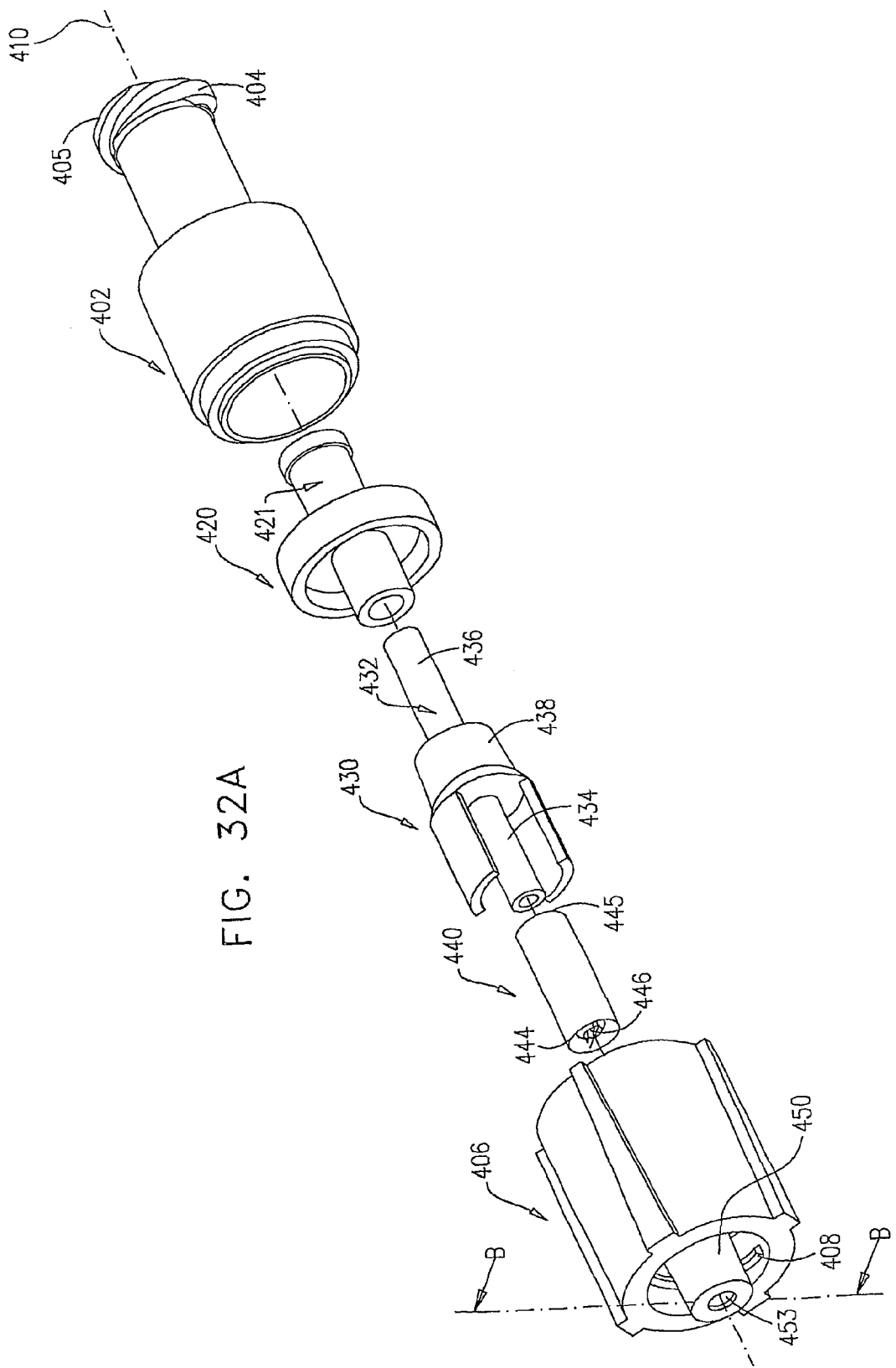

Reference is now made to FIG. 31, which is a simplified pictorial illustration of a fluid flow connector constructed and operative in accordance with yet another preferred embodiment of the invention, and to FIGS. 32A and 32B, which are simplified respective pictorial and sectional exploded view illustrations of the fluid flow connector of FIG. 31, FIG. 32B being taken along lines B-B in FIG. 32A.

As seen in FIGS. 31, 32A & 32B, there is provided a fluid flow connector 400 having a housing assembly including a rearward housing portion 402, having an externally-threaded portion 404 at a rearward end 405 thereof, and a forward housing portion 406 having an internally-threaded portion 408 at a forward end thereof. Rearward and forward housing portions 402 and 406 are preferably arranged along a common longitudinal axis 410 and are preferably heat welded together.

A resilient fluid flow conduit biasing (RFFCB) element 420 is disposed within the housing assembly and is arranged along longitudinal axis 410. The RFFCB element 420 includes a generally cylindrical portion 421 formed with an elongate bore 422.

An elongate rigid fluid flow conduit and actuator element 430 includes a cylindrical portion 432, formed with a fluid conduit defining bore 433 and having a forward part 434 and a rearward part 436 as well as a circumferential actuator portion 438. Rearward part 436 of element 430 is partially sealingly disposed within elongate bore 422.

A resilient fluid flow conduit sealing (RFFCS) element 440 is disposed within the housing assembly and is arranged along longitudinal axis 410 and is preferably slidingly disposed over the forward part 434 of cylindrical portion 432. The RFFCS element 440 is preferably formed with an interior bore 442, and with a forward face 444 and a rearwardly facing sealing aperture 445.

The forward face 444 of the RFFCS element 440 is preferably formed with a selectably closable slit 446 extending along longitudinal axis 410. Selectably closable slit 446 is preferably formed with at least two slit wall portions 447. It is appreciated that the two slit wall portions 447 in the state shown in FIG. 32B are not squeezed together, thereby defining an opening therebetween.

Preferably, the forward housing portion 406 includes a forward conduit 450, preferably integrally formed therewith. Forward conduit 450 is preferably formed with an interior bore 451, and has a forward end 452. The forward end 452 is formed with a forwardly facing aperture 453 and a rearwardly facing surface 454. RFFCS element 440 is preferably tightly and sealingly disposed within interior bore 451, whereby the periphery of forward face 444 of RFFCS element 440 tightly engages rearwardly facing surface 454.

Preferably, part of the RFFCB element 420 is pre-tensioned and thereby urges elongate rigid fluid flow conduit and actuator element 430 forwardly along longitudinal axis 410 to a closed position. In the closed position, the forward part 434 of the element 430 engages the two slit wall portions 447 of the selectably closable slit 446. This engagement forwardly displaces and squeezes the two slit wall portions 447 transversely to the longitudinal axis 410, thereby closing the slit 446.

Engagement of the forward part 434 of the element 430 with the slit 446 under the urging of RFFCB element 420 is operative to seal forwardly facing aperture 453.

Elongate rigid fluid flow conduit and actuator element 430 is arranged to be displaced rearwardly along longitudinal axis 410 by engagement of actuator portion 438 by a rearwardly facing end of a female luer (not shown), which may threadably engage internally-threaded portion 408 of forward housing portion 406.

Rearward displacement of elongate rigid fluid flow conduit and actuator element 430 produces corresponding rearward displacement of RFFCB element 420 along longitudinal axis 410 such that forward part 434 moves rearwardly out of engagement with the two slit wall portions 447 of the slit 446, thereby unsealing forwardly facing aperture 453 and allowing slit 446 to open for fluid communication between the fluid conduit defining bore 433 of elongate rigid fluid flow conduit and actuator element 430, interior bore 442 and forwardly facing aperture 453.

Reference is now made to FIGS. 33A and 33B, which are a simplified respective side view and a sectional illustration of a preferred structure of rearward housing portion 402 of the fluid flow connector 400 of FIG. 31, FIG. 33B being taken along lines B-B in FIG. 33A. As seen in FIGS. 33A & 33B, rearward housing portion 402 is an integrally formed element which is symmetric about a longitudinal axis, such as axis 410 (FIGS. 31-32B).

As noted hereinabove with reference to FIGS. 31-32B, the rearward housing portion 402 includes an externally-threaded portion 404 at a rearward end 405 thereof. Rearward housing portion 402 also includes a rearward conduit 455 extending forwardly from rearward end 405 along axis 410. An internally directed flange 456 is disposed at a location intermediate along rearward conduit 455 and serves as a stop, limiting forward penetration of a male luer (not shown) into conduit 455 from rearward end 405.

Rearward housing portion 402 also includes a forward conduit 457 which extends rearwardly from a forward end 458 of rearward housing portion 402 along axis 410. As seen clearly in FIG. 33B, rearward conduit 455 has an inner facing surface 459 and rearward conduit 455 extends partially into forward conduit 457. The exterior of rearward housing portion 402 is formed with a plurality of stepped circumferential radially outwardly, facing surfaces adjacent forward end 458, including a first circumferential ring 460, adjacent forward end 458, a second circumferential ring 461, having an outer diameter greater than that of first circumferential ring 460, rearwardly of ring 460, and a cylindrical wall 462 extending rearwardly of ring 461. A plurality of stepped circumferential forwardly facing surfaces are also defined adjacent forward end 458, including a ring 463 intermediate surfaces 460 and 461, and a ring 464, intermediate surfaces 461 and 462.

Figures 34A, 34B:
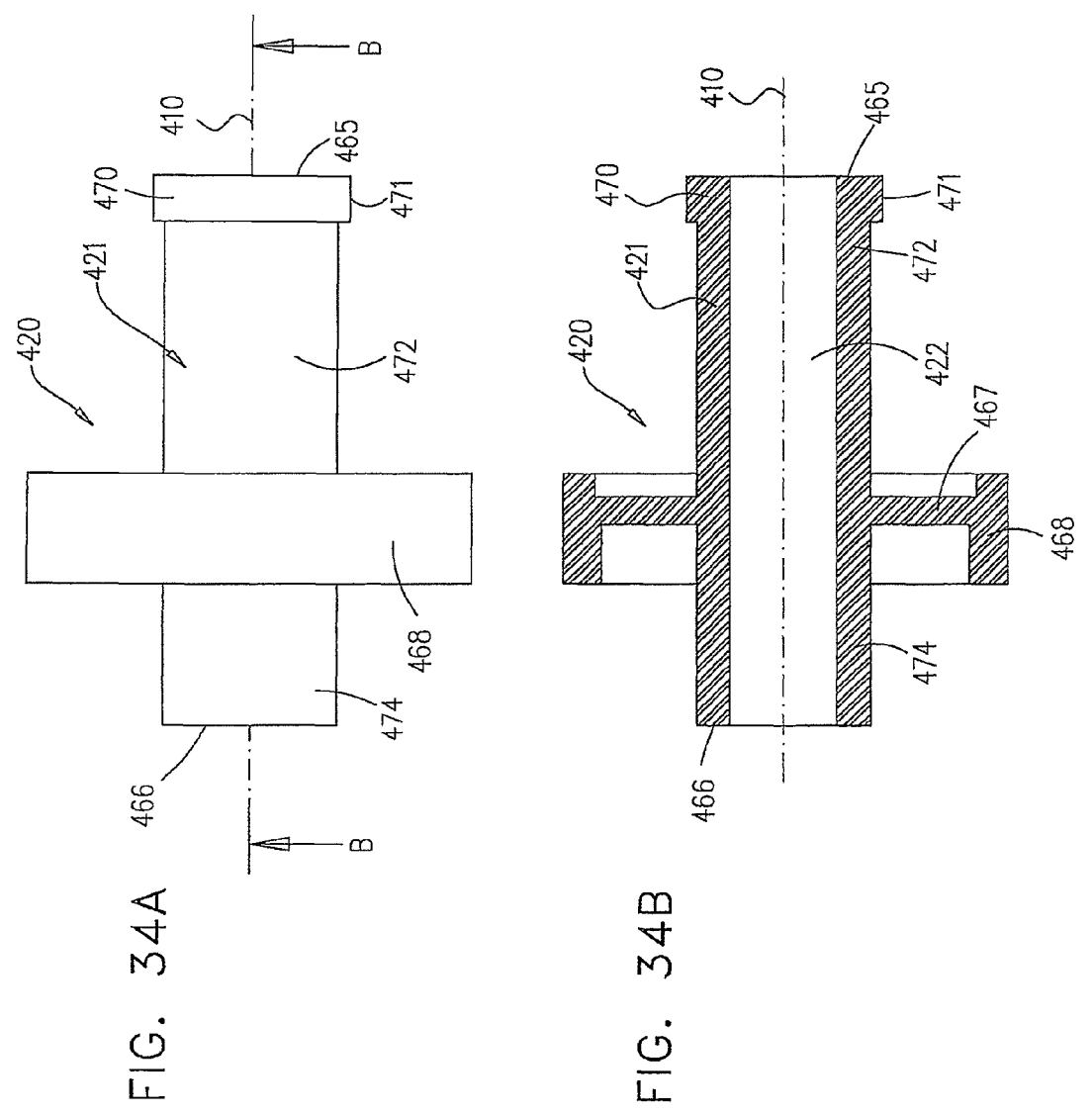

Reference is now made to FIGS. 34A and 34B, which illustrate resilient fluid flow conduit biasing (RFFCB) element 420, forming part of the fluid flow connector of FIGS. 31-32B, in an unstressed orientation, FIG. 34B being taken along lines B-B in FIG. 34A. As seen in FIGS. 34A & 34B, RFFCB element 420 is an integrally formed element, preferably formed of silicone rubber, which is symmetric about a longitudinal axis, such as axis 410 (FIGS. 31-32B).

As noted above, the RFFCB element 420 preferably includes a generally cylindrical portion 421 (FIGS. 32A & 32B) having an elongate bore 422 formed at the center thereof along axis 410, extending from a rearwardly facing end 465 to a forwardly facing end 466, cylindrical portion 432 of elongate rigid fluid flow conduit and actuator element 430 being partially and sealingly disposed therewithin. Extending radially outward from cylindrical portion 421 is a tensionable connecting portion 467, typically in the form of a disc when in an unstressed condition. Tensionable connecting portion 467 preferably terminates in a generally circularly cylindrical mounting portion 468.

Cylindrical portion 421 preferably includes a rear portion 470, having a circular cross section of a first diameter and a radially outer surface 471, and a rearward portion 472, forward of rear portion 470, and having a circular cross section of a second diameter, less than the first diameter, which terminates at a junction with tensionable connecting portion 467. Forward of the junction with tensionable connecting portion 467 is a forward portion 474, which terminates at forward end 466.

Figure 35A:
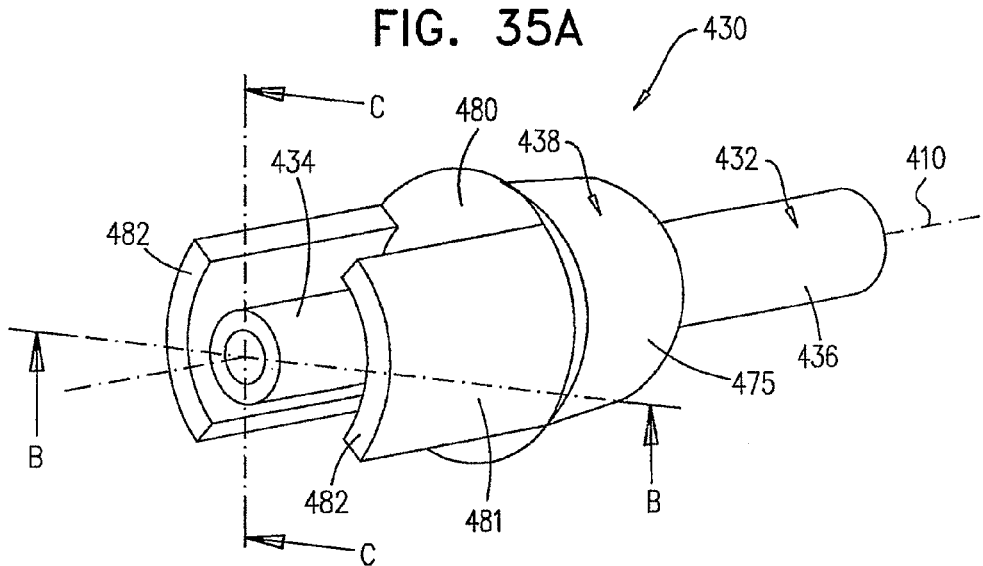
FIG. 35A is a simplified side view of a rigid fluid flow conduit and actuator element forming part of the fluid flow connector of FIG. 31.
Figure 35B:
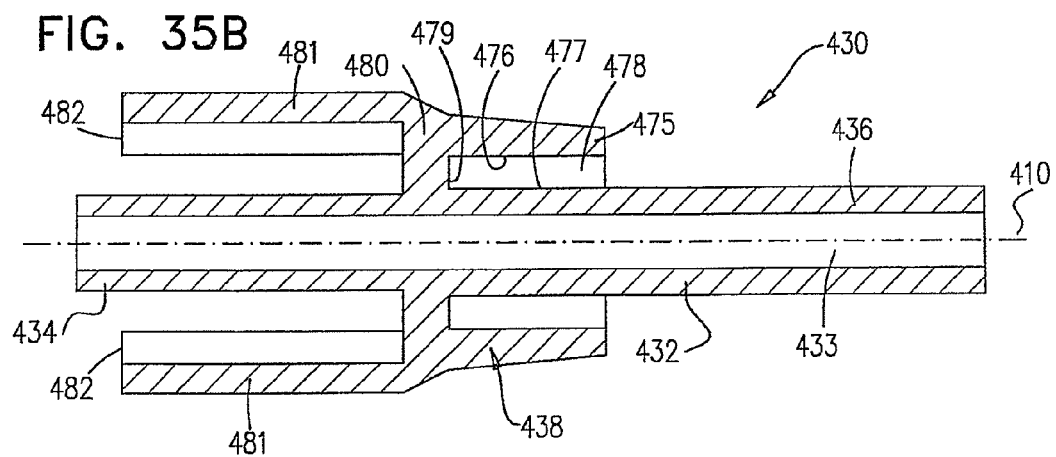
FIGS. 35B and 35C are simplified respective sectional illustrations of the rigid fluid flow conduit and actuator element, taken along mutually perpendicular section lines B-B and C-C in FIG. 35A.
Figure 35C:
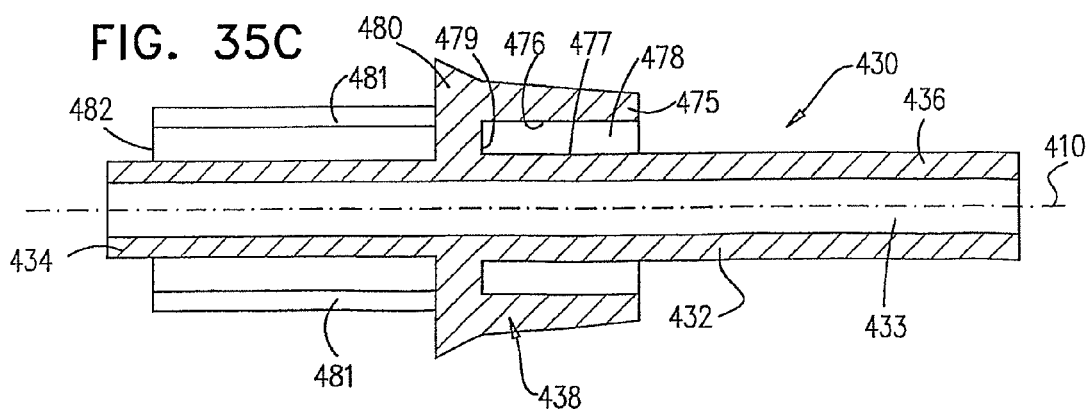

Reference is now made to FIGS. 35A-35C, which illustrate elongate rigid fluid flow conduit and actuator element 430. As noted above, element 430 includes a cylindrical portion 432, formed with a fluid conduit defining bore 433 and having a forward part 434 and a rearward part 436 as well as a circumferential actuator portion 438. Rearward part 436 of element 430 is partially sealingly disposed within elongate bore 422 of RFFCB element 420

Actuator portion 438 preferably includes a rearwardly facing cylindrical portion 475 whose interior facing surface 476 is spaced from an exterior facing surface 477 of rearward part 436 of cylindrical portion 432 and defines therewith a generally cylindrical recess 478 having an axially rearwardly facing wall surface 479 of a transverse wall 480. Forwardly of wall 480 are a pair of cylindrical sections 481 which extend forwardly of wall 480 and form part of an imaginary cylinder aligned about axis 410. Cylindrical sections 481 define forwardly facing engagement surfaces 482.

Figure 36A:
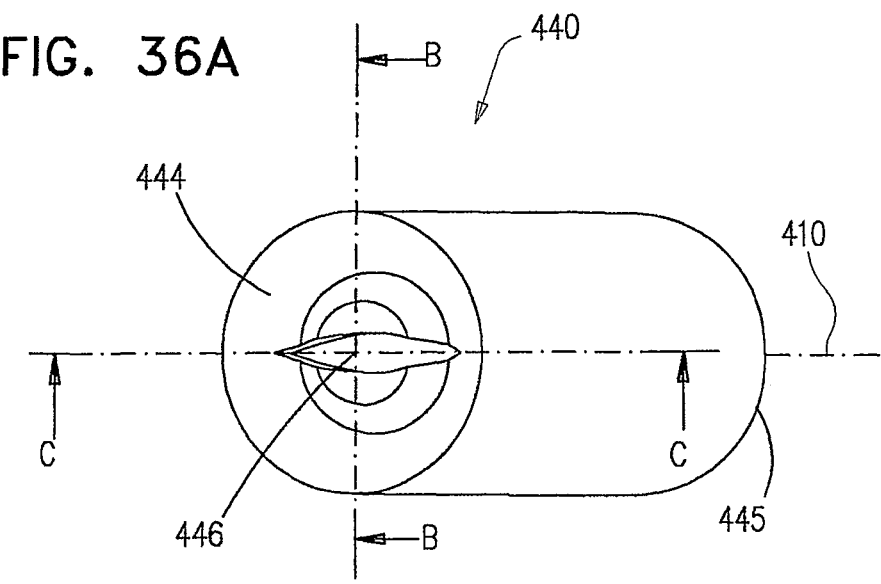
FIG. 36A is a simplified side view illustration of a resilient fluid flow conduit sealing (RFFCS) element forming part of the fluid flow connector of FIG. 31.
Figure 36B:
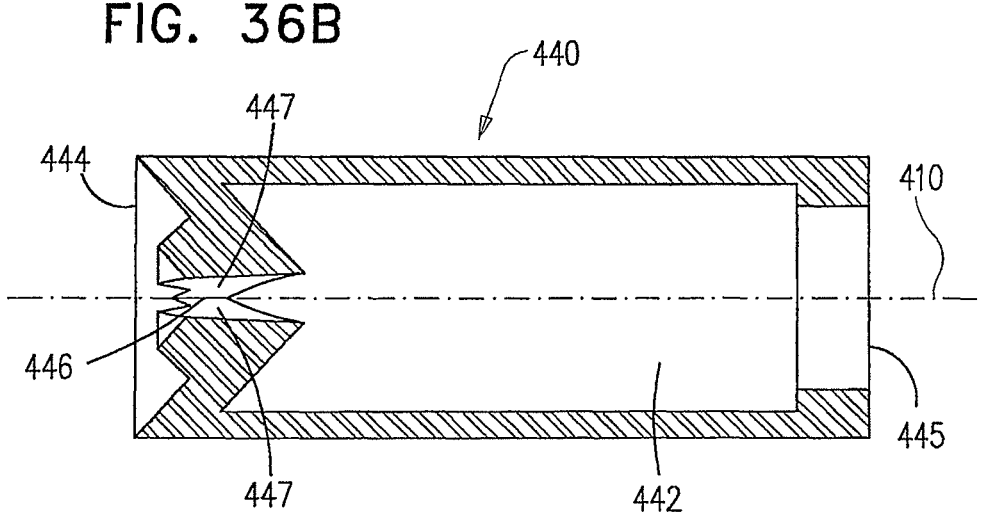
FIGS. 36B and 36C are simplified respective sectional illustrations of the resilient fluid flow conduit sealing (RFFCS) element, taken along mutually perpendicular section lines B-B and C-C in FIG. 36A.
Figure 36C:
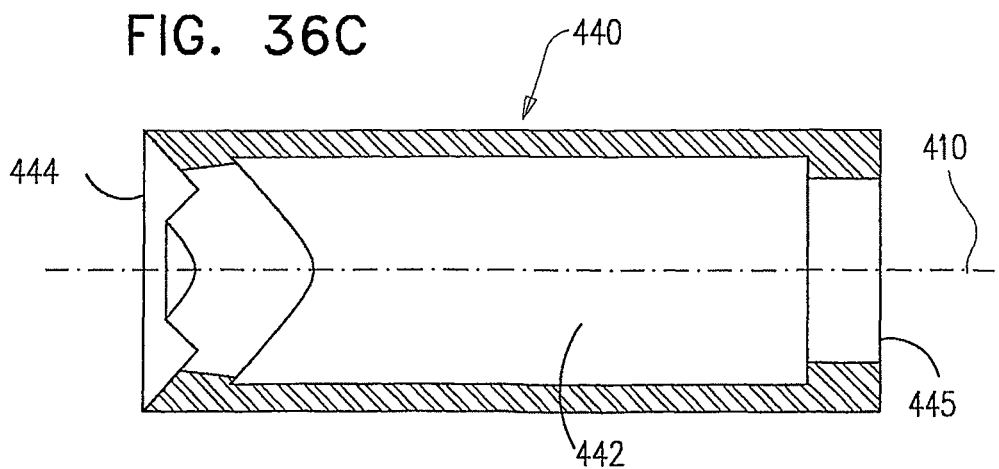

Reference is now made to FIGS. 36A-36C, which illustrate resilient fluid flow conduit sealing (RFFCS) element 440. As noted above, RFFCS element 440 is formed with an interior bore 442, and with a forward face 444 and a rearwardly facing sealing aperture 445.

The forward face 444 of the RFFCS element 440 is preferably formed with a selectably closable slit 446 extending along longitudinal axis 410. Selectably closable slit 446 is preferably formed with at least two slit wall portions 447 and preferably extends through forward face 444 along axis 410. As seen in FIGS. 36A & 36B, slit 446 is open when in an unstressed orientation.

Figure 37A:
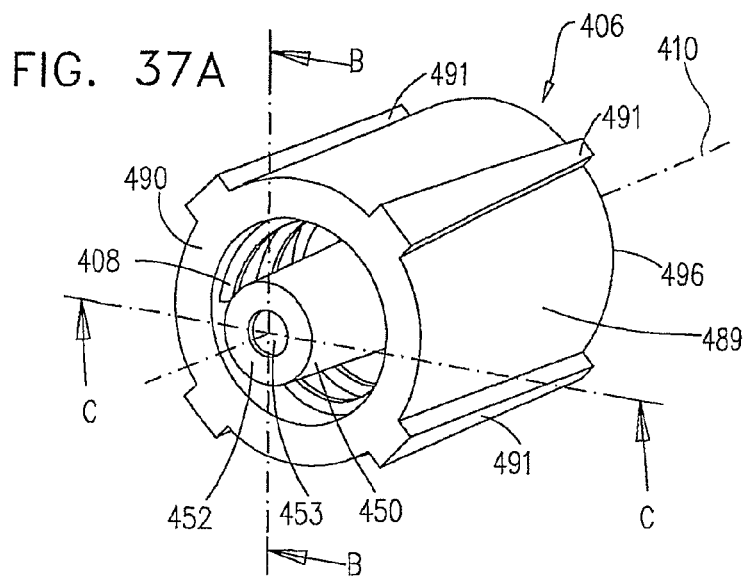
FIG. 37A is a simplified side view of a forward housing portion of the fluid flow connector of FIG. 31.
Figure 37B:
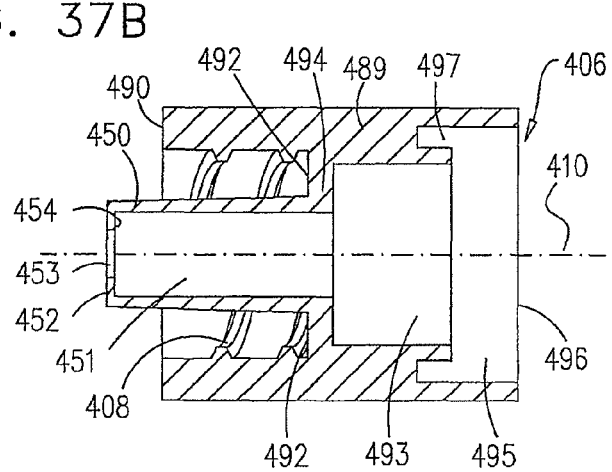
FIGS. 37B and 37C are simplified respective sectional illustrations of the forward housing portion, taken along mutually perpendicular section lines B-B and C-C in FIG. 37A.
Figure 37C:
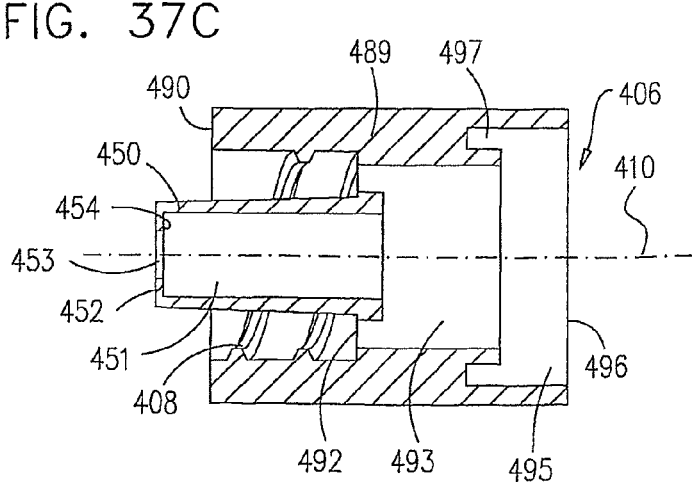
Figure 38A:
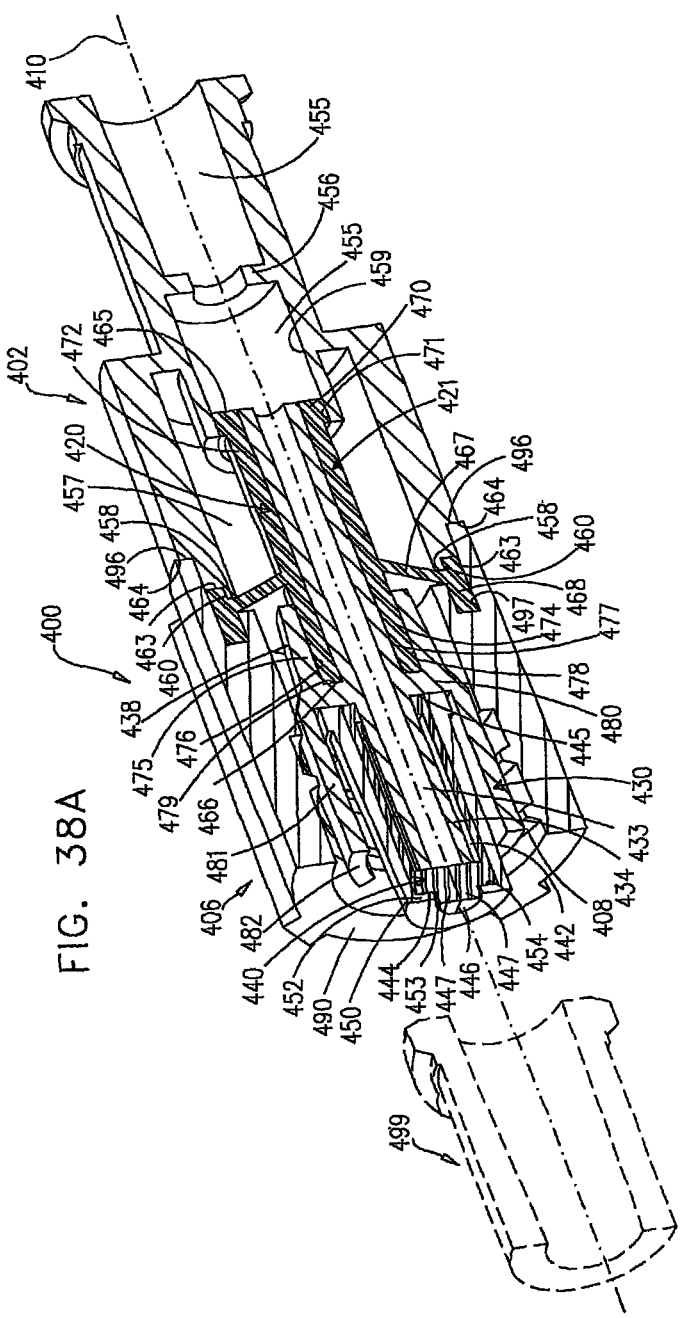
Figure 39A:
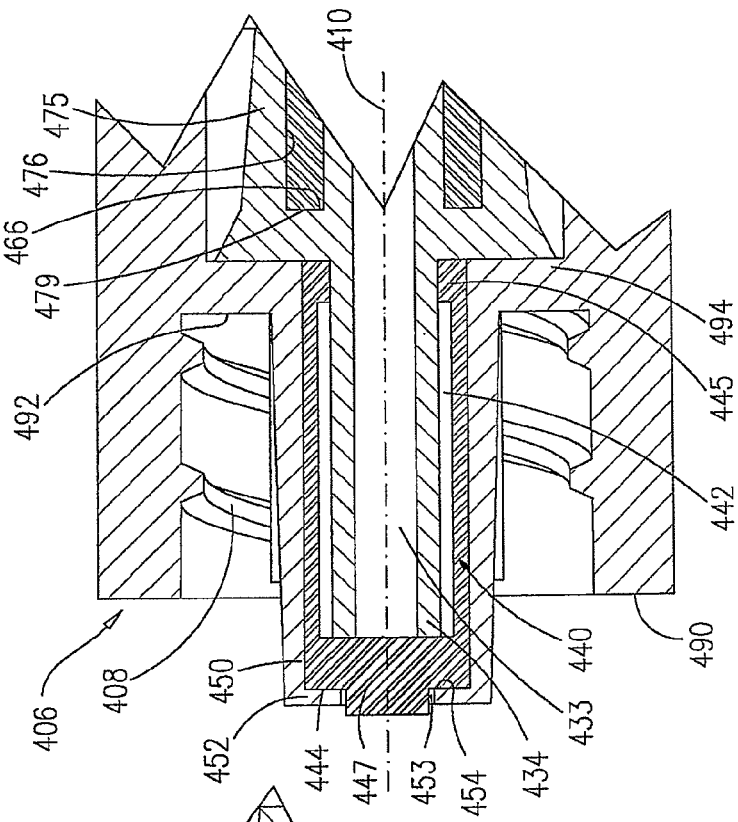
FIGS. 39A and 39B are simplified partial enlargements of respective FIGS. 38B and 38C.
Figure 39B:
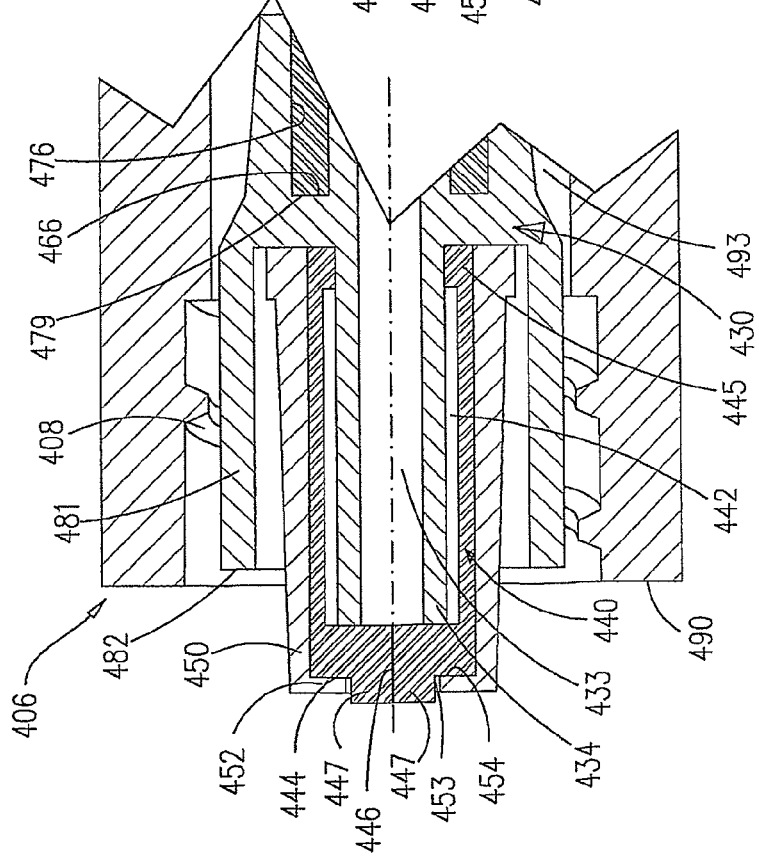

Reference is now made to FIGS. 37A, 37B and 37C, which illustrate the forward housing portion 406 (FIGS. 31-32B) of the fluid flow connector 400 of FIG. 31. Forward housing portion 406 preferably includes a generally cylindrical body 489 having a forwardmost face 490 and rearwardly tapered mutually spaced generally axial ribs 491 extending rearwardly from forwardmost face 490.

As seen in FIGS. 37A-37C, forward housing portion 406 is an integrally formed element which is generally symmetric about a longitudinal axis, such as axis 410 (FIGS. 31-32B), in most respects. As noted hereinabove with reference to FIGS. 31-32B, the forward housing portion 406 includes an internally-threaded portion 408 at a forward end thereof and a forward conduit 450 extending rearwardly therethrough along axis 410. Forward conduit 450 is preferably formed with an interior bore 451, and having a forward end 452. The forward end 452 is formed with a forwardly facing aperture 453 and a rearwardly facing surface 454.

Internally-threaded portion 408 terminates rearwardly at a circumferential shoulder 492 and communicates with a rearwardly extending generally circularly cylindrical internal bore 493. Forward conduit 450 is joined to the inwardly facing circularly cylindrical wall of bore 493 by a plurality of radially extending ribs 494, rearwardly of shoulder 492.

Forward housing portion 406 also includes a rearward conduit 495 which extends forwardly from a rearward face 496 of forward housing portion 406 along axis 410. As seen clearly in FIGS. 37B & 37C, rearward conduit 495 has an inner diameter greater than that of rearwardly extending generally circularly cylindrical internal bore 493, and rearwardly extending generally circularly cylindrical internal bore 493 extends partially into rearward conduit 495, defining a circumferential recess 497.

Reference is now made to FIGS. 38A, 38B, 38C, 39A and 39B, which are simplified sectional illustrations of the fluid flow connector 400 of FIG. 31 in a closed operative orientation, and to FIGS. 38D, 38E, 40A and 40B, which are simplified sectional illustrations of the fluid flow connector 400 of FIG. 31 in an open operative orientation in engagement with a female luer portion 499.

Referring initially specifically to FIGS. 38A, 38B, 38C, 39A and 39B, it is seen that RFFCB element 420 is maintained in a pre-tensioned state wherein generally circularly cylindrical mounting portion 468 is locked in place between rearward housing portion 402 and forward housing portion 406, which are welded together, as by ultrasonic welding. Specifically it is seen that rearward face 496 of forward housing portion 406 lies against ring 464 of rearward housing portion 402 and cylindrical mounting portion 468 is locked in a circumferential volume defined by circumferential recess 497 of forward housing portion 406, end 458 and surfaces 460 and 463 of rearward housing portion 402.

Forward portion 474 of RFFCB element 420 is seated in generally cylindrical recess 478 of elongate rigid fluid flow conduit and actuator element 430 such that forwardly facing edge 466 of RFFCB element 420 lies in engagement with rearwardly facing wall surface 479 of wall 480.

Axial pretensioning of RFFCB element 420 along axis 410 is achieved by axial pressure engagement of rearwardly facing wall surface 479 with forwardly facing edge 466 of RFFCB element 420 and by axial pressure engagement of forward part 434 of element 430 with selectably closable slit 446 of the RFFCS element 440. This arrangement stretches and thus tensions tensionable connecting portion 467, as seen from a consideration of FIGS. 38A-38C, 39A & 39B with FIGS. 34A & 34B.

Axial pressure engagement of forward part 434 of element 430 with selectably closable slit 446 of the RFFCS element 440 is operative to forwardly displace and tightly dispose the two slit wall portions 447 at least partially within forwardly facing aperture 453 and to squeeze the two slit wall portions 447 transversely to longitudinal axis 410, thereby closing slit 446.

Slidable sealing engagement is provided between radially outer surface 471 of rear portion 470 of RFFCB element 420 and inner facing surface 459 of rearward conduit 455. This sealing engagement preferably prevents fluid which enters the fluid flow connector via rearward conduit 455 from entering the volume within the forward conduit 457 lying rearward of connecting portion 467 and cylindrical mounting portion 468. Accordingly this volume is prevented from acting as a "dead space" which could undesirably retain such fluid.

Slidable sealing engagement is also provided between rearwardly facing sealing aperture 445 of RFFCS element 440 and exterior of forward part 434 of element 430.

It is appreciated that the fluid flow connector 400 in the state shown in FIGS. 38A-38C, 39A and 39B is capable of maintaining a pressurized fluid seal for pressurized fluid in rearward conduit 455 and in fluid conduit defining bore 433.

Reference is now made specifically to FIGS. 38D, 38E, 40A and 40B which are simplified sectional illustrations of the fluid flow connector 400 of FIG. 31 in an open operative orientation in engagement with a female luer portion 499.

It is seen that threaded engagement of the female luer portion 499 with the internally-threaded portion 408 causes elongate rigid fluid flow conduit and actuator element 430 to be rearwardly displaced. It is noted that rearwardly facing wall surface 479 of element 430 engages forwardly facing end 466 of RFFCB element 420, producing corresponding rearward displacement thereof along axis 410, resulting in increased tensioning of tensionable connecting portion 467 of RFFCB element 420.

Rearward displacement of element 430 along axis 410 produces disengagement of forward part 434 of element 430 from selectably closable slit 446 of the RFFCS element 440, allowing the two slit wall portions 447 to retract rearwardly of forwardly facing aperture 453 along axis 410 and transversely outward from longitudinal axis 410, thereby allowing the slit 446 to open.

Slidable sealing engagement continues to be provided between radially outer surface 471 of rear portion 470 of RFFCB element 420 and inner facing surface 459 of rearward conduit 455. This sealing engagement preferably prevents fluid which enters the fluid flow connector via rearward conduit 455 from entering the volume within the forward conduit 457 lying rearward of connecting portion 467 and cylindrical mounting portion 468. Accordingly this volume is prevented from acting as a "dead space" which could undesirably retain such fluid.

Slidable sealing engagement also continues to be provided between rearwardly facing sealing aperture 445 of RFFCS element 440 and exterior of forward part 434 of actuator element 430. This sealing engagement preferably prevents fluid which passes through bore 433 from entering the volume within interior bore 493 lying rearward of sealing ring 445. Accordingly this volume is prevented from acting as a "dead space" which could undesirably retain such fluid.

It is appreciated that the fluid flow connector 400, in the state shown in FIGS. 38D, 38E, 40A and 40B, provides a fluid flow connection for fluid supplied via rearward conduit 455 and fluid conduit defining bore 433, as by a male luer or a syringe, to female luer portion 499 via slit 446 and aperture 453.

Figure 41:
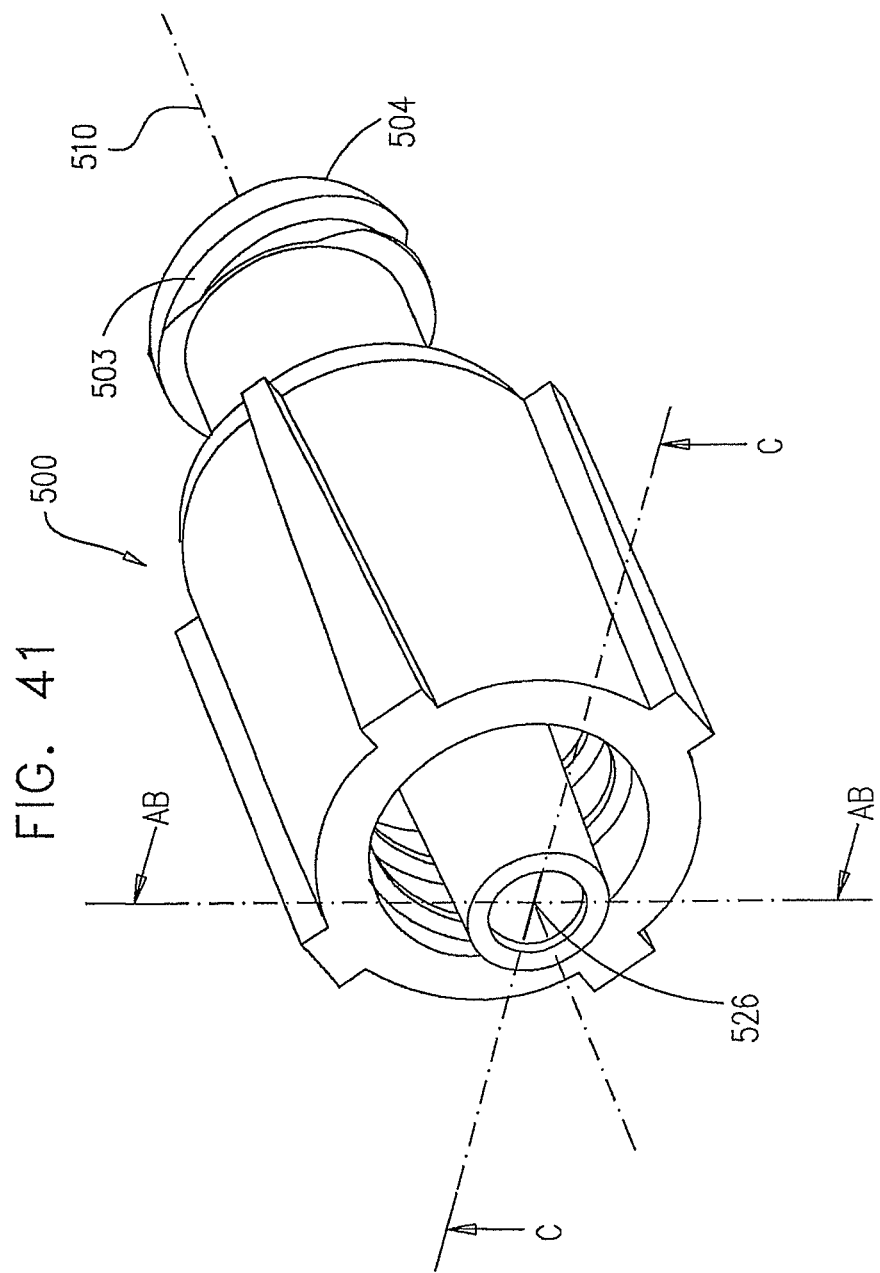
FIG. 41 is a simplified pictorial illustration of a fluid flow connector constructed and operative in accordance with yet another preferred embodiment of the invention.
Figure 42B:
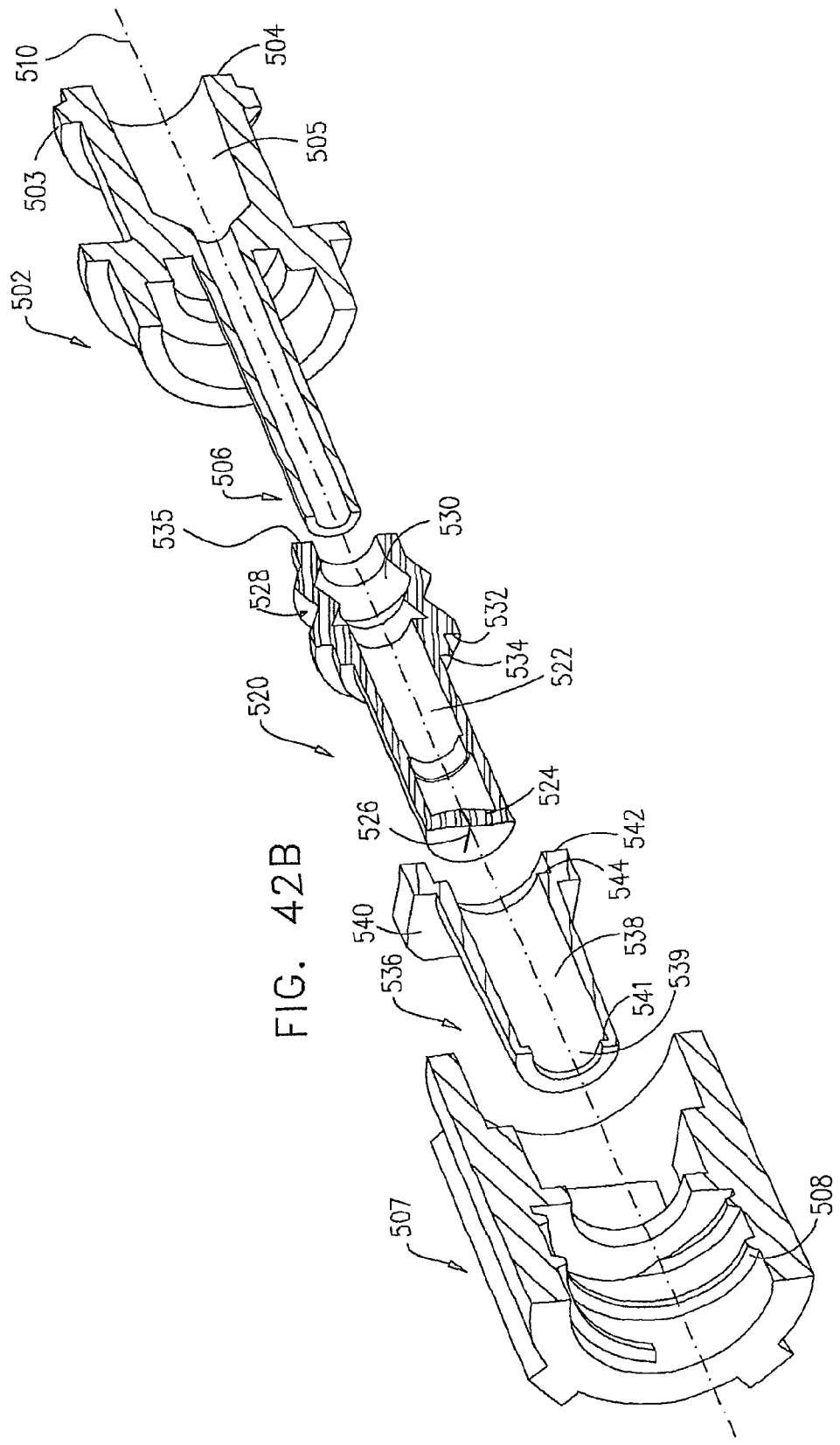

Reference is now made to FIG. 41, which is a simplified pictorial illustration of a fluid flow connector constructed and operative in accordance with yet another preferred embodiment of the invention, and to FIGS. 42A and 42B, which are simplified respective pictorial and sectional exploded view illustrations of the fluid flow connector of FIG. 41, FIG. 42B being taken along lines B-B in FIG. 42A.

As seen in FIGS. 41, 42A & 42B, there is provided a fluid flow connector 500 including a housing assembly including a rearward housing portion 502, having an externally-threaded portion 503 at a rearward end 504 thereof, a rearward conduit 505 extending forwardly from rearward end 504, an elongate fluid flow conduit portion 506 at a forward end thereof, and a forward housing portion 507, having an internally-threaded portion 508 at a forward end thereof. Rearward and forward housing portions 502 and 507 are preferably arranged along a common longitudinal axis 510 and are preferably heat welded together.

A resilient fluid flow conduit sealing and biasing (RFFCSB) element 520 disposed within the housing assembly and is arranged along longitudinal axis 510. The RFFCSB element 520 is formed with an elongate bore 522, and preferably has forward end wall 524 disposed forwardly of elongate bore 522.

The forward end wall 524 of the RFFCSB element 520 is preferably formed with a selectably openable slit 526 extending along longitudinal axis 510. As seen in FIG. 42B, disposed rearwardly of elongate bore 522 is a selectably compressible accordion type rearward portion 528 which defines an inner volume 530, communicating with elongate bore 522. An exterior surface of rearward portion 528 defines first and second concentric forwardly facing circumferential shoulders 532 and 534 and a rearwardly facing surface 535.

Elongate fluid flow conduit portion 506 is slidably disposed within elongate bore 522.

A forward conduit and actuator element 536 is provided for engagement with RFFCSB element 520. Forward conduit and actuator element 536 is preferably formed with an interior bore 538, a forwardly facing aperture 539 and a rearwardly facing generally square flange 540. A rearwardly facing shoulder 541 is defined by the periphery of aperture 539. First and second concentric rearwardly facing circumferential surfaces 542 and 544 are defined by flange 540 for engagement with corresponding first and second concentric forwardly facing circumferential shoulders 532 and 534 of RFFCSB element 520.

Forward conduit and actuator element 536 is arranged to be displaced rearwardly along longitudinal axis 510 by engagement therewith of a rearwardly facing end of a female luer (not shown), which may threadably engage internally-threaded portion 508 of forward housing portion 507.

Reference is now made to FIGS. 43A and 43B, which are a simplified respective side view and a sectional illustration of a preferred structure of rearward housing portion 502 of the fluid flow connector 500 of FIG. 41, FIG. 43B being taken along lines B-B in FIG. 43A. As seen in FIGS. 43A & 43B, rearward housing portion 502 is an integrally formed element which is symmetric about a longitudinal axis, such as axis 510 (FIGS. 41-42B).

As noted hereinabove with reference to FIGS. 41-42B, the rearward housing portion 502 includes an externally-threaded portion 503 at a rearward end 504 thereof, a rearward conduit 505 extending forwardly from rearward end 504 and an elongate fluid flow conduit portion 506 at a forward end thereof, extending forwardly from rearward conduit 505 along axis 510.

Rearward housing portion 502 also includes a forwardly facing circumferential recess 545 which surrounds part of elongate fluid flow conduit portion 506 about axis 510. Circumferential recess 545 includes a relatively narrow rearward portion 546 defining a forwardly facing circumferential surface 547 and a relatively wide forward portion 548.

Rearward housing portion 502 also includes a central flange 549 having a forwardly facing ring surface 550.

Reference is now made to FIGS. 44A, 44B and 44C, which illustrate resilient fluid flow conduit sealing and biasing (RFFCSB) element 520 forming part of the fluid flow connector 500 of FIGS. 41-42B in an unstressed orientation. As seen in FIGS. 44A-44C, RFFCSB element 520 is an integrally formed element, preferably formed of silicone rubber, which is symmetric about a longitudinal axis, such as axis 510 (FIGS. 41-42B), in all respects other than with respect to slit 526.

The RFFCSB element 520 preferably includes a generally elongate portion 560 at the center of which an elongate bore 522 is located along axis 510. Elongate bore 522 is formed with an integrally formed interior facing sealing ring 562 located intermediate along its length. As noted above, an exterior surface of selectably compressible accordion type rearward portion 528 defines first and second concentric forwardly facing circumferential shoulders 532 and 534 and a rearwardly facing surface 535. Elongate fluid flow conduit portion 506 is slidably and sealingly disposed within elongate bore 522 in engagement with sealing ring 562.

As noted above, the forward end wall 524 of the RFFCSB element 520 is preferably formed with a selectably openable slit 526 extending along longitudinal axis 510. The forward end wall 524 is preferably configured to define a rearwardly facing surface 564 having an elongate rearwardly facing ridge and a flat forwardly facing surface 566.

Figure 45A:
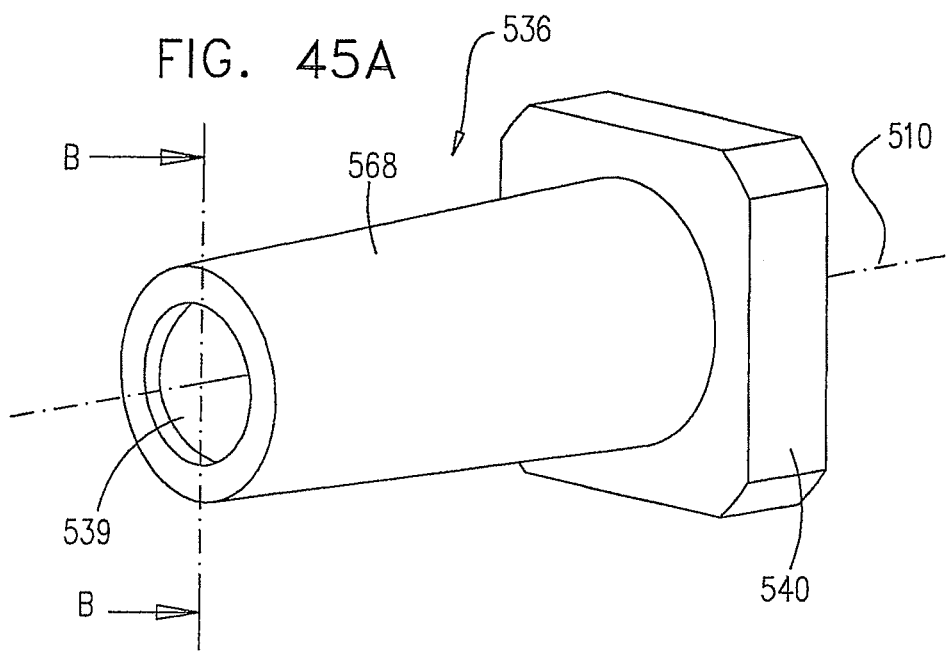
FIG. 45A is a simplified side view of a conduit and actuator element forming part of the fluid flow connector of FIG. 41.
Figure 45B:
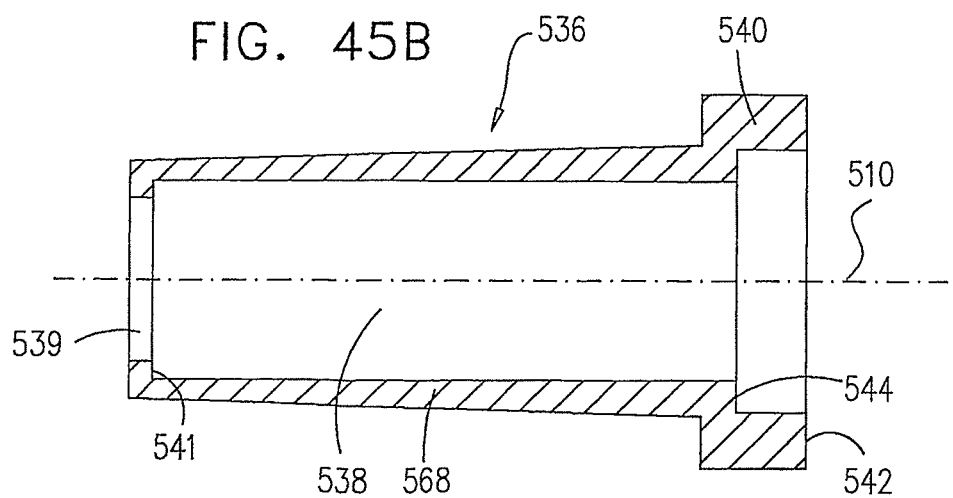
FIG. 45B is a simplified respective sectional illustration of the conduit and actuator element, taken along lines B-B in FIG. 45A.

Reference is now made to FIGS. 45A and 45B, which illustrate forward conduit and actuator element 536, forming part of the fluid flow connector 500. Forward conduit and actuator element 536 is preferably formed with a generally truncated conical forward section 568, including interior bore 538 and forwardly facing aperture 539, and a rearwardly facing, generally square flange 540 having rounded corners. A rearwardly facing shoulder 541 is defined by the periphery of aperture 539. First and second concentric rearwardly facing circumferential surfaces 542 and 544 are defined by flange 540 for engagement with corresponding first and second concentric forwardly facing circumferential shoulders 532 and 534 of RFFCSB element 520.

Figure 46A:
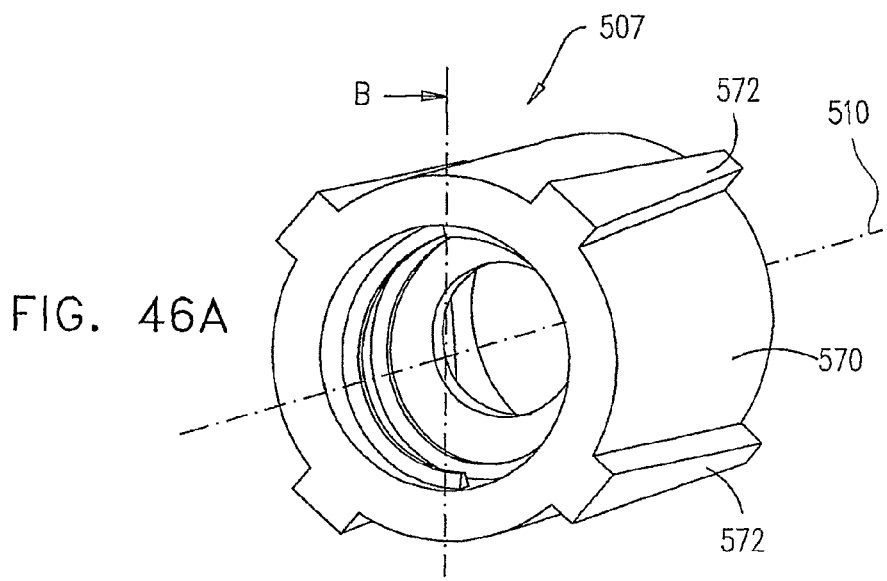
FIG. 46A is a simplified side view of a forward housing portion of the fluid flow connector of FIG. 41.
Figure 46B:
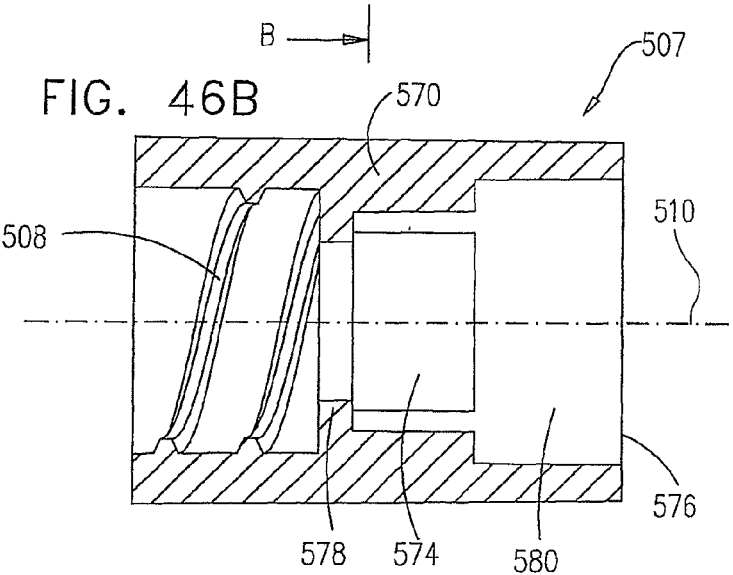
FIG. 46B is a simplified sectional illustration of the forward housing portion, taken along lines B-B in FIG. 46A.
Figure 46C:
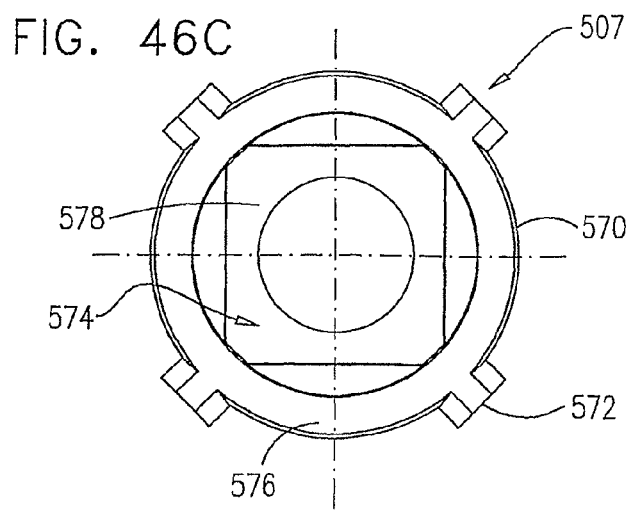
FIG. 46C is a simplified illustration of a rearwardly facing recess formed in the forward housing portion.
Figure 47A:
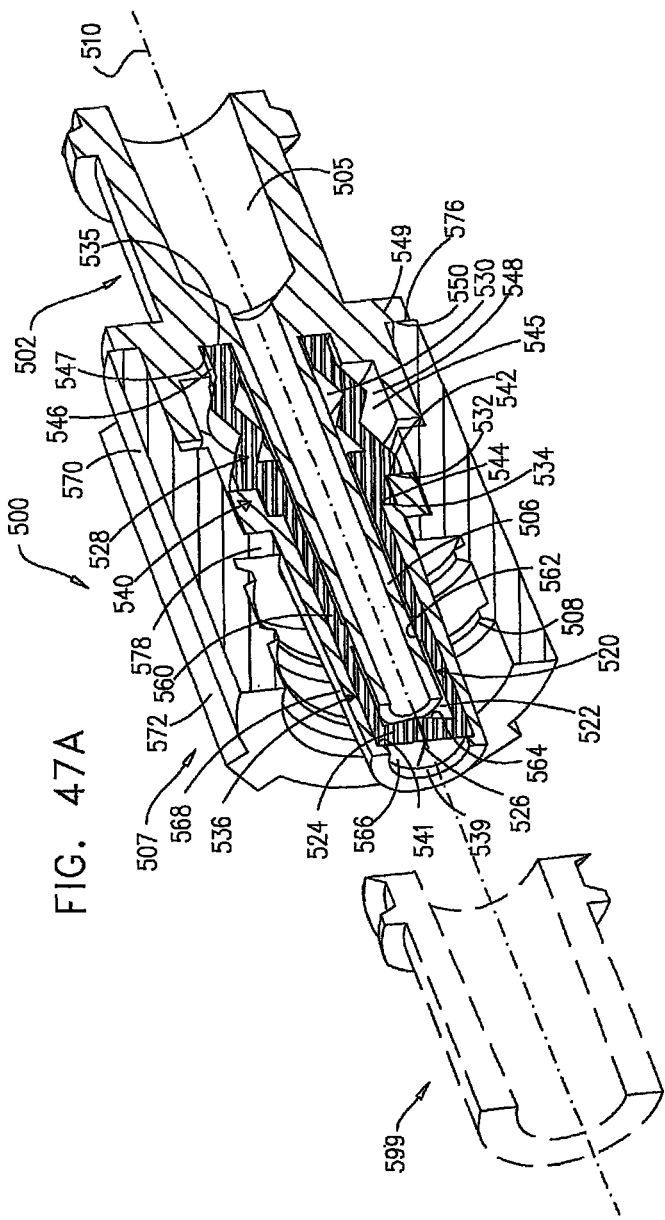

Reference is now made to FIGS. 46A-46C, which illustrate forward housing portion 507 (FIGS. 41-42B) of the fluid flow connector 500. Forward housing portion 507 preferably includes a generally cylindrical body 570 having rearwardly tapered mutually spaced generally axial ribs 572.

As seen in FIGS. 46A-46C, forward housing portion 507 is an integrally formed element which is generally symmetric about a longitudinal axis, such as axis 510 (FIGS. 41-42B), in all respects other than with respect to generally axial ribs 572, and a generally square recess 574 having rounded corners and arranged to accommodate generally square flange 540 (FIGS. 45A-45B). As noted hereinabove with reference to FIGS. 41-42B, the forward housing portion 507 includes an internally-threaded portion 508, at a forward end thereof, and a rearward end surface 576.

Internally-threaded portion 508 terminates rearwardly at a circumferential shoulder 578 and communicates with rearwardly extending generally square recess 574.

Forward housing portion 507 also includes a rearward conduit 580 which extends forwardly from rearward end surface 576 of forward housing portion 507 along axis 510. As seen clearly in FIG. 46B, rearward conduit 580 has an inner diameter greater than the maximum diameter of recess 574.

Reference is now made to FIGS. 47A, 47B, 47C, 49A and 49B, which are simplified sectional illustrations of the fluid flow connector 500 in a closed operative orientation, and to FIGS. 48A, 48B, 50A and 50B, which are simplified sectional illustrations of the fluid flow connector 500 in an open operative orientation in engagement with a female luer portion 599.

Referring initially specifically to FIGS. 47A, 47B, 47C, 49A and 49B, it is seen that RFFCSB element 520 is maintained in a non-stressed state and is held in place between rearward housing portion 502 and forward conduit and actuator element 536, which is in turn retained against forward movement by forward housing portion 507. Forward housing portion 507 and rearward housing portion 502 are welded together, as by ultrasonic welding. Specifically it is seen that rearward end surface 576 of forward housing portion 507 lies against forwardly facing ring surface 550 of central flange 549 of rearward housing portion 502.

It is also seen that rearwardly facing surface 535 of RFFCSB element 520 is seated against forwardly facing circumferential surface 547 of rearward housing portion 502, that shoulders 532 and 534 of RFFCSB element 520 engage corresponding surfaces 542 and 544 of forward conduit and actuator element 536 and that the peripheral edges of flat forwardly facing surface 566 of RFFCSB element engage rearwardly facing shoulder 541 of forward conduit and actuator element 536.

Slidable sealing engagement is provided between sealing ring 562 of RFFCSB element 520 and the exterior surface of elongate fluid flow conduit portion 506 of rearward housing portion 502.

It is appreciated that the fluid flow connector 500 in the state shown in FIGS. 47A-47C, 49A and 49B is capable of maintaining a pressurized fluid seal for pressurized fluid in elongate fluid flow conduit portion 506, rearward conduit 505 of rearward housing portion 502 and a volume inside RFFCSB element 520 forward of sealing ring 562. The pressure maintaining capability of the RFFCSB element 520 is enhanced by the particular configuration of the forward end wall 524, and particularly of the configuration of the rearwardly facing surface 564.

Reference is now made specifically to FIGS. 48A, 48B, 50A and 50B which are simplified sectional illustrations, of the fluid flow connector 500 in an open operative orientation in engagement with a female luer portion 599.

It is seen that threaded engagement of the female luer portion 599 with the internally-threaded portion 508 causes forward conduit and actuator element 536 to be rearwardly displaced. It is noted that circumferential surfaces 542 and 544 of element 536 engage shoulders 532 and 534 of RFFCSB element 520, and that rearwardly facing shoulder 541 engages the peripheral edges of flat forwardly facing surface 566 of RFFCSB element 520, a combination of which produces corresponding rearward displacement of the generally elongate portion 560 of RFFCSB element 520.

Rearward displacement of the generally elongate portion 560 of RFFCSB element 520 is operative to rearwardly compress selectably compressible accordion type rearward portion 528 of RFFCSB element 520 against forwardly facing circumferential surface 547 of rearward housing portion 502.

It is seen that rearward displacement of the generally elongate portion 560 of RFFCSB element 520 causes elongate fluid flow conduit portion 506 of rearward housing portion 502 to extend through selectably openable slit 526, and to at least partially extend through forwardly facing aperture 539 of element 536, thereby stretchingly displacing forward end wall 524 forwardly and radially outward from slit 526 to a longitudinal orientation, tightly and circumferentially disposed between the exterior surface of elongate fluid flow conduit portion 506 and aperture 539, thereby opening slit 526.

Slidable sealing engagement continues to be provided between sealing ring 562 of RFFCSB element 520 and the exterior surface of elongate fluid flow conduit portion 506 of rearward housing portion 502.

It is appreciated that the fluid flow connector 500, in the state shown in FIGS. 48A, 48B, 50A and 50B, provides a fluid flow connection for fluid supplied via rearward conduit 505 and fluid flow conduit portion 506, as by a male luer or a syringe, to female luer portion 599 via slit 526 and aperture 539. It is a particular feature of this embodiment that the volume of the fluid flow pathway of the fluid flow connector 500 does not substantially change upon connection to or disconnection from female luer portion 599, thus providing a generally neutral fluid displacement characteristic.

Reference is now made to FIG. 51, which is a simplified pictorial illustration of a fluid flow connector constructed and operative in accordance with yet another preferred embodiment of the invention, and to FIGS. 52A and 52B, which are simplified respective pictorial and sectional exploded view illustrations of the fluid flow connector of FIG. 51, FIG. 52B being taken along lines B-B in FIG. 52A.

As seen in FIGS. 51, 52A & 52B, there is provided a fluid flow connector 600 including a housing assembly including a rearward housing portion 602, having an externally-threaded portion 603 at a rearward end 604 thereof, and a forward housing portion 606 having an internally-threaded portion 608 at a forward end thereof. Rearward and forward housing portions 602 and 606 are preferably arranged along a common longitudinal axis 610 and are preferably heat welded together.

The rearward housing portion 602 is preferably formed with a rearward conduit 611 extending forwardly of rearward end 604 thereof and an elongate generally circularly cylindrical inner rod 612 at a forward end thereof. The elongate generally circularly cylindrical inner rod 612 is preferably formed with a rearward portion 614 having a rearwardly facing end 615 and a forward portion 616 having a forwardly facing end portion 617.

As seen in FIGS. 52A and 52B, the elongate generally circularly cylindrical inner rod 612 is also preferably formed with at least two elongate longitudinal recesses 618 extending from rearwardly facing end 615 to slightly rearward of forwardly facing end portion 617.

A resilient selectably compressible biasing (RSCB) element 620 is disposed within the housing assembly and is arranged along longitudinal axis 610.

A forward conduit and actuator element 636 is provided for engagement with RSCB element 620 and is preferably formed with an interior bore 637 having an inner facing surface 638, a forwardly facing edge 639 and a rearwardly facing flange 640. A rearwardly facing circumferential surface 642 is defined by flange 640 for engagement with RSCB element 620.

Forward conduit and actuator element 636 is arranged to be displaced rearwardly along longitudinal axis 610 by engagement therewith of a rearwardly facing end of a female luer (not shown), which may threadably engage internally-threaded portion 608 of forward housing portion 606.

Figure 53A:
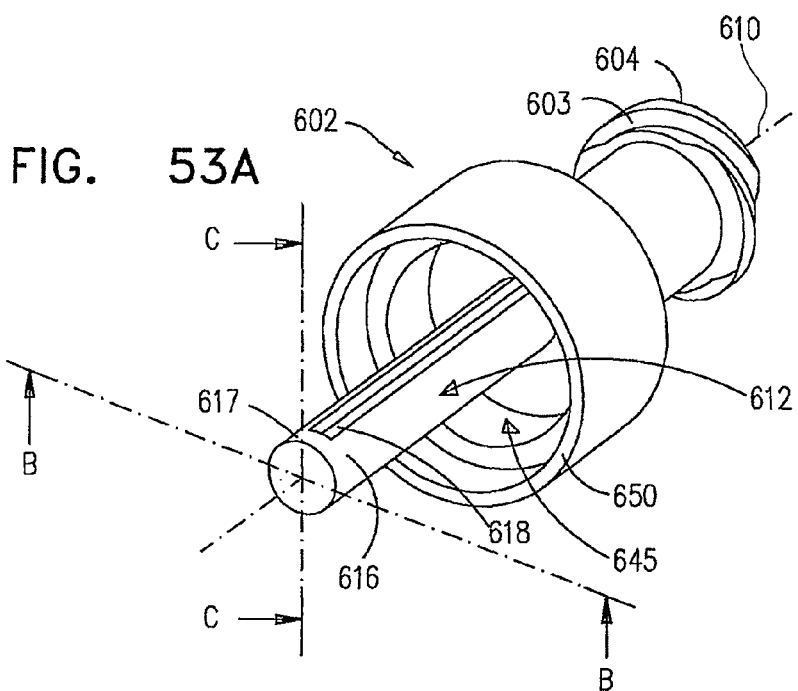
FIG. 53A is a simplified side view of a rearward housing portion, forming part of the fluid flow connector of FIG. 51.
Figure 53B:
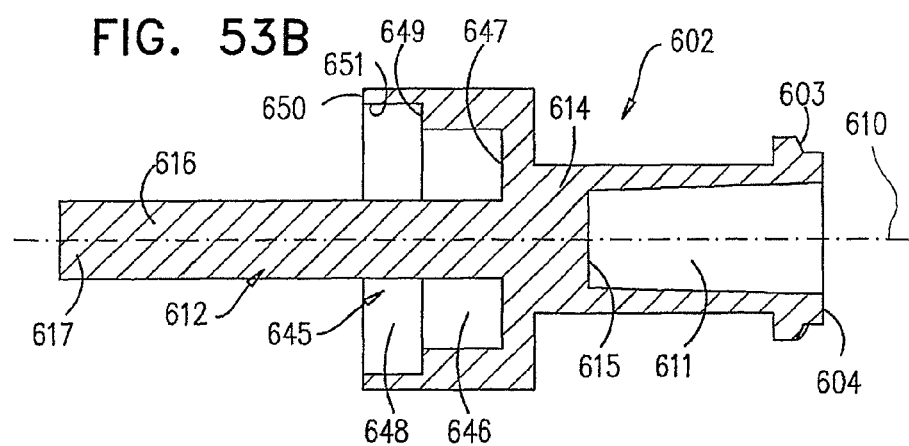
FIGS. 53B and 53C are simplified respective sectional illustrations of the rearward housing portion, taken along mutually perpendicular section lines B-B and C-C in FIG. 53A.
Figure 53C:
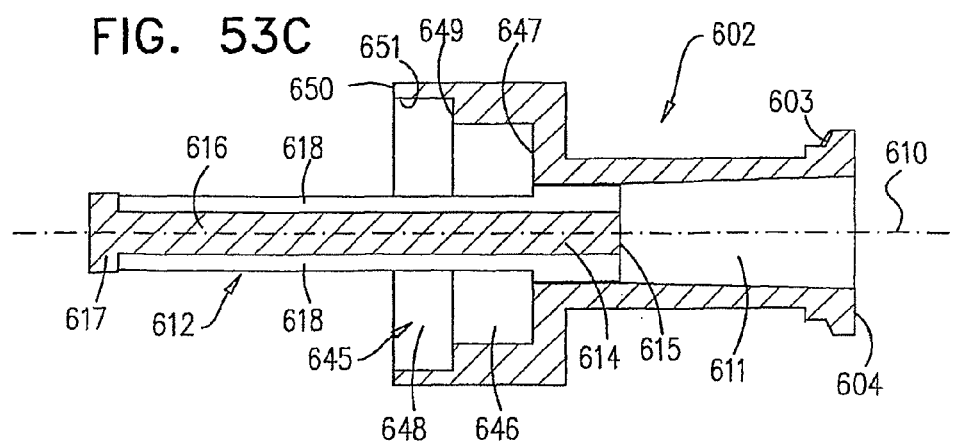

Reference is now made to FIGS. 53A, 53B and 53C which are simplified respective side view and sectional illustrations of a preferred structure of rearward housing portion 602 of the fluid flow connector 600 of FIG. 51. As seen in FIGS. 53A, 53B and 53C, rearward housing portion 602 is an integrally formed element which is generally symmetric about a longitudinal axis, such as axis 610 (FIGS. 51-52B), in all respects other than with respect to elongate longitudinal recesses 618.

As noted hereinabove with reference to FIGS. 51-52B, the rearward housing portion 602 includes an externally-threaded portion 603 at a rearward end 604 thereof, a rearward conduit 611 extending forwardly of rearward end 604 thereof, and an elongate generally circularly cylindrical inner rod 612 at a forward end thereof.

The inner rod 612 is preferably formed with a rearward portion 614 having a rearwardly facing end 615 and a forward portion 616 having a forwardly facing end portion 617, rearward portion 614 having a circular cross section of a diameter greater than that of the cross section of forward portion 616.

It is clearly seen in FIG. 53C that the elongate generally circularly cylindrical inner rod 612 is preferably formed with at least two elongate longitudinal recesses 618 extending from rearwardly facing end 615 to slightly rearward of forwardly facing end portion 617.

Rearward housing portion 602 also includes a forwardly facing circumferential recess 645 which surrounds part of elongate generally circularly cylindrical inner rod 612 about axis 610. Circumferential recess 645 includes a relatively narrow rearward portion 646 defining a first forwardly facing circumferential surface 647, and a relatively wide forward portion 648 defining a second forwardly facing circumferential surface 649. Rearward housing portion 602 also includes a forwardly facing ring surface 650, and an inner cylindrical wall surface 651 intermediate surfaces 649 and 650.

Figure 54A:
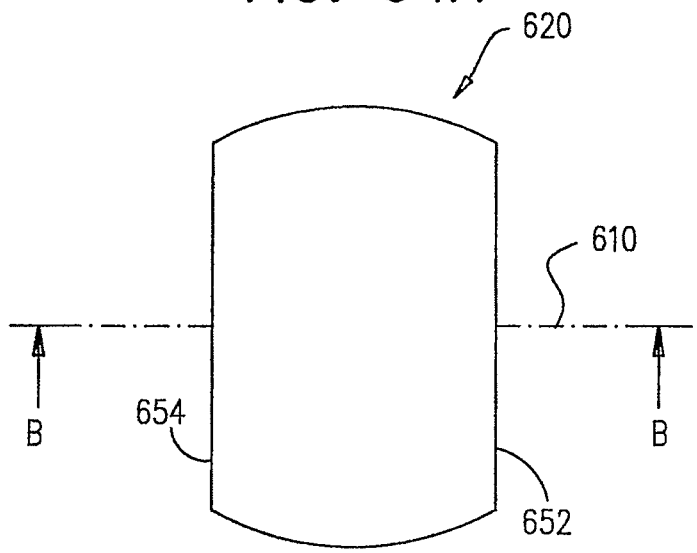
FIG. 54A is a simplified side view of a resilient selectably compressible biasing (RSCB) element forming part of the fluid flow connector of FIG. 51.
Figure 54B:
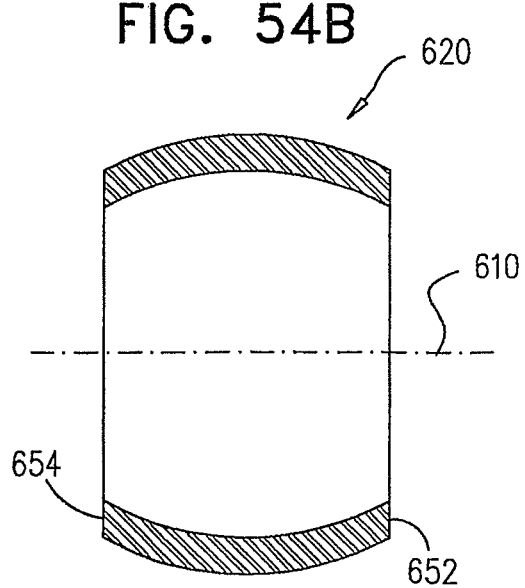
FIG. 54B is a simplified respective sectional illustration of the resilient selectably compressible biasing (RSCB) element, taken along lines B-B in FIG. 54A.

Reference is now made to FIGS. 54A and 54B, which illustrate resilient selectably compressible biasing (RSCB) element 620 forming part of the fluid flow connector 600 of FIGS. 51-52B in an uncompressed orientation. As seen in FIGS. 54A and 54B, RSCB element 620 is an integrally formed element, preferably formed of silicone rubber, which is symmetric about a longitudinal axis, such as axis 610 (FIGS. 51-52B). RSCB element 620 is preferably formed with a rearward end surface 652 and a forward end surface 654.

Figure 55A:
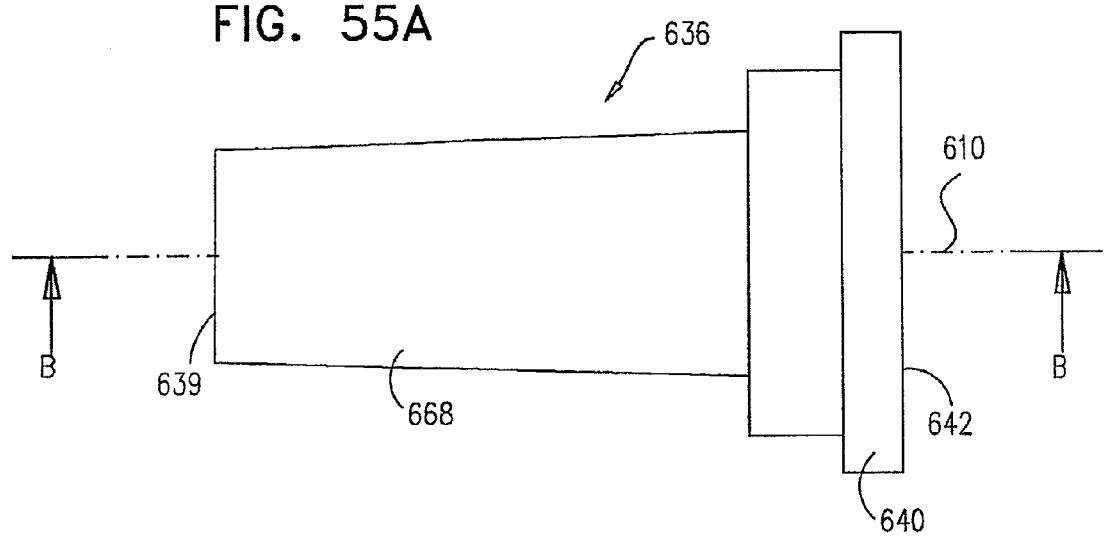
FIG. 55A is a simplified side view of a conduit and actuator element forming part of the fluid flow connector of FIG. 51.
Figure 55B:
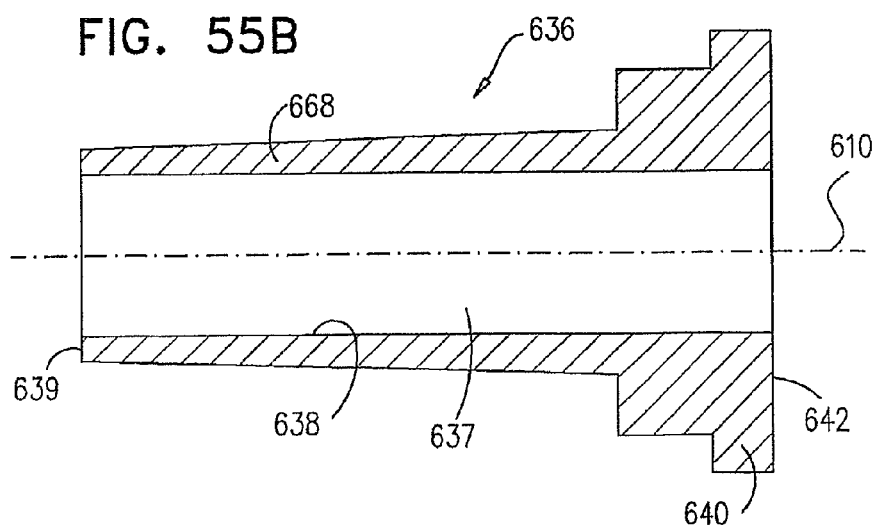
FIG. 55B is a simplified respective sectional illustration of the conduit and actuator element, taken along lines B-B in FIG. 55A.

Reference is now made to FIGS. 55A and 55B, which illustrate forward conduit and actuator element 636, forming part of the fluid flow connector 600. Forward conduit and actuator element 636 is preferably formed with a generally truncated conical forward section 668 and includes interior bore 637 having inner facing surface 638, forwardly facing edge 639, and a rearwardly facing flange 640. A rearwardly facing circumferential surface 642 is defined by flange 640 for engagement with RSCB element 620.

Figure 56A:
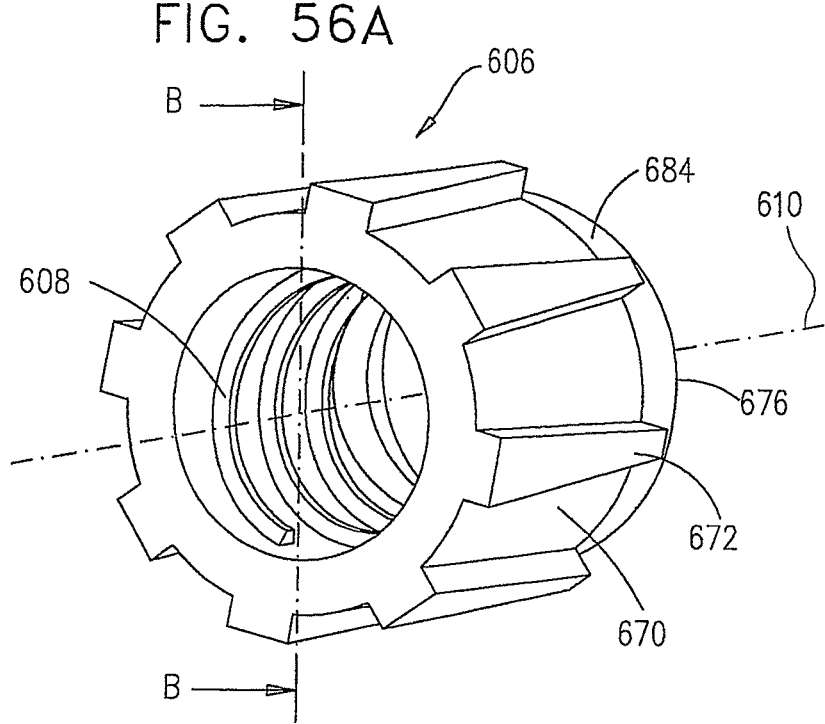
FIG. 56A is a simplified side view of a forward housing portion of the fluid flow connector of FIG. 51.
Figure 56B:
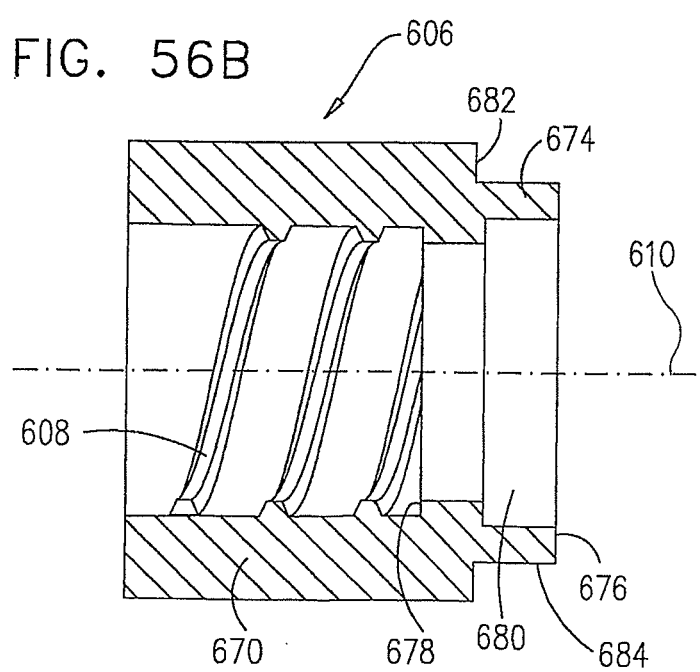
FIG. 56B is a simplified respective sectional illustration of the forward housing portion, taken along lines B-B in FIG. 56A.

Reference is now made to FIGS. 56A & 56B, which illustrate forward housing portion 606 (FIGS. 51-52B) of the fluid flow connector 600. Forward housing portion 606 preferably includes a generally cylindrical forward body portion 670 having rearwardly tapered mutually spaced generally axial ribs 672, and a generally cylindrical rearward body portion 674.

As seen in FIGS. 56A & 56B, forward housing portion 606 is an integrally formed element which is generally symmetric about a longitudinal axis, such as axis 610 (FIGS. 51-52B), in all respects other than with respect to generally axial ribs 672. As noted hereinabove with reference to FIGS. 51-52B, the forward housing portion 606 includes an internally-threaded portion 608 at a forward end thereof and a rearward end surface 676. Internally-threaded portion 608 terminates rearwardly at a circumferential shoulder 678.

Forward housing portion 606 also includes a rearward conduit 680 which extends forwardly from rearward end surface 676 of forward housing portion 606 along axis 610.

As seen clearly in FIGS. 56A & 56B, rearward body portion 674 has an exterior diameter lesser than that of forward body portion 670, thereby defining a rearwardly facing circumferential shoulder 682, and an exterior cylindrical wall surface 684.

Reference is now made to FIGS. 57A, 57B, 57C, 59A and 59B, which are simplified sectional illustrations of the fluid flow connector 600 in a closed operative orientation, and to FIGS. 58A, 58B, 60A and 60B, which are simplified sectional illustrations of the fluid flow connector 600 in an open operative orientation in engagement with a female luer portion 699.

Referring initially specifically to FIGS. 57A, 57B, 57C, 59A and 59B, it is seen that RSCB element 620 is maintained in a non-compressed state and is held in place between rearward housing portion 602 and forward conduit and actuator element 636, which is in turn retained against forward movement by forward housing portion 606. Forward housing portion 606 and rearward housing portion 602 are welded together, as by ultrasonic welding.

Figure 57A:
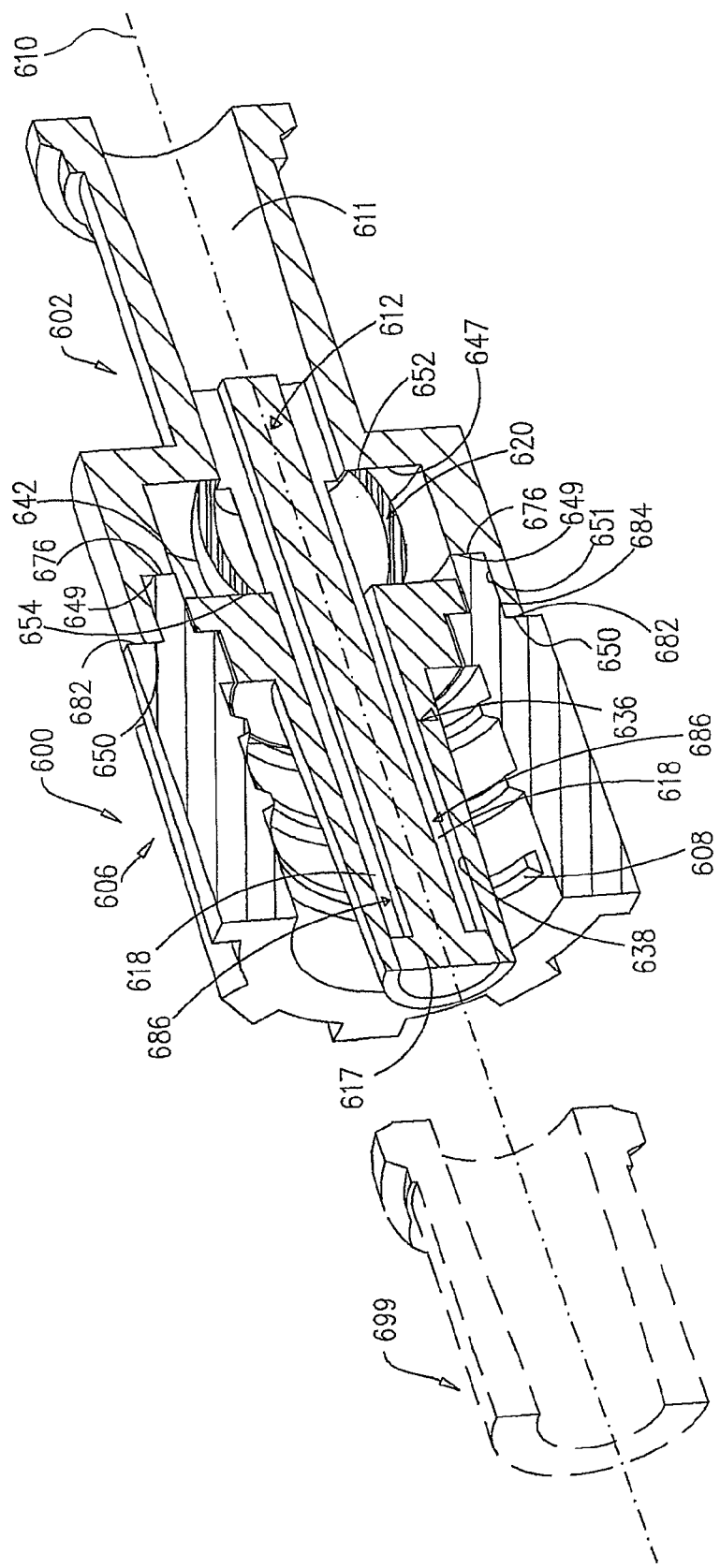

As seen clearly in FIGS. 57A-57C, rearward end surface 676 of forward housing portion 606 lies against forwardly facing circumferential surface 649 of rearward housing portion 602, exterior cylindrical wall surface 684 of forward housing portion 606 lies against inner cylindrical wall surface 651 of rearward housing portion 602, and that rearwardly facing circumferential shoulder 682 of forward housing portion 606 lies against forwardly facing ring surface 650 of rearward housing portion 602.

It is also seen in FIGS. 57A-57C that rearward end surface 652 of RSCB element 620 is seated against forwardly facing circumferential surface 647 of rearward housing portion 602, and that forward end surface 654 of RSCB element 620 engages rearwardly facing circumferential surface 642 of forward conduit and actuator element 636.

As seen clearly in FIGS. 57A & 57B, the at least two elongate longitudinal recesses 618 of inner rod 612 and the inner facing surface 638 of interior bore 637 of forward conduit and actuator element 636 define at least two longitudinal fluid flow conduits 686 therebetween. Forward sealing of longitudinal fluid flow conduits 686 is provided by sealing engagement of forwardly facing end portion 617 of cylindrical inner rod 612 with the inner facing surface 638 of interior bore 637 of forward conduit and actuator element 636.

It is appreciated that the fluid flow connector 600 in the state shown in FIGS. 57A, 57B, 57C, 59A and 59B is capable of maintaining a pressurized fluid seal for pressurized fluid in longitudinal fluid flow conduits 686 and rearward conduit 611 of rearward housing portion 602.

Reference is now made specifically to FIGS. 58A, 58B, 60A and 60B which are simplified sectional illustrations of the fluid flow connector 600 in an open operative orientation in engagement with a female luer portion 699.

It is seen that threaded engagement of the female luer portion 699 with the internally-threaded portion 608 causes forward conduit and actuator element 636 to be rearwardly displaced. It is noted that forward end surface 654 of RSCB element 620 is engaged by rearwardly facing circumferential surface 642 of element 636, rearward displacement of which is operative to rearwardly compress RSCB element 620 against forwardly facing circumferential surface 647 of rearward housing portion 602.

It is seen that rearward displacement of forward conduit and actuator element 636 causes inner facing surface 638 of interior bore 637 to move rearwardly out of engagement with forwardly facing end portion 617 of cylindrical inner rod 612, thereby allowing fluid communication between fluid flow conduits 686 and female luer portion 699.

It is appreciated that the fluid flow connector 600, in the state shown in FIGS. 58A, 58B, 60A and 60B, provides a fluid flow connection for fluid supplied via rearward conduit 611 and fluid flow conduits 686, as by a male luer or a syringe, to female luer portion 699.

Figure 61:
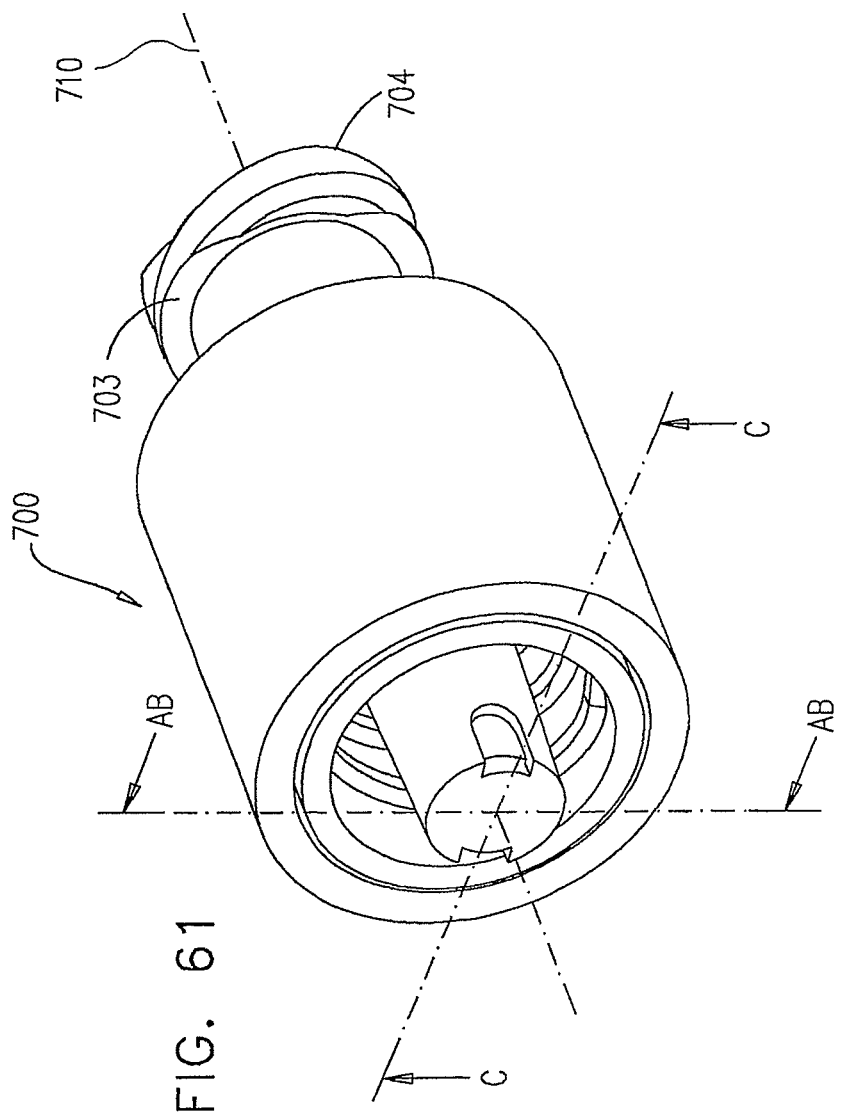
FIG. 61 is a simplified pictorial illustration of a fluid flow connector constructed and operative in accordance with yet another preferred embodiment of the invention.
Figure 62A:
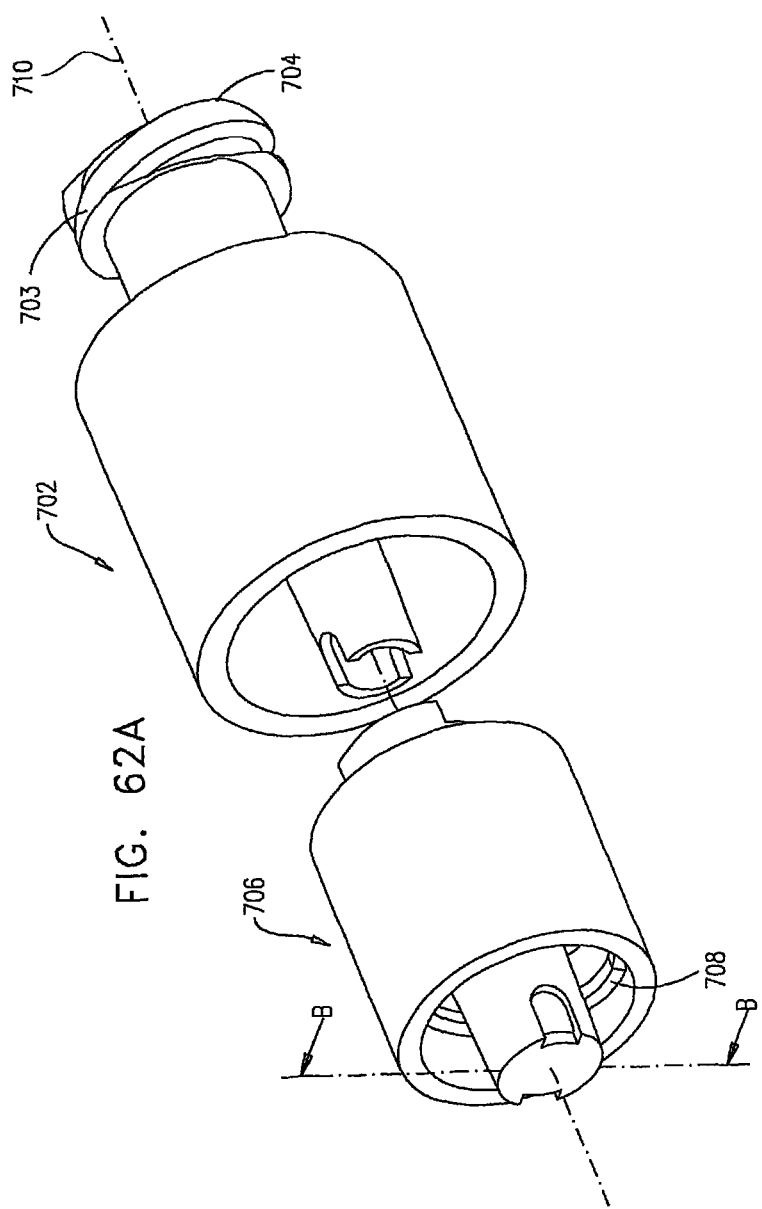
Figure 63A:
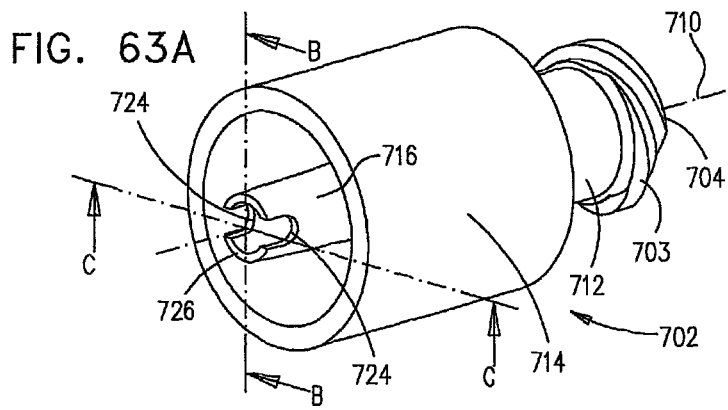
FIG. 63A is a simplified side view of a rearward housing portion, forming part of the fluid flow connector of FIG. 61.
Figure 63B:
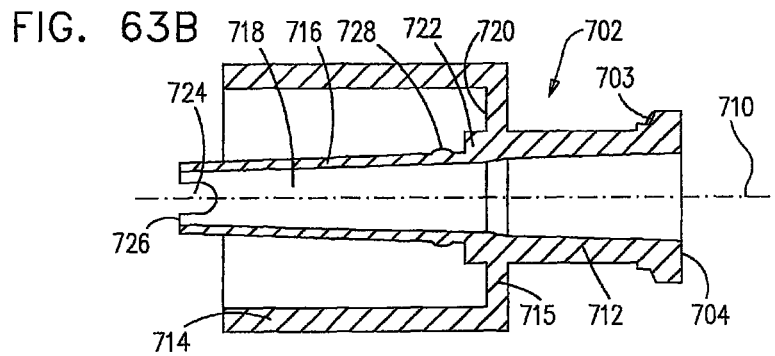
FIGS. 63B and 63C are simplified respective sectional illustrations of the rearward housing portion, taken along mutually perpendicular section lines B-B and C-C in FIG. 63A.
Figure 63C:
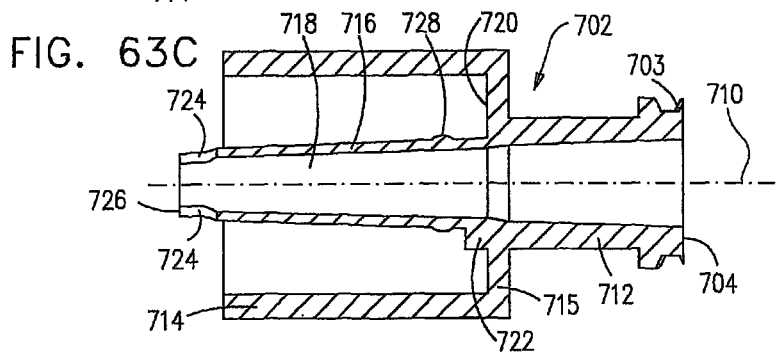
Figure 63D:
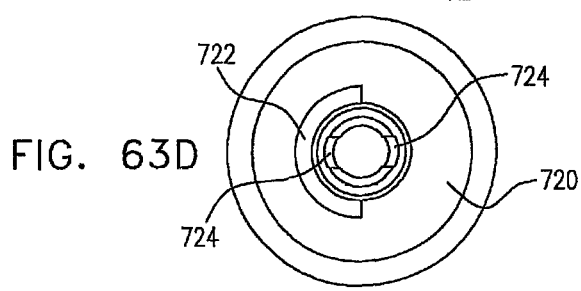
FIG. 63D is a simplified rearwardly facing end view of the rearward housing portion, forming part of the fluid flow connector of FIG. 61.
Figure 64A:
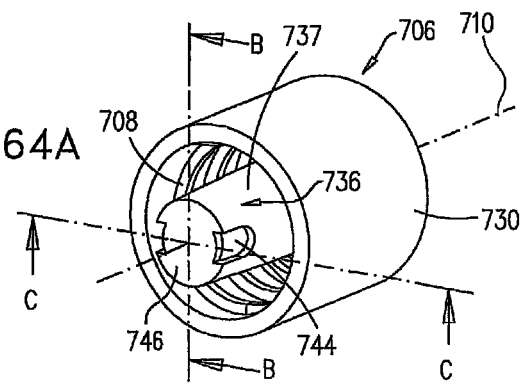
FIG. 64A is a simplified side view of a forward housing portion, forming part of the fluid flow connector of FIG. 61.
Figure 64B:
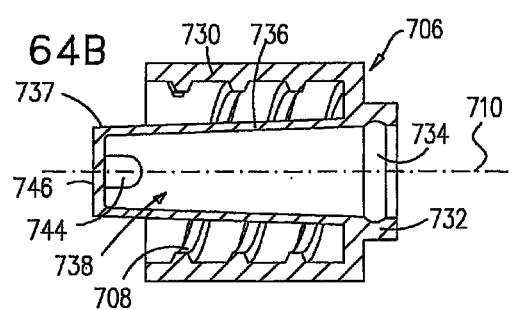
FIGS. 64B and 64C are simplified respective sectional illustrations of the forward housing portion, taken along mutually perpendicular section lines B-B and C-C in FIG. 64A.
Figure 64C:
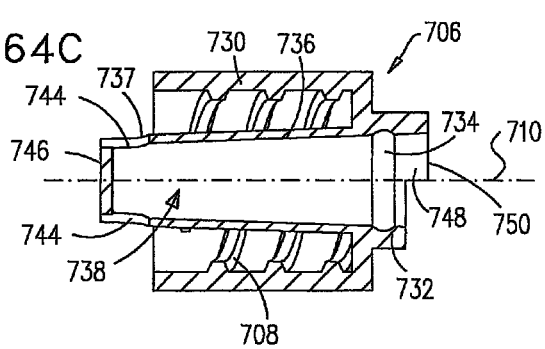
Figure 64D:
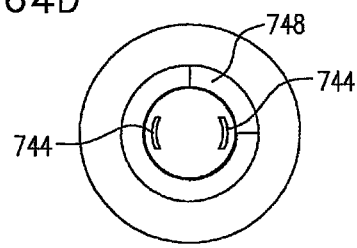
FIG. 64D is a simplified forwardly facing end view of the forward housing portion, forming part of the fluid flow connector of FIG. 61.
Figure 65A:
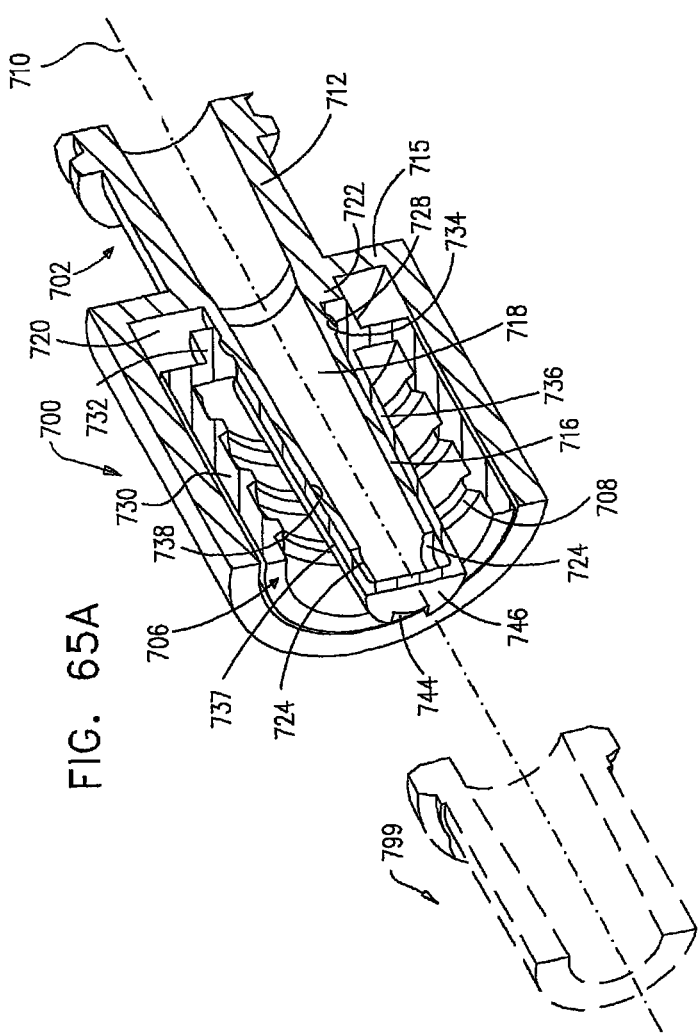

Reference is now made to FIG. 61, which is a simplified pictorial illustration of a fluid flow connector constructed and operative in accordance with yet another preferred embodiment of the invention, and to FIGS. 62A and 62B, which are simplified respective pictorial and sectional exploded view illustrations of the fluid flow connector of FIG. 61, FIG. 62B being taken along lines B-B in FIG. 62A.

As seen in FIGS. 61, 62A & 62B, there is provided a fluid flow connector 700 including a housing assembly including a rearward housing portion 702, having an externally-threaded portion 703 at a rearward end 704 thereof, and a forward housing portion 706 having an internally-threaded portion 708 at a forward end thereof. Rearward and forward housing portions 702 and 706 are preferably arranged along a common longitudinal axis 710 and are preferably snap fitted together.

Referring additionally to FIGS. 63A-63D, it is seen that the rearward housing portion 702 is an integrally formed element which is generally symmetric about a longitudinal axis, such as axis 710 (FIGS. 61-62B), but has certain non-symmetric structural features as described hereinbelow.

Rearward housing portion 702 is preferably formed with a rearward portion 712 extending forwardly of externally-threaded portion 703 thereof and with a generally cylindrical portion 714 extending forwardly of rearward portion 712 and joined thereto by a generally annular wall 715. An elongate generally conical hollow forwardly open shaft 716 extends forwardly along axis 710 interiorly of generally cylindrical portion 714. Formed in externally-threaded portion 703, rearward portion 712 and shaft 716 is a forwardly tapered conduit 718.

Wall 715 defines a forwardly facing surface 720. Forward of forwardly facing surface 720 of wall 715 there is provided a forwardly extending rotation limiting protrusion 722 which lies adjacent shaft 716 along a part of the periphery thereof.

Formed on opposite forward edges of forwardly tapered conduit 718 are a pair of cut-outs 724 which extend to a forward edge 726 of shaft 716. Formed on an outer surface of shaft 716, rearwardly of cut-outs 724 and forwardly of a forwardly facing surface 720 of wall 715, is an annular protrusion 728.

Reference is now made additionally to FIGS. 64A-64D, which illustrate forward housing portion 706 (FIGS. 61-62B) of the fluid flow connector 700. Forward housing portion 706 preferably includes a generally cylindrical main body portion 730 and a generally cylindrical rearward body portion 732, having an annular recess 734 configured for snap fit, rotational engagement with annular protrusion 728.

Forward housing portion 706 also includes an elongate generally conical hollow forwardly closed shaft 736, which extends forwardly along axis 710 mainly interiorly of generally cylindrical main body portion 730 and defines an outer generally conical surface 737. Formed in shaft 736 is a forwardly tapered volume 738, which is sized to rotationally and sealingly accept shaft 716 of rearward housing portion 702, when annular protrusion 728 is in snap fit engagement with annular recess 734.

Formed on opposite forward sides of forwardly tapered conduit 738 are a pair of cut-outs 744 which extend to a forward wall 746 of shaft 736. Formed rearwardly of rearward body portion 732 of forward housing portion 706 is a rotation limiting portion 748 having a rear wall 750 which slidingly engages forwardly facing surface 720 of wall 715 of rearward housing portion 702 and cooperates with forwardly extending rotation limiting protrusion 722 of the rearward housing portion 702 to limit the extent of mutual rotation of the forward and rearward housing portions 706 and 702 respectively about axis 710.

Reference is now made to FIGS. 65A, 65B, 65C, 66A and 66B, which are simplified sectional illustrations of the fluid flow connector 700 in a closed operative orientation, and to FIGS. 65D, 65E, 67A and 67B, which are simplified sectional illustrations of the fluid flow connector 700 in an open operative orientation in engagement with a female luer portion 799.

Referring initially specifically to FIGS. 65A, 65B, 65C, 66A and 66B, it is seen that annular protrusion 728 is in snap fit engagement with annular recess 734 and that forward edge 726 of shaft 716 lies in engagement with a rearwardly facing surface of forward wall 746 of shaft 736. Cut-outs 724 of shaft 716 are not aligned with cut-outs 744 of shaft 736. Mutual sealing of shaft 716 within volume 738 of shaft 736 thus seals conduit 718, rendering it capable of maintaining a pressurized fluid seal for pressurized fluid therein.

Reference is now made specifically to FIGS. 65D, 65E, 67A and 67B, which are simplified sectional illustrations of the fluid flow connector 700 in an open operative orientation in engagement with a female luer portion 799. It is seen that threaded engagement of the female luer portion 799 with the internally-threaded portion 708 causes frictional locking engagement between an inner conical surface of female luer portion 799 with outer generally conical surface 737, thereby rotating forward housing portion 706 about axis 710 relative to rearward housing portion 702. This rotation continues until mutually facing surfaces of rotation limiting protrusions 722 and 748 come into touching engagement. At this point, cut-outs 724 of shaft 716 lie in alignment with cut-outs 744 of shaft 736, thereby opening conduit 718 and permitting fluid flow therethrough.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

The invention claimed is:

1. A fluid flow connector comprising:
   a housing assembly having a first end and a second end arranged along a common longitudinal axis;
   a forward conduit and actuator element at least partially disposed within said housing assembly, said forward conduit and actuator element having a forward edge;
   a resilient fluid flow conduit sealing and biasing element locked within said forward conduit and actuator element, said resilient fluid flow conduit sealing and biasing element having a forward end positioned alongside said forward edge, said forward end being formed with a selectably closable slit extending along said longitudinal axis; and
   a rigid fluid flow conduit member disposed within said resilient fluid flow conduit sealing and biasing element,
   said forward conduit and actuator element and said resilient fluid flow conduit sealing and biasing element being positionable in a forward position wherein said selectably closable slit is closed; and
   said forward conduit and actuator element and said resilient fluid flow conduit sealing and biasing element being positionable in a rearward position, wherein said rigid fluid flow conduit member at least partially extends through said selectably closable slit causing said selectably closable slit to open and wherein
   said resilient fluid flow conduit sealing and biasing element is formed with an elongate bore and a forward end wall having a rearwardly facing surface, said slit being formed within said forward end wall;
   said forward conduit and actuator element is formed with an interior bore and a forwardly facing aperture; and
   when said forward conduit and actuator element and said resilient fluid flow conduit sealing and biasing element are positioned in said rearward position, said rigid fluid flow conduit member extends through said slit, and at least partially extends through said forwardly facing aperture, thereby stretchingly displacing said forward end wall forwardly and radially outward from said slit to a longitudinal orientation, tightly and circumferentially disposed between an exterior surface of said rigid fluid flow conduit member and said aperture, thereby unsealing said rigid fluid flow conduit member.

2. A fluid flow connector according to claim 1 and wherein said forward conduit and actuator element is arranged for displacement between said forward position and said rearward position along said common longitudinal axis.

3. A fluid flow connector according to claim 1 and wherein said resilient fluid flow conduit sealing and biasing element is arranged for partial displacement between said forward position and said rearward position along said common longitudinal axis.

4. A fluid flow connector according to claim 1 and wherein said first end is an internally-threaded end and said second end is an externally-threaded end.

5. A fluid flow connector according to claim 1 and wherein when said forward conduit and actuator element and said resilient fluid flow conduit sealing and biasing element are positioned in said rearward position, said forward conduit and actuator element is engaged by a displacement actuator and said rigid fluid flow conduit member at least partially extends through said selectably closable slit, thereby opening said selectably closable slit.

6. A fluid flow connector according to claim 5 and wherein when said forward conduit and actuator element and said resilient fluid flow conduit sealing and biasing element are positioned in said forward position, said forward conduit and actuator element is not engaged by said displacement actuator and said selectably closable slit is closed.

7. A fluid flow connector according to claim 1 and wherein said housing assembly also includes a rearward conduit which extends forwardly from said second end along said axis.

8. A fluid flow connector according to claim 7 and wherein said rigid fluid flow conduit member is integrally formed within said housing assembly and extends forwardly from said rearward conduit.

9. A fluid flow connector according to claim 1 and wherein said resilient fluid flow conduit sealing and biasing element is formed with a selectably compressible accordion type rearward portion disposed rearwardly of said elongate bore, said selectably compressible accordion type rearward portion defining an inner volume, communicating with said elongate bore.

10. A fluid flow connector according to claim 9 and wherein when said forward conduit and actuator element and said resilient fluid flow conduit sealing and biasing element are positioned in said rearward position and said forward conduit and actuator element is engaged by a displacement actuator, said selectably compressible accordion type rearward portion is rearwardly compressed against a forwardly facing circumferential surface of said housing assembly.

11. A fluid flow connector according to claim 1 and wherein said forward conduit and actuator element is arranged to be displaced rearwardly from said forward position to said rearward position along said axis by engagement of said forward conduit and actuator element by a rearwardly facing end of an external conduit.

12. A fluid flow connector according to claim 11 and wherein:
   said first end is an internally-threaded end; and
   said engagement of said external conduit with said forward conduit and actuator element is via said internally-threaded end.

13. A fluid flow connector according to claim 1 and wherein said resilient fluid flow conduit sealing and biasing element includes a generally elongate portion having an elongate bore formed therewithin along said axis, said elongate bore including an integrally formed interior facing sealing ring.

14. A fluid flow connector according to claim 13 and wherein said rigid fluid flow conduit member is slidably and sealingly disposed within said elongate bore in engagement with said sealing ring.

15. A fluid flow connector according to claim 13 and wherein said sealing ring and an exterior surface of said rigid fluid flow conduit member are in slidable sealing engagement.

16. A fluid flow connector according to claim 13 and wherein:
said housing assembly also includes a rearward conduit which extends forwardly from said second end along said axis;
said resilient fluid flow conduit sealing and biasing element is formed with a forward end wall having a rearwardly facing surface, said slit being formed within said forward end wall; and
said fluid flow connector maintains a pressurized fluid seal for pressurized fluid in said rearward conduit, said rigid fluid flow conduit member, and a volume inside said resilient fluid flow conduit sealing and biasing element forward of said sealing ring, said pressurized fluid seal being provided by said sealing ring and by said rearwardly facing surface of said forward end wall.

17. A fluid flow connector according to claim 1 and wherein:
said housing assembly also includes a rearward conduit which extends forwardly from said second end along said axis;
said forward conduit and actuator element is formed with an interior bore and a forwardly facing aperture;
said forward conduit and actuator element is arranged to be displaced rearwardly from said forward position to said rearward position along said axis by engagement of said forward conduit and actuator element by a rearwardly facing end of an external conduit; and
when said forward conduit and actuator element and said resilient fluid flow conduit sealing and biasing element are in said rearward position, a fluid flow connection is open for fluid supplied via said rearward conduit and said rigid fluid flow conduit member to said external conduit via said slit and said aperture, wherein a volume of said fluid flow connection does not substantially change upon opening or closing of said fluid flow connection, thus providing a generally neutral fluid displacement characteristic.

* * * * *